(12) United States Patent
Zhou

(10) Patent No.: US 9,789,295 B2
(45) Date of Patent: *Oct. 17, 2017

(54) CUSTOMIZED SKIN CARE AND METHOD TO PROVIDE SAME

(71) Applicant: Yuchen Zhou, San Jose, CA (US)

(72) Inventor: Yuchen Zhou, San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/193,059

(22) Filed: Jun. 26, 2016

(65) Prior Publication Data

US 2016/0331308 A1    Nov. 17, 2016

Related U.S. Application Data

(63) Continuation-in-part of application No. 13/492,852, filed on Jun. 9, 2012, now Pat. No. 9,623,225, which
(Continued)

(51) Int. Cl.
*A61M 35/00* (2006.01)
*A61H 23/00* (2006.01)
(Continued)

(52) U.S. Cl.
CPC ............ *A61M 35/003* (2013.01); *A61B 5/002* (2013.01); *A61B 5/0022* (2013.01); *A61B 5/0077* (2013.01); *A61B 5/103* (2013.01); *A61B 5/441* (2013.01); *A61B 5/4836* (2013.01); *A61H 7/002* (2013.01); *A61H 23/00* (2013.01); *A61M 37/00* (2013.01); *A61N 7/00* (2013.01); *G06F 19/3406* (2013.01); *G06F 19/3456* (2013.01);
(Continued)

(58) Field of Classification Search
CPC .... A61H 2201/105; A61H 7/00; A61H 7/001; A61H 7/002; A61H 7/003; A61H 7/004; A61H 7/005; A61H 23/00; A61H 23/02; A61H 23/0245; A61H 2201/0119; A61H 2201/0153; A61H 2201/0157; A61H 2201/02; A61H 2201/02; A47K 5/1217; B67D 7/0044; B67D 7/0046; B05B 11/3081; B05B 11/3082; B05B 83/66; B05B 83/68; B05B 83/682; A61M 35/003; A61M 2005/14208; A61M 11/00; A61F 2007/0087; A61F 7/00; A61F 2007/00

See application file for complete search history.

(56) References Cited

U.S. PATENT DOCUMENTS 4,984,568 A    1/1991   Persaud
5,785,960 A *  7/1998   Rigg .................... A45D 44/005
                                              366/160.1
(Continued)

FOREIGN PATENT DOCUMENTS

TW        M414957 U    11/2011

*Primary Examiner* — Justine Yu
*Assistant Examiner* — Tu Vo

(57) ABSTRACT

Methods to provide customized skin care by using specimen dispensing device to dispense specimens from removable dispensers for the purpose of treating skin of a user are presented. Methods to utilize the embedded memory and electrical interface of the dispensing device and dispensers to produce customizable skin care products that give better skin treatment results are also presented. The invention may also be applied to health care and personal care needs.

20 Claims, 83 Drawing Sheets

Related U.S. Application Data is a continuation-in-part of application No. 13/317,136, filed on Oct. 11, 2011, now abandoned, application No. 15/193,059, which is a continuation-in-part of application No. 13/396,381, filed on Feb. 14, 2012, now Pat. No. 9,492,645, which is a continuation-in-part of application No. 13/317,136, filed on Oct. 11, 2011, now abandoned.

(60) Provisional application No. 61/456,164, filed on Nov. 2, 2010, provisional application No. 61/464,520, filed on Mar. 3, 2011.

(51) Int. Cl.

| | |
|---|---|
| *A61H 23/02* | (2006.01) |
| *A61B 5/00* | (2006.01) |
| *A61H 7/00* | (2006.01) |
| *A61B 5/103* | (2006.01) |
| *A61M 37/00* | (2006.01) |
| *A61N 7/00* | (2006.01) |
| *G06F 19/00* | (2011.01) |
| *G06Q 50/00* | (2012.01) |
| *A61N 1/00* | (2006.01) |
| *A61N 1/04* | (2006.01) |
| *A61N 5/06* | (2006.01) |
| *A61N 1/32* | (2006.01) |
| *A61F 7/00* | (2006.01) |
| *A61H 9/00* | (2006.01) |
| *G01S 19/19* | (2010.01) |

(52) U.S. Cl.
CPC ......... *G06F 19/3462* (2013.01); *G06Q 50/01* (2013.01); *A61F 2007/0087* (2013.01); *A61H 7/003* (2013.01); *A61H 9/0007* (2013.01); *A61H 23/006* (2013.01); *A61H 23/0245* (2013.01); *A61H 2201/0153* (2013.01); *A61H 2201/0157* (2013.01); *A61H 2201/02* (2013.01); *A61H 2201/0207* (2013.01); *A61H 2201/0214* (2013.01); *A61H 2201/0228* (2013.01); *A61H 2201/0292* (2013.01); *A61H 2201/10* (2013.01); *A61H 2201/1409* (2013.01); *A61H 2201/5046* (2013.01); *A61H 2201/5048* (2013.01); *A61H 2201/5064* (2013.01); *A61H 2201/5097* (2013.01); *A61H 2205/022* (2013.01); *A61M 37/0092* (2013.01); *A61M 2205/3584* (2013.01); *A61M 2205/50* (2013.01); *A61N 1/0408* (2013.01); *A61N 1/328* (2013.01); *A61N 5/0616* (2013.01); *A61N 2005/0644* (2013.01); *A61N 2007/0034* (2013.01); *G01S 19/19* (2013.01)

(56) References Cited

U.S. PATENT DOCUMENTS

| | | | | |
|---|---|---|---|---|
| 5,903,465 | A * | 5/1999 | Brown | A45D 44/005 700/242 |
| 6,177,093 | B1 * | 1/2001 | Lombardi | A61K 8/00 424/401 |
| 6,437,866 | B1 * | 8/2002 | Flynn | A45D 44/005 356/326 |
| 6,510,366 | B1 * | 1/2003 | Murray | A45D 44/00 700/233 |
| 6,571,003 | B1 * | 5/2003 | Hillebrand | A61B 5/0064 382/100 |
| 6,622,064 | B2 * | 9/2003 | Bartholomew | A45D 29/00 222/144 |
| 6,715,642 | B2 | 4/2004 | Engel | |
| 6,782,307 | B2 * | 8/2004 | Wilmott | A61K 8/044 700/233 |
| 6,935,386 | B2 * | 8/2005 | Miller | B01F 13/1055 141/104 |
| 7,711,610 | B2 * | 5/2010 | Iwaki | G06Q 30/06 424/401 |
| 8,224,481 | B2 | 7/2012 | Bylsma | |
| 8,564,778 | B1 * | 10/2013 | Igarashi | A45D 44/005 356/402 |
| 8,693,768 | B1 * | 4/2014 | LaForgia | A45D 44/005 222/1 |
| 9,007,588 | B1 * | 4/2015 | Igarashi | G05D 11/132 356/402 |
| 9,205,283 | B2 * | 12/2015 | Miklatzky | A45D 19/02 |
| 2001/0028308 | A1 | 10/2001 | De La Huerga | |
| 2005/0191252 | A1 | 9/2005 | Mitsui | |
| 2006/0276731 | A1 | 12/2006 | Thiebaut et al. | |
| 2007/0185553 | A1 | 8/2007 | Kennedy | |
| 2009/0200395 | A1 | 8/2009 | Duru | |
| 2009/0210322 | A1 * | 8/2009 | Stark | A61Q 1/02 705/26.1 |
| 2010/0185322 | A1 * | 7/2010 | Bylsma | A61M 5/1413 700/239 |
| 2011/0220139 | A1 * | 9/2011 | Samain | A45D 40/18 132/200 |
| 2011/0226803 | A1 * | 9/2011 | Schwartz | A45D 34/00 222/1 |
| 2011/0247718 | A1 * | 10/2011 | Samain | A45D 44/005 141/1 |
| 2011/0251526 | A1 | 10/2011 | Kim | |
| 2011/0251537 | A1 | 10/2011 | Yeo | |
| 2011/0288680 | A1 * | 11/2011 | Samain | A45D 44/005 700/239 |
| 2013/0037043 | A1 * | 2/2013 | Samain | G06F 19/3462 132/200 |
| 2014/0081462 | A1 * | 3/2014 | Igarashi | A45D 44/005 700/265 |
| 2014/0081463 | A1 * | 3/2014 | Igarashi | A45D 44/005 700/265 |
| 2015/0021356 | A1 * | 1/2015 | Witchell | G01F 1/42 222/23 |
| 2016/0058156 | A1 * | 3/2016 | Chiasson | A45D 40/24 132/200 |
| 2016/0107133 | A1 * | 4/2016 | Sugino | B01F 13/1063 366/142 |

\* cited by examiner

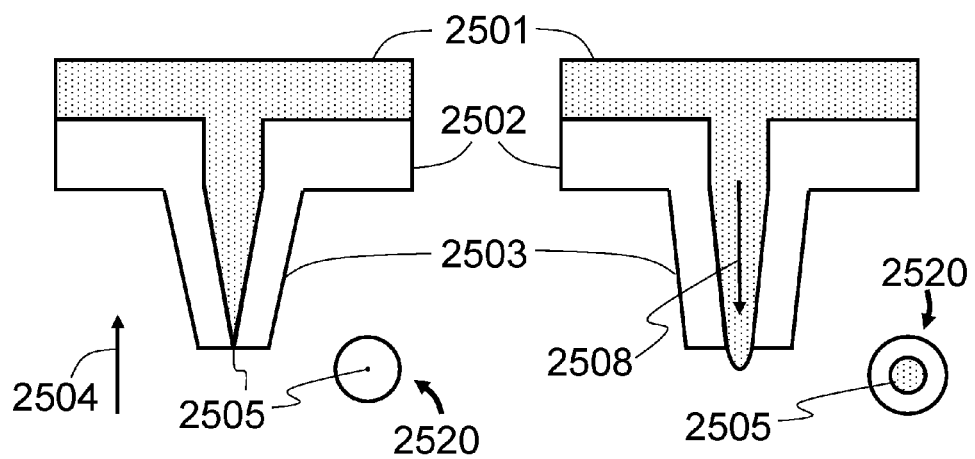
FIG. 25A     FIG. 25B
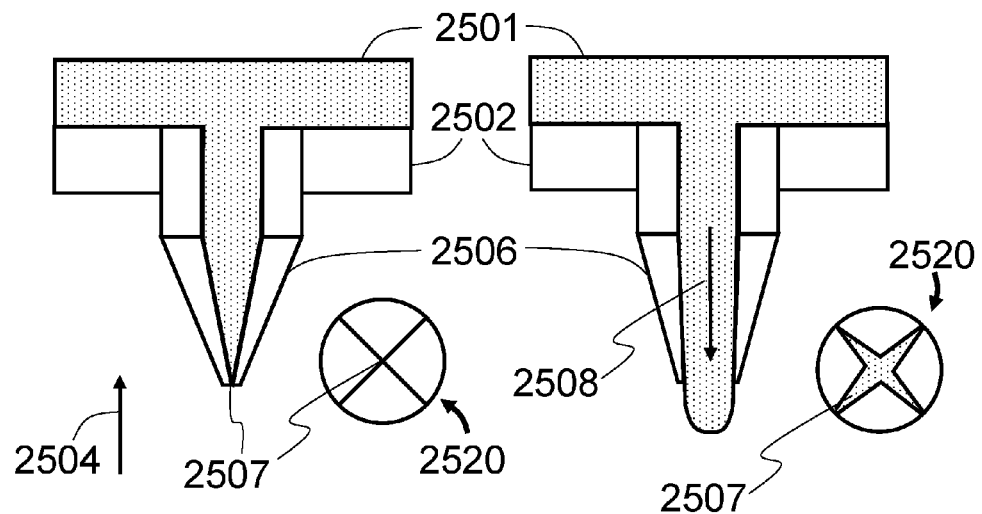
FIG. 25C     FIG. 25D

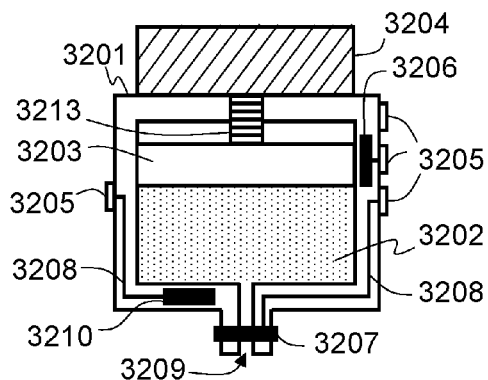
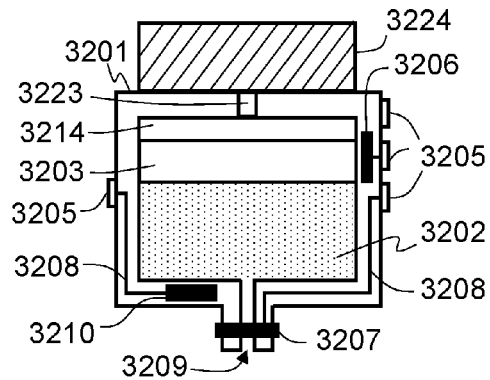
FIG. 32A  FIG. 32B
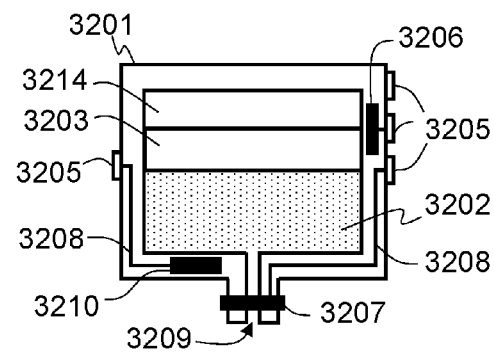
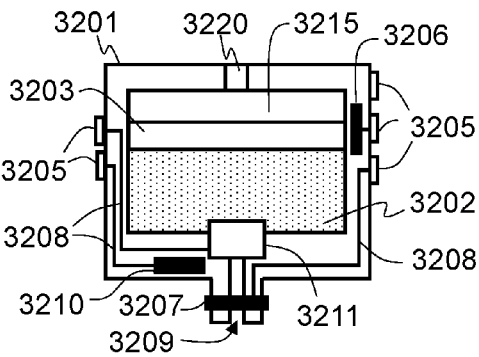
FIG. 32C  FIG. 32D

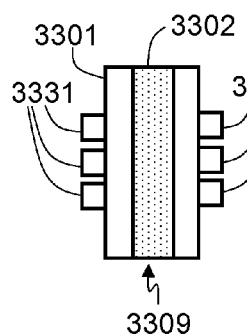 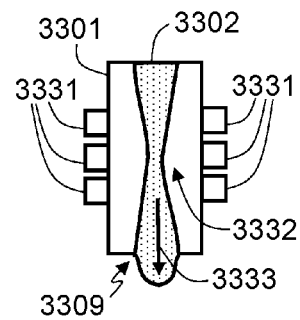 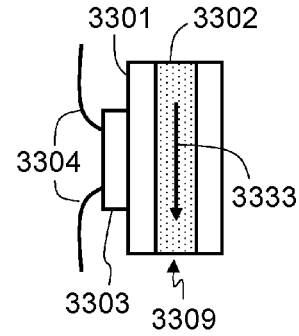
*FIG. 33A*  *FIG. 33B*  *FIG. 33C*
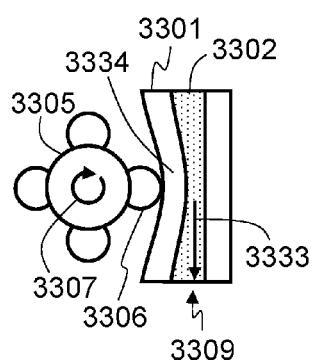 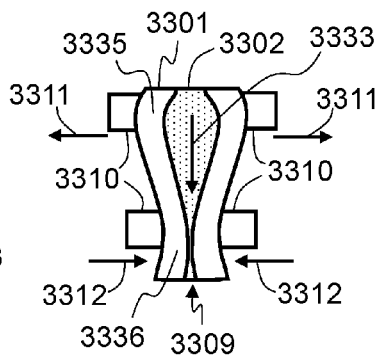 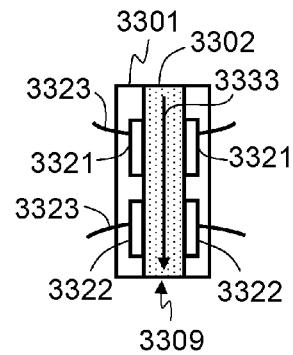
*FIG. 33D*  *FIG. 33E*  *FIG. 33F*

CUSTOMIZED SKIN CARE AND METHOD TO PROVIDE SAME

CROSS-REFERENCE TO RELATED APPLICATIONS

The present application is a Continuation-In-Part of the commonly assigned application bearing Ser. No. 13/492,852, filed on Jun. 9, 2012, entitled "SPECIMEN DISPENSING DEVICE," which is incorporated herein by reference. Application Ser. No. 13/492,852 is a Continuation-In-Part of the commonly assigned application bearing Ser. No. 13/317,136, filed on Oct. 11, 2011, entitled "Integrated skin-treatment specimen dispenser with electrical interface," which claims the benefit of the provisional application bearing Ser. No. 61/456,164, filed on Nov. 2, 2010.

The present application is also a Continuation-In-Part of the commonly assigned application bearing Ser. No. 13/396,381, filed on Feb. 14, 2012, entitled "SKIN TREATMENT DEVICE WITH AN INTEGRATED SPECIMEN DISPENSER", which is a Continuation-In-Part of the commonly assigned application bearing Ser. No. 13/317,136, filed on Oct. 11, 2011, entitled "Integrated skin-treatment specimen dispenser with electrical interface," that claims the benefit of the provisional application bearing Ser. No. 61/456,164, filed on Nov. 2, 2010. Application Ser. No. 13/396,381 also claims the benefit of the provisional application bearing Ser. No. 61/464,520, filed on Mar. 3, 2011.

FIELD OF THE INVENTION

The present invention generally relates to electrical and electronic skin care technology and more particularly to a skin care specimen dispenser and its application in achieving personalized or customized specimen according to each individual user's own unique skin condition, skin feature and skin care need.

BACKGROUND

Skin care products in today's market are generally in the forms of lotion, cream, serum, powder, solid, gel, liquid or other physical forms. It is a universal practice in the commercially available skin care products that these products are marketed and provided to users in these forms without specification or means that are designed to meet the specific skin condition of different individual users. Consequently, the different skin types of different users after using the same skin care product can usually produce different skin care results, even though the functional ingredients of the same product are identical. For example, a skin care product marketed as "anti-aging" usually targets the aging signs of the facial skin, including wrinkles, age spots, fine lines, brown spots, smile lines, and puffy eyes, etc. By using a product targeting to reduce multiple signs of aging, which generally includes multiple active ingredients, with a single or a group of ingredients functioning to reduce certain type of aging sign, a user with stronger wrinkles or a user with stronger puffy eyes may not experience the same level of effectiveness of aging sign reduction as compared to a normal user with a more evenly weighted aging signs.

The inventor realizes that the way that the existing skin-care products are produced and marketed, and the method that is generally practiced by users on daily basis are lack of the ability to customize the skin care product composition and application method to match to the unique skin condition and unique skin care need of each individual user. By enabling this ability to customize the skin care product composition and application method to each individual skin care need, more effectiveness from the skin care product and better skin care result shall be achieved than the existing method of using existing skin-care products.

It is an object of this invention to include the step of each individual user skin analysis in the skin care process and to provide a specimen dispensing device that utilizes the unique personal skin data of each individual user resulting from said skin analysis and enables the customizability of skin care products and dispensing of skin care specimen. It is an object of this invention to provide the said specimen dispensing device in combination with skin treatment members to enhance skin care results. It is an object of this invention to utilized personal computing devices, personal communication devices, databases, internet cloud, social networks and professional skin care service providers to achieve the customized skin care for each individual user.

It is yet another object of this invention to provide a specimen dispensing device that enables the customizability of other health care or personal products according to each individual user's unique skin care need by utilizing data communication protocols that can associate and correlate the functions and efficacies of different specimens with the unique skin conditions of different users.

SUMMARY OF THE INVENTION

In this invention, we described a specimen dispensing device that can achieve individually customizable skin care product. We also described methods to achieve individually customized skin care specimen according to each individual user's own unique skin care need. Similar methods and devices can also be used for other health care and personal care needs, as long as the ability to individually customize a specimen can make a beneficial improvement in the health care or personal care effectiveness and provide better care result.

The most preferred specimen dispensing device for dispensing one or more types of specimen to a target skin area of a human being according to this invention may include: a device body; a dispenser containing the specimen; a specimen outlet existing on the device body, the outlet being operatively connected to the dispenser, where the specimen passes through during a dispensing operation; at least one electrical contact being electrically connected to an electronic circuit included in the dispenser; at least one first information storage component located in the dispenser storing first type of information; a control unit containing electronic circuits and embedded software; an electrical connection between the dispenser and the control unit; at least one second information storage component located in the control unit storing second type of information; and at least one information processing component in the control unit controls the dispensing of specimen from the dispenser by processing the first type and second type of information.

The dispenser can be a removable and replaceable dispenser; a refillable dispenser; a disposable and for one-time use only dispenser; a dispenser having multiple sub-dispensers containing same or different specimens, the sub-dispensers being individually selectable to dispense specimen therein; a dispenser with multiple specimen compartments containing same or different specimens, each of the compartments being individually selectable to dispense specimen therein; a dispenser that resides within the device body; or a dispenser that is externally attached to the device body.

The specimen can be any of: liquid, gel, serum, cream, lotion, paste and powder. It can be used for a variety of treatments such as biological body area, body function, organ, skin, bone, tissue and cell.

The specimen is dispensed from the dispenser by any means of: a manually exerted or a pre-loaded force to the dispenser, wherein the control unit controls the dispensing by limited the amount of specimen being dispensed from one or more of the specimen containing compartments or sub-dispensers; an electrically powered driving mechanism that is part of the dispenser and operated by the control unit; and an electrically powered driving mechanism that is part of the device body and electrically controlled by the control unit.

The first type of information is related to the specimen, and is further related to how the specimen is dispensed, including but not limited to any of: information of the specimen such as: specimen brand, name, type, original, composition, production date and expiration date, specimen level within the dispenser and ordering information, number of sub-dispensers and compartments, information of specimen within sub-dispensers and compartments; information of optimal or pre-set operational mode of the different sub-dispensers or difference different specimen compartments within a single dispenser, where the operational mode can be, but not limited to, timing and/or flow speed of specimen application from each different dispenser or each different compartment, amount of specimen to be dispensed from each different dispenser or each different compartment; information of historic usage data of the device, the dispenser and specimen; information that is created or input by the user, manufacturer, or a health care professional; information transferred from the control unit; biometrics information of the user; and information enabling anti-fake, anti-piracy, authenticity confirmation.

The first type of information is transmitted to the information processing component in the control unit by using a standardized protocol, for example as illustrated by dispenser data structures 5400, 5500, 5550 as in FIG. 54 through FIG. 55B. The protocol can be designed such that different specimen information in any individual compartment or individual sub-dispenser is arranged in the same digital format. The same digital format can be an ordered number and/or character sequence of information that contains an allocate space in a sequence for any of the possibly needed information of any given specimen to be dispensed from the device. The protocol can be used to standardize the communication between any specimen dispenser made by different vendors and any dispensing devices made by other vendors to achieve compatibility and to reduce cost of operation.

The first information storage component can be any of: a digital data storage device, such as flash memory, phase-change memory, resistive RAM, MRAM, DRAM, SRAM, magnetic data storage device; an analog data storage device; an optically recognizable markings such as letters, numbers, bar code, graphics, color patterns, RF ID, physical indentations or protrusions and chemicals; a hard coded dispensing regulation component such as an electronic chip, a circuit component, a mechanical valve or a non-volatile memory.

The second type of information is related to the target skin area of a human being, such as device operation data, user skin information data, user personal and biometrics information, dispenser identification data, date, time, season, weather and other user-specific data, application schedule and reminder message. The second type of information may be transmitted to and stored in the control unit by using a standardized protocol, for example as illustrated by user data structure 5300 of FIG. 53.

The second information storage component can be any of: a digital data storage device such as flash memory, phase-change memory, resistive RAM, MRAM, DRAM, SRAM, magnetic data storage device; an analog data storage device; an optically recognizable markings such as letters, numbers, bar code, graphics, color patterns, RF ID, physical indentations or protrusions, and chemicals.

The control unit includes means for displaying information to a user through visual, skin contact or sound effects; means for receiving the first type of information stored in the first information storage component and the second type of information stored in the second information storage component; and means for processing the first type information and the second type of information by the information processing component and for providing instructions to control the dispenser to dispense the specimen in a specific manner. The control unit may further include: means for sending data to be stored in the dispenser, wherein data stored in the container is retrievable; means or providing user interface, power supply and charging functions; and means for sending messages wirelessly to a second device such as, but not limited to a computer, a mobile device, a smart phone, or a data center.

The information processing component includes embedded software for processing the first type and second type of information. The embedded software, first type of information and second type of information may be retrieved or updated through a data interface within the device. The retrieval and update can be done by any of, a computer, a mobile device, a smart phone, or a data center. The data interface can be any of: a wireless transmitter/receiver within the control unit; a data communication component that utilizes the wireless charging circuitry to transmit digital or analog data; and one or more electrical contacts that connect to the control unit.

The dispensing surface of the device may be a skin treatment member which can produce any of: ultrasonic vibration, sub-sonic vibration, electrical voltage or current application, heating, cooling, light emission, air blowing, brushing, tapping, shaking, pulsating or scrubbing. In descriptions hereafter, the word "dispenser" and the word "cartridge" is used as equivalent terms interchangeably in descriptions of the embodiments of this invention.

BRIEF DESCRIPTION OF THE DRAWINGS

FIG. 25A illustrates a first type of specimen dispenser outlet being closed when specimen is not under dispensing pressure or force;

FIG. 25B illustrates a first type of specimen dispenser outlet being opened when specimen is under dispensing pressure or force;

FIG. 25C illustrates a second type of specimen dispenser outlet being closed when specimen is not under dispensing pressure or force;

FIG. 25D illustrates a second type of specimen dispenser outlet being opened when specimen is under dispensing pressure or force;

FIG. 32A illustrates cross-sectional view of a specimen dispenser having surface electrical contacts, embedded electrical components and an externally attached mechanical specimen driver;

FIG. 32B illustrates cross-sectional view of a specimen dispenser having surface electrical contacts, embedded electrical components and an externally attached air pump specimen driver;

FIG. 32C illustrates cross-sectional view of a specimen dispenser having surface electrical contacts, embedded electrical components and specimen driving by internal propellant;

FIG. 32D illustrates cross-sectional view of a specimen dispenser having surface electrical contacts, embedded electrical components and specimen driving by a pump located in proximity to the dispenser outlet;

FIG. 33A illustrates a specimen pump including thermal excitation circuits and electrical components around a specimen conduit;

FIG. 33B illustrates specimen being dispensed by heating from circuits and electrical component on a specimen conduit and specimen contained therein;

FIG. 33C illustrates a specimen pump including a piezo element attached to a specimen conduit and specimen contained therein;

FIG. 33D illustrates a specimen pump including a rotary motor and a flexible conduit and specimen contained therein;

FIG. 33E illustrates a specimen pump including alternating valves and a flexible conduit and specimen contained therein;

FIG. 33F illustrates a specimen pump including electrodes embedded in a conduit and specimen contained therein;

FIG. 74B illustrates a method to identify a dispenser by magnetic sensing;

FIG. 75 illustrates a method to realize personalized dispensing scheme;

FIG. 76 illustrates a method to realize personalized composition dispenser set;

FIG. 77 illustrates another method to realize personalized dispensing scheme;

FIG. 78 illustrates yet another method to realize personalized dispensing scheme;

FIG. 79 illustrates another method to realize personalized composition dispenser set;

FIG. 80 illustrates yet another method to realize personalized composition dispenser set;

FIG. 81 illustrates yet another method to realize personalized dispensing scheme;

FIG. 82A illustrates a method to apply ultrasound treatment on top of a skin care mask covering a user's skin area;

FIG. 82B illustrates another method to apply ultrasound treatment on top of a skin care mask covering a user's skin area;

FIG. 83A illustrates an example of pusher based on threaded rod;

FIG. 83B illustrates an example of pusher based on rollers;

Figure 83A:
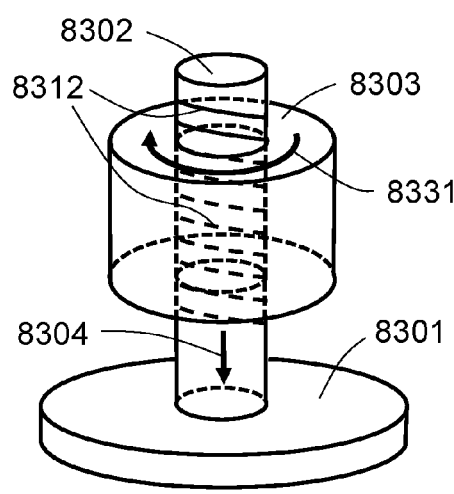
Figure 83B:
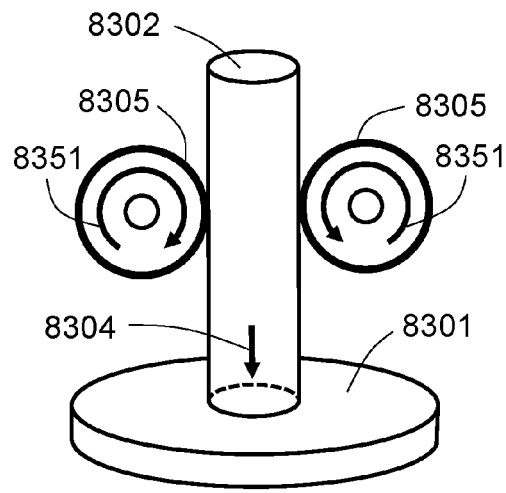
Figure 83C:
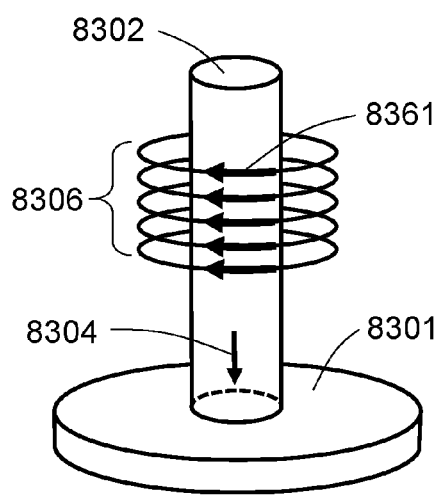

FIG. 83C illustrates an example of pusher based on electromagnetic force; and

Figure 83D:
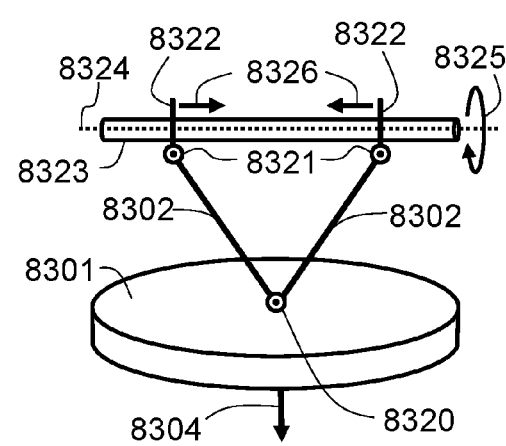

FIG. 83D illustrates an example of pusher based on hinges.

DETAILED DESCRIPTION OF THE INVENTION

While a novel specimen dispensing device for skin care and skin treatment is disclosed, methods to utilize the embedded memory and electrical interface of the device to produce customizable skin care products and give better skin treatment results are presented. The invention has applicability to other health care and personal care needs, including utilizing the information of: (1) individual personal information, (2) individual personal illness information, (3) individual personal symptom information, (4) individual personal health information, (5) individual physical and bodily conditions information, together with the information of: (1) medication, (2) personal care products that are specifically targeted to treat illness or symptoms, (3) products that are to improve health conditions, to improve physical or bodily conditions, in ways that produce treatment recipes that are uniquely adjusted according to each individual's own health care or personal care need. The present invention may be embodied in many different forms, designs or configurations, for the purpose of promoting an understanding of the principles of the invention, reference will be made to the embodiments illustrated in the drawings and specific language will be used to describe the same. It will nevertheless be understood that no limitation or restriction of the scope of the invention is thereby intended. Any alterations and further implementations of the principles of the invention as described herein are contemplated as would normally occur to one skilled in the art to which the invention relates.

Figure 1:
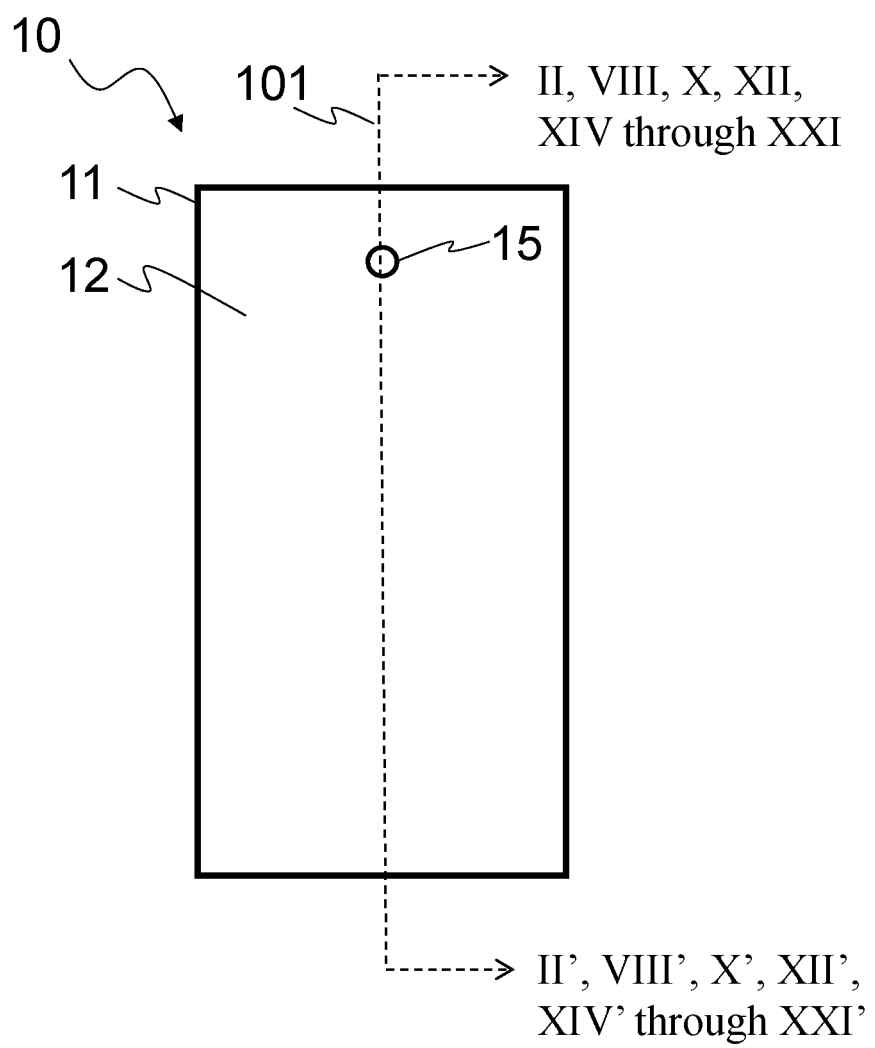
FIG. 1 is a schematic diagram illustrating a front view of the specimen dispensing device according to the embodiments of the present invention.
Figure 2:
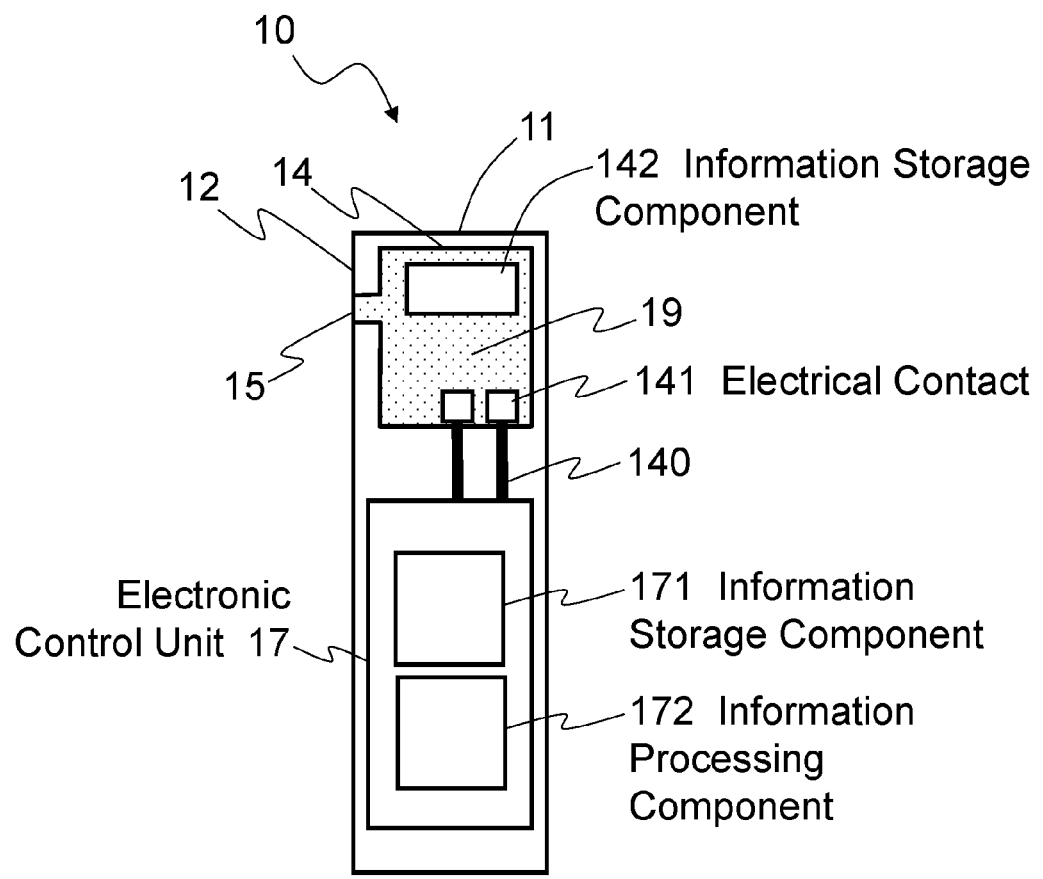
FIG. 2 is a schematic diagram illustrating a cross-sectional view of the specimen dispensing device of FIG. 1 according to the first preferred embodiment of the present invention.

FIG. 1 and FIG. 2 illustrate a specimen dispenser being integrated within a specimen dispensing device 10. FIG. 1 is a schematic diagram illustrating a front view of the specimen dispensing device 10, where the outside rectangle shape is shown merely for description purpose and in practice can be any other shapes as needed. FIG. 2 is a schematic diagram illustrating a cross-sectional view along the center line 101 of FIG. 1.

The specimen dispensing device, as illustrated in FIG. 1 and FIG. 2, which represents the one of the best modes of this invention, contains the following components or aspects: a device body 11, a dispensing surface 12, a dispenser 14, at least one electrical contact 141 that is part of the dispenser 14, at least one type of information storage component 142 included or embedded in the dispenser 14, a specimen outlet 15, an electronic control unit 17, an electrical interface 140, at least one information storage component 171 included in the control unit 17, and at least one information processing component 172 included in the control unit 17.

The device body 11 provides a case or housing for the dispenser and the internal electronics. It can be made of metal, alloy, glass, plastics or any other solid materials.

The dispensing surface 12 is a surface which allows the dispensed specimen 19 to temporarily reside upon after being dispensed from dispenser 14 through the outlet 15 of device 10 before transferring to target skin area of a user of the dispensing device 10. However, in other embodiment, the specimen can be dispensed directly onto the target skin without staying on surface 12, for example through a spray function, whereas the specimen 19 is dispensed from the outlet 15 through a spray action and directly upon the target skin area of the user of the dispensing device 10.

The skin treatment specimen dispenser 14, which can be in any shape, contains skin treatment specimen 19 which can be, but not limited to, liquid, gel, cream, paste, serum, lotion and powder.

The at least one electrical contact 141 resides on the dispenser 14 and is electrically connected to electronic circuits and components, including the information storage component 142, that are embedded in dispenser 14.

The at least one type of information storage component 142 included in the dispenser 14 stores information including how the specimen 19 is designed to be dispensed from the dispensing device 10 according to the user's own unique skin care need. The information stored in information storage component 142 can be, but not limited to, dispensing amount, dispensing speed, timing of dispense and specimen information.

The specimen outlet 15 is one hole or an array of holes, which is located on the surface 12 and is embedded in the body 11. In operation, the skin treatment specimen 19 is dispensed through the outlet 15.

The electronic control unit 17 contains electrical circuits, electronic components and necessary software or firmware stored in the electronic components.

The electrical interface 140 is located between the dispenser 14 and the electronic control unit 17 such that the dispensing of specimen 19 from the dispenser 14 can be entirely or partially controlled by the electronic control unit 17.

The at least one information storage component 171 included in the control unit 17 is located in, and electronically coupled to, the control unit 17. It stores information related to how to control the dispensing of specimen 19 from dispenser 14, such information can be, but not limited to, software or firmware, device operation data, user skin information data, user personal and biometrics information, dispenser identification data, date, time, season, and other user-specific data such as preference, schedule, reminder message and avoidance. Such stored information may be updated as needed, by user, by a manufacturer, by a skin care specialist, by a dermatologist, or by a health care professional. The user skin information stored in information component 171 is acquired after a skin analysis of the user's skin condition.

Figure 51:
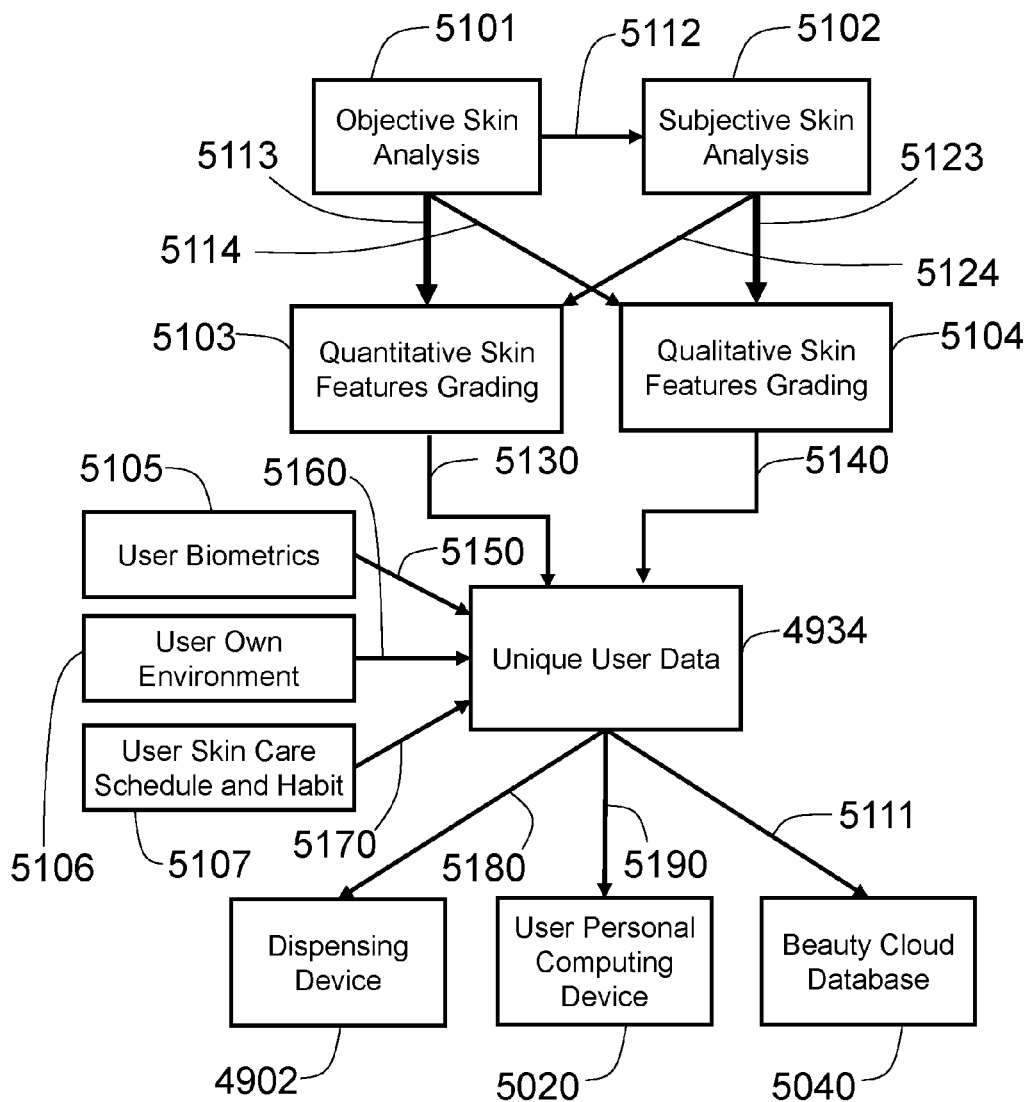
FIG. 51 illustrates methods to analyze a user's skin condition, as well as generation and storage of unique user data.

Now referring to FIG. 51. FIG. 51 illustrates a method to analyze a user's skin condition, as well as generation and storage of unique user data 4934. In the user skin analysis method of FIG. 51, skin analysis step is characterized into two practices: objective skin analysis 5101 and subjective skin analysis 5102. Objective skin analysis 5101 includes practices to analyze a user's skin condition by any of: skin analysis instruments, physical tools, skin feature measuring or grading equipment, which analyze the user's skin condition by a set of standards that are not affected by human judgement. Subjective analysis 5102 includes practices to analyze a user's skin condition through visual examination of user's skin, verbal or visual communication with the user regarding the user skin condition, by any of: a skin care specialist, a skin dermatologist, a computer interface allowing user to perform self-evaluation. Subjective analysis 5102 results include any of: an opinion, an evaluation, a judgement, a recommendation, or an adjustment by any of: a skin care specialist, a skin dermatologist, or the user's own preference, desire, habit, and life style. FIG. 51 shows that the results from the practice of objective skin analysis 5101 of the user's skin, can be brought into a subjective skin analysis step 5102 as shown by step 5112, where the user' skin analysis results may be further modified by the subjective skin analysis step S102.

Results from user' skin analysis by the objective skin analysis 5101 and subjective skin analysis 5102 may each be forwarded to a grading step of the condition of various skin features as indicated by steps of 5113, 5114, 5123 and 5124. The grading step may provide a quantitative skin feature grading 5103, which grades the user's skin features according to a set of standards and into numeric or digital information, for example grade 1 through 10 in step of 1, where grade 1 is mildest and grade 10 is strongest of a specific skin feature. The grading step may also provide a qualitative skin feature grading 5104, which grades the user's skin features according to a set of standards and into qualitative grades, for example, very serious, serious, normal, good, and very good, whereas the qualitative grades may be less precise or provides less detail as compared to quantitative grades and may sometimes be based on personal opinion and experience of a skin specialist, a skin dermatologist, or the user.

The qualitative grades from the qualitative skin features grading 5104 may also be stored or transmitted in later steps by numeric or character data, for example grade 1 through grade 5 in step of 1 representing qualitative grades of very serious, serious, normal, good, and very good.

Skin features as being analyzed in user' skin analysis by the objective skin analysis 5101 and subjective skin analysis 5102, and graded by quantitative skin feature grading 5103 and qualitative skin feature grading 5104 may include any of, but not limited to: fine lines, wrinkles, skin contours due to aging, loss of fat, skin drooping, brown/dark spots, discoloration, dryness, oiliness, hydration level, skin symptoms (for example, acne, blister, infection), skin chemical PH value, skin surface chemical composition, skin surface bio-composition (old skin, microbes, bacteria). Results from quantitative skin feature grading 5103 and qualitative skin feature grading 5104 may also include any of: the number, the size, the location, the strength or severity, and the distribution of each skin feature. The skin features may not be limited to facial skin but also other parts of the user's body. For different users undergoing the same skin analysis steps and skin feature grading steps, the types of skin features or skin conditions may be same or similar. However, the quantitative grade or the qualitative grade of each skin feature after quantitative skin feature grading 5103 and qualitative skin feature grading 5104 may be different for different user. For example, after quantitative skin feature grading 5103, a first user may have a fine line grade of 10 and a wrinkle grade of 1, i.e. more fine lines issue, while a second user may have a fine line grade of 2 and wrinkle grade of 10, i.e. more wrinkles issue, whereas first and second users may require different skin care specimen composition due to different skin feature strength.

User's skin features and their grades after quantitative skin feature grading 5103 or qualitative skin feature grading 5104 may be further transferred as shown by step 5130 and step 5140 and be compiled into unique user data 4934. Additionally, user's biometrics data 5105, user's own living or working environment data 5106, user's own skin care schedule or skin care habit data 5107, may also be transferred, as shown by steps 5150, 5160 and 5170 respectively, to be compiled into the unique user data 4934.

The unique user data 4934 may include any of, but not limited to: quantitative and qualitative grading of user's skin features, degree of improvement required or needed in quantitative values or qualitative grades of each feature, user's biometrics data, user's own living or working environment data, user's own skin care schedule or skin care habit data. The unique user data 4934 may be compiled in a format of a standard data communication protocol, for example the user data structure 5300 of FIG. 53, for data transmission, data storage and interfacing through various devices and specimen dispensers. The unique user data 4934 may be transmitted as shown by step 5180 and stored in a specimen dispensing device 4902, for example the information storage component 171 included in the control unit 17 of FIG. 2. The unique user data 4934 may be transmitted as shown by step 5190 and stored in a user person computing device 5020, for example a computer, or a mobile phone. The unique user data 4934 may be transmitted as shown by step 5111 and stored in a database 5040 that is part of an internet cloud service, for example a remote server that hosts a database which can accept and provide data through internet connection, and being part of a user data cloud service, i.e. beauty cloud.

Now referring to FIG. 52A through FIG. 52F, which illustrate examples of objective skin analysis 5101 and subjective skin analysis 5102.

Figure 52A:
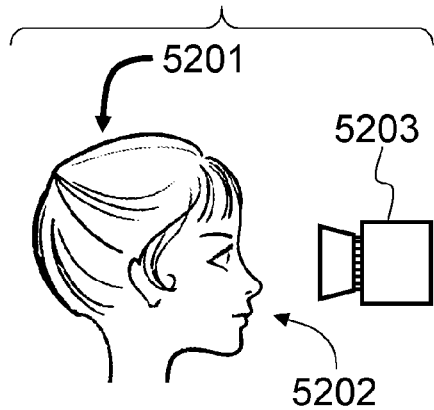
FIG. 52A illustrates skin analysis by imaging.

FIG. 52A illustrates an example of skin analysis of the facial skin 5202 of a user 5201 by an imaging system 5203. Imaging system 5203 can be a camera based system. Imaging system 5203 may capture photos or images of the skin 5202 under various lighting conditions, from various angles, with various distances from the user 5202, with various resolutions, and with various optical or digital zoom of the different areas of skin 5202. After images are captured, images may be further processed by pattern recognition software or hardware, for example a computing device or computer, to classify the skin features existing on user 5201 skin 5202 and also grade each of such features according to the size, location, distribution, strength, severity and overall appearance following a set of skin feature evaluation standards. Such image process and skin feature recognition and grading may also be regarded as part of the objective skin analysis 5101, and quantitative skin feature grading 5103 of FIG. 51. Alternatively, the captured images may be reviewed and evaluated by a person, including, but not limited to, a skin care specialist, a skin dermatologist, or the user 5201, and an estimation of existing skin features and their corresponding grades may be generated with the experience and expertise of the person. Such image evaluation and skin features estimation and grading may also be regarded as part of the subjective skin analysis 5102, and qualitative skin feature grading 5104 of FIG. 51.

Figure 52B:
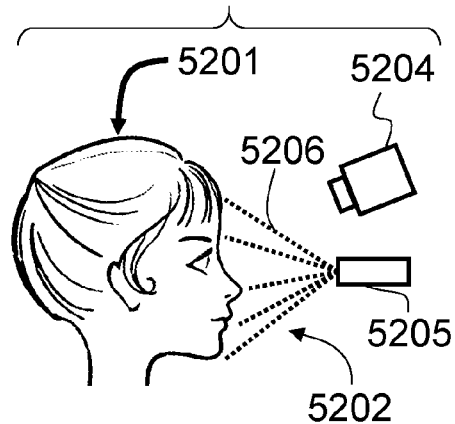
FIG. 52B illustrates skin analysis by radiation scanning.

FIG. 52B illustrates an example of skin analysis by radiation scanning. Radiation emitter 5205 emits radiation beams 5206 towards skin 5202 or user 5201. Radiation detector 5204 detects the radiation signal from the radiation beams 5206 being reflected from the skin 5202 of user 5201, whereas the radiation signal detected by the optical detector 5204 is converted into electrical signal for further electrical signal and data process. The radiation emitter 5205 may move in the directions that are substantially parallel to the skin 5202 surface to effectively produce scanning of the skin 5202 area radiation beams 5206, whereas the radiation detector 5204 may move in substantially same speed and directions as the radiation emitter 5205. The radiation beams 5206 emitted from radiation emitter 5205 may change its directions such that that radiation beams 5206 may effectively scan the areas of the skin 5202, whereas the radiation detector 5204 may be stationary relative to the radiation emitter 5205 when directions of radiation beams 5206 changes. Reflected radiation signal detected by radiation detector 5204 and generated electrical signal by the radiation detector 5204 may be processed into information of one or more skin features with characteristics of the skin features including any of: feature existence, strength, severity, formation, composition, malignancy, depth into skin 5202. During scanning of the radiation beams 5206 over the areas of skin 5202, reflected radiation signal of 5206 detected by radiation detector 5204 may be also correlated with any of: the direction of the radiation beams 5206, the spatial location of the radiation emitter 5205, the spatial location of the radiation detector 5204, relative to skin 5202, to generate information of detected skin features including any of: size, location, distribution, and overall appearance. Radiation emitter 5206 radiation source may be any of: LED, laser, lamp, x-ray generator, and particle generator. Radiation beams 5206 may be any of: microwave, visible light, infrared light, ultra-violet light, x-ray, and particles of electron, alpha particle, ions, or molecules. Radiation detector 5204 may contain any of: CCD, CMOS sensor, photo diode, x-ray detector, electron detector, particle detector, ion detector, and molecule detector. Reflected signal from skin 5202 may also contain excited radiation from certain chemicals, elements, compositions that are contained within the skin features, or existing in the skin 5202, by the excitation from incident radiation 5206. The Electrical signal generated by radiation detector 5204 may be any of: strength of detected radiation signal, spectrum of detected radiation signal, spectrum of the blackbody radiation signal from the skin 5202, wavelength of detected radiation signal, and existence of radiation signal at specific frequencies, for example excited radiation at certain frequency that is indication of existence of certain chemicals, elements or compositions. Such skin feature detection and grading may be regarded as part of the objective skin analysis 5101, and quantitative skin feature grading 5103 of FIG. 51.

Figure 52C:
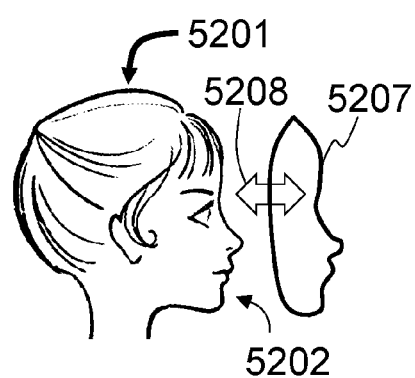
FIG. 52C illustrates skin analysis by skin feature mapping.

FIG. 52C illustrates an example of skin analysis by skin feature mapping on skin 5202 of user 5201. A skin mask 5207, which is a facial mask as in FIG. 52C, is disposed on top of the facial skin 5202 and later removed from the facial skin 5202, as indicated by the two-ends arrow 5208. Skin features, for example, fine lines, wrinkles, humps and sagging areas, brown spots, and other skin features that is topographically different than normal skin surrounding these feature, may have their locations, sizes, heights and numbers, transferred into the topographical features within the facial mask 5207. Facial mask 5207 may then be brought into an optical examination system, for example, a microscope, an optical scanner, to be further analyzed on the transferred topographical features that correspond to the skin features of the skin 5202 of user 5201. The results of such analysis may then be used for analysis steps 5101, 5102 and skin feature grading steps 5103 and 5104 of FIG. 51. Facial mask 5207 may also be brought into a topographical examination system, for example, a scanning needle based two-dimensional or three-dimensional scanning system that measures the topographical information of the surface of the mask 5207, and converts that information into digital data. The digital data of such analysis may then be used for analysis steps 5101, 5102 and skin feature grading steps 5103 and 5104 of FIG. 51. A specific example is that the mask 5207 is a thin thickness facial mask, which is soft and compliant to the face of the user 5201, for example, when the mask is hydrated. After the mask 5207 being disposed upon facial skin 5202 of user 5201 and tightly pressed against skin 5202 to eliminate all possible spaces between mask 5207 and skin 5202, thus facial features on skin 5202 may transfer their physical properties to the mask, which is similar to a hard stencil transferring physical features to an overlaying soft substrate. When mask 5207 is removed from the skin 5202, transferred physical properties of the skin features stay as topographical features of the mask 5207. In one embodiment, face mask 5207 is removed after substantially losing partial or majority of the water content within the mask, whereas the topographic features transferred from skin features are hardened into the material of the mask 5207. Afterwards, face mask 5207 may be analyzed by optical or topographical examination systems as described above.

Figure 52D:
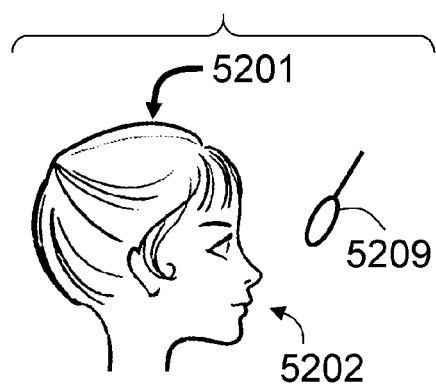
FIG. 52D illustrates skin analysis by biological or chemical analysis.

FIG. 52D illustrates an example of skin analysis by biological analysis, where a sampling tool 5209, for example a cotton swab, is brought into contact with the skin 5202 of user 5201 at one or more locations on the skin 5202 to pick up surface chemicals, objects, or materials from skin 5202. After the sampling tool 5209 is removed from skin 5202, the sampling tool 5209 may be brought into a biological analysis system that is capable of measuring the existence and amount of chemicals, molecules, bacteria, skin debris, and other skin surface bearing materials deposited from the environment of the user 5201. The data from such biological analysis may then be used for analysis steps 5101, 5102 and skin feature grading steps 5103 and 5104 of FIG. 51.

Figure 52E:
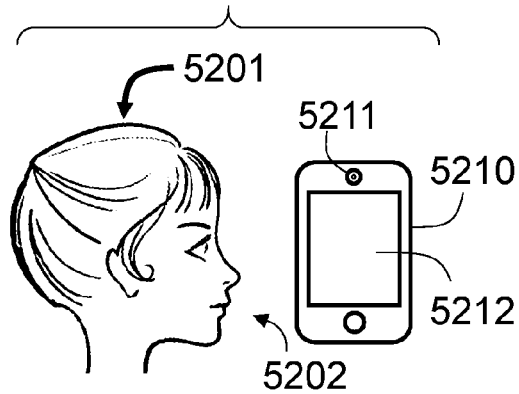
FIG. 52E illustrates skin analysis by user self-analysis aided by a computing device.

FIG. 52E illustrates an example of skin analysis by user 5201 self-analysis aided by a computing device 5210. Device 5210 may be any of: a computer, a mobile phone, and a tablet computing device. Device 5210 may have an imaging device 5211, for example a camera. Imaging device 5211 may be built into the device 5210 as a component of the computing device 5210. Imaging device 5211 may be externally attached to an electrical interface of the computing device 5210 through electrical wires. Imaging device 5211 may also be a device external to the computing device 5210 and communicating with computing device 5210 through wired or wireless data connections, for example through any of: internet, WIFI, Bluetooth, Infrared, or RF coupling through RF coupling coils. Imaging device 5211 may capture images of skin 5202 of user 5201 similarly as the imaging system 5203 captures images of skin 5202 in FIG. 52A. Captured images by imaging device 5211 may be transferred to the computing device 5210 and may be saved in a database within the computing device 5210. Afterwards, images may be further processed by pattern recognition software within computing device 5210 to classify the skin features existing on skin 5202 of user 5201 and may also grade each of such skin features according to the size, location, distribution, strength, severity and overall appearances following a set of skin feature evaluation standards. Such image process and skin feature recognition and grading may also be regarded as part of the quantitative skin feature grading 5103 of FIG. 51. Alternatively, the captured images may be reviewed and evaluated by a person, including any one of, but not limited to, a skin care specialist, a skin dermatologist, and the user 5201, and an estimation of existing skin features and their corresponding grades may be generated with the experience and expertise of the person. Such image evaluation and skin features estimation and grading may also be regarded as part of the qualitative skin feature grading 5104 of FIG. 51. Said person that evaluates the images may be local as the user 5201 to evaluate the images on a display 5212, or at a remote location where the images are transmitted to the said person through a data network, for example internet. Display 5212 may provide user 5201 and any person providing said evaluation the ability to view the captured images. Device 5210 may also provide a user interface to user 5201 or any person providing said evaluation which enables any of: displaying information to user 5201, acquiring user 5201 input, for example display 5212 is also a touch screen and user 5201 may touch displayed information on display 5212 and provide information regarding skin 5202 or information regarding user 5201 that relates to skin care of skin 5202. Information acquired from user 5201 by device 5210, for example through user 5201 input via a touch screen display 5212 or another type of electronic input device like a mouse or a keyboard, may be used towards the subjective skin analysis 5102 and qualitative skin feature grading 5104 of FIG. 51. Further, such acquired information from user 5201 may be transmitted to a remote person, for example, a skin care specialist or a dermatologist, for an evaluation by the remote person, whereas the evaluation of said remote personal may be used towards the subjective skin analysis 5102, qualitative skin feature grading 5104, and unique user data 4934 of FIG. 51.

Figure 52F:
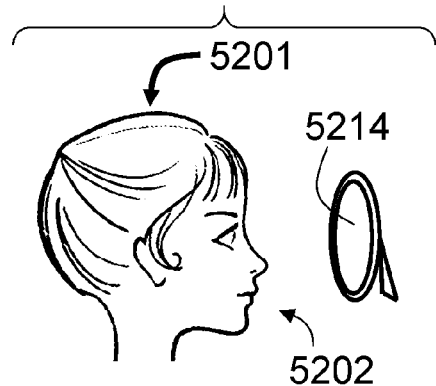
FIG. 52F illustrates skin analysis by visual evaluation.

FIG. 52F illustrates an example of skin analysis by visual evaluation, whereas the user 5201 provides self-evaluation with using a visualization tool 5214, for example a mirror, to visually inspect skin 5202. Visual evaluation as in FIG. 52F may also be conducted by another person, for example a skin care specialist, or a dermatologist, without using mirror 5214. Results from the visual evaluation may be used towards the subjective skin analysis 5102 and qualitative skin feature grading 5104, and unique user data 4934 of FIG. 51

Now referring back to FIG. 2, where the at least one information processing component 172 is also located in and electronically coupled to the control unit 17. It retrieves the first information stored in the information storage component 142 and the second information stored in the information storage component 171, and then processes both the retrieved first and second information and provides commands and instructions to control the dispensing of specimen 19 from the dispenser 14.

The electronic control unit 17 controls the dispensing of specimen 19 from dispenser 14, through outlet 15. The control unit 17 may also provide user interface, power supply and charging functions. Additionally, the electronic control unit 17 may send electrical signals to the specimen dispenser 14 or receives electrical signals from the specimen dispenser 14, to achieve required skin treatment procedure through electrical interface 140 that electrically connects to the electrical contacts 141 on dispenser 14.

The dispenser 14 may have any of the below features: (1) it can be removable, in other words, it may be taken out and installed back into the device 10 by the user; (2) the specimen 19 may be replenished within dispenser 14 by the user, or a health care professional, after depletion of the specimen during usage, i.e. dispenser 14 may be re-used; (3) dispenser 14 may be disposable and for one-time use only, where specimen 19 is pre-filled within the dispenser before usage; (4) the dispenser 14 can be configured as having multiple sub-dispensers containing same or different specimens such that the sub-dispensers can be individually selected to dispense contained specimen; (5) the dispenser 14 can be configured as a single dispenser with multiple specimen compartments that may contain same or different specimens, such that each compartment within the dispenser can be individually selected and dispense specimen; (6) the dispensing of the specimen 19 is fulfilled by a manually exerted or a pre-loaded force to the dispenser, upon which a pressure generation component that is part of the dispenser, for example a lead, a lever, a gauge, a cap, a piston, a spring, compressed air or a stretched pouch, forces the specimen 19 to flow out of the dispenser through the outlet 15, where the control unit 17 controls the dispensing by limiting the amount of specimen being dispensed from one or more of the specimen containing compartments or sub-dispensers; (7) the dispensing of the specimen 19 is fulfilled by an electrically powered driving mechanism that is part of the dispenser and operated by the electrical interface 140 located within the device 10 body; (8) the dispensing of the specimen 19 is fulfilled by an electrically powered driving mechanism that is a part of the device and electrically controlled by the control unit 17. The driving mechanism provides mechanical force to dispenser 14 to make the specimen 19 flow out of the dispenser through the outlet 15.

In other words, dispenser 14 can be any of: a removable and replaceable dispenser; a refillable dispenser; a disposable and for one-time only dispenser; an integrated dispenser having multiple sub-dispensers containing same or different specimens, the sub-dispensers being individually selectable to dispense specimen therein; and an integrated dispenser with multiple specimen compartments containing same or different specimens, each of the compartments being individually selectable to dispense specimen therein.

Figure 14:
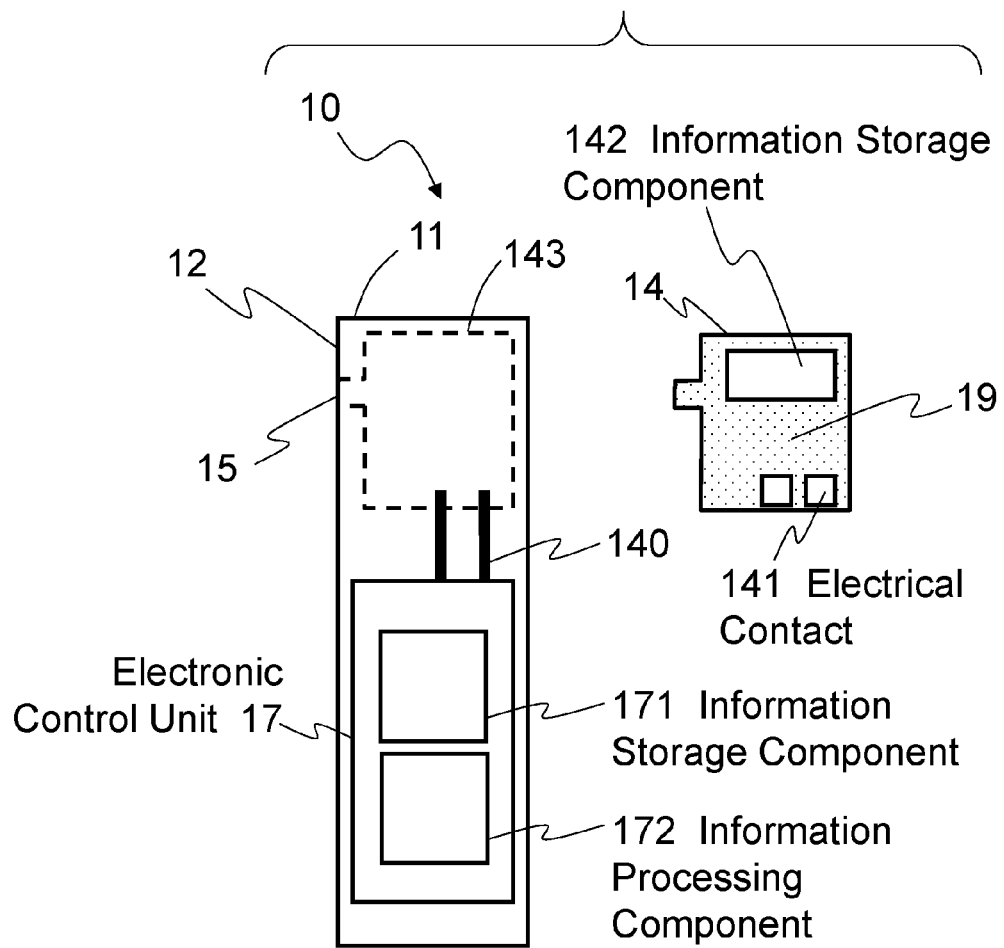
FIG. 14 illustrates the dispenser being removable from inside a dispensing device.

Now referring to FIG. 14. FIG. 14 illustrates the dispenser 14 may be removed from or installed into the dispensing device 10 of FIG. 2. Dispenser 14 that contains the specimen 19 therein, together with the information storage component 412 and electrical contacts 141 that are embedded in the dispenser 14, may be installed into the dispenser containment space 143, which is marked as the dashed line in FIG. 14, within the dispensing device 10. With the dispenser 14 installed into the containment space 143 of dispensing device 10, electrical interface 140 may make direct physical contact with the electrical contacts 141. Alternatively, in another embodiment, the control unit 17 of device 10 may communicate with embedded electronics within dispenser 14, including the information storage component 142, through a wireless communication method, whereas such wireless communication method may include, but not limited to, WIFI, Bluetooth, RFID, infrared, inductive coupling or fiber optics interface, and whereas a direct contact through electrical interface 140 may not be needed. When dispenser 14 is installed into the dispensing device 10, the device body 11 of device 10 may completely enclose the dispenser 14 inside. Dispenser 14 containing the specimen 19 therein, together with the information storage component 412 and electrical contacts 141 that are embedded in the dispenser 14, may also be removed from the dispenser containment space 143 and outside of the device body of dispensing device 10 as shown in FIG. 14.

Figure 15:
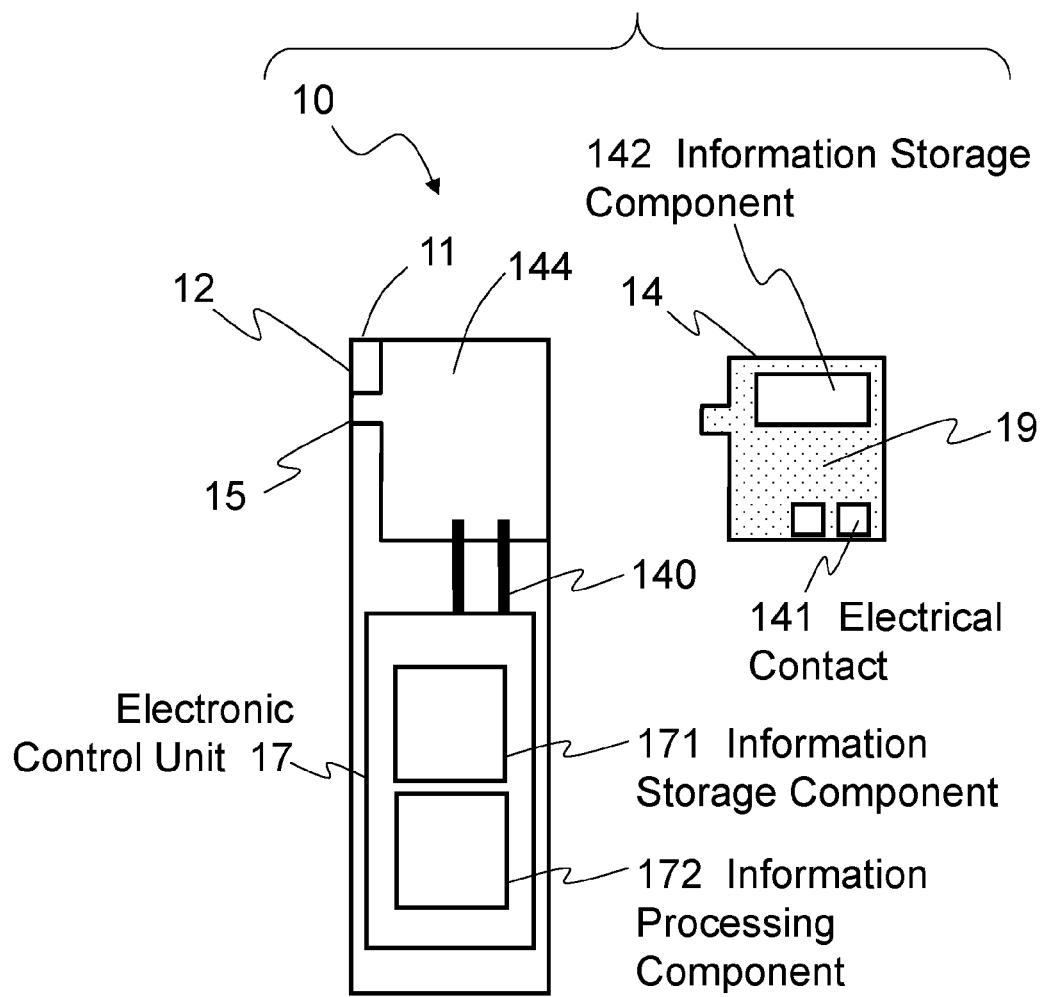
FIG. 15 illustrates the dispenser being externally attached to, or removed from, a dispensing device.

FIG. 15 illustrates the dispenser 14 may be removed from, or externally attached to, the device body 11 of the dispensing device 10 of FIG. 15. Dispenser 14 that contains the specimen 19 therein, together with the information storage component 412 and electrical contacts 141 that are embedded in the dispenser 14, may be attached to the dispensing device 10 by occupying completely the dispenser containment space 144, which is marked as the dispenser 14 shaped empty space in the dispensing device 10 in FIG. 15. With the dispenser 14 attached to the dispensing device 10, electrical interface 140 may make direct physical contact with the electrical contacts 141. Alternatively, in another embodiment, the control unit 17 of device 10 may communicate with embedded electronics within dispenser 14, including the information storage component 142, through a wireless communication method, whereas the wireless communication method may include, but not limited to, WIFI, Bluetooth, RFID, infrared, inductive coupling or fiber optics interface, and whereas a direct contact through electrical interface 140 may not be needed. When dispenser 14 is externally attached to the dispensing device 10, the dispenser 14 may be visible as being part of the device body. Dispenser 14 containing the specimen 19 therein, together with the information storage component 412 and electrical contacts 141 that are embedded in the dispenser 14, may also be removed and detached from the device body 11 of dispensing device 10 as shown in FIG. 15.

Figure 22A:
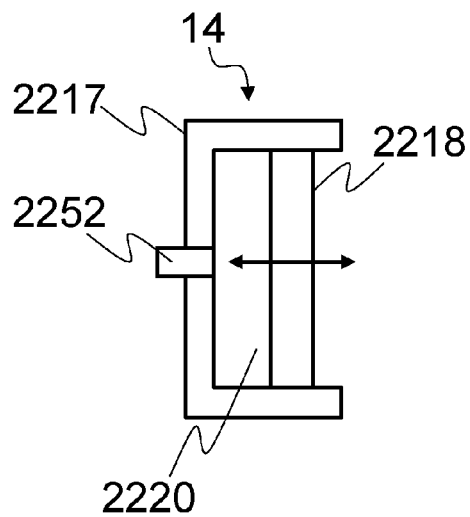
FIG. 22A illustrates a specimen dispenser in the form of a mechanically operated cartridge.

Now referring to FIG. 22A. FIG. 22A illustrates a specimen dispenser 14 of FIG. 2, also referred to as cartridge, in the form of a mechanically operated cartridge. FIG. 22A shows the cartridge 14 having an outside housing 2217, an outlet 2252 and a piston 2218 that moves in the direction towards or away from the interior wall of the housing 2217 where the outlet 2252 is located. Specimen dispenser 14 and specimen outlet 2252 are similar as the cartridge 14 and outlet 15 of FIG. 2. Skin care specimen is stored in the space 2220 enclosed by the interior wall and the piston 2218. When the piston 2218 moves towards the interior wall where the outlet 2252 is located and reduces the volume within the space 2220, specimen is dispensed through outlet 2252 to outside the cartridge 14 due to pressure added to the specimen by the piston 2218. Movement of the piston 2218 is mechanical, which can be realized through pushing and pulling force from a button-type or a roller-type leverage structures existing externally on the device body 11 of FIG. 2, and thus the specimen dispensing can be manually controlled by the user. Alternatively, the pushing and pulling force can be applied through electric motor component residing within the device body 11 of FIG. 2, and thus the specimen dispensing can be operated by an electrical-switch-type or a touch-sensor-type electronic interface located externally on the device body 11 of FIG. 2.

Figure 22B:
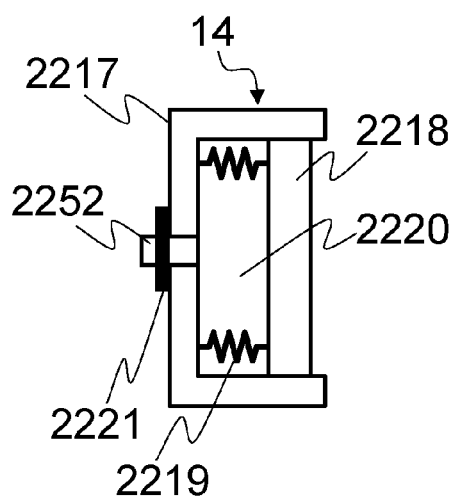
FIG. 22B illustrates a specimen dispenser in the form of a cartridge having a first type preloaded dispensing force and a specimen flow gate.

FIG. 22B illustrates a specimen dispenser 14, also referred to as cartridge, in the form of a cartridge having a first type preloaded dispensing force and specimen flow gate. It is similar to FIG. 22A, but the pushing force is applied by embedded loading force, as exampled by the spring like structure 2219 in FIG. 22B. The loading force can be applied from either side of the piston 2218, where FIG. 22B is only one of many variations. In addition, the loading force can be implemented as, including but not limited to, spring, rubber cushion, rubber band or compressed air. The loading force applies a pressure on the specimen within the space 2220, and the specimen can be dispensed through outlet 2252 automatically as soon as the outlet 252 is set to an open mode. To control and limit flow of specimen, a switch structure such as a valve 2221, also referred to as specimen flow gate, is coupled to the outlet 2252, which is able to close and open the flow path of specimen through outlet 252. The valve 2221 can be a slit valve, a one-way valve, or a double-way valve. Operation of the valve 2221 can be realized through a button-type or a roller-type leverage structures existing externally on the device body 11 of FIG. 2, and the specimen dispensing can be operated manually. Alternatively, valve 2221 can be operated through an electric motor component residing within the device body 11 of FIG. 2, and thus the specimen can be operated by an electrical-switch-type or a touch-sensor-type electronic interface existing externally on the device body 11 of FIG. 2. Operation of the valve 2221 can be realized as a pressure operation valve similar to the valve 2325 through valve switch 2324 of FIG. 23B, and can be operated manually. Alternatively, valve 2221 can be operated through an electrically driven switch that user operates through an electrical interface.

Figure 22C:
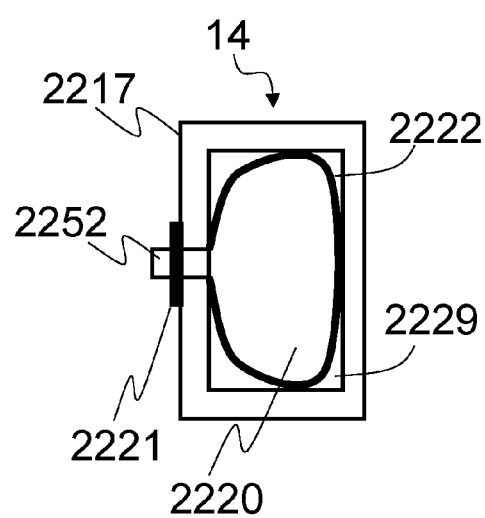
FIG. 22C illustrates a specimen dispenser in the form of a cartridge having a second type preloaded dispensing force and a specimen flow gate.

FIG. 22C illustrates a specimen dispenser 14, also referred to as cartridge, in the form of a cartridge having a second type preloaded dispensing force and specimen flow gate. It is similar to FIG. 22B, but replacing the piston and loading structure with a simple self-contracting pouch 2222 existing within the enclosed housing 2217. The specimen is contained in the internal space 2220 of the pouch 2222. The self-contracting pouch 2222 can be, but not limited to, a dilated rubber pocket. The self-contracting force of the pouch 2222 produces enough pressure to dispense the specimen when the valve 2221, also referred to as specimen flow gate, opens up the flow through the outlet 2252. Alternatively, the pouch 2222 provides containment as a bladder, while the space 2229 may be filled with pressurized air or gas, which is capable of shrinking the volume of the pouch 2222 and squeezing out the specimen within 2220 through the outlet 2252 when the flow gate 2221 is turned on. Flow gate 2221 of FIG. 22C is same as flow gate 2221 in FIG. 22B.

Figure 22D:
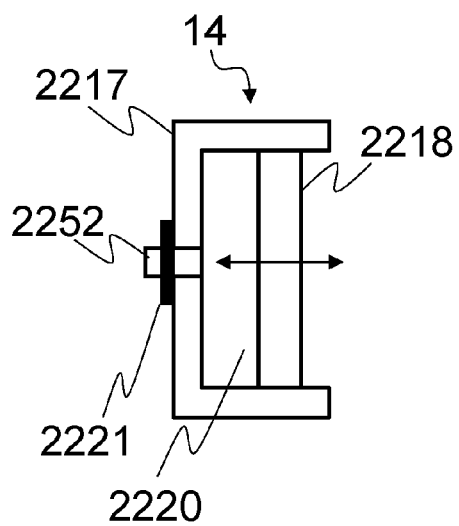
FIG. 22D illustrates a specimen dispenser in the form of a mechanically operated cartridge having a specimen flow gate.

FIG. 22D illustrates a specimen dispenser 14, also referred to as cartridge, in the form of a mechanically operated cartridge having a specimen flow gate. FIG. 22D is a variation of FIG. 22A with a valve 2221, also referred to as specimen flow gate, coupled to the outlet 2252. The valve 2221 can be operated simultaneously with the piston 2218 to produce more precise specimen flow through the outlet 2252. Operation of valve 2221 can be achieved through the same mechanical or electronic interface that user uses to operate piston 2218. Flow gate 2221 of FIG. 22D is same as flow gate 2221 in FIG. 22B.

Figure 23A:
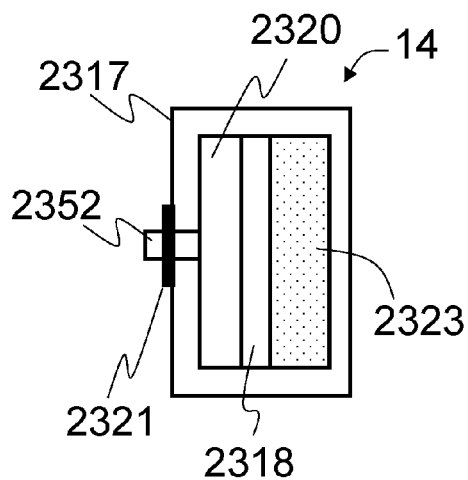
FIG. 23A illustrates a specimen dispenser in the form of a cartridge having a propellant driven piston and a specimen flow gate.

FIG. 23A illustrates a specimen dispenser 14, also referred to as cartridge, in the form of a cartridge having a propellant 2323 driven piston 2318 and a specimen flow gate 2321. FIG. 23A shows the cartridge 14 having an outside housing 2317, a specimen outlet 2352 and a piston 2318 that moves in the direction towards or away from the interior wall of the housing 2317 where the outlet 2352 is located. Specimen dispenser 14 and specimen outlet 2352 are similar as the cartridge 14 and outlet 15 of FIG. 2. Skin care specimen 19 of FIG. 2 is stored in the space 2320 enclosed by the interior wall of the housing 2317, and the piston 2318 surface facing the outlet 2352. When the piston 2318 moves towards the interior wall where the outlet 2352 is located, and reduces the volume within the space 2320, specimen is dispensed through outlet 2352 to outside the cartridge 14 due to pressure added to the specimen by the piston 2318. In FIG. 23A, movement of the piston 2218 towards the outlet 2352 is driven by a pre-filled pressurized propellant 2323, for example a compressed gas, which fills the space defined by the interior wall of the housing 2317, and the piston 2318 surface facing away from the outlet 2352. During a specimen dispensing operation, flow gate 2321 opens up and allows specimen within space 2320 to flow outside of the cartridge 14 through outlet 2352. As the specimen flows outside of cartridge, specimen pressure reduces in the space 2320 and piston 2318 further moves towards the interior wall of the housing 2317 where the outlet 2352 is located due to a higher pressure from the pressurized propellant 2323. If flow gate 2321 continuously opens, the piston 2318 will continue moving until reaching the interior wall of the housing 2317 where the outlet 2352 is located and finish dispensing specimen from space 2320. When the flow gate 2321 shuts off, with specimen still remaining in space 2320, the specimen space 2320 reduces to the size where the pressure in the specimen space 2320 equals pressure in the propellant 2323, and piston 2318 stops moving. Turn on and shut off operations of the flow gate 2321 may be performed through a mechanical switch operated by user manually, or by an electrically driven switch that user operates through an electrical interface.

Figure 23B:
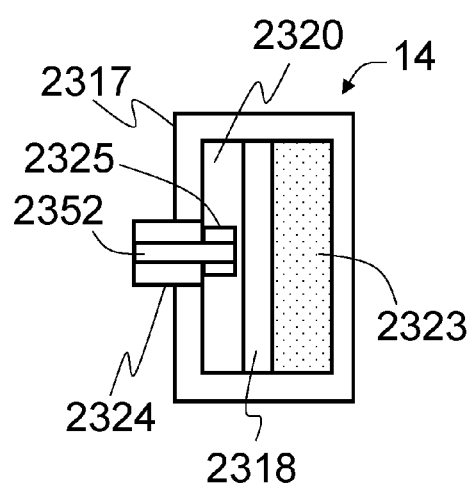
FIG. 23B illustrates a specimen dispenser in the form of a cartridge having a propellant driven piston and a flow valve controlled by externally applied pressure.

FIG. 23B illustrates a specimen dispenser 14, also referred to as cartridge, in the form of a cartridge having a propellant 2323 driven piston 2318 and a flow valve 2325 controlled by externally applied pressure. Specimen dispenser 14 and specimen outlet 2352 are similar as the cartridge 14 and outlet 15 of FIG. 2. FIG. 23B is a variation of FIG. 23A and operates similarly as FIG. 23A, with the exception that the flow gate 2321 being replaced by a flow valve 2325. Flow valve 2325 is in shut off state by default. An externally attached valve switch 2324 is used to turn on the flow valve 2325 and allow the specimen to be dispensed from the space 2320. Valve switch 2324 is mechanically operated, whereas an externally applied pressure on valve switch 2324 may produce a mechanical response from the flow valve 2325 and causes the flow valve 2325 to turn on. After the externally applied pressure is removed from the valve switch 2324, flow valve 2325 will return to shut off state. Outlet 2352 pass through both valve switch 2324 and flow valve 2325 and reaches into the specimen space 2320.

Figure 23C:
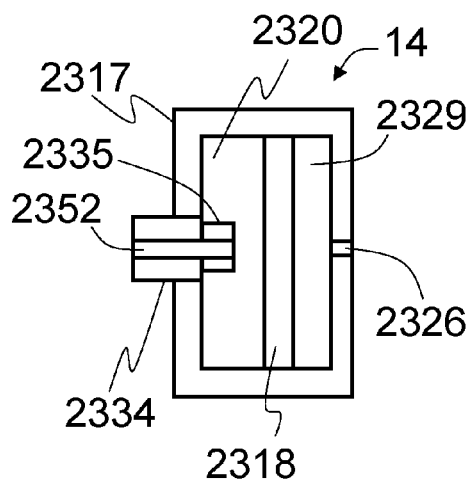
FIG. 23C illustrates a specimen dispenser in the form of a cartridge having an airless pump and a piston.

FIG. 23C illustrates a specimen dispenser 14, also referred to as cartridge, in the form of a cartridge having an airless pump 2335 and a piston 2318. FIG. 23C shows a cartridge 14 structure similar as in FIG. 23B, except the flow valve 2325 and valve switch 2324 of FIG. 23B are replaced by an airless pump 2335 and pump lever 2334 in FIG. 23C. Also, the propellant 2323 of FIG. 23B is replaced by air in space 2329 in FIG. 23C, whereas the air is filled in space 2329 from outside the cartridge 14 through an air inlet 2326 in the wall of the housing 2317. During operation, airless pump 2335 is in shut off state by default, until an external pressure is applied on the pump lever 2334, which further operates the airless pump 2335 to extract specimen from the space 2320 and dispenses the extracted specimen through the outlet 2352 to outside the cartridge 14. A typical airless pump 2335 will output a certain amount of specimen upon every pressure event on the pump lever 2334, for example a pressing of the pump lever 2334 towards inside the cartridge 14 will produce a given amount of specimen out of space 2320. After specimen is dispensed from the space 2320, pressure within 2320 reduces below air pressure within air of space 2329 and allows the piston 2318 to move towards the interior wall where the outlet 2352 is located, and reduces the volume within the space 2320. More air flows from outside the cartridge 14 through the air inlet 2326 and fills in cartridge 14 space 2329.

Figure 23D:
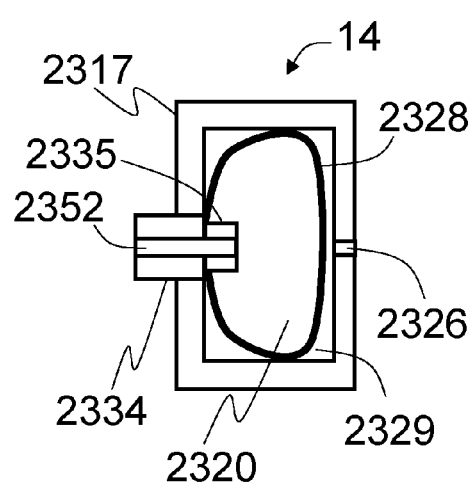
FIG. 23D illustrates a specimen dispenser in the form of a cartridge having a an airless pump and a specimen containment pouch.

FIG. 23D illustrates a specimen dispenser 14, also referred to as cartridge, in the form of a cartridge having an airless pump and a specimen containment pouch. Cartridge 14 of FIG. 23D operates similarly as in FIG. 23C, except that the piston 2318 of FIG. 23C is replaced by a pouch 2328 in FIG. 23D, and space 2320 is enclosed within the pouch 2328 as in FIG. 23D. During a dispensing operation, where an external pressure is applied on the pump lever 2334, the airless pump 2335 extracts specimen from the space 2320 and dispenses the extracted specimen through the outlet 2352 to outside the cartridge 14. After specimen is dispensed from the space 2320, pressure within 2320 reduces below air pressure within air 2329, and causing the pouch 2328 to contract due to air pressure of space 2329 being higher, and reduces the volume within the space 2320. Then, more air flows from outside through the air inlet 2326 and fill in space 2329.

Figure 24A:
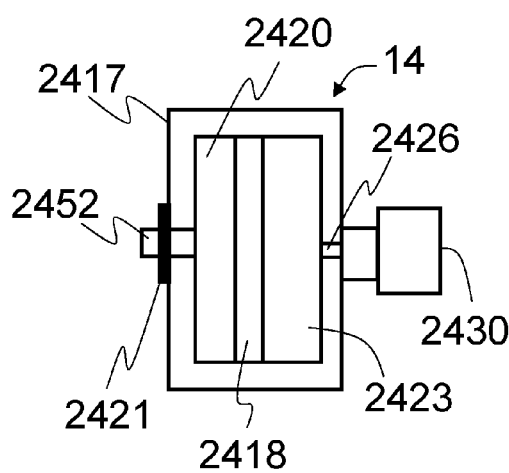
FIG. 24A illustrates a specimen dispenser in the form of a cartridge having a pressured air driven piston, an air pump and a specimen flow gate.
Figure 24B:
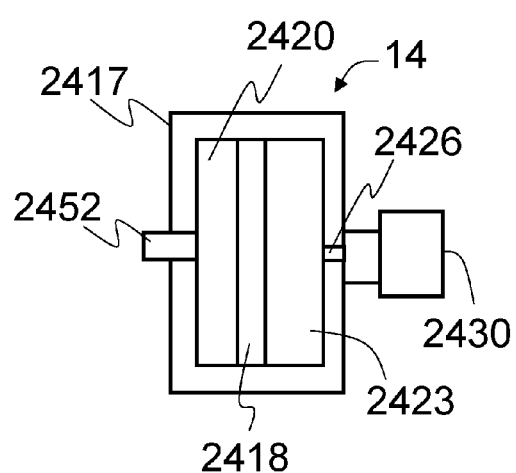
FIG. 24B illustrates a specimen dispenser in the form of a cartridge having a pressured air driven piston and an air pump.

FIG. 24A illustrates a specimen dispenser 14, also referred to as cartridge, in the form of a cartridge having a pressured air 2423 driven piston 2418, an air pump 2430 and a specimen flow gate 2421. Cartridge 14 of FIG. 24A operates substantially similar to cartridge 14 of FIG. 23A, except that the propellant 2323 of FIG. 23A is replaced by a pressured air 2423. An air inlet 2426 existing in the wall of the housing 2417 allows air pump 2430 to inject air into the cartridge 14 space between the piston 2418 surface, which opposes space 2420 that contains specimen, and the housing 2417, to produce a pressured air 2423. Pressured air 2423 functions substantially similar to the propellant 2323 in FIG. 23A. Piston 2418 and flow gate 2421 also function similarly as the piston 2318 and flow gate 2321 in FIG. 23A FIG. 24B illustrates a specimen dispenser 14, also referred to as cartridge, in the form of a cartridge having a pressured air 2423 driven piston 2418 and an air pump 2430. Cartridge 14 of FIG. 24B has similar structure as cartridge 14 of FIG. 24A, except that the flow gate 2421 of FIG. 24A is removed from FIG. 24B. During operation, when no air is injected into the cartridge 14 by the air pump 2430 to cause the pressure of the air of 2423 to increase, piston 2418 does not move and specimen in space 2420 does not flow outside of the cartridge 14 through the outlet 2452. When air pump 2430 injects air into cartridge 14 and increase pressure in air 2423, due to higher air pressure of 2423 than specimen pressure in space 2420, piston 2418 moves towards the interior wall of the housing 2417 where the outlet 2452 is located and forces specimen contained in space 2420 to dispense and flow out of the cartridge 14 through outlet 2452. When air pump 2430 stops injecting air into the cartridge 14, the piston will continue moving and specimen being dispensed from space 2420 until pressure in air 2423 reduces to the level that is same as the pressure in specimen within space 2420. In the case where air injection from air pump 2430 continues, specimen in 2420 may be depleted and the piston stops moving when reaching the interior wall of the housing 2317 where the outlet 2352 is located.

For the specimen outlets 2252, 2352 and 2452 in the specimen dispensers as described in FIG. 22A through FIG. 24B, it is desirable to be able to dispense the specimen through the outlets, while also being able to eliminate back-flow of specimen into the cartridges through the outlets, and being able to avoid contaminants entering the cartridges through the outlets. FIG. 25A through FIG. 28D illustrate the local cross-section views of any one of the specimen outlets 2252, 2352 and 2452, and any specimen outlet of any specimen dispenser or any specimen dispenser holder as described in any prior or later figures or embodiment of this invention, which also includes but not limited to, FIG. 31A through FIG. 48B, whereas the cross-section is along center plane that passes through a center line of the outlet and the center plane divides the outlet into two substantially equivalent portions.

FIG. 25A illustrates a first type of specimen dispenser outlet being closed when specimen is not under dispensing pressure or force. Specimen outlet nozzle 2503 is located in the specimen dispenser housing 2502, which is same as the dispenser housing 2217, 2317 and 2417, or cartridge housing, of cartridge 14 in FIG. 22A through FIG. 24B. Specimen outlet 2505 of FIG. 25A is a closable opening as shown being closed in FIG. 25A when specimen 2501 is not being dispensed from the cartridge where specimen 2501 is contained. View 2520 shows the bottom-up view of the outlet 2505 and nozzle 2503 when viewed along direction 2504 towards inside the nozzle 2503. In FIG. 25A, nozzle 2503 may be composed of one or more flexible or expandable material made of any of: rubber, polymer, plastics, cloth, or metallic mesh, which expands and opens up the outlet 2505 when the pressure in specimen 2501 increases above a threshold level during a dispensing procedure as described in FIG. 22A through FIG. 24B.

FIG. 25B illustrates the first type of specimen dispenser outlet 2505 as in FIG. 25A being opened when specimen is under dispensing pressure as described in FIG. 22A through FIG. 24B. The nozzle 2503 opens due to pressure added to the specimen 2501 and allows specimen 2501 to flow out of the outlet 2505 in 2508 direction. View 2520 in FIG. 25B that shows the view of nozzle 2503 and outlet 2505 along 2504 direction illustrates the specimen 2501 flowing out of the outlet 2505.

FIG. 25C illustrates a second type of specimen dispenser outlet being closed when specimen is not under dispensing pressure or force. Specimen outlet nozzle 2506 is located in the specimen dispenser housing 2502, which is same as the dispenser housing 2217, 2317 and 2417, or cartridge housing, of cartridge 14 in FIG. 22A through FIG. 24B. Specimen outlet 2507 of FIG. 25C is a closable opening as shown being closed in FIG. 25C when specimen 2501 is not being dispensed from the cartridge where specimen 2501 is contained. View 2520 of FIG. 25C shows the bottom-up view of the outlet 2507 and nozzle 2506 when viewed along direction 2504 towards inside the nozzle 2507 of FIG. 25C. In FIG. 25C, nozzle 2506 may be composed of two or more rigid or semi-rigid nozzle pieces that have built-in tension which forces pieces to close up the nozzle 2506 and outlet 2507 when specimen 2501 is not being pressurized, whereas the nozzle pieces may be made of any of: rubber, polymer, plastics, or metals, which bend away from the center line of the nozzle and open up the outlet 2507 when the pressure in specimen 2501 increases above a threshold level during a dispensing procedure as described in FIG. 22A through FIG. 24B.

FIG. 25D illustrates a second type of specimen dispenser outlet 2507 as in FIG. 25C being opened when specimen 2501 is under dispensing pressure as described in FIG. 22A through FIG. 24B. The nozzle pieces of nozzle 2506 open up and bend away from each other due to pressure added to the specimen 2501 and allows specimen 2501 to flow out of the outlet 2507 in 2508 direction. View 2520 in FIG. 25D that shows the view of nozzle 2506 and outlet 2507 along 2504 direction of FIG. 25C illustrates the specimen 2501 flowing out of the outlet 2507.

Figures 26A, 26B:
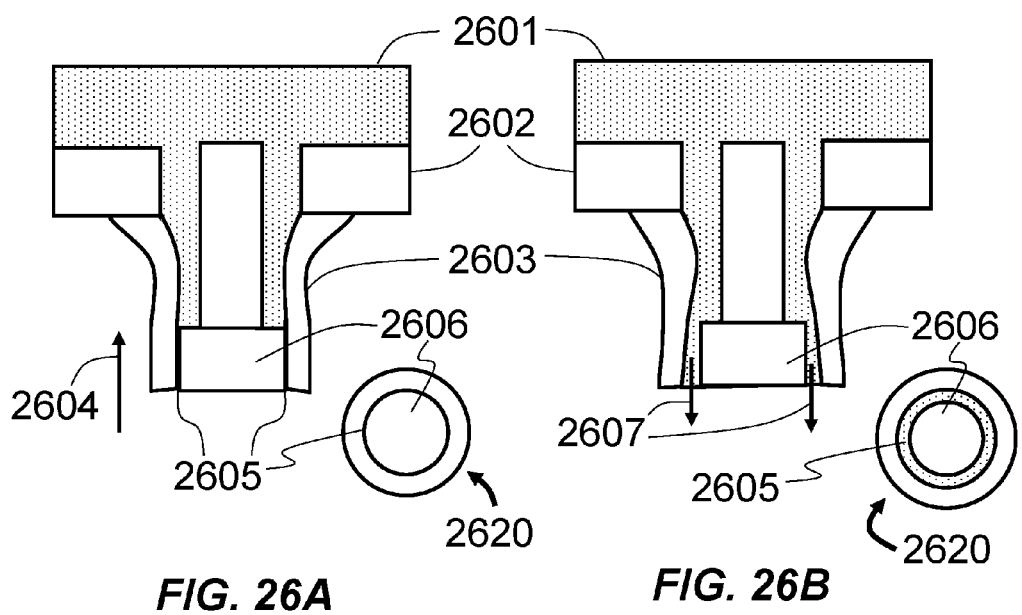
FIG. 26A illustrates a third type of specimen dispenser outlet being closed when specimen is not under dispensing pressure or force.
FIG. 26B illustrates a third type of specimen dispenser outlet being opened when specimen is under dispensing pressure or force.

FIG. 26A illustrates a third type of specimen dispenser outlet being closed when specimen is not under dispensing pressure or force. Specimen outlet nozzle 2603 is located in the specimen dispenser housing 2602, which is same as the dispenser housing 2217, 2317 and 2417, or cartridge housing, of cartridge 14 in FIG. 22A through FIG. 24B. Specimen outlet 2605 of FIG. 26A is a closable opening as shown being closed in FIG. 26A with the wall of outlet nozzle 2603 being pressing against a center flow stopper 2606, when specimen 2601 is not being dispensed from the cartridge where specimen 2601 is contained. Compared to FIG. 25A, outlet 2605 is a ring shape opening instead of a circular opening, whereas the center flow stopper 2606 enlarges the opening of wall of nozzle 2603, as compared to nozzle 2503 of FIG. 25A, provides a tighter seal of the outlet 2605 when closed, with additional contracting force being introduced in the wall of nozzle 2603 by the center stopper 2606. View 2620 of FIG. 26A shows the bottom-up view of the outlet 2605 and nozzle 2603 when viewed along direction 2604 towards inside the nozzle 2603. In FIG. 26A, nozzle 2603 may be composed of one or more flexible or expandable material made of any of: rubber, polymer, plastics, cloth, or metallic mesh, which expands and opens up the outlet 2605 when the pressure in specimen 2601 increases above a threshold level during a dispensing procedure as described in FIG. 22A through FIG. 24B. Center stopper 2606 is attached to the specimen dispenser housing 2602 inside the dispenser by fixture not shown in FIG. 26A.

FIG. 26B illustrates the third type of specimen dispenser outlet 2605 as in FIG. 26A being opened when specimen 2601 is under dispensing pressure as described in FIG. 22A through FIG. 24B. The nozzle 2603 opens up space between wall of nozzle 2603 and center stopper 2606 due to pressure added to the specimen 2601 and allows specimen 2601 to flow out of the outlet 2605 in 2607 direction. View 2620 in FIG. 26B that shows the view of nozzle 2603 and outlet 2605 along 2604 direction illustrates the specimen 2601 flowing out of the outlet 2605.

Figures 26C, 26D:
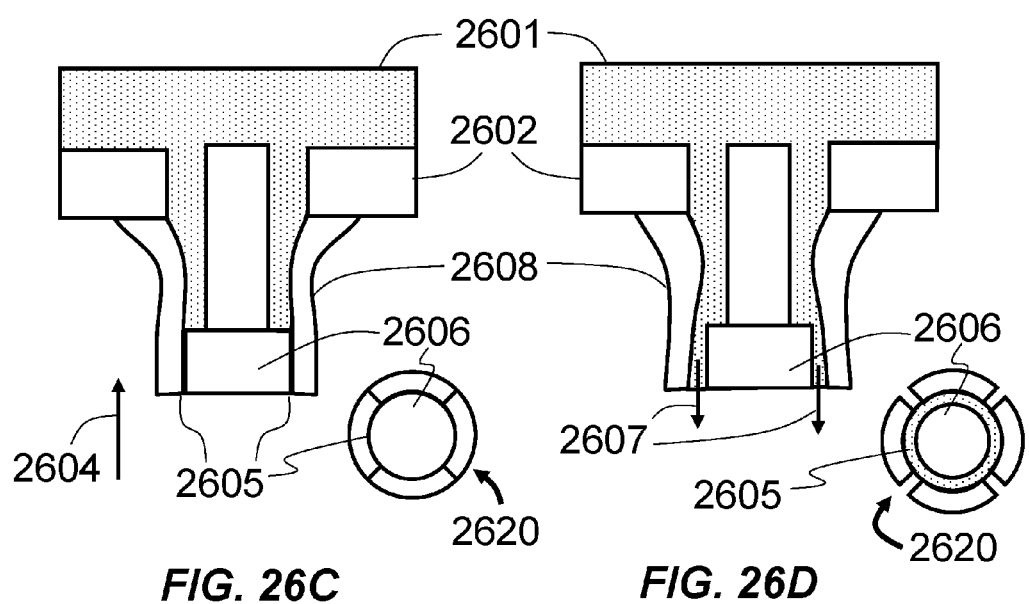
FIG. 26C illustrates a fourth type of specimen dispenser outlet being closed when specimen is not under dispensing pressure or force.
FIG. 26D illustrates a fourth type of specimen dispenser outlet being opened when specimen is under dispensing pressure or force.

FIG. 26C illustrates a fourth type of specimen dispenser outlet being closed when specimen is not under dispensing pressure or force or force. Specimen outlet nozzle 2608 is located in the specimen dispenser housing 2602, which is same as the dispenser housing 2217, 2317 and 2417, or cartridge housing, of cartridge 14 in FIG. 22A through FIG. 24B. In FIG. 26C, nozzle 2608 may be composed of two or more rigid or semi-rigid nozzle pieces that have built-in tension which forces pieces to close up the nozzle 2608 and outlet 2605 when specimen 2601 is not being pressurized. Specimen outlet 2605 of FIG. 26C is a closable opening as shown being closed in FIG. 26C with the nozzle pieces of nozzle 2608 being pressing against a center flow stopper 2606, when specimen 2601 is not being dispensed from the cartridge where specimen 2601 is contained. Compared to FIG. 25C, outlet 2605 of FIG. 26C is a ring shape opening instead of a circular opening, whereas the center flow stopper 2606 of FIG. 26C enlarges the opening of nozzle pieces of nozzle 2608, as compared to nozzle 2506 of FIG. 25C, provides a tighter seal of the outlet 2605 when closed, with additional contracting force being introduced in the nozzle pieces of nozzle 2608 by the center stopper 2606. View 2620 of FIG. 26C shows the bottom-up view of the outlet 2605 and nozzle 2608 when viewed along direction 2604 towards inside the nozzle 2608 of FIG. 26C. The nozzle pieces of nozzle 2608 may be made of any of: rubber, polymer, plastics, or metals, which bend away from the center line of the nozzle and open up the outlet 2605 when the pressure in specimen 2601 increases above a threshold level during a dispensing procedure as described in FIG. 22A through FIG. 24B. Center stopper 2606 is attached to the specimen dispenser housing 2602 inside the dispenser by fixture not shown in FIG. 26C.

FIG. 26D illustrates the fourth type of specimen dispenser outlet 2605 as in FIG. 26C being opened when specimen 2601 is under dispensing pressure as described in FIG. 22A through FIG. 24B. The nozzle pieces of nozzle 2608 open up and bend away from the center stopper 2606 due to pressure added to the specimen 2601 and allows specimen 2601 to flow out of the outlet 2605 in 2607 direction. View 2620 in FIG. 26D that shows the view of nozzle 2608 and outlet 2605 along 2604 direction of FIG. 26C illustrates the specimen 2601 flowing out of the outlet 2606.

Figures 27A, 27B:
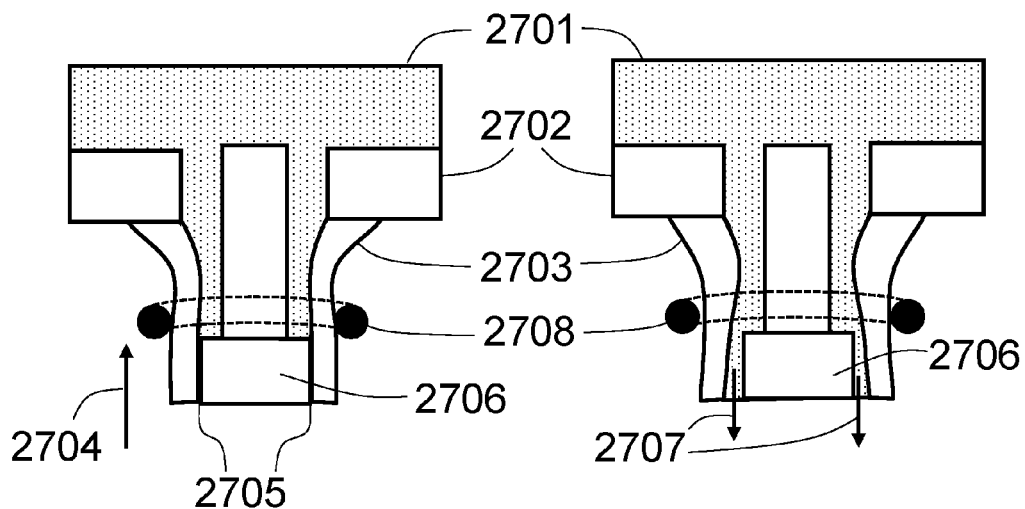
FIG. 27A illustrates a fifth type of specimen dispenser outlet being closed when specimen is not under dispensing pressure or force.
FIG. 27B illustrates a fifth type of specimen dispenser outlet being opened when specimen is under dispensing pressure or force.

FIG. 27A illustrates a fifth type of specimen dispenser outlet being closed when specimen is not under dispensing pressure or force. FIG. 27B illustrates a fifth type of specimen dispenser outlet 2705 being opened when specimen 2701 is under dispensing pressure or force. In one embodiment, the material, structure and function of nozzle 2703 of FIG. 27A and FIG. 27B is substantially similar as the nozzle 2603 in FIG. 26A and FIG. 26B, whereas specimen 2701, specimen dispenser housing 2702, center stopper 2706 and outlet 2705 are functioning substantially similar as specimen 2601, specimen dispenser housing 2602, center stopper 2606 and outlet 2605 as in FIG. 26A and FIG. 26B. The O-ring 2708, which may be made of any of: rubber, polymer, plastics, cloth, or metallic mesh, metal spring, plastic spring, being disposed around the nozzle 2703 as illustrated in FIG. 27A and FIG. 27B is used to provide additional contracting force on the nozzle to achieve a better seal of specimen 2701 by a tighter contact between center stopper 2706 and wall of nozzle 2703. In another embodiment, the material, structure and function of nozzle 2703 of FIG. 27A and FIG. 27B is substantially similar as the nozzle 2608 in FIG. 26C and FIG. 26D, whereas specimen 2701, specimen dispenser housing 2702, center stopper 2706 and outlet 2705 are functioning substantially similar as specimen 2601, specimen dispenser housing 2602, center stopper 2606 and outlet 2605 as in FIG. 26C and FIG. 26D. The O-ring 2708 is then used to provide additional contracting force on the nozzle pieces of nozzle 2703 to achieve a better seal of specimen 2701 by a tighter contact between center stopper 2706 and nozzle pieces of nozzle 2703.

Figures 27C, 27D:
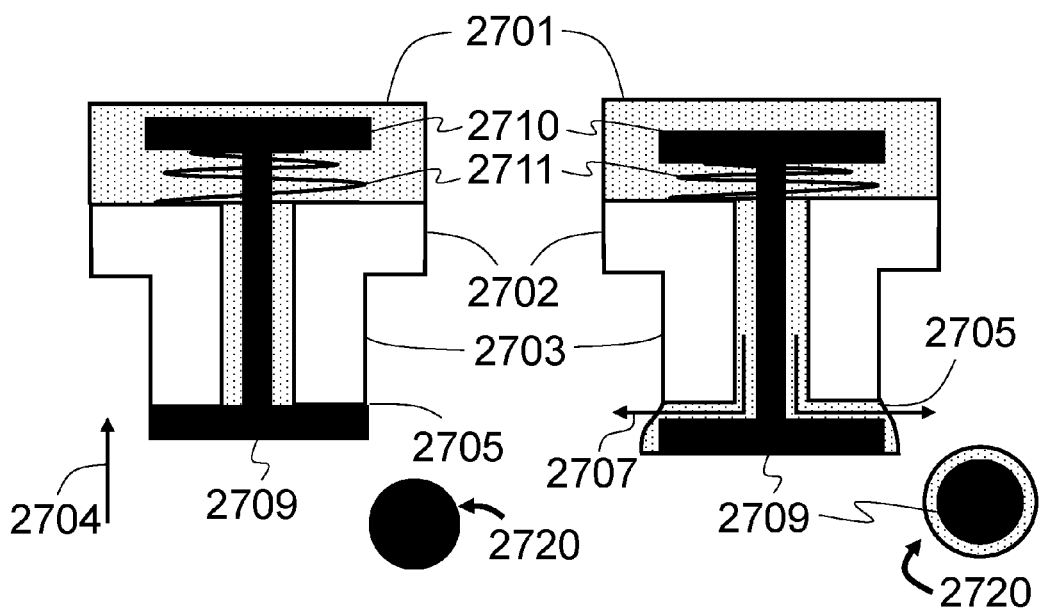
FIG. 27C illustrates a sixth type of specimen dispenser outlet being closed when specimen is not under dispensing pressure or force.
FIG. 27D illustrates a sixth type of specimen dispenser outlet being opened when specimen is under dispensing pressure or force.

FIG. 27C illustrates a sixth type of specimen dispenser outlet being closed when specimen 2701 is not under dispensing pressure or force. Specimen outlet nozzle 2703 is located in the specimen dispenser housing 2702, which is same as the dispenser housing 2217, 2317 and 2417, or cartridge housing, of cartridge 14 in FIG. 22A through FIG. 24B. Specimen outlet 2705 of FIG. 25A is a closable opening as shown being closed in FIG. 25A, with a flow gate 2710 being pressing against the bottom edge of the nozzle 2703. A spring 2711, or any other force-exertion mechanism, is coupled to the flow gate 2710 and presses against dispenser housing 2703, such that the force produced by the spring 2711 on the flow gate 2710 causes the flow grate 2710 bottom cover to be pulled towards the bottom edge of the nozzle 2703, when specimen 2701 is not being dispensed from the cartridge where specimen 2701 is contained. Spring 2711 may be in compression state even as flow gate 2710 closes the flow of specimen 2701 to produce a tight shut off of the specimen 2710. View 2720 of FIG. 27A shows the bottom-up view of the flow gate bottom surface 2709 when viewed along direction 2704 towards inside the nozzle 2703. In FIG. 27A, flow gate 2710 may be composed of one or more rigid or semi-rigid material made of any of: rubber, polymer, plastics, or metal. Spring 2711 may further compress and allows flow gate 2710 to move in direction opposing 2704 and opens up the outlet 2705 when the pressure in specimen 2701 increases above a threshold level during a dispensing procedure as described in FIG. 22A through FIG. 24B.

FIG. 27D illustrates the sixth type of specimen dispenser outlet 2705 as in FIG. 27C being opened when specimen 2701 is under dispensing pressure as described in FIG. 22A through FIG. 24B. The flow gate 2710 under the increase pressure within specimen 2701, forces the spring 2711 bottom cover to further compress and the flow gate 2710 moves in direction against 2704 and moves away from the bottom edge of nozzle 2703 to allow specimen 2701 to flow out of the outlet 2705 in 2707 direction at the side edge of the nozzle 2701. View 2720 in FIG. 27D that shows the view of bottom surface 2709 of flow gate 2710 along 2704 direction of FIG. 26C and illustrates the specimen 2701 flowing out of the outlet 2705 at the bottom circular edge of flow gate 2710 and nozzle 2703.

Figures 28A, 28B:
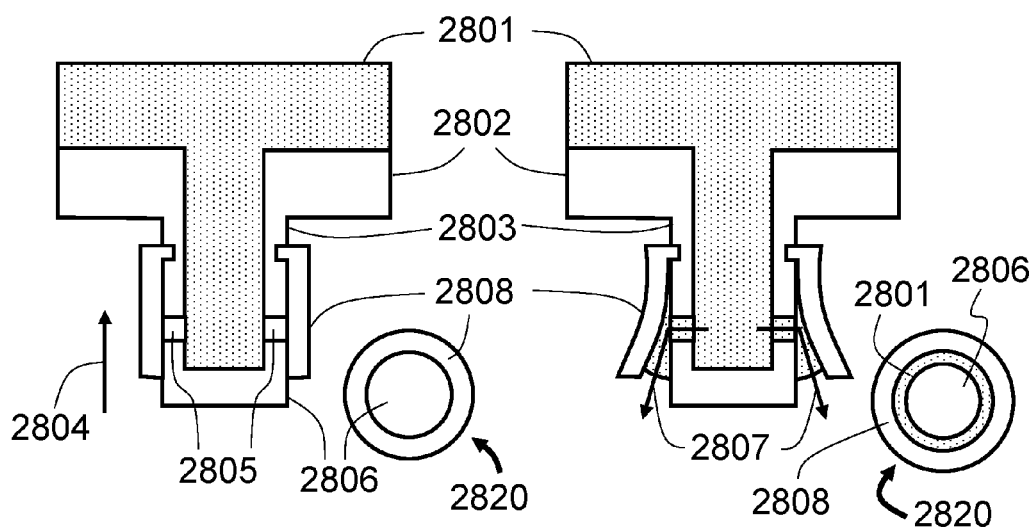
FIG. 28A illustrates a seventh type of specimen dispenser outlet being closed when specimen is not under dispensing pressure or force.
FIG. 28B illustrates a seventh type of specimen dispenser outlet being opened when specimen is under dispensing pressure or force.

FIG. 28A illustrates a seventh type of specimen dispenser outlet being closed when specimen is not under dispensing pressure or force. Specimen outlet nozzle 2803 is located in, or being part of, the specimen dispenser housing 2802, which is same as the dispenser housing 2217, 2317 and 2417, or cartridge housing, of cartridge 14 in FIG. 22A through FIG. 24B. Specimen outlet 2805 of FIG. 28A is in the form of one or more of openings on the side wall of the outlet nozzle 2803, as shown in FIG. 28A, whereas the outlet 2805 openings of FIG. 28A are covered by a flow stopper 2808 that is pressing against the outlet 2805 openings to avoid out-flow of specimen 2801 through the outlet 2805 openings when specimen 2801 is not being dispensed from the cartridge where specimen 2601 is contained. Nozzle 2803 is preferred to be in a cylinder shape, with the outlet 2805 openings being clearance holes that reside on side wall of the cylinder of the nozzle 2803 and connect from inside of the nozzle 2803 to the outside of the nozzle 2803, while the bottom end of the nozzle 2803 is sealed. The flow stopper 2808 may be a flexible tubing shaped material that covers the cylindrical side wall of the nozzle. Flow stopper 2808 is preferred by be stretched and experiencing a contracting or tensile stress within the stopper 2808, such that the flow stopper 2808 portion that covers the outlet 2805 openings on the side wall of nozzle 2803 provides sufficient pressure against specimen 2801 to avoid specimen 2801 out-flow from outlet 2805 when specimen 2801 is not under dispensing pressure. View 2820 of FIG. 28A shows the bottom-up view of the nozzle 2803 bottom end 2806 and flow stopper 2808 when viewed along direction 2804 towards inside the nozzle 2603. In FIG. 28A, nozzle 2803 may be any rigid material and may be same material as the housing 2802. Flow stopper 2808 that may be composed of one or more flexible or expandable material made of any of: rubber, polymer, latex, plastics, cloth, or metallic mesh, which expands around the nozzle 2803 openings and opens up the outlet 2805 when the pressure in specimen 2801 increases above a threshold level during a dispensing procedure as described in FIG. 22A through FIG. 24B.

FIG. 28B illustrates a seventh type of specimen dispenser outlet 2805 as in FIG. 28A being opened when specimen 2801 is under dispensing pressure as described in FIG. 22A through FIG. 24B. The flow stopper 2808 covering the side wall of the nozzle 2803 expands and opens up space between wall of nozzle 2603 and the flow stopper 2808 due to pressure added to the specimen 2801 and allows specimen 2801 to flow out of the outlet 2805 in 2807 direction. View 2820 in FIG. 28B that shows the view of nozzle 2803 bottom end 2806 and flow stopper 2808 along 2804 direction of FIG. 28A illustrates the flow stopper 2808 expands and allowing specimen 2801 to flow out of the outlet 2805.

FIG. 28C illustrates an eighth type of specimen dispenser outlet being closed when specimen is not under dispensing pressure or force. Specimen outlet nozzle 2803 is located in, or being part of, the specimen dispenser housing 2802, which is same as the dispenser housing 2217, 2317 and 2417, or cartridge housing, of cartridge 14 in FIG. 22A through FIG. 24B. Outlet nozzle 2803 has a bottom opening, which is covered by a capping shaped flow stopper 2808. Flow stopper 2808 may have a side portion that may attach to the side wall of the nozzle 2803, and a bottom portion 2809 which is attached to the side portion of the flow stopper 2808 and covers the bottom opening of the nozzle 2803. There may be one or more openings between the bottom portion 2809 and the side portion of the flow stopper 2803 to allow specimen 2801 to be dispensed through. Specimen outlet 2805 of FIG. 28C is in the form of one or more of openings between the bottom portion 2809 and the side portion of the flow stopper 2808, as shown in FIG. 28C. Nozzle 2803 is preferred to be in a cylinder shape and the flow stopper 2808 is a flexible tubing shaped material that covers the cylindrical side wall of the nozzle. Flow stopper 2808 and its bottom portion 2809 are preferred by be stretched and experience a contracting or tensile stress within the stopper 2808 and bottom portions when attached to the side wall of the nozzle 2803, such that the bottom portion 2809 and side portion of flow stopper 2808 close the openings in between them with sufficient tensile force that works against specimen 2801 out-flow from outlet 2805. View 2820 of FIG. 28C shows the bottom-up view of the bottom portion 2809 of the flow stopper 2808 when viewed along direction 2804 towards inside the nozzle 2603. In FIG. 28C, nozzle 2803 may be any rigid material and may be same material as the housing 2802. Flow stopper 2808 and the bottom portion 2809 may be composed of one or more flexible or expandable material made of any of: rubber, polymer, latex, plastics, cloth, or metallic mesh, whereas the bottom portion 2809 expands around the outlet 2805 openings and opens up the outlet 2805 when the pressure in specimen 2801 increases above a threshold level during a dispensing procedure as described in FIG. 22A through FIG. 24B.

Figures 28C, 28D:
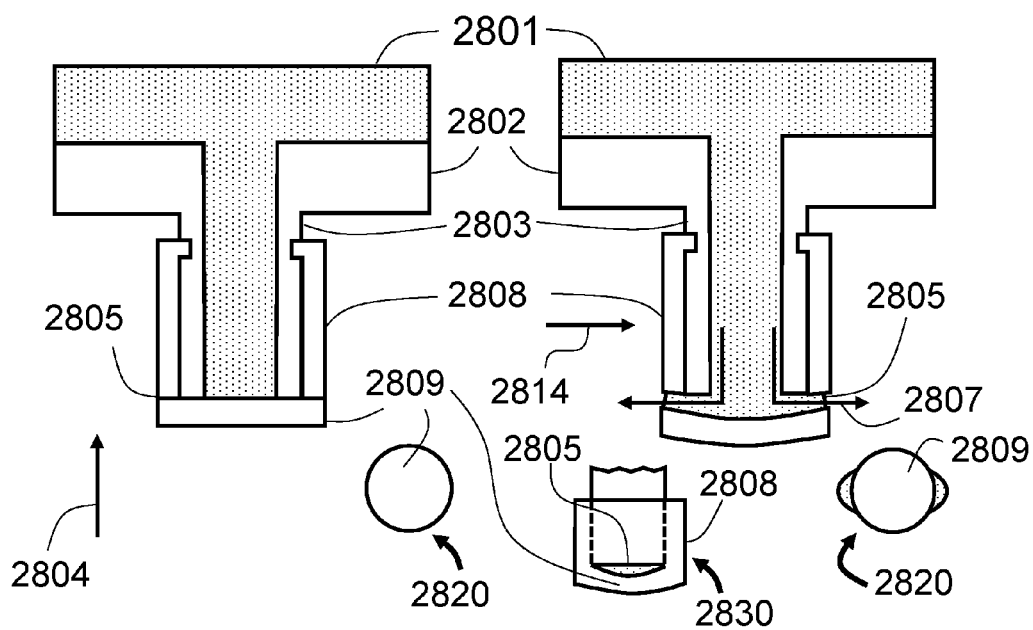
FIG. 28C illustrates an eighth type of specimen dispenser outlet being closed when specimen is not under dispensing pressure or force.
FIG. 28D illustrates an eighth type of specimen dispenser outlet being opened when specimen is under dispensing pressure or force.

FIG. 28D illustrates an eighth type of specimen dispenser outlet 2805 as in FIG. 28C being opened when specimen 2801 is under dispensing pressure as described in FIG. 22A through FIG. 24B. The flow stopper 2808 bottom portion 2809 covering the bottom opening of the nozzle 2803 expands and opens up space between the bottom portion 2809 and side portion of flow stopper due to pressure added to the specimen 2801 and allows specimen 2801 to flow out of the outlet 2805 in 2807 direction. View 2820 in FIG. 28D that shows the view of bottom portion 2809 of flow stopper 2808 along 2804 direction of FIG. 28C illustrates the flow stopper 2808 bottom portion 2809 expands and allowing specimen 2801 flowing out of the outlet 2805. View 2830 in FIG. 28D shows the side view of bottom portion 2809 attached to the side portion of flow stopper 2808 along 2814 direction of FIG. 28D illustrates the flow stopper 2808 bottom portion 2809 expands and allowing specimen 2801 flowing out of the outlet 2805 on the side portion of the flow stopper 2808 with the slit opening between bottom portion 2809 and side portion of flow stopper 2808.

Figure 29:
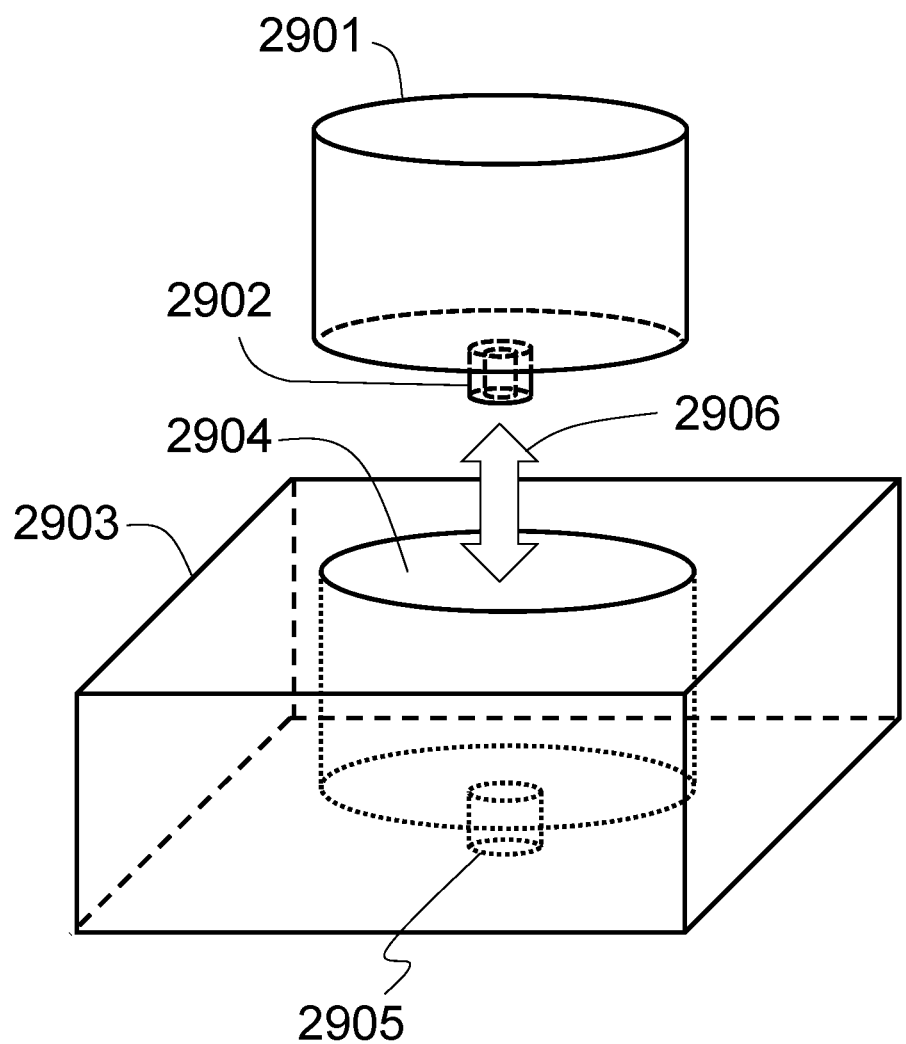
FIG. 29 illustrates a specimen dispenser in the form of a removable specimen cartridge being inserted into or removed from a designated cartridge slot in a device body.

FIG. 29 illustrates a specimen dispenser 2901 in the form of a removable specimen cartridge being inserted into or removed from a designated cartridge slot 2904 in a device body 2903. Specimen dispenser 2901 and slot 2904 are substantially cylindrical shape as in FIG. 29, which is only for the description purpose, while the actual shapes of specimen dispenser 2901 and slot 2904 may differ from cylinder with only requirement of dispenser 2901 can fit into the slot 2904. Device body 2903 is substantially similar as the device body 11 of device 10 as in FIG. 1 and FIG. 2. Specimen dispenser 2901 and specimen outlet 2902 at the bottom of the dispenser are substantially similar as specimen dispenser 14 and any of the specimen outlet 2252, 2352 and 2452 in FIG. 22A through FIG. 24B. The nozzle portion of specimen outlet 2902 may have sufficiently similar structures and functions as any of the outlet nozzles 2503, 2506, 2606, 2608, 2703, and 2803 as described in FIG. 25A through FIG. 28D. In FIG. 29, the dispenser 2901 is inserted into the device body 2903 and positioned into the slot 2904, with the specimen outlet 2902 of the cartridge aligned to and inserted into the outlet 2905 of the device body 2903. Directions of 2906 show how specimen dispenser 2901 is inserted into, or removed from, the slot 2904 of the device body 2903. Specimen is contained within the specimen dispenser 2901 and dispensed through the specimen outlet 2902 and consequently the device specimen outlet 2905 when specimen dispenser 2901 is positioned within the slot 2904 of device body 2903. Dispensing of specimen from dispenser 2901 may be through any methods as described in FIG. 22A through FIG. 24B.

Figure 30:
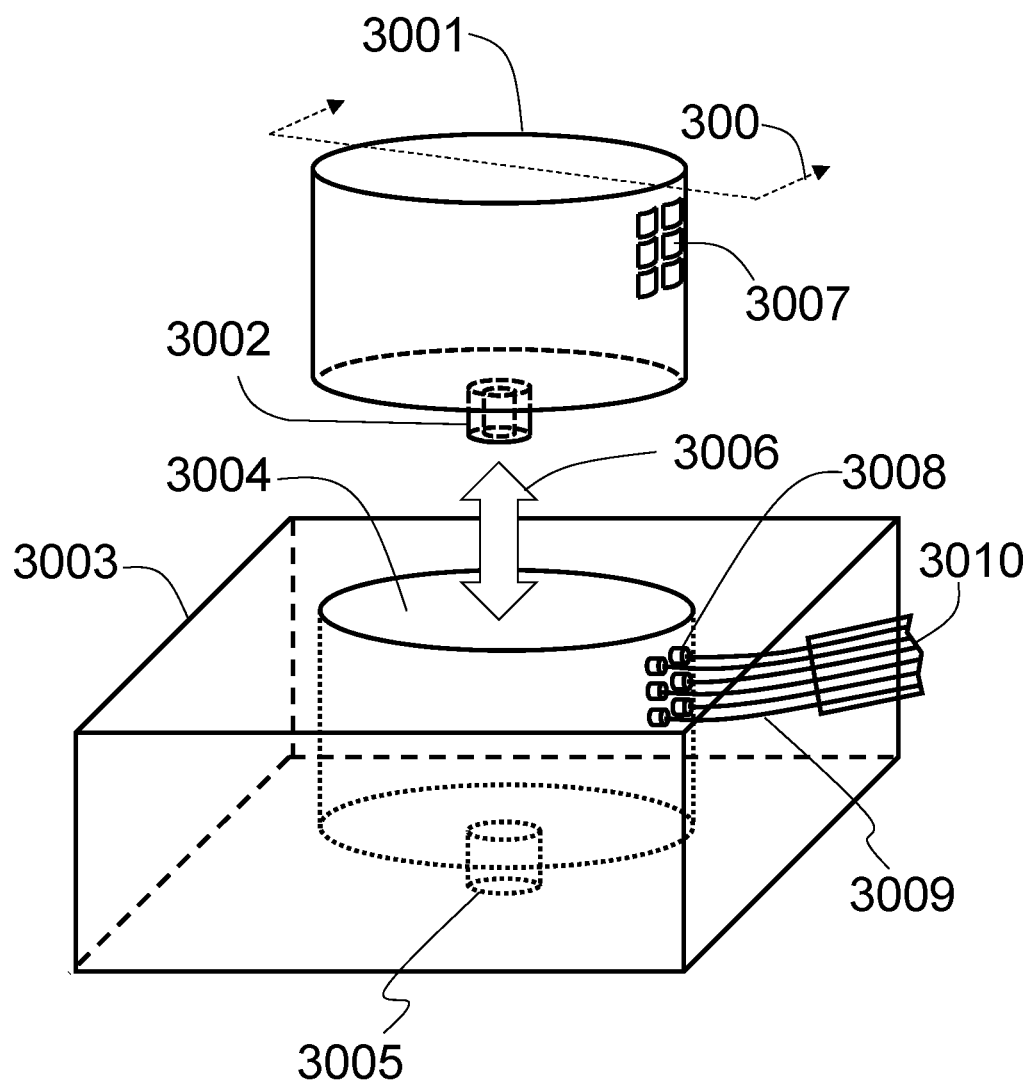
FIG. 30 illustrates a specimen dispenser in the form of a removable specimen cartridge having surface electrical contacts, being inserted into or removed from a designated cartridge slot in a device body.

FIG. 30 illustrates a specimen dispenser 3001 in the form of a removable specimen cartridge having surface electrical contacts 3007, being inserted into or removed from a designated cartridge slot 3004 in a device body 3003. Specimen dispenser 3001 and slot 3004 are substantially cylindrical shape as in FIG. 30, which is only for the description purpose, while the actual shapes of specimen dispenser 3001 and slot 3004 may differ from cylinder with only requirement of dispenser 3001 can fit into the slot 3004. FIG. 30 describes an embodiment that is substantially similar as FIG. 14 and FIG. 15, but having more structural details. Device body 3003 is substantially similar as the device body 11 of device 10 as in FIG. 1 and FIG. 2. Specimen dispenser 3001 and specimen outlet 3002 at the bottom of the dispenser are substantially similar as specimen dispenser 14 and any of the specimen outlet 2252, 2352 and 2452 in FIG. 22A through FIG. 24B. The nozzle portion of specimen outlet 3002 may have sufficiently similar structures and functions as any of the outlet nozzles 2503, 2506, 2606, 2608, 2703, and 2803 as described in FIG. 25A through FIG. 28D. The dispenser 3001 being inserted into, or removed from, the slot 3004 in the device body 3003 is substantially similar as the dispenser 14 of FIG. 14 and FIG. 15 being inserted into, or removed from, the slot 143 of device 10 as in FIG. 14 or slot 144 of device 10 as in FIG. 15. The surface electrical pads 3007 on the external wall of the dispenser 3001 make contact with the electrical contacts 3008, which are built in the side wall of the slot 3004, when the dispenser 3001 is inserted into the slot 3004. The electrical connections 3009 in contact with the contacts 3008 connect the contacts 3008 to other electronic components within the device body 3003. The electrical connections 3009 may be contained in bundle 3010 in the form of electrical wires 3009 contained in a cable 3010, or as electrical paths 3009 contained in a flat flexible substrate 3010. The surface pads 3007 are substantially similar as electrical contact 141 of FIG. 14 and FIG. 15. The contacts 3008, electrical connections 3009 and bundle 3010 together are substantially similar as electrical connection 140 of FIG. 14 and FIG. 15. The electrical connections 3009 in bundle 3010 will ultimately connect to other electronics that is substantially similar as the control unit 17 of FIG. 14 and FIG. 15. The surface pads 3007 may connect to other electronic components embedded in the dispenser 3001, which may include components that are similar to the information storage component 142 of FIG. 14 and FIG. 15. The surface pads 3007 may also connect to electronic components embedded in the dispenser 3001, which may provide any of: dispensing control of specimen, specimen flow gate, specimen volume sensing. In FIG. 30, the dispenser 3001 is inserted into the device body 3003 and positioned into the slot 3004, with the specimen outlet 3002 of the cartridge aligned to and inserted into the outlet 3005 of the device body 3003. The contacts 3008 make physical contact with the pads 3007, and electrical signals can be sent to, or retrieved from, the embedded electronic components of the dispenser 3001 through the connections 3009 by electronics, for example control unit 17 as in FIG. 14 and FIG. 15, contained in the device body 3003. Directions of 3006 show how specimen dispenser 3001 is inserted into, or removed from, the slot 3004 of the device body 3003. Specimen is contained within the specimen dispenser 3001 and dispensed through the specimen outlet 3002 and consequently the device specimen outlet 3005 when specimen dispenser 3001 is positioned within the slot 3004 of device body 3003. Dispensing of specimen from dispenser 3001 may be through any methods as described in FIG. 22A through FIG. 24B, or any methods as described in FIG. 31A through FIG. 35D.

Figure 31A:
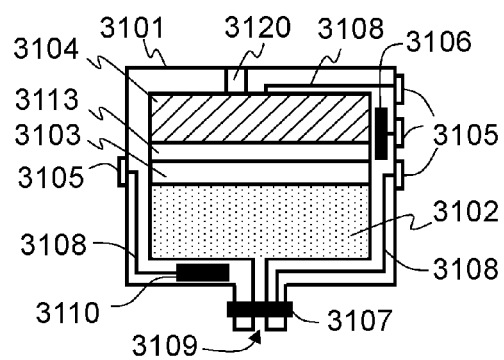
FIG. 31A illustrates cross-sectional view of a specimen dispenser having surface electrical contacts, embedded electrical components and an embedded electrically operated specimen driver.

FIG. 31A illustrates cross-sectional view of specimen dispenser 3001 of FIG. 30 with a cross-section plane along a center line 300 as in FIG. 30 that divides the cartridge 3001 of FIG. 30 into substantially equal halves, whereas specimen dispenser 3001 of FIG. 30 having surface electrical contacts 3105, embedded electrical or mechanical components 3106, 3107, 3110, and an embedded electrically operated specimen driver 3104. In FIG. 31A, specimen dispenser is formed by an enclosing housing 3101. A specimen driver 3104 is enclosed in the housing 3101. Specimen 3102 is also enclosed within the housing 3101 by the wall of the housing 3101 and a piston 3103, which is also enclosed in the housing 3101. Specimen driver 3104 is preferred to be positioned against an internal wall of the housing 3101. A propellant 3113 exists in between the specimen driver 3104 and the piston 3103. The specimen driver 3104 is capable of increasing the pressure in the propellant 3113, which in turn produces pressure and force on piston 3103 that tends to move piston 3103 inside the housing 3101 in the direction towards the specimen outlet 3109. Specimen outlet 3109 is located in the housing 3101 wall that is orthogonal to the piston 3103 moving directions. The outlet 3109 contains a flow gate 3107, which can open or shut off the specimen 3102 flow towards outside the housing 3101 through the outlet 3109. In a dispensing operation, flow gate 3107 opens, and the pressurized propellant 3113 forces piston 3103 to move in direction towards the outlet 3109 to increase space occupied by propellant 3113 and reduces pressure in the propellant 3113, whereas the piston 3103 movement forces the specimen 3102 to flow outside of the housing 3102 through the outlet 3109. When flow gate 3107 shuts off, specimen 3102 is contained within the housing 3101 and pressure in the propellant 3113 does not produce a movement of the piston 3103 due to specimen 3102 is blocked by the flow gate 3107 and pressure built up in the specimen 3102 equals pressure in the propellant 3113. The specimen driver 3104 may increase the pressure within propellant 3113 by releasing more propellant material into the space occupied by propellant 3113. In such case, the specimen driver 3104 may comprise a container that contains compressed propellant 3113 material, for example compressed liquid gas or air, and specimen driver 3104 may release the propellant 3113 material from the compressed form into the space of the housing 3101 occupied by the propellant 3113. The specimen driver 3104 may also increase the pressure within propellant 3113 by pumping air from outside of the housing 3101 into the space occupied by the propellant 3113. In such case, an air intake 3120 may exists in the housing wall that specimen driver 3104 resides, whereas the specimen driver 3104 draws air from outside of the housing 3101 through the air intake 3120 into the housing 3101, and then pumps the drawn air into the propellant 3113 space, whereas propellant 3113 is also air, to increase the pressure in propellant 3113. FIG. 31A also shows that the dispenser housing 3101 has surface electrical contacts 3105, whereas electrical connections 3108 may connect the electrical contacts 3105 to one or more of: the specimen driver 3104, the embedded electronic component 3106, a specimen remaining volume sensor 3110, and the flow gate 3107. As illustrated in FIG. 31A, through the electrical contacts 3105 and the connections 3108, one or more of the components, including but not limited to: the specimen driver 3104, the embedded electronic component 3106, a specimen remaining volume sensor 3110, and the flow gate 3107, may be controlled electrically by an electrical control unit, for example control unit 17 of FIG. 14 and FIG. 15, that is external to the housing 3101. The embedded electronic component 3106 may be any of: a control unit that controls specimen driver 3104, the specimen remaining volume sensor 3110, or the flow gate 3107 through circuits embedded in the housing 3101; a logic unit; a data processor; a CPU; a memory; a data communication device including WIFI chip, RFID chip and Bluetooth chip; an information storage device that is similar to the same component 142 as in FIG. 14 and FIG. 15.

Figure 31B:
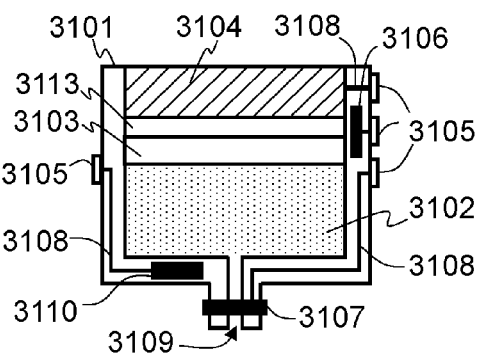
FIG. 31B illustrates cross-sectional view of a specimen dispenser having surface electrical contacts, embedded electrical components and an exposed electrically operated specimen driver.

FIG. 31B illustrates cross-sectional view of a specimen dispenser 3001 of FIG. 30 with a cross-section plane along a center line 300 as in FIG. 30 that divides the cartridge 3001 of FIG. 30 into substantially equal halves, whereas specimen dispenser 3001 of FIG. 30 having surface electrical contacts 3105, embedded electrical or mechanical components 3106, 3107, 3110, and an exposed electrically operated specimen driver 3104. Dispenser of FIG. 31B is substantially similar in both structure and function of components as the dispenser of FIG. 31A with components of FIG. 31B being functioning identically as the components having same numeral numbers as in FIG. 31A, with the only exception that the housing 3101 is not fully enclosed and having an opening where the specimen driver 3104 is located therein. The specimen driver 3104 of FIG. 31B is exposed to air outside of housing 3101 and does not require an air intake 3120 as in FIG. 31A to pump air into the propellant 3113 of FIG. 31B. The specimen driver 3104 of FIG. 31B may be externally inserted into the housing 3101 opening during assembly of the dispenser, rather than requiring an assembly process to fully enclose the specimen driver 3104 by the dispenser housing 3101 as in FIG. 31A.

Figure 31C:
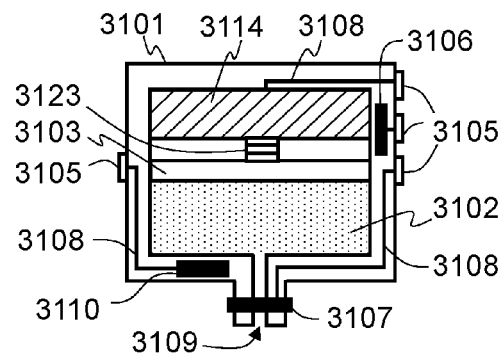
FIG. 31C illustrates cross-sectional view of a specimen dispenser having surface electrical contacts, embedded electrical components and an embedded electrical-mechanical specimen driver.

FIG. 31C illustrates cross-sectional view of a specimen dispenser 3001 of FIG. 30 with a cross-section plane along a center line 300 as in FIG. 30 that divides the cartridge 3001 of FIG. 30 into substantially equal halves, whereas specimen dispenser 3001 of FIG. 30 having surface electrical contacts 3105, embedded electrical or mechanical components 3106, 3107, 3110, and an embedded electrical-mechanical specimen driver 3114. In FIG. 31C, specimen dispenser is formed by an enclosing housing 3101. A specimen electrical-mechanical driver 3114 is enclosed in the housing 3101. Specimen 3102 is also enclosed within the housing 3101 by the wall of the housing 3101 and a piston 3103, which is also enclosed in the housing 3101. Specimen driver 3114 is preferred to be positioned against an internal wall of the housing 3101. A mechanical pusher 3123 exists in between the specimen driver 3114 and the piston 3103 and in direct contact with the piston 3103, whereas the length or size of the pusher 3123 may increase during a dispensing operation where such increase of length or size of the pusher 3123 is produced by the specimen driver 3114.

Now referring to FIG. 83A, which shows a first example of the pusher 3123 of FIG. 31C. Pusher 8302 and piston 8301 of FIG. 83A are same as the pusher 3123 and piston 3103 of FIG. 31C. The pusher 8302 of FIG. 83A is a threaded rod with threads 8312 that occupies a substantial length of the pusher rod 8302, making the pusher 8302 being similar to a screw, whereas the specimen driver 3114 of FIG. 31C couples to the threads 8312 of pusher 8302 through an threaded rotary motor 8303, such that the motor 8303 threads match to the threads 8312 of the pusher 8302. The specimen driver 3114 of FIG. 31C produces a rotary motion of the motor 8303 in the direction of 8331 and threads of motor 8303 push the threads 8312 of pusher 8302 to produce a downward movement of the pusher 8304 in 8304 direction which in turn pushes the piston 8301 in direction 8304, which is towards the outlet 3109 as in FIG. 31C.

Now referring to FIG. 83B, which shows a second example of the pusher 3123 of FIG. 31C. Pusher 8302 and piston 8301 of FIG. 83B are same as the pusher 3123 and piston 3103 of FIG. 31C. The pusher 8302 of FIG. 83B may be a rod, whereas the specimen driver 3114 of FIG. 83B couples to the rod pusher 8302 through one or more rotary wheels 8305, such that the wheels 8305 rotation initiated by the specimen driver 3114 of FIG. 31C in the directions 8351 of FIG. 83B produces a downward movement of the pusher rod 8302 in the direction 8304 due to the friction force between the wheels 8305 surface pushing against the rod 8302 surface, which in turn pushes piston 8301 in direction 8304, which is towards the outlet 3109 as in FIG. 31C. Pusher 8302 may also have threads or gear teeth on its surface, whereas the threads or gear teeth of the pusher 8302 surface may couple to threads or gear teeth that may exist on the surface of the wheels 8305, which may be gear wheels.

Now referring to FIG. 83C, which shows a third example of the pusher 3123 of FIG. 31C. Pusher 8302 and piston 8301 of FIG. 83C are same as the pusher 3123 and piston 3103 of FIG. 31C. The pusher 8302 of FIG. 83C may be a metal rod, or a rod made of partially or entirely of permanent magnet, whereas the specimen driver 3114 of FIG. 31C electromagnetically couples to the rod pusher 8302 through one or more sets of electrical coils or voice coils 8306, for example the rod 8302 may pass through a center clearance of the coils 8306 as shown in FIG. 83C. When an electric current 8361 is applied by the specimen driver 3114 of FIG. 31C, and the current 8361 passes through one or more of the electrical coils 8306, the current 8361 within the coils 8306 produces magnetic field which through electromagnetic interactions with the metal or permanent magnet rod pusher 8302 causes a downward movement of the piston 8301 in direction 8304, which is towards the outlet 3109 as in FIG. 31C. Pusher 8302 of FIG. 83C may be in other shapes, for example ring, block or tube, that electromagnetically couple to the coils 8306.

Now referring to FIG. 83D, which shows a fourth example of the pusher 3123 of FIG. 31C. Pusher 8302 and piston 8301 of FIG. 83D are same as the pusher 3123 and piston 3103 of FIG. 31C. The pusher 8302 of FIG. 83D is a cross-frame structure that has two of more hinged arms joining at a hinge 8320 that is fixed on the surface of the piston 8301. The pusher 8302 has least two top moving sections 8322, each of the top moving sections is connected to a hinged arm at a joint hinge 8321. The top moving sections 8322 are coupled to a threaded rod 8323. Specimen driver 3114 of FIG. 31C causes a rotation of the threaded rod 8323 in direction 8325 along the rod 8323 center line 8324, such rotation produces a movement of each of the top sections 8322 moving in directions 8326 and reduces the spacing between the top sections 8322 on the rod 8323. The closing up of spacing of top sections 8322, through the hinges 8321 and 8320, causes the arms of the pusher 8302 to extend in vertical direction in FIG. 83D and causes a downwards movement of the piston 8301 in direction 8304, which is towards the outlet 3109 as in FIG. 31C.

Now referring back to FIG. 31C, specimen outlet 3109 is located in the housing 3101 wall that is orthogonal to the piston 3103 moving directions. The outlet 3109 contains a flow gate 3107, which can open and shut off the specimen 3102 flow towards outside the housing 3101 through the outlet 3109. In a dispensing operation, flow gate 3107 opens, and the pusher 3123 forces piston 3103 to move in direction towards the outlet 3109, whereas the piston 3103 movement forces the specimen 3102 to flow outside of the housing 3101 through the outlet 3109. When flow gate 3107 shuts off, specimen 3102 is contained within the housing 3101 and pusher 3123 does not produce a movement of the piston 3103 due to specimen 3102 is blocked by the flow gate 3107. FIG. 31C also shows that the dispenser housing 3101 has surface electrical contacts 3105, whereas electrical connections 3108 may connect the electrical contacts 3105 to one or more of: the specimen driver 3114, the embedded electronic component 3106, a specimen remaining volume sensor 3110, and the flow gate 3107. As illustrated in FIG. 31C, through the electrical contacts 3105 and the connections 3108, one or more of the components, including but not limited to: the specimen driver 3114, the embedded electronic component 3106, a specimen remaining volume sensor 3110, and the flow gate 3107, may be controlled electrically by an electrical control unit, for example control unit 17 in FIG. 14 and FIG. 15, that is external to the housing 3101. The embedded electronic component 3106 may be any of: a control unit that controls specimen driver 3114 or the specimen remaining volume sensor 3110 or the flow gate 3107 through circuits embedded in the housing 3101, a logic unit, a data processor, a CPU, a memory, a data communication device including WIFI chip, RFID chip and Bluetooth chip, an information storage device that is similar to the same component 142 as in FIG. 14 and FIG. 15

Figure 31D:
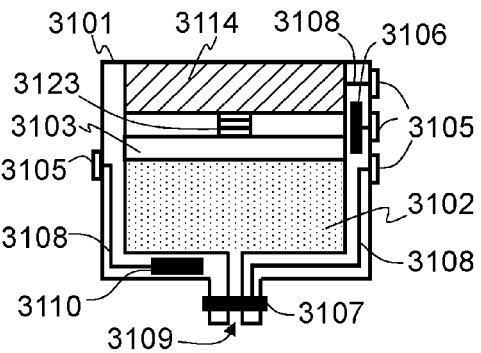
FIG. 31D illustrates cross-sectional view of a specimen dispenser having surface electrical contacts, embedded electrical components and an exposed attached electrical-mechanical specimen driver.

FIG. 31D illustrates cross-sectional view of a specimen dispenser 3001 of FIG. 30 with a cross-section plane along a center line 300 as in FIG. 30 that divides the cartridge 3001 of FIG. 30 into substantially equal halves, whereas specimen dispenser 3001 of FIG. 30 having surface electrical contacts 3105, embedded electrical or mechanical components 3106, 3107, 3110, and an exposed attached electrical-mechanical specimen driver 3114. Dispenser of FIG. 31D is substantially similar in both structure and function of components as the dispenser of FIG. 31C with components of FIG. 31D being functioning identically as the components having same numeral numbers as in FIG. 31C, with the only exception that the housing 3101 is not fully closed and with an opening where the specimen driver 3114 is located therein. The specimen driver 3114 of FIG. 31D is exposed to air outside of housing 3101, and may be externally inserted into the housing 3101 opening during assembly of the dispenser, rather than requiring an assembly process to fully enclose the specimen driver 3114 by the dispenser housing 3101 as in FIG. 31C.

FIG. 32A illustrates cross-sectional view of a specimen dispenser 3001 of FIG. 30 with a cross-section plane along a center line 300 as in FIG. 30 that divides the cartridge 3001 of FIG. 30 into substantially equal halves, whereas specimen dispenser 3001 of FIG. 30 having surface electrical contacts 3205, embedded electrical or mechanical components 3206, 3207, 3210, and an externally attached mechanical specimen driver 3204. In FIG. 32A, specimen dispenser is formed by an closed housing 3201. A specimen mechanical driver 3204 is externally attached to the housing 3201. Specimen 3202 is enclosed within the housing 3201 by the wall of the housing 3201 and a piston 3203, which is also enclosed in the housing 3201. Specimen driver 3204 is coupled to a mechanical pusher 3213 that extends from the specimen driver 3204 and into the housing 3201 to be in direct contact with the piston 3203, whereas the length or size of the pusher 3223 may increase during a dispensing operation where such increase of length or size of the pusher 3223 is produced by the specimen driver 3204. Pusher 3213 and specimen driver 3204 function substantially similar to pusher 3123 and specimen driver 3114 of FIG. 31C. Examples of pusher 3213 function to push the piston 3203 can also be found in FIG. 92A through FIG. 92D, where pushers 9202, pistons 9201 are same as pusher 3213 and piston 3203 of FIG. 32A. The mechanical specimen driver 3204 may be manually operated by the user of the device 3003 as in FIG. 30 to produce mechanical movements, for example movement 9231, 9251, 9225 as shown in FIG. 92A, FIG. 92B and FIG. 92D. The mechanical specimen driver 3204 may also be electrically operated by a control unit, for example control unit 17 of FIG. 14 and FIG. 15, that is enclosed in the device body 3003 of FIG. 30, through electrical connections, where the control unit produces mechanical movements, for example movement 9231, 9251, 9225 as shown in FIG. 92A, FIG. 92B and FIG. 92D, or electrical signal, for example current 9261 as shown in FIG. 92C. The mechanical specimen driver 3204 as in FIG. 32A may be part of the device body 3003 of FIG. 30 that attaches to the housing 3201 as in FIG. 32A of dispenser 3001 of FIG. 30 externally after cartridge dispenser 3001 is inserted into the slot 3004 as illustrated in FIG. 30.

In FIG. 32A, specimen outlet 3209 is located in the housing 3201 wall that is orthogonal to the piston 3203 moving directions. The outlet 3209 contains a flow gate 3207, which can open and shut off the specimen 3202 flow towards outside the housing 3201 through the outlet 3209. In a dispensing operation, flow gate 3207 opens, and the pusher 3213 forces piston 3203 to move in direction towards the outlet 3209, whereas the piston 3203 movement forces the specimen 3202 to flow outside of the housing 3201 through the outlet 3209. When flow gate 3207 shuts off, specimen 3202 is contained within the housing 3201 and pusher 3213 does not produce a movement of the piston 3203 due to specimen 3202 is blocked by the flow gate 3207. FIG. 32A also shows that the dispenser housing 3201 has surface electrical contacts 3205, whereas electrical connections 3208 may connect the electrical contacts 3205 to one or more of: the embedded electronic component 3206, a specimen remaining volume sensor 3210, and the flow gate 3207. As illustrated in FIG. 32A, through the electrical contacts 3205 and the connections 3208, one or more of the components, including but not limited to: the embedded electronic component 3206, a specimen remaining volume sensor 3210, and the flow gate 3207, may be controlled electrically by an electrical control unit, for example control unit 17 in FIG. 14 and FIG. 15, that is external to the housing 3201. The embedded electronic component 3206 may be any of: a control unit that controls the specimen remaining volume sensor 3210 or the flow gate 3207 through circuits embedded in the housing 3201, a logic unit, a data processor, a CPU, a memory, a data communication device including WIFI chip, RFID chip and Bluetooth chip, an information storage device that is similar to the same component 142 as in FIG. 14 and FIG. 15.

FIG. 32B illustrates cross-sectional view of a specimen dispenser 3001 of FIG. 30 with a cross-section plane along a center line 300 that divides the cartridge 3001 of FIG. 30 into substantially equal halves, whereas specimen dispenser 3001 of FIG. 30 having surface electrical contacts 3205, embedded electrical or mechanical components 3206, 3207, 3210, and an externally attached air pump specimen driver 3224. Dispenser of FIG. 32B is substantially similar in the structure and function of components as the dispenser of FIG. 32A with components of FIG. 32B being functioning identically as the components having same numeral numbers as in FIG. 32A, with the exception that the specimen driver 3224 drives the piston 3203 moving downwards in FIG. 32B and forces dispensing of specimen 3202 by injecting air 3214 into the housing 3201 through an air intake 3223 located next to the specimen driver 3224 in the housing 3201, rather than by a mechanical pusher 3213 as in FIG. 32A. The specimen driver 3224 of FIG. 32B injects air into the housing 3201 space between the piston 3203 and housing 3201 occupied by air 3214 and increases the pressure in air 3214. When flow gate 3207 of FIG. 32B opens, pressure in air 3214 produces a movement of piston 3203 towards outlet 3209 and forces specimen 3202 to be dispensed out of the housing 3201 through the outlet 3209.

FIG. 32C illustrates cross-sectional view of a specimen dispenser 3001 of FIG. 30 with a cross-section plane along a center line 300 that divides the cartridge 3001 of FIG. 30 into substantially equal halves, whereas specimen dispenser 3001 of FIG. 30 having surface electrical contacts 3205, embedded electrical or mechanical components 3206, 3207, 3210, and specimen driving by internal propellant 3214. Dispenser of FIG. 32C is substantially similar in the structure and function of components as the dispenser of FIG. 32B with components of FIG. 32C being functioning identically as the components having same numeral numbers as in FIG. 32B, with the exception that the specimen driver 3224 and air intake 3223 as in FIG. 32B are removed and replaced by an internal propellant 3214 as illustrated in FIG. 32C. The propellant 3214 exists in the space between the piston 3203 and housing 3201 and is pressurized. The propellant 3214 may be made of compressed air or other types of gas, and produces a constantly applied pressure on the piston 3203. When flow gate 3207 of FIG. 32C opens, pressure from propellant 3214 on the piston 3203 produces a movement of piston 3203 towards outlet 3209 and forces specimen 3202 to be dispensed out of the housing 3201 through the outlet 3209.

FIG. 32D illustrates cross-sectional view of a specimen dispenser 3001 of FIG. 30 with a cross-section plane along a center line 300 that divides the cartridge 3001 of FIG. 30 into substantially equal halves, whereas specimen dispenser 3001 of FIG. 30 having surface electrical contacts 3205, embedded electrical or mechanical components 3206, 3207, 3210, 3211 and specimen driving by a pump 3211 located in proximity to the dispenser outlet 3209. In FIG. 32D, specimen dispenser is formed by an closed housing 3201. A specimen pump 3211 is embedded in the housing 3201 and in close proximity to the outlet 3209. Specimen 3202 is enclosed within the housing 3201 by the wall of the housing 3201 and a piston 3203, which is also enclosed in the housing 3201. An air chamber 3215 existing in between the space enclosed by the wall of the housing 3201 and the side of the piston 3203 opposing the specimen 3202, and the air chamber 3215 is connected to external air through an air intake 3220 located in the housing 3201. Specimen pump 3211 is capable of pumping specimen 3202 out of the housing 3201 through the outlet 3209 when the flow gate 3207 is open. The specimen pump 3211 may be operated electrically through electrical connection 3208 that connects the specimen pump 3211 to the surface pad 3205 and consequently a control unit located in the device body 3003 of FIG. 30. Alternatively, specimen pump 3211 may be operated by electrical components embedded in housing 3201, for example a control unit 3206, through electrical connections embedded in the housing 3201. When specimen 3202 is pumped out of the housing 3201 by the specimen pump 3211 through the outlet 3209, the decreased pressure in specimen 3202 causes the piston 3203 to move in the direction towards the outlet 3209 due to the air pressure in air chamber 3215 being higher than in the specimen 3202, and more external air enters the air chamber 3215 through the air intake 3220.

Now referring to FIG. 33A through FIG. 33F. The specimen conduit 3301 of FIG. 33A through FIG. 33F connects the specimen 3202 of FIG. 32D from inside the housing 3201 to the outlet 3209 as in FIG. 32D. Outlet 3309 of FIG. 33A through FIG. 33F is same as outlet 3209 of FIG. 32D.

FIG. 33A illustrates an example of specimen pump 3211 of FIG. 32D, which includes a thermal excitation circuits 3331 around a specimen conduit 3301. Thermal excitation circuits 3331 may be positioned in close proximity to, or directly in contact with, the conduit 3301. Electric current may be applied through the circuits 3331 via the electrical connections 3208 as in FIG. 32D to generate local heating of the conduit 3301 and the specimen 3302 contained within the conduit. Heating by the thermal excitation circuits 3331 may be through direct heat generation of the current flowing through the circuits 3331, whereas the circuits 3331 function as heating coil and said current lowing through the circuits 3331 may be a DC current. Heating by the thermal excitation circuits 3331 may also be from a low frequency AC current with AC frequency less than 100 Megahertz (MHz). In such case, conduit 3301 experiences heat radiation from the circuits 3331 or heat transfer through direct contact with the circuits 3331, while specimen 3302 is heated by heat transfer from the conduit 3301 through direct contact. Alternatively, heating by the thermal excitation circuits 3331 can be through an AC current flowing through the circuits 3331 at an RF frequency larger than 100 MHz, whereas the RF frequency AC current flowing through the circuits 3331 generates microwave that heat certain molecules of the specimen 3302 directly through a process of dielectric heating, for example the AC frequency is 2.45 Gigahertz (GHz) or 915 MHz and molecules in specimen 3302 being heated are any of: water, fat, and other substances that absorb energy from the microwave. In such case, the thermal excitation circuits 3331 may heat the specimen 3302 contained in the conduit 3301 directly through microwave generated by the circuits 3331, and conduit 3301 may be less heated or affected by the microwave than the specimen 3302. When the specimen 3302 of FIG. 33A is heated locally within the conduit 3301, the material of the specimen 3302 contained within the conduit 3301 may increase volume and forces increased volume of the specimen 3302 to move outside the conduit 3301 and through the outlet 3309, and thus specimen 3302 is dispensed from the conduit 3301 through the outlet 3309. After specimen 3302 dispensing, the heating may stop to allow conduit 3301 and the specimen 3302 to cool down, and to allow more specimen to replenish the space within the conduit 3301 for the next dispensing event of specimen 3302 by heating.

FIG. 33B illustrates an example of specimen pump 3211 of FIG. 32D, with specimen being dispensed by heating from circuits 3331 on a specimen conduit 3301 and specimen contained therein. FIG. 33B shows an alternative method of dispensing specimen 3302 of FIG. 33A through heating by the circuits 3331, whereas the electric current flowing through the circuits 3331 causes a local heating of the conduit 3301. Material of the conduit 3301 of FIG. 33B has the property of thermal expansion, as shown by the 3332 in FIG. 33B, during heating, and thus the local heating of the conduit 3301 by the circuit 3331 produces a narrowed conduit 3301 internal width and a smaller conduit 3301 volume that holds the specimen 3302. Due to this reduced internal volume of conduit 3301, specimen 3302 is forced, or squeezed, to flow out of the conduit 3301 and through the outlet 3309 in direction of 3333, and thus specimen 3302 is dispensed from the conduit 3301 through the outlet 3309. After specimen 3302 dispensing, the heating may stop to allow conduit 3301 to cool down, and to allow more specimen to replenish the space within the conduit 3301 for the next dispensing event of specimen 3302 by heating.

FIG. 33C illustrates an example of specimen pump 3211 of FIG. 32D, including a piezo element 3303 attached to a specimen conduit 3301 and specimen 3302 contained therein. At least two electrical connections 3304, which are similar as electrical connections 3208 of FIG. 32D, are electrically coupled to the at least two electrodes of the piezo element 3303. With an AC voltage applied between the electrical connections 3304, with the AC voltage having a frequency more than 20 kHz, the piezo element 3303 produces ultrasonic vibrations that couples with the specimen conduit 3301 through direct contact between piezo element 3303 and the specimen conduit 3301, which further couples to the specimen 3302 contained within the specimen conduit 3301. With the specimen conduit 3301 having a design of its shape, material property, and dimensions of the containment where specimen 3302 resides, specimen conduit 3301 functions as a fluidic channel, for example a micro-fluidic channel, where the ultrasonic vibration from the piezo element 3303 produces pushing force to cause a fluidic flow that forces the specimen 3302 to flow in the direction 3333 and out of the conduit 3301 through the outlet 3309.

FIG. 33D illustrates an example of specimen pump 3211 of FIG. 32D, including a rotary motor 3305 and a flexible conduit 3301 and specimen 3302 contained therein. At least one motor arm 3306 is located on the circumference of the motor 3305, such that when the motor 3305 rotates in the 3307 direction, the at least one arm 3306 comes into contact with the external wall of the flexible conduit 3301. With a continued rotation of the motor 3305 and movement of the arm 3306, the conduit 3301 is compressed as shown by the conduit compression 3334 in FIG. 33D, whereas such compression 3334 of the conduit 3301 moves from top to down along the direction 3333 until arm 3306 moves away from the conduit 3301 following the rotation 3307 of the motor 3305, at which time the compression 3334 may return to the original non-compressed shape of conduit 3301 wall. The compression 3334 movement forces, or squeezes, the specimen 3302 to flow in the direction of 3333 outside of the conduit 3301 and through the outlet 3309. Rotation 3307 of motor 3305 may be electrically driven through the electrical connections 3308 of FIG. 32D.

FIG. 33E illustrates an example of specimen pump 3211 of FIG. 32D, including alternating valves 3310 and a flexible conduit 3301 and specimen 3302 contained therein. Valves 3310 may be placed on only one side of the conduit 3301, or two sides of the conduit 3301 as shown in FIG. 33E. At least two valves 3310 are positioned at two different locations on the conduit 3301 wall along the 3333 direction. FIG. 33E shows that a set of upper valves 3310 move away from each other along the 3311 directions, which in turn cause the flexible conduit 3301 walls connected to the upper valves 3310 to bend accordingly as shown by 3335 and the wall spacing of the conduit 3301 between the upper valves 3310 increases. Such increase of conduit 3301 spacing at upper valves 3310 location leads to decrease specimen 3302 pressure, which causes more specimen 3302 to move into the increase spacing area of the conduit from inside the housing 3201 as in FIG. 32D. Meanwhile, FIG. 33E shows that a set of lower valves 3310 move closer to each other along the 3312 directions, which in turn cause the flexible conduit 3301 walls connected to the upper valves 3310 to bend accordingly as shown by 3336 and the wall spacing of the conduit 3301 between the lower valves 3310 decrease, preferably to zero wall spacing. Such decrease of conduit 3301 spacing at lower valves 3310 location forces, or squeezes, the specimen 3302 originally in the conduit 3301 space at the lower valves 3310 location out of the conduit 3301 and through the outlet 3309 in 3333 direction.

Following the FIG. 33E valve movements, the upper valves 3310 may reverse their movement to 3312 directions to be closer to each other and reduces the wall spacing of conduit 3301 at upper valves 3310 location, preferably to zero wall spacing. Meanwhile, the lower valves 3310 may also reverse their movement to 3311 directions to be away from each other and increases the wall spacing of conduit 3301 at lower valves 3310 location. The reversed movements of the upper and lower valves 3310 cause the specimen 3302 originally contained within the conduit 3301 space around the upper valves 3310 location to move to the conduit 3301 space around the lower valves 3310 location. Then, a following valve movements as shown in FIG. 33E may force, or squeeze, the specimen 3302 in the conduit 3301 space at the lower valves 3310 location out of the conduit 3301 and through the outlet 3309 in 3333 direction. A repeated movements and reverse movements of the valves 3310 may provide a pumping function to pump the specimen 3202 out of the housing 3201 through the outlet 3209 of FIG. 32D. Movements of the valves 3310 in directions 3311 and 3312 may be produced by a driver connected to the valves 3310, or being part of valves 3310, which are controlled by electrical signal from the electrical connections 3208 of FIG. 32D.

FIG. 33F illustrates an example of specimen pump 3211 of FIG. 32D, including electrodes 3321 and 3322 embedded in a conduit 3301 and specimen 3302 contained therein. Each of the electrodes 3321 and 3322 may have an electrical connection 3323 attached, which are similar as the electrical connection 3208 of FIG. 32D. A first electrical voltage may be applied to the upper electrodes 3321 through the electrical connections 3323, which may produce a first dielectric polarization in the specimen 3302, or may inject a first electric charge, for example electrons, in the specimen 3302 when the electrodes 3321 are in contact with the specimen 3302. Then a second electrical voltage may be applied to the lower electrodes 3322 through the electrical connections 3323, which may produce an electric field in the specimen 3302 that provide an electrical attraction to the first dielectric polarization in the specimen 3302, or provides an electrical attraction to the first electric charge, for example a positive voltage on the electrodes 3322. Such electrical attraction may cause the specimen 3302 to move in the direction 3333 and eventually out of the conduit 3301 through the outlet 3309. The first and second voltages may be applied in the form of pulses or AC voltage. The first and second voltages may have different amplitude, polarity, pulse width or frequency.

Now referring back to FIG. 32D, specimen outlet 3209 is located in the housing 3201 wall that is orthogonal to the piston 3203 moving directions. The outlet 3209 contains a flow gate 3207, which can open and shut off the specimen 3202 flow towards outside the housing 3201 through the outlet 3209. In a dispensing operation, flow gate 3207 opens, and the pump 3211 forces the specimen 3202 to flow outside of the housing 3201 through the outlet 3209. When flow gate 3207 shuts off, specimen 3202 is contained within the housing 3201 and pump 3211 does not produce a dispensing of the specimen 3202 or a movement of the piston 3203 due to specimen 3202 is blocked by the flow gate 3207. FIG. 32D also shows that the dispenser housing 3201 has surface electrical contacts 3205, whereas electrical connections 3208 may connect the electrical contacts 3205 to one or more of: the embedded electronic component 3206, a specimen remaining volume sensor 3210, the specimen pump 3211, and the flow gate 3207. As illustrated in FIG. 32D, through the electrical contacts 3205 and the connections 3208, one or more of the components, including but not limited to: the embedded electronic component 3206, a specimen remaining volume sensor 3210, the specimen pump 3211, and the flow gate 3207, may be controlled electrically by an electrical control unit, for example control unit 17 in FIG. 14 and FIG. 15, that is external to the housing 3201. The embedded electronic component 3206 may be any of: a control unit that controls the specimen remaining volume sensor 3210 or the flow gate 3207 or the specimen pump 3211 through circuits embedded in the housing 3201, a logic unit, a data processor, a CPU, a memory, a data communication device including WIFI chip, RFID chip and Bluetooth chip, an information storage device that is similar to the same component 142 as in FIG. 14 and FIG. 15.

Figure 34A:
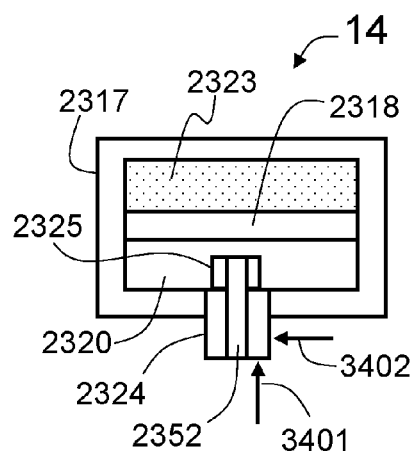
FIG. 34A illustrates a specimen dispenser in the form of a cartridge having a propellant driven piston, and a flow valve controlled by externally applied different types of pressure.

To control specimen dispensing from dispensers having various mechanically operated flow valves as shown in FIG. 23B through FIG. 23D, FIG. 34A illustrates a specimen dispenser that is identical to the dispenser 14 of FIG. 23B, in the form of a cartridge having a propellant 2323 driven piston 2318 and a flow valve 2325 being controlled by externally applied different types of pressure. FIG. 23B being used in FIG. 34A is only for description purpose. Principles as described in FIG. 34A and FIG. 34B may be applied to other specimen dispensers with mechanically operated flow values without limitation. Same as in FIG. 23B, FIG. 34A shows that the valve switch 2324 is mechanically operated, whereas an externally applied pressure, for example first pressure applied on valve switch 2324 in direction 3401 or second pressure in direction 3402, will be transferred to a mechanical response from the flow valve 2325 and causes the flow valve 2325 to turn on. When the flow value 2325 is turned on, the specimen 2320 is forced out of the outlet 2352 by the propellant 2323 pressure on the piston 2318. After the externally applied pressure is removed from the valve switch 2324, flow value 2325 will return of shut off state. Outlet 2352 pass through both valve switch 2324 and flow valve 2325 and reaches into the specimen space 2320.

Figure 34B:
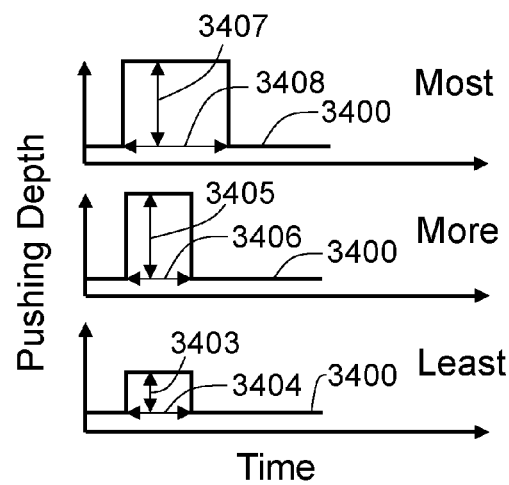
FIG. 34B illustrates methods to control the specimen dispense amount from the cartridge of FIG. 34A.
Figure 34C:
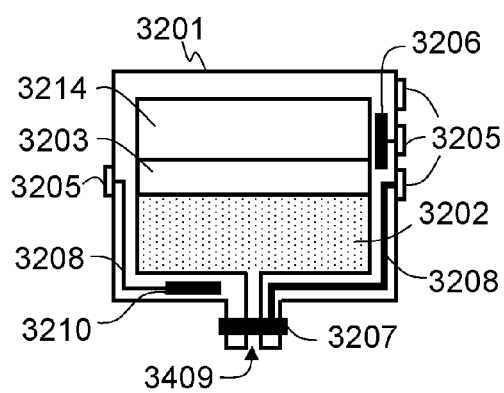
FIG. 34C illustrates a specimen dispenser having surface electrical contacts, embedded electrical components, a propellant driven piston and electrical signal controlled flow gate.

FIG. 34B illustrates methods to control the specimen 2320 dispense amount from the dispenser of FIG. 34A by controlling the pressure applied to the valve switch 2324. Each of the three plots of the FIG. 34B has an identical horizontal axis to represent time of pressure applied to the valve switch 2324 in either 3401 or 3402 direction of FIG. 34A. Each of the three plots of the FIG. 34B has an identical vertical axis to represent degree of pressure applied to the valve switch 2324 of FIG. 34A, with the degree of pressure being labeled as the pushing depth of the valve switch 2324, whereas for the mechanically operation valve switch 2324, the more mechanical movement of the valve switch 2324 produced by the pressure in either 3401 or 3402 directions, with the movement being labeled as pushing depth in FIG. 34B, the larger the opening that is produced in the flow valve 2325, and the more amount of specimen 2320 is dispensed from dispenser 14 in a unit time. Each plot of FIG. 34B shows a pulse function representing the application and pushing depth applied to valve switch 2324 in FIG. 34A. The bottom level 3400 represents zero pressure applied to valve switch 2324 and flow gating 2325 being shut off. The arrows 3403, 3405, 3407 arising from the bottom level 3400 represent three different pushing depth of the pressure, which are also the amplitudes of the three pulses indicating different flow valve 2325 open degrees, with 3407 being the widest opening and 3403 being the smallest opening in flow valve 2325. The arrows 3404, 3406, 3408 represent the time that pressure is applied to the valve switch 2324, which are also the pulse width of the three plots and indicate the flow valve 2325 open time, with 3408 being the longest and 3404 being the shortest in open time of the flow valve 2325. For lower plot of FIG. 34B showing a pressure pulse applied to valve switching having a pulse amplitude 3403 and pulse width 3404, it has the shortest flow gate 2325 opening time 3404 and smallest pushing depth 3403, and thus produces least amount of specimen 2320 dispensing from cartridge 14. For middle plot of FIG. 34B showing a pressure pulse applied to valve switching having a pulse amplitude 3405, it has the same flow gate 2325 opening time 3406 and larger pushing depth 3405 compared to 3404 and 3403 of the lower plot of FIG. 34B, and thus produces more amount of specimen 2320 dispensing from cartridge 14 than in lower plot of FIG. 34B. For upper plot of FIG. 34B showing a pressure pulse applied to valve switching having a pulse amplitude 3407 and pulse width 3408, it has the a longer flow gate 2325 opening time 3408 and same pushing depth 3407 compared to 3406 and 3405 of the middle plot of FIG. 34B, and thus produces even more amount of specimen 2320 dispensing from cartridge 14 than in middle plot, and also the most amount of the specimen 2320 dispensing from cartridge 14 among the three plots of FIG. 34B.

Figure 35A:
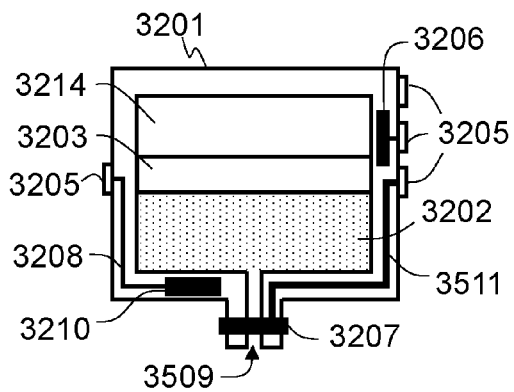
FIG. 35A illustrates a specimen dispenser having surface electrical contacts, embedded electrical components, an embedded electrically operated specimen driver and digital electrical signal controlled flow gate.
Figure 35B:
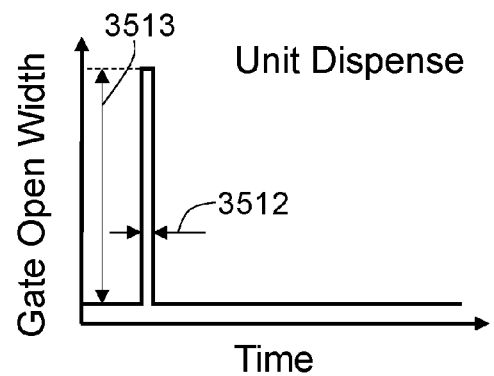
FIG. 35B illustrates method to produce the specimen dispensing from the dispenser of FIG. 35A in a unit volume by a single pulse of electrical signal.
Figure 35C:
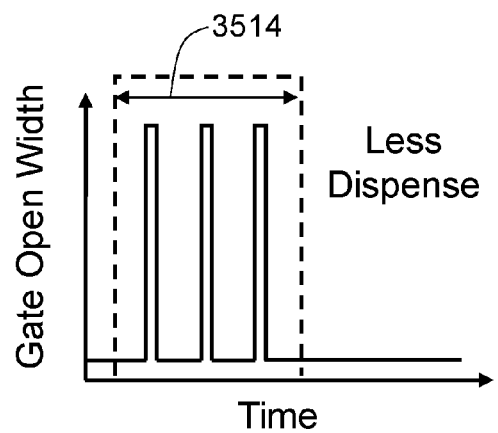
FIG. 35C illustrates method to produce the specimen dispensing in a first amount from the dispenser of FIG. 35A by a number of pulses of electrical signal.
Figure 35D:
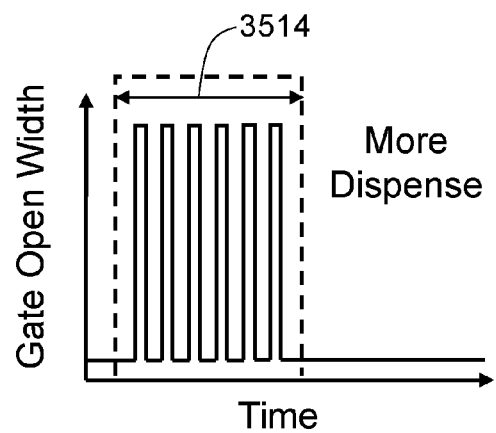
FIG. 35D illustrates method to produce the specimen dispensing in a second amount from the dispenser of FIG. 35A by another number of pulses of electrical signal.

To control specimen dispensing from dispensers having various electrically operated specimen flow gate, for example flow gates 3107 and 3207 as shown in FIG. 31A through FIG. 32D, FIG. 34C illustrates a specimen dispenser that is identical to the dispenser of FIG. 32C, in the form of a specimen dispenser having surface electrical contacts 3205, embedded electrical components 3206, 3210, a propellant 3214 driven piston 3203 and electrical signal controlled flow gate 3207. FIG. 32C being used in FIG. 34C is only for description purpose. Principles as described in FIG. 34C and FIG. 34D may be applied to other specimen dispensers with electrically operated specimen flow gates without limitation. Same as in FIG. 32C, FIG. 34C shows that the flow gate 3207 may be electrically operated, whereas a first electrical signal applied to the flow gate 3207 though the connection 3208 which further connects to the contact pads 3205, is capable of turning on the flow gate 3207 to allow the specimen 3202 to be dispensed from the dispenser housing 3201. The first electrical signal applied to the flow gate 3207 may be applied by an electrical control unit, for example control unit 17 as in FIG. 14 and FIG. 15, that is external to the housing 3201. After the applied first electrical signal is removed from the flow gate 3207, flow gate 3207 may return to shut off state to stop specimen 3202 dispensing from the dispenser housing 3201. Alternatively, a second electrical signal may be applied to the flow gate 3207 through the connection 3208 to change the flow gate 3207 into shut off state.

FIG. 34D illustrates methods to control the specimen 3202 dispensing amount from the dispenser of FIG. 34C by an electrical signal applied to the flow gate 3207 of FIG. 34C. Each of the three plots of the FIG. 34D has an identical horizontal axis to represent time of the electrical signal applied to the flow gate 3207 of FIG. 34C. Each of the three plots of the FIG. 34D has an identical vertical axis to represent the flow gate 3207 open width, which may be related to the amplitude of the electrical signal applied to the flow gate 3207, for example a higher amplitude electric voltage or electric current applied to the flow gate 3207 may produce a wider opening of the flow gate 3207 to allow more amount of specimen 3202 to be dispensed from dispenser housing 3201 of FIG. 34C in a unit time. Each plot of FIG. 34D shows a pulse function representing the duration of the electrical signal applied to the flow gate 3207 in FIG. 34C, and electrical signal generated open width of the flow gate 3207 in FIG. 34C, whereas the pulse of each plot may also be treated as a pulse of the electrical signal applied to the flow gate 3207 with a pulse duration and pulse amplitude. The bottom level 3410 represents zero opening of the flow gate 3207, or shut off of the flow gate 3207. The arrows 3413, 3415, 3417 arising from the bottom level 3410 represent three different opening width of flow gate 3207, which indicate three different electrical signals applied to the flow gate 3207, with 3417 being the widest opening and 3413 being the smallest opening in flow gate 3207. The arrows 3414, 3416, 3418 represent the duration of the flow gate 3207 opening in each of the plots, which also indicate the pulse duration of the electrical signals applied to flow gate 3207, with 3418 being the longest and 3414 being the shortest pulse duration. For lower plot of FIG. 34D showing flow gate 3207 opening cause by application of electrical signal to the flow gate 3207, it has a pulse amplitude 3413 and pulse width 3414, it has the shortest flow gate 3207 opening duration 3414 and smallest flow gate 3207 opening width 3413, and thus produces least amount of specimen 3202 dispensing from dispenser of FIG. 34C. For middle plot of FIG. 34D showing flow gate 3207 opening cause by application of electrical signal to the flow gate 3207 having a pulse amplitude 3415 and pulse duration 3416, it has the same flow gate 3207 opening duration 3416 and wider opening 3415 compared to 3414 and 3413 of the lower plot of FIG. 34D, and thus produces more amount of specimen 3202 dispensing from dispenser of FIG. 34C than in lower plot. For upper plot of FIG. 34D showing flow gate 3207 opening cause by application of electrical signal to the flow gate 3207 having a pulse amplitude 3417 and pulse duration 3418, it has the a longer flow gate 3207 opening duration 3418 and same opening width 3417 compared to 3416 and 3415 of the middle plot of FIG. 34D, and thus produces even more amount of specimen 3202 dispensing from dispenser of FIG. 34C than in middle plot, and also most amount of the specimen 3202 dispensing from dispenser of FIG. 34C among the three plots of FIG. 34D.

FIG. 35A through FIG. 35D illustrate dispensing various amounts of specimen 3202 from dispenser housing 3201 of FIG. 34C and FIG. 32C with a method that is different than what was described in FIG. 34D.

FIG. 35A illustrates specimen dispenser same as FIG. 34C having surface electrical contacts 3205, embedded electrical components 3206, 3210, a propellant 3214 driven piston 3203 and electrical signal controlled flow gate 3207. FIG. 35A dispenser is only for description purpose. Principles as described in FIG. 35A through FIG. 35D may be applied to other specimen dispensers with electrically operated specimen flow gates without limitation.

FIG. 35B illustrates specimen 3202 dispensing from the dispenser of FIG. 35A in a unit volume by a single pulse of electrical signal applied to the flow gate 3207 of FIG. 35A. FIG. 35B is similar to any one of the plots of the FIG. 34D, with the pulse width 3512 representing the duration of the flow gate 3207 being open, and pulse amplitude 3513 representing the open width of the flow gate 3207. Pulse width 3512 together the pulse amplitude 3513 determine a specific amount of specimen 3202 being dispensed from the dispenser in FIG. 35A, which is also referred to as a Unit Dispense of the specimen 3202.

FIG. 35C illustrates the method to produce the specimen 3202 dispensing in a first amount from the dispenser of FIG. 35A by a number of pulses of the electrical signal applied to the flow gate 3207. In FIG. 35C, dispensing of the specimen 3202 is always produced by a number of repeated pulses of FIG. 35B within a given time slot 3514. For FIG. 35C, three pulses are used as example to show that three Unit Dispenses are performed according the FIG. 35B unit dispense scheme, which is referred to as Less Dispense.

FIG. 35D illustrates method to produce the specimen 3202 dispensing in a second amount from the dispenser of FIG. 35A by another number of pulses of electrical signal applied to the flow gate 3207. In FIG. 35D, dispensing of the specimen 3202 within the same duration of a given time slot 3514 as in FIG. 35C, six pulses are used as example to show that six Unit Dispenses are performed according the FIG. 35B unit dispense scheme, which is referred to as More Dispense. With the six Unit Dispenses within time slot 3514, the amount of the total specimen 3202 dispensed in FIG. 35D is twice the amount of the total specimen 3202 dispensed in FIG. 35C.

Figure 34D:
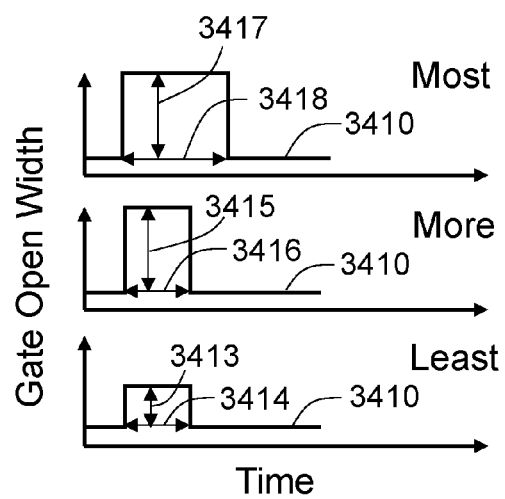
FIG. 34D illustrates methods to control the specimen dispense amount from the cartridge of FIG. 34C by an electrical signal.

According the method of using different number of Unit Dispense pulses to dispense various amount of specimen 3202 as illustrated in FIG. 35C and FIG. 35D, the dispensing of specimen 3202 from specimen dispenser can now be digitally controlled with a volume precision determined by the Unit Dispense specimen volume. For example, for a specimen dispenser that is capable of producing 1 microliter (uL) specimen 3203 volume in each Unit Dispense, a first user requiring a 5 uL specimen will need five Unit Dispenses, while a second user requiring an 8 uL will need eight Unit Dispenses. While for a specimen dispenser that is capable of producing 0.1 uL specimen 3203 volume in each Unit Dispense, the first user may ask for 5.1 uL composed of 51 Unit Dispenses for a better accuracy to meet first user's need, while the second user may ask for 8.3 uL composed of 83 Unit Dispenses for better accuracy to meet second user's need. The dispensing method as demonstrated in FIG. 35B through FIG. 35D may couple with the pulse amplitude variations, as shown in FIG. 34D to achieve more level of precision of specimen 3203 dispensing amount control, which not only utilizes the number of Unit Dispense pulses as shown in FIG. 35C and FIG. 35D to control the amount of specimen 3202 dispensing, the gate open width of a Unit Dispense may also vary, such that for the same number of Unit Dispensing pulses, the specimen amount dispensed may be different depending on the gate open width of each of the Unit Dispense pulse. For example, to achieve a 5.3 uL dispensing of the specimen 3203, five pulses of a first Unit Dispense having a first gate open width that enables 1 uL dispense for each Unit Dispense, and three pulses a second Unit Dispense having a second gate open width that enables 0.1 uL dispense for each Unit Dispense, may be combined in various sequence to produce the 5.3 uL dispensed specimen 3202 volume.

Figure 3:
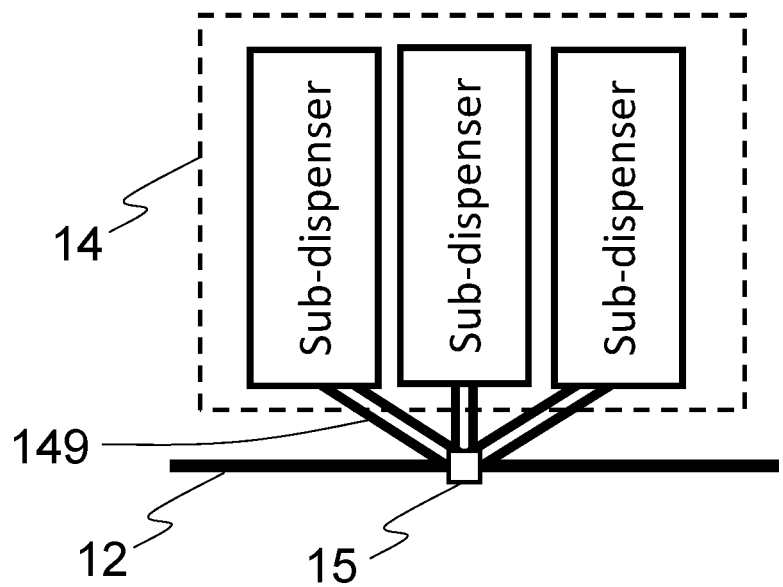
FIG. 3 is a schematic diagram illustrating a specimen dispenser having multiple sub-dispensers.

Now referring back to FIG. 3. FIG. 3 is a schematic diagram illustrating a specimen dispenser 14 which has multiple sub-dispensers. The sub-dispensers are physically separated dispensers by themselves. Each sub-dispenser has a conduit 149 that connects to the outlet 15 on the surface 12, where the conduits 149 converge at or in close proximity to the outlet 15. Before the convergence point, the conduits 149 are separated to avoid cross-contamination of the specimen from different sub-dispensers. The sub-dispensers are referred to as dispenser 14 as a whole entity. However, when dispenser 14 is replaced, all sub-dispensers may be replaced together, or replaced individually.

Figure 4:
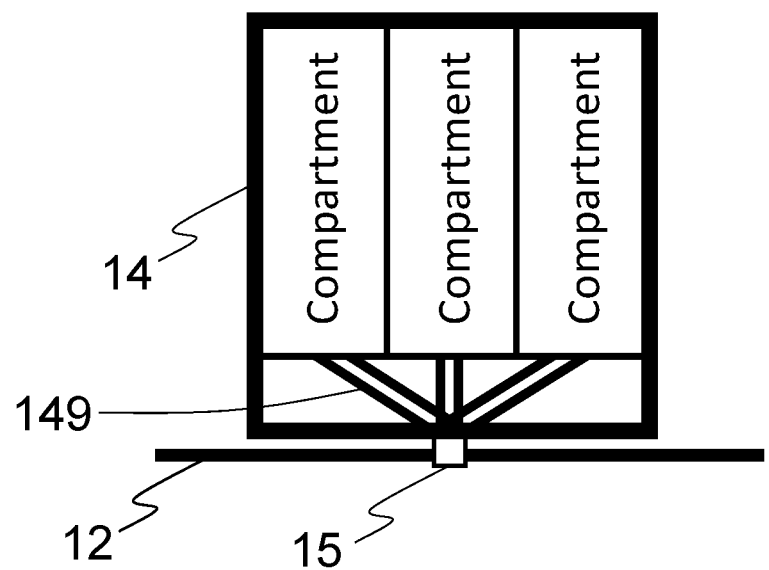
FIG. 4 is a schematic diagram illustrating a specimen dispenser having multiple compartments.

FIG. 4 is a schematic diagram illustrating a specimen dispenser 14 having multiple compartments. The dispenser 14 has a physical containment body where the compartments reside. During specimen dispensing, the compartments may function similar as independent dispensers by themselves. Each compartment has a conduit 149 that connects to the outlet 15 on the surface 12, where the part of or entire conduit 149 may exist within the dispenser body. The conduits 149 from different compartments converge at or in close proximity to the outlet 15. Before the convergence point, the conduits 149 are separated to avoid cross-contamination of the specimen from different sub-dispensers. When the dispenser 14 is replaced, specimens in all compartments are replaced together.

Figure 36:
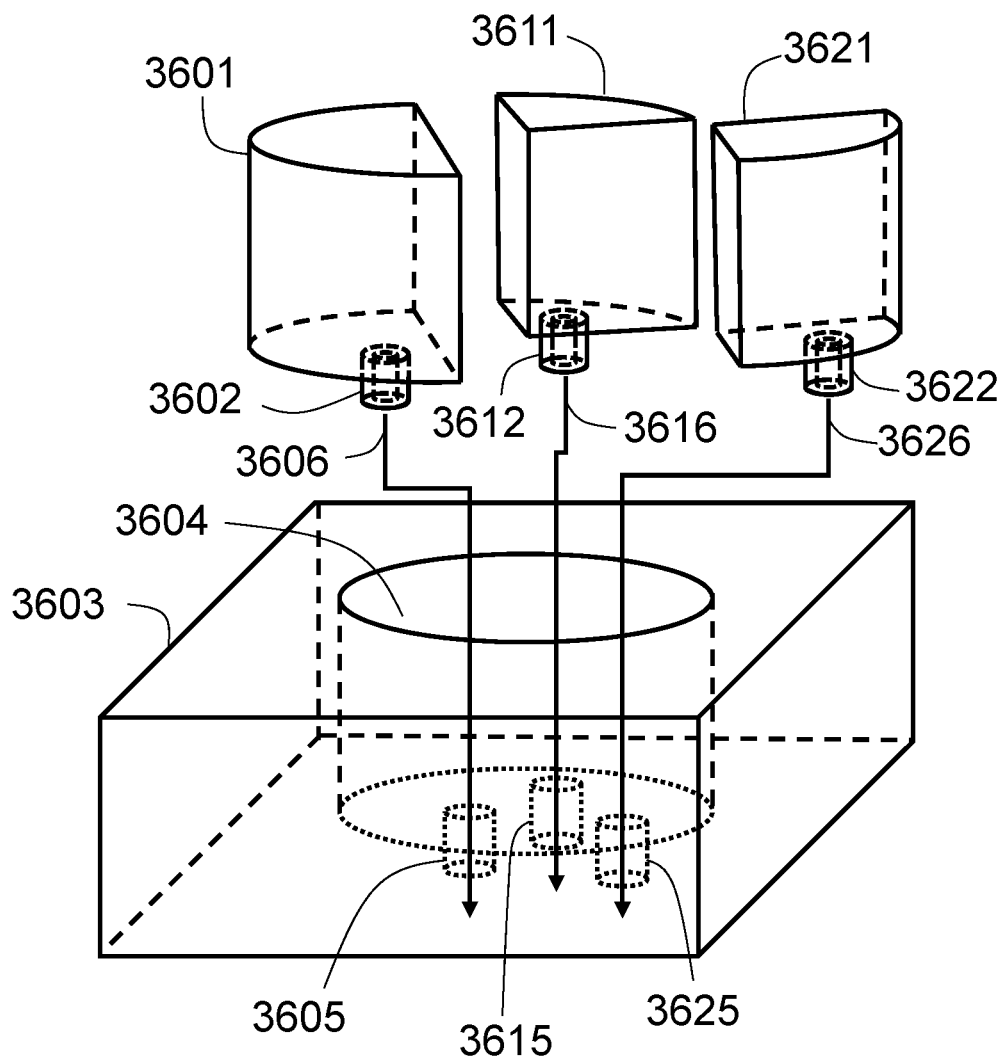
FIG. 36 illustrates removable specimen dispensers being inserted into a cartridge slot in a device body with each cartridge having a separate specimen outlet in the device body.

FIG. 36 illustrates removable specimen cartridges, also referred to as specimen dispensers or specimen sub-dispensers, 3601, 3611, and 3621, being inserted into a slot 3604 in a device body 3603 with each dispense having a separate specimen outlet 3605, 3615 and 3625, in the device body 3603, whereas the device body 3603 as in FIG. 36 only shows partial body of a specimen dispensing device where a specimen dispenser is contained. FIG. 36 is substantially similar as FIG. 29 with the exception of having multiple dispensers 3601, 3611, and 3621 that may combine into a single dispenser set. The device body 3603 of FIG. 36 is substantially similar as the device body 11 of device 10 as in FIG. 1 and FIG. 2. Specimen dispensers 3601, 3611, and 3621, and specimen outlets 3602, 3612 and 3622, at the bottom of each corresponding dispensers respectively, are substantially similar as specimen dispenser 14 and any of the specimen outlet 2252, 2352 and 2452 as in FIG. 22A through FIG. 24B. The nozzle portion of specimen outlet 3602, 3612 and 3622 may have sufficiently similar structures and functions as any of the outlet nozzles 2503, 2506, 2606, 2608, 2703, and 2803 as described in FIG. 25A through FIG. 28D. In FIG. 36, the dispensers 3601, 3611, 3621 are inserted into the device body 3603 and positioned into the slot 3604 as a dispenser set, with the specimen dispenser outlets 3602, 3612 and 3622 aligned to and inserted into the outlets 3605, 3615 and 3625 of the device body 3603. Directions of 3606, 3616, and 3626 show how specimen dispensers 3601, 3611 and 3621 are inserted into the slot 3604 of the device body 3603, with specimen dispenser outlets, 3602, 3612, 3622 inserted into the device outlets 3605, 3615 and 3625. Specimen is contained within each of the specimen dispensers 3601, 3611 and 3621, and dispensed through the specimen outlets 3602, 3612, 3622, and consequently the device specimen outlets 3605, 3615 and 3625 when specimen dispensers 3601, 3611 and 3621 are positioned within the slot 3604 of device body 3603. Dispensing of specimen from dispenser 3601, 3611 and 3621 may be through any methods as described in FIG. 22A through FIG. 24B.

Figure 37:
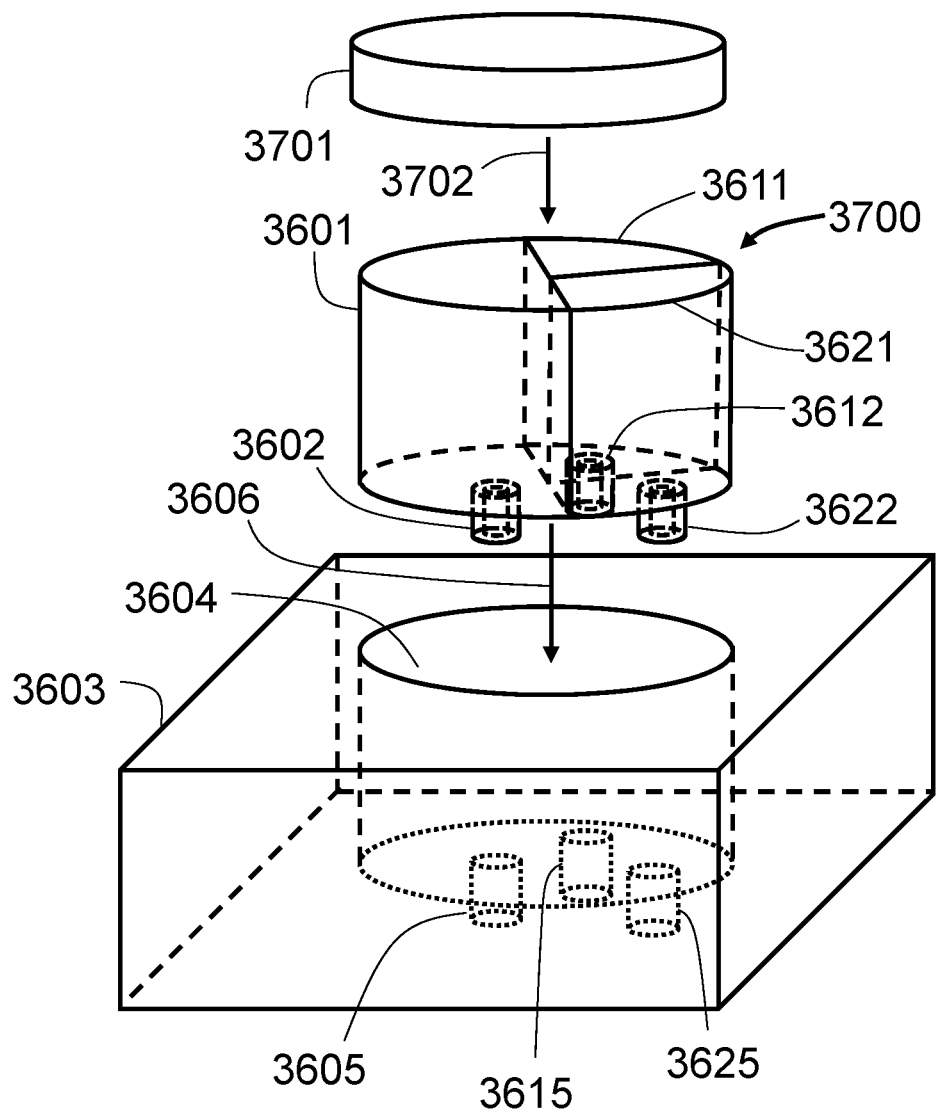
FIG. 37 illustrates specimen cartridges of FIG. 36 being combined into a set and inserted into a cartridge slot in a device body.

FIG. 37 illustrates the specimen dispensers 3601, 3611 and 3621 of FIG. 36 being combined into a single dispenser set 3700 and inserted into the slot 3604 of device body 3603, whereas the device body 3603 as in FIG. 37 only shows partial body of a specimen dispensing device where a specimen dispenser is contained. Dispensers 3601, 3611 and 3621, dispenser outlet 3602, 3612, and 3622, device body 3603, slot 3604 and device outlets 3605, 36015, 3625, are identical to the corresponding entities having same labeled numbers in FIG. 36. FIG. 37 illustrates that the specimen dispensers 3601, 3611 and 3621 are combined into a single dispenser set 3700, whereas the dispensers 3601, 3611 and 3621 may have features including any of: matching external physical shapes, external mechanical hooking points that attach one dispenser to another, or magnetic hooking points that are made of permanent magnets or magnetic materials that attract one dispenser to another, which may enable the dispensers to be assembled or grouped into the dispenser set 3700 easily. FIG. 37 shows an example of the dispensers 3601, 3611, 3621 are grouped into a cylinder shape dispenser set 3700, and dispenser set 3700 is inserted into the slot 3604 of the device body 3603 with each of the dispenser outlets 3602, 3612, 3622 being inserted into the device outlets 3605, 3615 and 3625. After the dispenser set 3700 is inserted into the slot 3604 of device body 3603, each dispenser 3601, 3611, or 3621 may be driven individually by internal or external driving mechanisms or methods, for example any of the methods as described in FIG. 22A through FIG. 24B, and in FIG. 31A through FIG. 35D, to dispense specimen individually through the device outlets 3605, 3615, 3625, and dispenser outlets 3602, 3612 or 3622 may have any of the nozzles as described in FIG. 25A through FIG. 28D. Alternatively, after the dispenser set 3700 is inserted into the slot 3604 of device body 3603, as illustrated in FIG. 37, a single driving mechanism 3701, may be applied, as direction 3702 shows, to all the dispensers 3601, 3611, and 3621 at the same time, and driving mechanism 3701 may be used to drive all dispensers 3601, 3611, and 3621 simultaneously by methods that may be of the methods as described in FIG. 22A through FIG. 24B, and in FIG. 31A through FIG. 35D, to dispense specimen simultaneously through the device outlets 3605, 3615, 3625. For example, the driving mechanism 3701 may be a push button that user may manually as shown in FIG. 37, or through an electronic driving mechanism, dispense specimen from all the three dispensers 3601, 3611, and 3621 simultaneously, for example by dispensing mechanisms in FIG. 22A through FIG. 24B. When dispensers 3601, 3611, and 3621 are dispensing specimen simultaneously, flow gates at the nozzle of the dispenser outlets 3602, 3612 and 3622, similar to the flow gates of 2221, 2321, 2421, from FIG. 22A through FIG. 24B, may be used to control the flow rate of specimen from different dispensers 3601, 3611, and 3621 to be different.

It needs to be noted that the device outlets 3605, 3615, 3625 are shown in FIG. 36 and FIG. 37, and in other figures of this invention, for description purpose only, whereas in other embodiments device outlets 3605, 3615, 3625 may take the form of simple clearances in the device body 3603 and the dispenser outlets 3602, 3612 or 3622 stay atop and in contact with the device outlets 3605, 3615, 3625 top rim to allow specimen to be dispensed through the device outlets 3605, 3615, 3625. Alternatively, device outlets 3605, 3615, 3625 may not exist and a large enough device clearance allowing the dispenser outlets 3602, 3612, and 3622 to be directly exposed to the air outside the device body 3603, and the specimen is dispensed from dispensers 3601, 3611 and 3621 to outside of the device body 3903 through dispenser outlets 3602, 3612, and 3622 directly and through the large enough device clearance.

Figure 38:
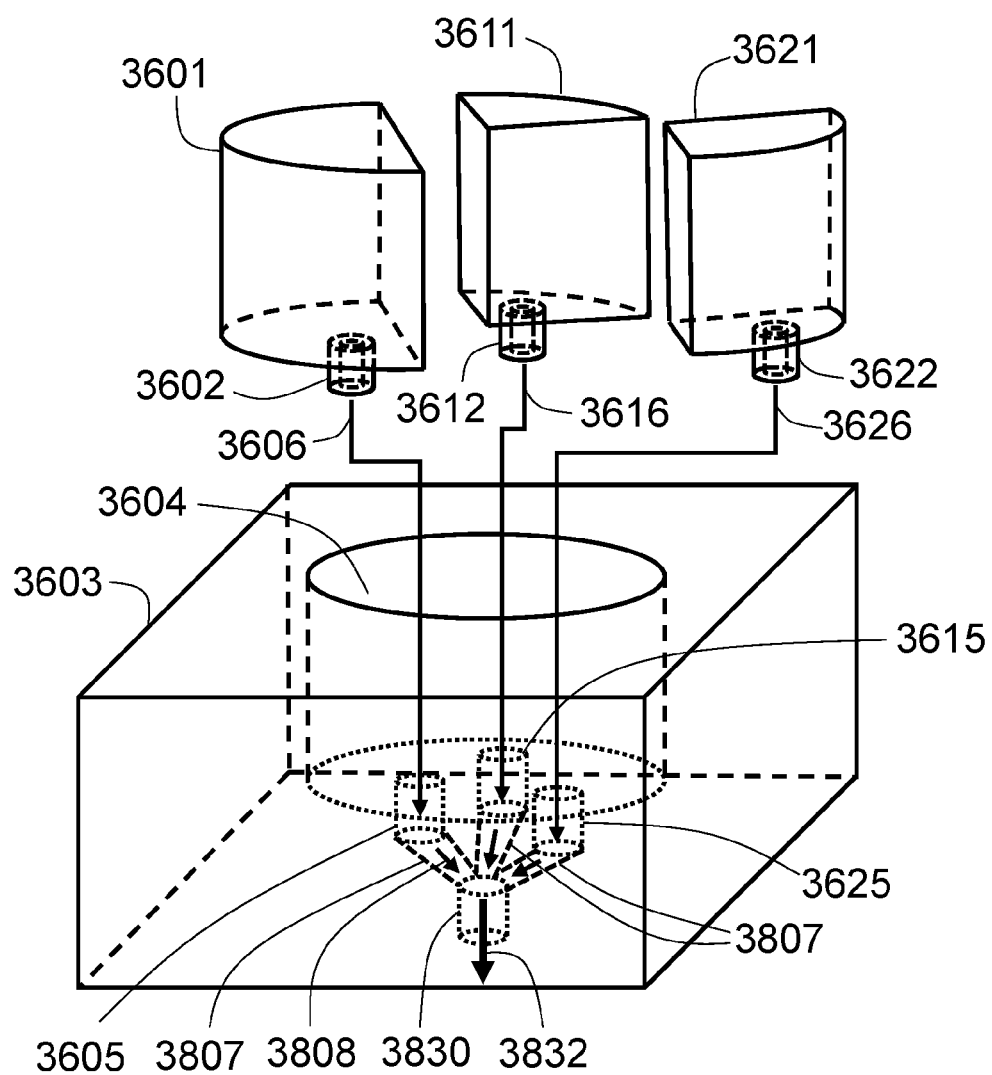
FIG. 38 illustrates removable specimen dispensers being inserted into a cartridge slot in a device body with a combined specimen outlet in the device body.

FIG. 38 illustrates removable specimen dispensers 3601, 3611, 3621, being inserted into a slot 3604 in a device body 3603 with a combined specimen outlet 3830 in the device body 3603, whereas the device body 3603 as in FIG. 38 only shows partial body of a specimen dispensing device wherein a specimen dispenser is contained. FIG. 38 is substantially similar to FIG. 36, with entities of FIG. 38 having same description and functions as the corresponding entities of FIG. 36 that are labeled with same numbers as the entities of FIG. 38. In addition to FIG. 36 device body 3603, the device outlets 3605, 3615 and 3625 as FIG. 38 have conduits 3807 that connect the device outlets 3605, 3615 and 3625 into a single combined specimen outlet 3830 in the device body 3603. When specimen is dispensed from the dispensers 3601, 3611, 3621 through dispenser outlets 3602, 3612, 3622 and device outlets 3605, 3615, 3625, the specimen flow through the conduits 3807 in directions 3808 and specimen from different dispensers combine at the combined outlet 3830 and flow out side of the device body 3603 in direction 3832.

In another embodiment, dispenser outlets 3602, 3612 and 3622 bottom surface may be in tight contact with the top surface of the dispenser holder outlets 3605, 3615 and 3625 after dispensers 3601, 3611 and 3621 are inserted into slot 3604, and specimen is dispensed from dispensers 3601, 3611 and 3621 through dispenser outlets 3602, 3612 and 3622 and then the device outlets 3605, 3615 and 3625 and then the combined outlet 3830.

Similarly as in FIG. 37, after dispensers 3601, 3611, and 3621 are inserted in the device body 3603, each dispenser 3601, 3611, or 3621 may dispense specimen individually. Alternatively, a driving mechanism similar to 3701 of FIG. 37 may be applied to one or more dispensers 3601, 3611, 3621 of FIG. 38. For example, user may manually, or through an electronic driving mechanism, dispense specimen from one or more of the dispensers 3601, 3611, and 3621 simultaneously, whereas dispensing mechanisms in FIG. 22A through FIG. 24B may be used to dispense specimen from dispensers 3601, 3611, 3621 simultaneously. When dispensers 3601, 3611, and 3621 are dispensing specimen simultaneously, flow gates at the nozzle of the dispenser outlets 3602, 3612 and 3622, similar to the flow gates of 2221, 2321, 2421, from FIG. 22A through FIG. 24B, may be used to control the flow rate of specimen from different dispensers 3601, 3611, and 3621 to be different.

Figure 39:
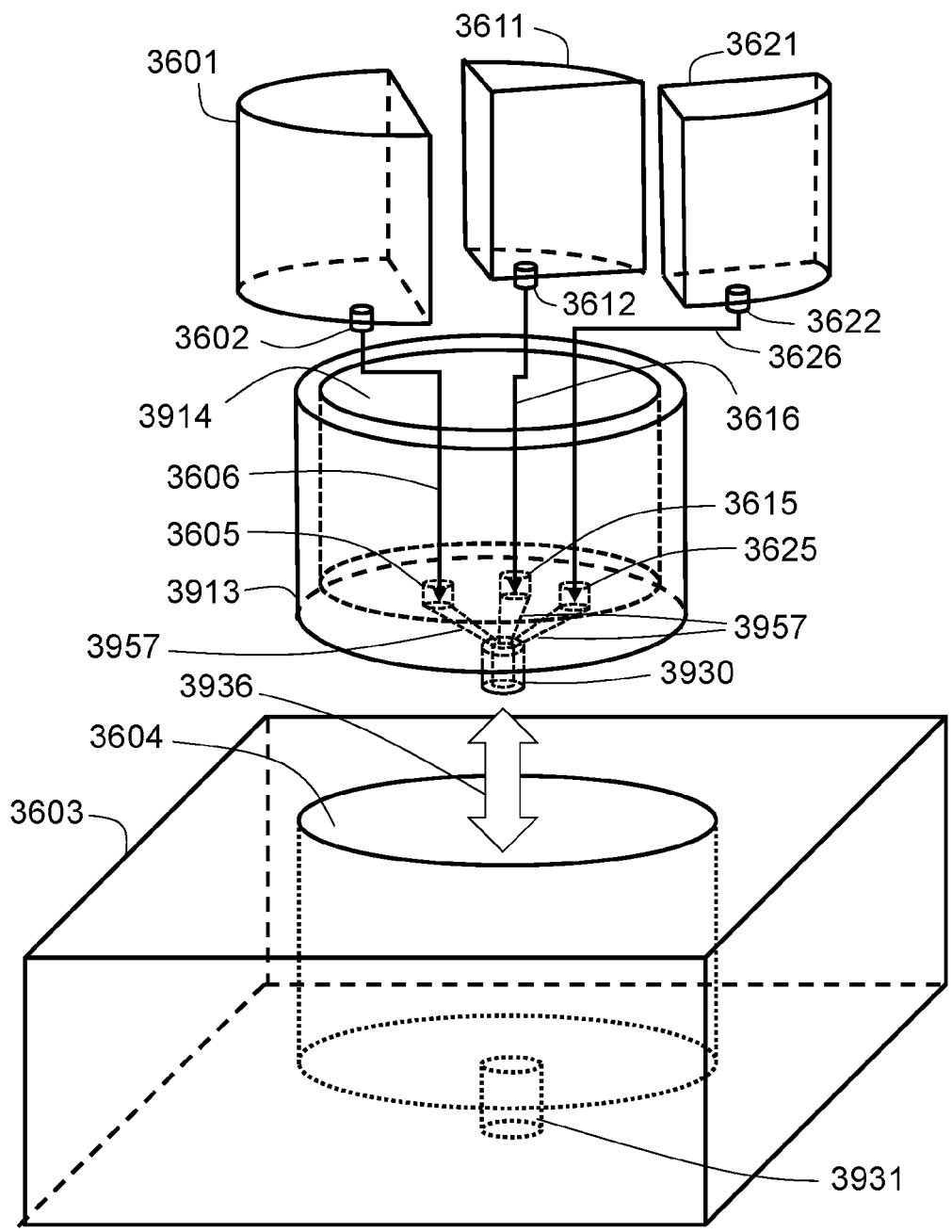
FIG. 39 illustrates removable specimen sub-dispensers being inserted into a dispenser holder having a combined specimen outlet in the dispenser holder, whereas the dispenser holder being inserted into or removed from a dispenser slot in a device body.

FIG. 39 illustrates removable specimen sub-dispensers 3601, 3611, 3621 being inserted into a dispenser holder 3613 having a combined specimen outlet 3630 in the dispenser holder 3613, whereas the dispenser holder 3613 being inserted into or removed from a dispenser slot 3604 in a device body 3603, whereas the device body 3603 as in FIG. 39 only shows partial body of a specimen dispensing device where a specimen dispenser is contained. FIG. 39 illustration is substantially similar as in FIG. 36 and FIG. 37, with the differences being: (1) the specimen dispensers, 3601, 3611, 3621, are first inserted into a slot 3914 within the dispenser holder 3913, with the dispenser outlets 3602, 3612 and 3622, being inserted into the dispenser holder outlets 3605, 3615 and 3625 along directions of 3606, 3616 and 3626; (2) each of dispenser holder outlets 3605, 3615 and 3625 is connected to a combined outlet 3930 of the dispenser holder 3913 through a conduit 3957, with specimen from each of the dispensers, 3601, 3611, 3621 being dispensed through dispenser outlets 3602, 3612 and 3622, then through dispenser holder outlets 3605, 3615 and 3625, and then through the conduits 3957, and then mixed at and dispensed through the dispenser holder combined outlet 3930; (3) the dispenser holder with holding the specimen dispensers, 3601, 3611, 3621 is then inserted into, or removed from, the slot 3604 of the device body 3603 along direction 3936, with the combined outlet 3930 fitting inside device outlet 3931, whereas specimen dispensed from the combined outlet 3930 further passes the device outlet 3931 and outside the device body 3603. The dispenser holder 3913, holding the specimen dispensers 3601, 3611, and 3621 in slot 3914, functionally forms a single dispenser set of the dispensers, 3601, 3611, 3621.

In another embodiment, dispenser outlets 3602, 3612 and 3622 bottom surface may be in tight contact with the top surface of the dispenser holder outlets 3605, 3615 and 3625 after dispensers 3601, 3611 and 3621 are inserted into slot 3914, and specimen is dispensed from dispensers 3601, 3611 and 3621 through dispenser outlets 3602, 3612 and 3622 and then the dispenser holder outlets 3605, 3615 and 3625 and then the combined outlet 3930. In yet another embodiment, dispenser holder combined outlet 3930 bottom surface may be in tight contact with the top surface of the device outlet 3931 after dispenser holder 3913 is inserted into slot 3604, and specimen is dispensed from dispensers 3601, 3611 and 3621 through dispenser holder combined outlet 3930, and then the device outlet 3931.

Similarly as in FIG. 37, after dispensers 3601, 3611, and 3621 are inserted in the dispenser holder 3913, and specimen holder 3913 inserted in the device body 3603, each dispenser 3601, 3611, or 3621 may dispense specimen individually. Alternatively, a driving mechanism similar to 3701 of FIG. 37 may be applied to one or more dispensers 3601, 3611, 3621 of FIG. 39. For example, user may manually, or through an electronic driving mechanism, dispense specimen from one or more of the dispensers 3601, 3611, and 3621 simultaneously, whereas dispensing mechanisms in FIG. 22A through FIG. 24B may be used to dispense specimen from dispensers 3601, 3611, 3621 simultaneously. When dispensers 3601, 3611, and 3621 are dispensing specimen simultaneously, flow gates at the nozzle of the dispenser outlets 3602, 3612 and 3622, similar to the flow gates of 2221, 2321, 2421, from FIG. 22A through FIG. 24B, may be used to control the flow rate of specimen from different dispensers 3601, 3611, and 3621 to be different.

Figure 40:
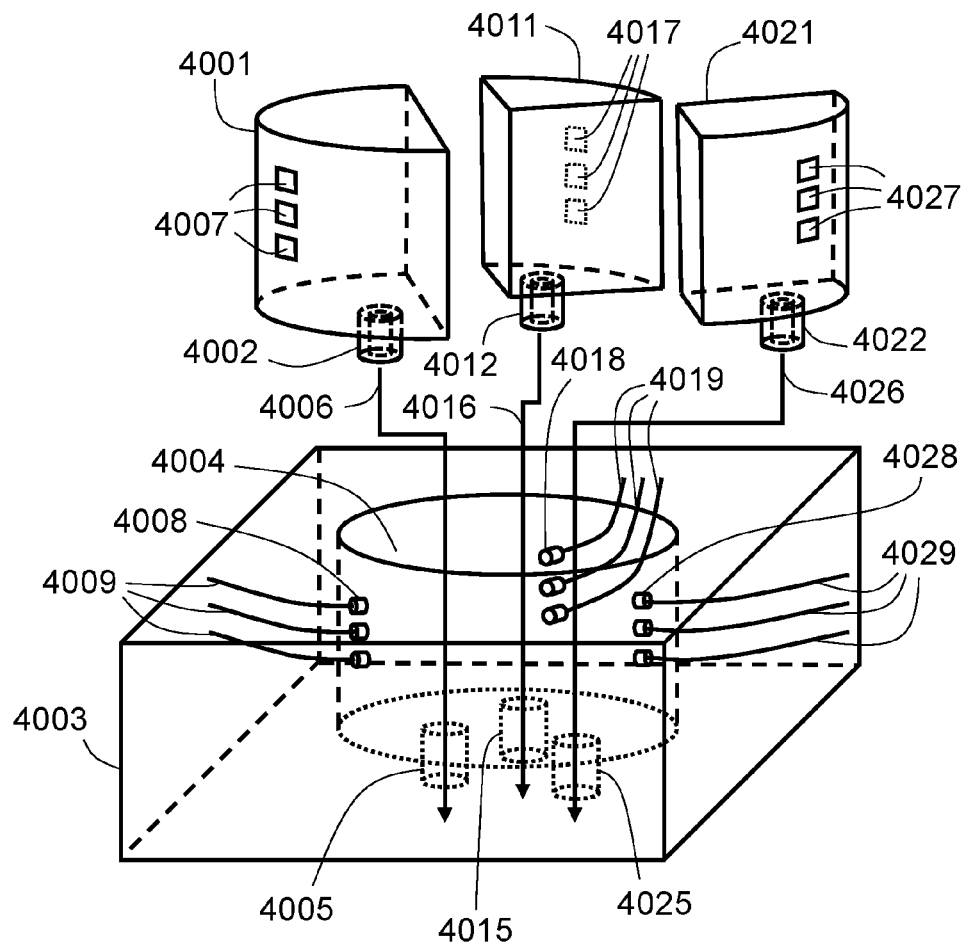
FIG. 40 illustrates removable specimen dispensers each having surface electrodes being inserted into a dispenser slot having electrical contacts, and with each dispenser having a separate specimen outlet, in a device body.

FIG. 40 illustrates removable specimen dispensers, 4001, 4011, 4021, each respectively having surface electrodes 4007, 4017, 4027, being inserted into a slot 4004 in a device body 4003, whereas the slot 4004 has electrical contacts 4008, 4018, and 4028 embedded in the inside wall of the slot 4004. Each of dispensers 4001, 4011 and 4021 has a separate specimen outlet 4002, 4012 and 4022. FIG. 40 is substantially similar to FIG. 30 with the exception of having multiple dispensers 4001, 4011, and 4021 that may combine into a single dispenser set. The device body 4003 as in FIG. 40 only shows partial body of a specimen dispensing device where a specimen dispenser is contained. The device body 4003 of FIG. 40 is substantially similar as the device body 11 of device 10 as in FIG. 1 and FIG. 2. Specimen dispensers 4001, 4011, and 4021 may be substantially similar to any of the specimen dispensers as described in FIG. 31A through FIG. 35D. The nozzle portion of specimen outlets 4002, 4012 and 4022 may have sufficiently similar structures and functions as any of the outlet nozzles 2503, 2506, 2606, 2608, 2703, and 2803 as described in FIG. 25A through FIG. 28D. In FIG. 40, the dispensers 4001, 4011, 4021 are inserted into the device body 4003 and positioned into the slot 4004 as a dispenser set, with the specimen dispenser outlets 4002, 4012 and 4022 aligned to and inserted into the outlets 4005, 4015 and 4025 of the device body 4003. Directions of 4006, 4016, and 4026 show how specimen dispensers 4001, 4011 and 4021 are inserted into the slot 4004 of the device body 4003, with specimen dispenser outlets, 4002, 4012, 4022 inserted into the device outlets 4005, 4015 and 4025. Specimen is contained within each of the specimen dispensers 4001, 4011 and 4021, and dispensed through the specimen outlets 4002, 4012, 4022, and final through the device specimen outlets 4005, 4015 and 4025 when specimen dispensers 4001, 4011 and 4021 are positioned within the slot 4004 of device body 4003. Dispensing of specimen from dispenser 4001, 4011 and 4021 may be through any methods as described in FIG. 31A through FIG. 35D.

The surface electrical pads 4007, 4017, 4027, on the external walls of the dispensers 4001, 4011, 4021 respectively make contact with the electrical contacts 4008, 4018, 4128 embedded in the inside wall of the slot 4004 when the dispensers 4001, 4011, 4021 are inserted into the slot 4004. The electrical connections 4009, 4019, 4029, which are respectively in contact with the electrical contacts 4008, 4018, 4128, may connect the electrical contacts 4008, 4018, 4128, and ultimately the electrical pads 4007, 4017 and 4027, to other electronic components within the device body 4003. The electrical contacts 4008, 4018, 4128 and electrical connections 4009, 4019, 4029 are substantially similar as the contacts 3008 and connections 3009 of FIG. 30, as well as electrical connection 140 of FIG. 14 and FIG. 15. The surface electrical pads 4007, 4017, 4027, are also substantially similar as electrical contact pads 3007 of FIG. 30 as well as contact pads 141 of FIG. 14 and FIG. 15. The electrical connections 4009, 4019, 4029, may ultimately connect to other electronics that is substantially similar as the control unit 17 of FIG. 14 and FIG. 15. The surface pads 4007, 4017, 4027, may also connect to other electronic components embedded in the dispensers 4001, 4011, 4021, as described in FIG. 31A through FIG. 35D. In FIG. 40, after the electrical contacts 4008, 4018, 4128, make physical contact with the electrical pads 4007, 4017, 4027, electrical signals can be sent to, or retrieved from, the embedded electronic components of the dispensers 4001, 4011, 4021, through the connections 4009, 4019, 4029, by electronics, for example control unit 17 as in FIG. 14 and FIG. 15, contained in the device body 4003.

Similar as in FIG. 36, even though FIG. 40 shows dispenser outlets 4002, 4012 and 4022 are inserted into the device outlets 4005, 4015 and 4025, another embodiment may provide dispenser outlets 4002, 4012 and 4022 bottom surface being in tight contact with the top surface of the device outlets 4005, 4015 and 4025 after dispensers 4001, 4011 and 4021 are inserted into slot 4004, and specimen is dispensed from dispensers 4001, 4011 and 4021 through dispenser outlets 4002, 4012 and 4022 and then the device outlets 4005, 4015 and 4025.

FIG. 40 shows each dispenser of 4001, 4011, or 4021, dispenses through separate device outlet 4005, 4015 and 4025. Alternatively, another embodiment of the FIG. 40 may provide a device body 4003 that has a combined device outlet similar to 3830 of FIG. 38, while conduits similar to conduits 3807 of FIG. 38 connect the outlets 4005, 4015 and 4025, which are then substantially similar as outlets 3805, 3815 and 3825 of FIG. 38, to said combined outlet and specimen from each dispenser of 4001, 4011, or 4021 are mixed inside and dispensed through said combined outlet in the device body, which is substantially similar to the dispensing process of specimen through the outlets 3805, 3815, 3825 and combined outlet 3830 of FIG. 38.

Figure 41:
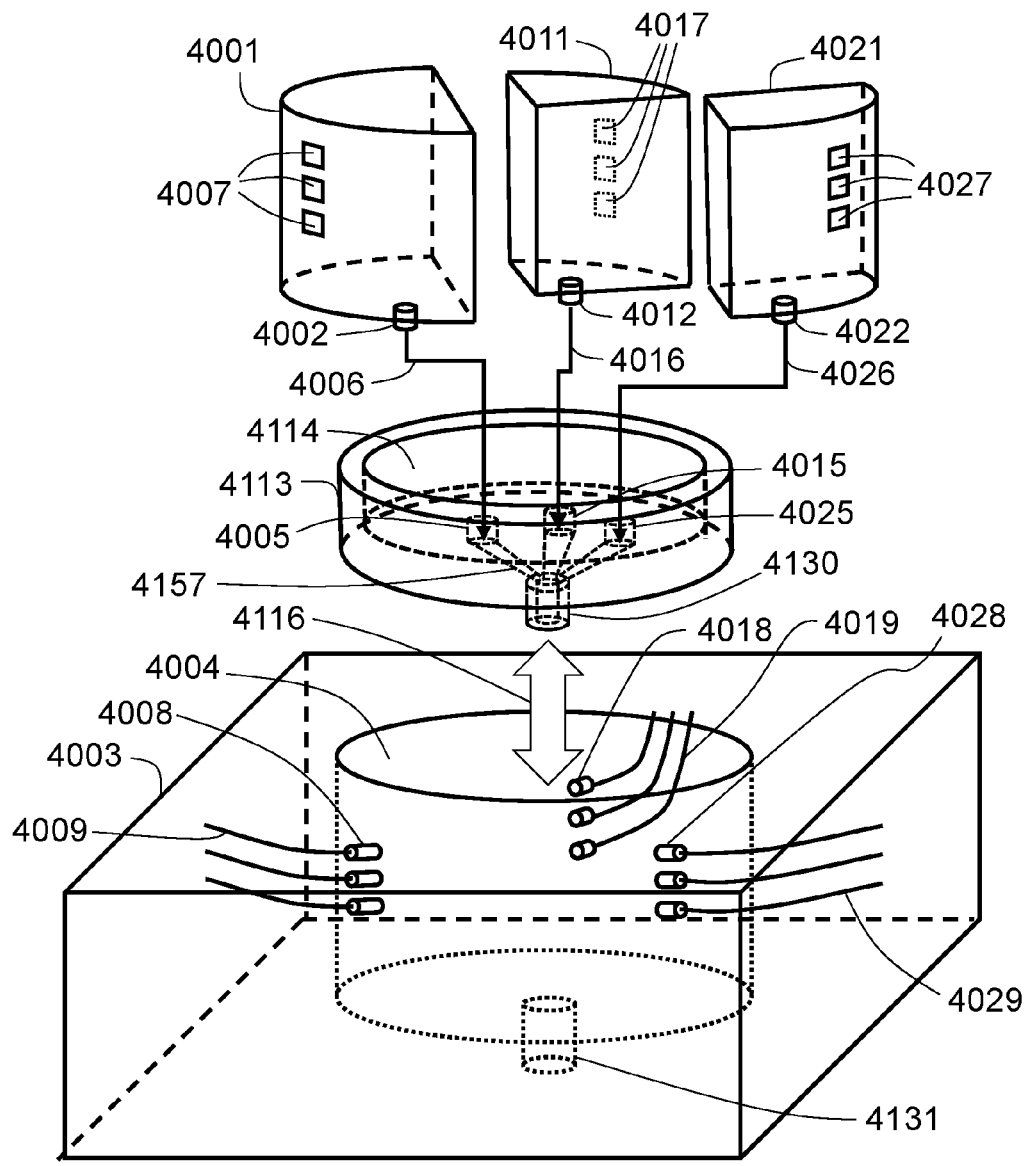
FIG. 41 illustrates removable specimen sub-dispensers each having surface electrodes being inserted into a dispenser holder having a combined specimen outlet, whereas the dispenser holder being inserted into or removed from a device dispenser slot having electrical contacts.

FIG. 41 illustrates removable specimen dispensers, 4001, 4011, 4021, each respectively having surface electrodes 4007, 4017, 4027, being inserted into a dispenser holder 4113 having a combined specimen outlet 4130, whereas the dispenser holder 4113 being inserted into a slot 4004, which has electrical contacts 4008, 4018, and 4028, in a device body 4003, whereas the device body 4003 as in FIG. 41 only shows partial body of a specimen dispensing device where a specimen dispenser is contained. FIG. 41 illustration is substantially similar as FIG. 40, with the variations being: (1) the specimen dispensers, 4001, 4011, 4021, are first inserted into a slot 4114 within the dispenser holder 4113, with the dispenser outlets 4002, 4012 and 4022 being inserted into the dispenser holder outlets 4005, 4015 and 4025 along directions of 4006, 4016 and 4026; (2) each of dispenser holder outlets 4005, 4015 and 4025 is connected to a combined outlet 4130 of the dispenser holder 4113 through a conduit 4157, with specimen from each of the dispensers, 4001, 4011, 4021 being dispensed through dispenser outlets 4002, 4012 and 4022, then through dispenser holder outlets 4005, 4015 and 4025, and then through the conduits 4157, and then mixed at and dispensed through the dispenser holder combined outlet 4130; (3) the dispenser holder 4113 with holding the specimen dispensers, 4001, 4011, 4021 is then inserted into, or removed from, the slot 4004 of the device body 4003 along direction 4116, with the combined outlet 4130 fitting inside device outlet 4131, whereas specimen dispensed from the combined outlet 4130 further passes the device outlet 4131 and outside the device body 4003. The dispenser holder 4113, holding the specimen dispensers 4001, 4011, and 4021 in slot 4114, functionally forms a single dispenser set of the dispensers, 4001, 4011, 4021.

After the dispenser holder 4113, holding the specimen dispensers 4001, 4011, and 4021 in slot 4114, being inserted into the slot 4004 of the device body 4003, same as in FIG. 40, the surface electrical pads 4007, 4017, 4027, on the external walls of the dispensers 4001, 4011, 4021 respectively make direct contact with the electrical contacts 4008, 4018, 4128 built-in the side wall of the slot 4004, and the electrical connections 4009, 4019, 4029, which are respectively in contact with the electrical contacts 4008, 4018, 4128, may connect the electrical contacts 4008, 4018, 4128, to other electronic components within the device body 4003.

In another embodiment, dispenser outlets 4002, 4012 and 4022 bottom surface may be in tight contact with the top surface of the dispenser holder outlets 4005, 4015 and 4025 after dispensers 4001, 4011 and 4021 are inserted into slot 4114, and specimen is dispensed from dispensers 4001, 4011 and 4021 through dispenser outlets 4002, 4012 and 4022 and then the dispenser holder outlets 4005, 4015 and 4025 and then the combined outlet 4130. In yet another embodiment, dispenser holder 4113 combined outlet 4130 bottom surface may be in tight contact with the top surface of the device outlet 4131 after dispenser holder 4113 is inserted into slot 4004, and specimen is dispensed from dispensers 4001, 4011 and 4021 through dispenser holder combined outlet 4130, and then the device outlet 4131.

Figure 42:
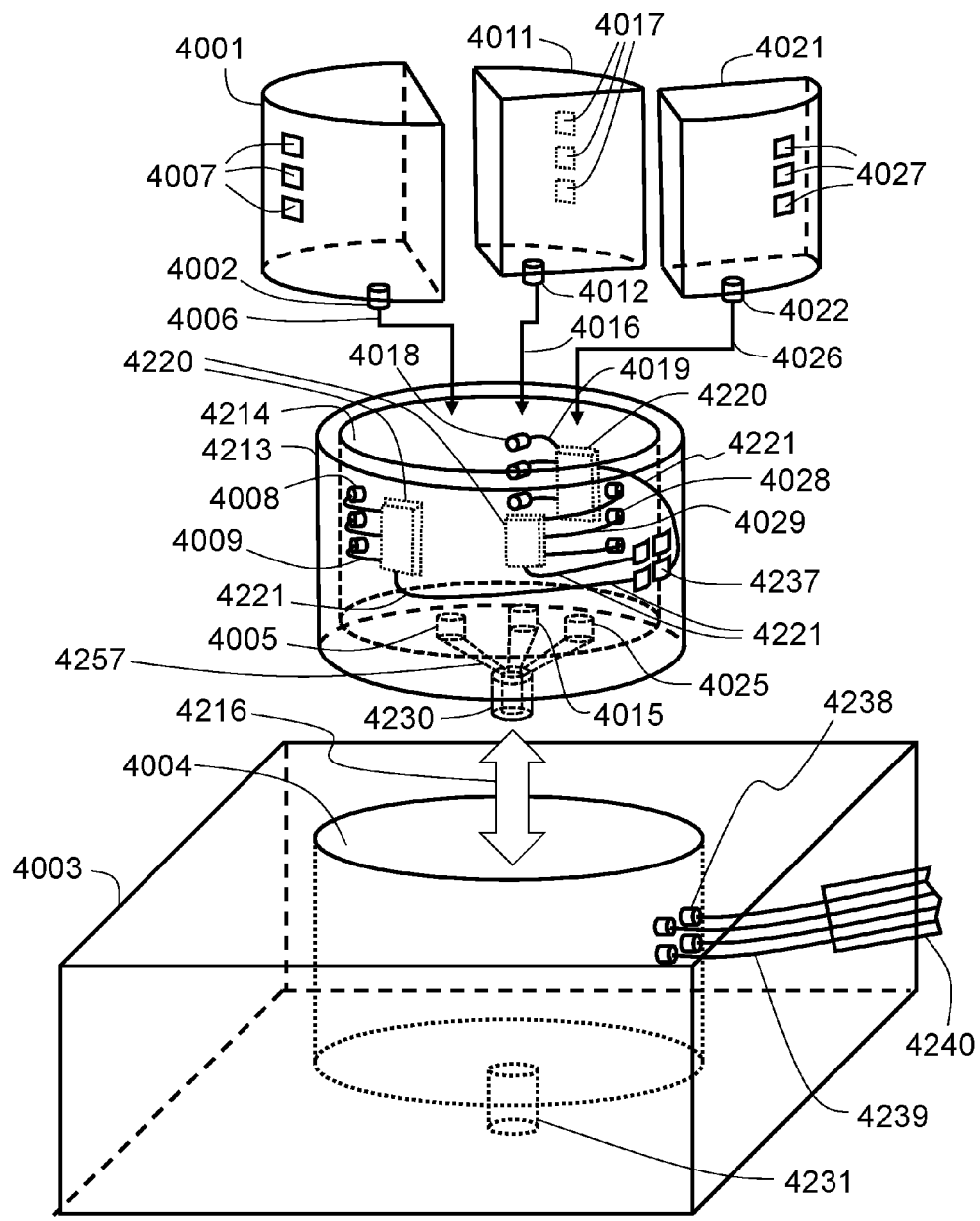
FIG. 42 illustrates removable specimen sub-dispensers each having surface electrodes being inserted into a dispenser holder having a combined specimen outlet, internal and external electrical contacts, and embedded electronics, whereas the dispenser holder being inserted into or removed from a device dispenser slot having electrical contacts.

FIG. 42 illustrates removable specimen dispensers, 4001, 4011, 4021, each respectively having surface electrodes 4007, 4017, 4027, being inserted into a dispenser holder 4213, which may have a combined specimen outlet 4230, internal electrical contacts 4008, 4018, 4028, and external electrical contacts 4237, and embedded electronics 4220, whereas the dispenser holder 4213 being inserted into or removed from a dispenser slot 4004 having electrical contacts 4238 in a device body 4003, whereas the device body 4003 as in FIG. 42 only shows partial body of a specimen dispensing device where a specimen dispenser is contained. FIG. 42 illustration is similar as FIG. 40, with the variations being: (1) the specimen dispensers, 4001, 4011, 4021, are first inserted into a slot 4214 within the dispenser holder 4213, with the dispenser outlets 4002, 4012 and 4022 being inserted into the dispenser holder outlets 4005, 4015 and 4025 along directions of 4006, 4016 and 4026; (2) each of dispenser holder outlets 4005, 4015 and 4025 is connected to a combined outlet 4230 of the dispenser holder 4213 through a conduit 4257, with specimen from each of the dispensers, 4001, 4011, 4021 being dispensed through dispenser outlets 4002, 4012 and 4022, then through dispenser holder outlets 4005, 4015 and 4025, and then through the conduits 4257, and then mixed at and dispensed through the dispenser holder combined outlet 4230; (3) the dispenser holder with holding the specimen dispensers, 4001, 4011, 4021 is then inserted into, or removed from, the slot 4004 of the device body 4003 along direction 4216, with the combined outlet 4230 fitting inside device outlet 4231, whereas specimen dispensed from the combined outlet 4230 further passes the device outlet 4231 and outside the device body. The dispenser holder 4213, holding the specimen dispensers 4001, 4011, and 4021 in slot 4214, functionally forms a single dispenser set of the dispensers, 4001, 4011, 4021; (4) after the dispensers, 4001, 4011, 4021 being inserted into the slot 4214 of dispenser holder 4213, the surface electrical pads 4007, 4017, 4027, on the external walls of the dispensers 4001, 4011, 4021 respectively make direct contact with the electrical contacts 4008, 4018, 4228 embedded in the inside wall of the slot 4214, and the electrical connections 4009, 4019, 4029, which are respectively in contact with the electrical contacts 4008, 4018, 4228, may connect the electrical contacts 4008, 4018, 4228, to other embedded electronic components 4220 within the dispenser holder 4214, whereas the embedded electronics components 4220 may provide the function of any of: (a) data communication through electrical connections 4221 and the surface contact pads 4237 with any electronics contained in the device body 4003; (b) identification and authentication of the dispensers, 4001, 4011, 4021 and specimen contained therein; (c) obtaining information regarding specimen contained in each of the dispensers, 4001, 4011, 4021 for any of: remaining volume, specimen type, specimen physical or chemical properties such as viscosity, temperature, composition and pressure; (d) storing and providing information regarding specimen contained in each of the dispensers, 4001, 4011, 4021 for any of: physical or chemical properties such as viscosity, temperature, composition and pressure specimen, purpose of specimen for skin care treatment, method of dispensing or mixing specimen, method of using specimen for a specific skin condition; and (e) providing electric power to the dispensers, 4001, 4011, 4021, and driving of specimen dispensing from the dispensers, 4001, 4011, 4021; (5) surface electrical pad 4237 may exist on the external surface of the dispenser holder 4213, and electrical connections 4221 may connect the surface electrical pads 4237 with the embedded electrical components 4220, whereas the electrical pads 4237 and electrical connections 4221 may provide the function of any of: data communication to and from the electrical components 4220, providing electric power to the electrical components 4220, and electrical driving of specimen dispensing from dispensers 4001, 4011, 4021 through commanding the electrical components 4220; (6) after the dispenser holder 4213, holding the specimen dispensers 4001, 4011, and 4021 in slot 4214, being inserted into the slot 4004 of the device body 4003, the surface electrical pads 4237, on the external wall of the dispenser holder 4237 make direct contact with the electrical contacts 4238 embedded in the inside wall of the slot 4004, and the electrical connections 4239 which are in contact with the electrical contacts 4238, may connect the electrical contacts 4238, to other electronic components within the device body 4003.

The electrical contacts 4238 and electrical connections 4239 are substantially similar as the contacts 3008 and connections 3009 of FIG. 30, as well as electrical connection 140 of FIG. 14 and FIG. 15. The electrical connections 4239 may be contained in bundle 4240 in the form of electrical wires 4239 contained in a cable 4249, or as electrical paths 4239 contained in a flat flexible substrate 4240. The electrical connections 4239 may ultimately connect to other electronics that is substantially similar as the control unit 17 of FIG. 14 and FIG. 15. After the dispensers 4001, 4011, 4021 are inserted into the dispenser holder 4213 slot 4214, and the dispenser holder 4213 being inserted in the device body 4003 slot 4004, 4027, electrical signals may be sent to, or retrieved from, the embedded electronic components 4220, and consequently the embedded electronic components within the dispensers 4001, 4011, 4021, through the connections 4239, 4221 and 4009, 4019, 4029, by electronics, for example control unit 17 as in FIG. 14 and FIG. 15, contained in the device body 4003.

In another embodiment of FIG. 42, dispenser outlets 4002, 4012 and 4022 bottom surface may be in tight contact with the top surface of the dispenser holder outlets 4005, 4015 and 4025 after dispensers 4001, 4011 and 4021 are inserted into slot 4214, and specimen is dispensed from dispensers 4001, 4011 and 4021 through dispenser outlets 4002, 4012 and 4022 and then the dispenser holder outlets 4005, 4015 and 4025 and then the combined outlet 4230. In yet another embodiment, dispenser holder combined outlet 4230 bottom surface may be in tight contact with the top surface of the device outlet 4231 after dispenser holder 4213 is inserted into slot 4004, and specimen is dispensed from dispensers 4001, 4011 and 4021 through dispenser holder combined outlet 4230, and then the device outlet 4231.

Figure 43:
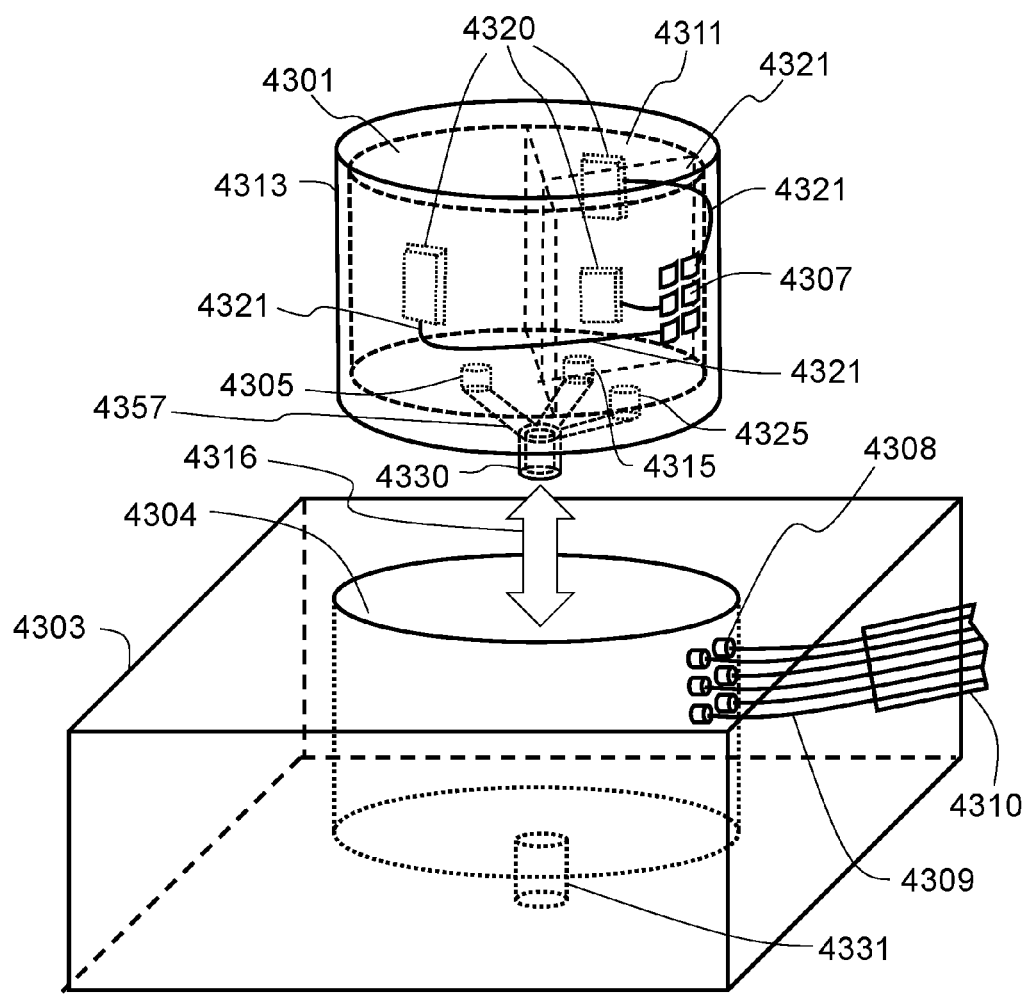
FIG. 43 illustrates removable specimen dispenser having sub-compartments and surface electrodes being inserted into or removed from a device body slot having electrical contacts.

FIG. 43 illustrates removable specimen dispenser 4313, which may have sub-compartments 4301, 4311, 4321 contained therein, and surface contact pads 4307, being inserted into or removed from a slot 4304 in a device body 4303, whereas the slot 4304 has electrical contacts 4308 embedded in the inside wall, and whereas the device body 4303 as in FIG. 43 only shows partial body of a specimen dispensing device where specimen dispenser is contained. Sub-compartments 4301, 4311, 4321 may be enclosed in the body of specimen dispenser 4313, and may be stationary and not removable from the specimen dispenser 4313. Each of the Sub-compartments 4301, 4311, 4321 may have an embedded electronic component 4320 with electrical connections 4321 connecting the electronic component s 4320 to the surface contact pads 4307, whereas the embedded electronic component 4320 may provide function of any of: (a) data communication through electrical connections 4321 and the surface contact pads 4307 with any electronics contained in the device body 4303; (b) identification and authentication of sub-compartments 4301, 4311, 4321 and specimen contained therein; (c) obtaining information regarding specimen contained in each of sub-compartments 4301, 4311, 4321 for any of: remaining volume, specimen type, specimen physical or chemical properties such as viscosity, temperature, composition and pressure; (d) storing and providing information regarding specimen contained in each of sub-compartments 4301, 4311, 4321 for any of: physical or chemical properties such as viscosity, temperature, composition and pressure specimen, purpose of specimen for skin care treatment, method of dispensing or mixing specimen, method of using specimen for a specific skin condition; and (e) providing electric power to sub-compartments 4301, 4311, 4321, and driving of specimen dispensing from sub-compartments 4301, 4311, 4321.

Each of the sub-compartments 4301, 4311, 4321 may have an outlet 4305, 4315, or 4325 respectively. Conduits 4357 may connect each of the outlets 4305, 4315, 4325 to the outlet 4330 of dispenser 4313, whereas specimen is dispensed from inside the sub-compartments 4301, 4311, 4321 through the outlets 4305, 4315, 4325, and then through the conduits 4357, and then mixed at and dispensed through the dispenser outlet 4330 outside the body of dispenser 4313. FIG. 43 is similar as FIG. 30 with the exception of having multiple sub-compartments 4301, 4311, and 4321 that are enclosed in the dispenser 4313. The device body 4303 of FIG. 43 is substantially similar as the device body 11 of device 10 as in FIG. 1 and FIG. 2, or device body 3003 of FIG. 30. Dispensing of specimen from sub-compartments 4301, 4311 and 4321 may be through any methods, and substantially similar specimen driving mechanism as described in any of the specimen dispensers in FIG. 31A through FIG. 35D. The nozzle portion of specimen outlet 4330 of dispenser 4313 may have sufficiently similar structures and functions as any of the outlet nozzles 2503, 2506, 2606, 2608, 2703, and 2803 as described in FIG. 25A through FIG. 28D. In FIG. 43, the dispenser 4313 is inserted into the device body 4303 and positioned into the slot 4304, with the specimen dispenser outlet 4330 aligned to and inserted into the outlets 4331 of the device body 4303. Direction of 4316 shows how specimen dispenser 4313 is inserted into the slot 4304 of the device body 4303, with specimen dispenser outlets 4330 inserted into the device outlets 4331. Specimen contained within each of the specimen sub-compartments 4301, 4311 and 4321, is dispensed through the specimen outlets 4305, 4315, 4325, then through the conduits 4357, then through the dispenser outlet 4330, and then the device specimen outlet 4331.

The surface electrical pads 4307 on the external walls of the dispenser 4313 may make contact with the electrical contacts 4308 built-in the inside wall of the slot 4304 when the dispenser 4313 is inserted into the slot 4304. The electrical connections 4309 in contact with the electrical contacts 4308 may connect the electrical contacts 4308 to other electronic components within the device body 4303. The electrical contacts 4308 and electrical connections 4309 are substantially similar as the contacts 3008 and connections 3009 of FIG. 30, as well as electrical connection 143 of FIG. 14 and FIG. 15. The electrical connections 4309 may be contained in bundle 4310 in the form of electrical wires 4309 contained in a cable 4310, or as electrical paths 4309 contained in a flat flexible substrate 4310. The surface electrical pads 4307 are also substantially similar as electrical contact pads 3007 of FIG. 30 as well as contact pads 141 of FIG. 14 and FIG. 15. The electrical connections 4309 may ultimately connect to other electronics in device body 4303 that is substantially similar as the control unit 17 of FIG. 14 and FIG. 15. In FIG. 43, after the electrical contacts 4308 make physical contact with the electrical pads 4307, electrical signals can be sent to, or retrieved from, the embedded electronic components 4320 of the dispenser 4313 through the connections 4321 and 4309, by electronics, for example control unit 17 as in FIG. 14 and FIG. 15, contained in the device body 4303.

Similar as in FIG. 36, even though FIG. 43 shows dispenser outlet 4330 are inserted into the device outlet 4331, another embodiment may provide dispenser outlet 4330 bottom surface being in tight contact with the top surface of the device outlet 4331 after dispenser 4313 is inserted into slot 4304, and specimen is dispensed from dispensers 4313 through dispenser outlet 4330 and then the device outlets 4331.

Figure 44:
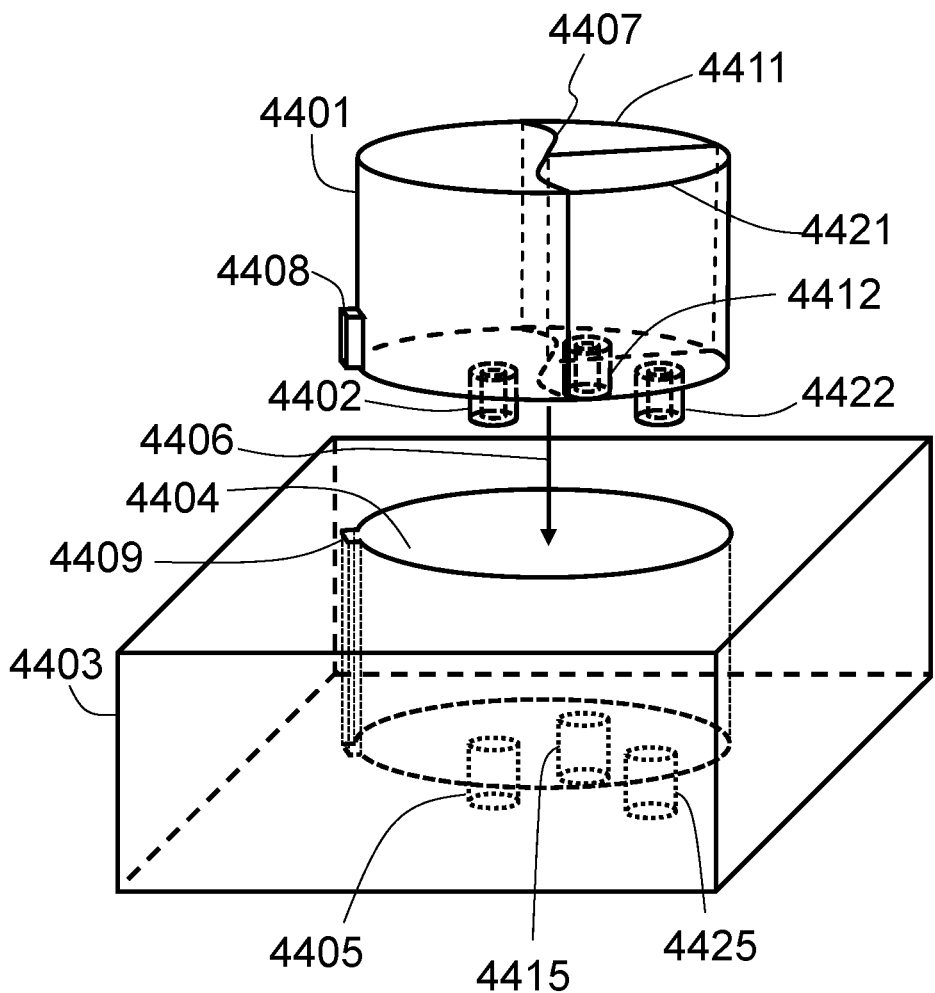
FIG. 44 illustrates specimen dispensers being combined into a set and inserted into a dispenser slot in a device body, whereas physical features are used to assist dispenser positioning and alignment.

FIG. 44 illustrates specimen dispensers 4401, 4411, and 4421 being combined into a set and inserted into a dispenser slot 4404 in a device body 4403, whereas physical features 4407, 4408 and 4409 are used to assist dispenser positioning and alignment. FIG. 44 is sufficiently similar as FIG. 37, with dispensers 4401, 4411, 4421, dispenser outlets 4402, 4412, 4422, slot 4404, device body 4403, and device outlets 4405, 4415, 4425 being sufficiently identical to the dispensers 3601, 3611, 3621, dispenser outlets 3602, 3612, 3622, slot 3604, device body 3603, and device outlets 3605, 3615, 3625 of FIG. 37. Dispensers 4401, 4411, 4421 are inserted in the slot 4404 of device body 4403 along 4406 direction, which is also sufficiently similar as dispensers 3601, 3611, 3621 being inserted in the slot 3604 of device body 3603 along 3606 direction as in FIG. 37.

Dispensers 4401, 4411, 4421 of FIG. 44 may have physical features 4407, which may be the curvatures of the physical shapes of the dispensers 4401, 4411, 4421 as shown in FIG. 44, that enable the dispensers 4401, 4411, 4421 to be assembled into a dispenser set in a specific configuration or orientation, whereas changing of the relative orientations of the dispensers 4401, 4411, 4421 from this specific configuration or orientation may render the dispenser set not cylindrical or not physically possible to be inserted into the slot 4404 of device body 4403. Dispensers 4401, 4411, 4421 of FIG. 44 may have also physical features 4408, which may take the form of an alignment ridge 4408 on the dispenser 4401 as shown in FIG. 44, that is preferred to be matching to another physical feature 4409 in the slot 4404 inside wall, for example the alignment slot 4409 in the slot 4404 inside wall. The matching physical features 4408 and 4409 may help align the dispensers 4401, 4411, 4421 during their insertion into the slot 4404, such that the dispenser outlets 4402, 4412, 4422 may be aligned precisely to the locations of the device outlets 4405, 4415, 4425 during the insertion of the dispensers 4401, 4411, 4421, whereas a user inserting the dispensers 4401, 4411, 4421 does not need extra effort to align the dispenser outlets 4402, 4412, 4422 to the device outlets 4405, 4415, 4425. For example, as FIG. 44 shows, dispensers 4401, 4411, 4421 are first assembled into a dispenser set according to the physical feature 4407, and then the dispenser set is inserted into the slot 4404 with the alignment ridge 4408 on dispenser 4401 aligned to and sliding into the alignment slot 4409. With the dispensers 4401, 4411, 4421 in the form of the dispenser set sliding into the slot 4404, alignment ridge 4408 sliding within alignment slot 4409 enables the dispenser 4401 having the outlet 4402 automatically aligned to, and inserted into, the device outlet 4405. Due the dispensers 4411, 4421 are specifically oriented in the configuration of FIG. 44 relative to the dispenser 4401 by curvature 4407, and confined by the slot 4404 inside wall, the dispensers 4411, 4421 outlets 4412 and 4422 are also automatically aligned to, and inserted into, the device outlets 4415 and 4425. The physical features 4408 that enable alignment of dispenser set alignment to the slot 4404 may exist on one or more dispensers of a dispenser set, with matching physical features 4409 existing at various locations of the inside wall of slot 4404. The physical features similar to 4407, 4408, 4409 and together with the confinement of the internal wall of slot 4404 may enable each of the dispensers 4401, 4411, 4421 be inserted into the slot 4404 individually and aligned into specific orientations automatically.

Physical features 4407, 4408, 4409 of FIG. 44 mainly serve to achieve fast and easy handling of dispensers for a user during replacement and insertion of the dispensers, with eliminating the possibility of putting wrong dispenser at a wrong location, or any possibility of confusion of whether a dispenser should be used in a cartridge set. Physical features 4407, 4408, 4409 may include any type of physical shapes, physical protrusions, physical indentations, physical grooves. For different dispenser sets that have different size dispensers, or different number of dispensers, within each different set, physical features 4407, 4408, 4409 may take different forms, shapes, locations, and sizes. Additionally, the physical features 4407, 4408, 4409 may also be, or combined with any of: colors of dispensers, or optical patterns on the dispensers' external surfaces, that may match to certain color or optical patterns in or around the slot 4404 to enable easy matching. For example, the dispensers 4401, 4411, 4421 may be in color sequence of white, gray and green, whereas colored patterns of white, gray and green sections around the top opening of the slot 4404 may be used to indicate the corresponding designated locations of the dispensers 4401 (white), 4411 (gray), 4421 (green), and user may use such color matching to insert the dispensers 4401, 4411, 4421 into slot 4404 at corresponding color matching locations, which may also have the physical features 4407, 4408 and 4409 simultaneously for fast insertion and dispenser set assembly.

Evan through FIG. 44 uses FIG. 37 type of configuration for description purpose, the method as described in FIG. 44 may be readily applied to the dispensers 3601, 3611, 3621 with device body 3603 or dispenser holder 3913 as in FIG. 36 through FIG. 39. The method as described in FIG. 44 may also be readily applied to the dispensers 4001, 4011, 4021, 4313 with device body 4003, 4303, or dispenser holders 4113, 4213 as in FIG. 40 through FIG. 43, wherein in addition to alignment of dispenser outlets to device outlets, fast and reliable alignment of dispenser surface electrical pads to electrical contacts in the slot wall of the device body may also be achieved by a user with using the physical features 4407, 4408, 4409, and possibly together with color and optical patterns, as described in FIG. 44.

Figure 45:
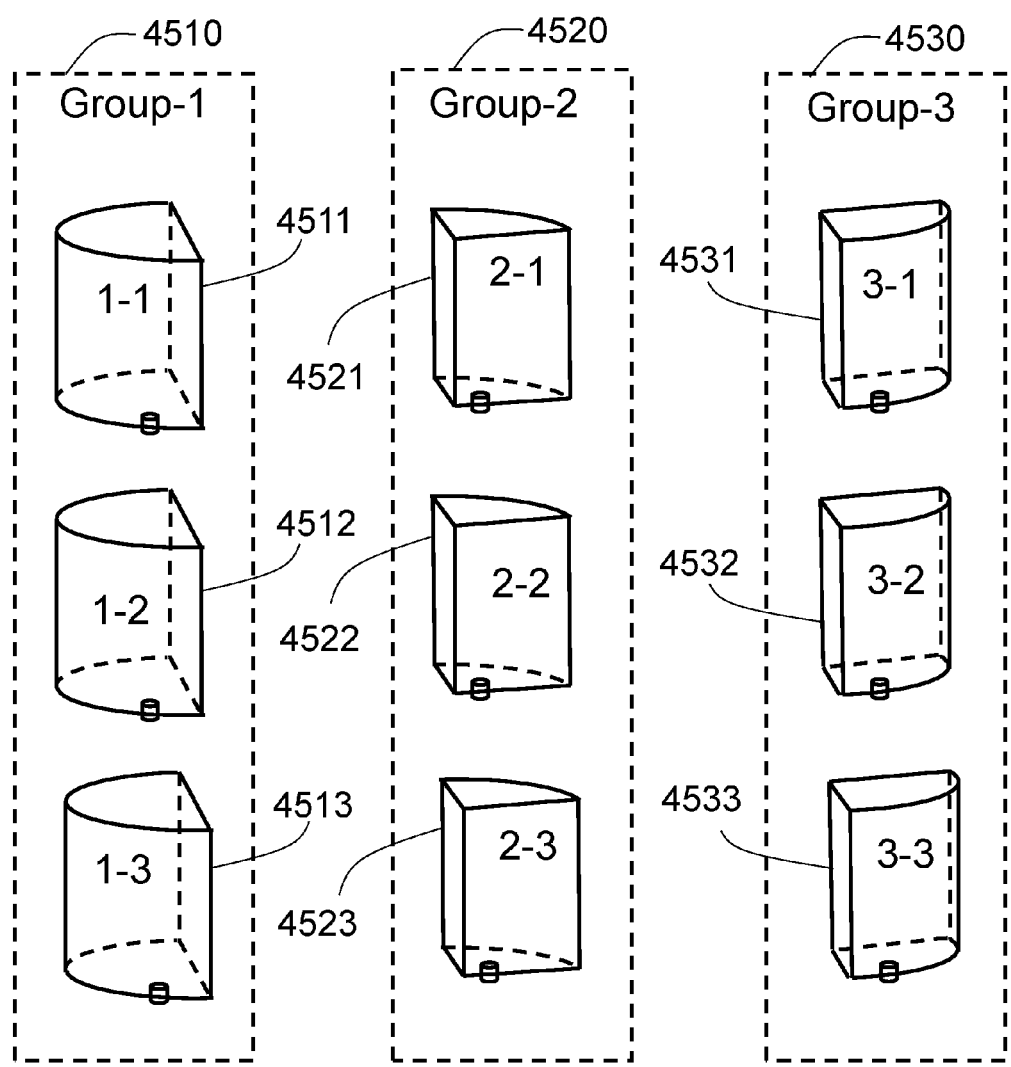
FIG. 45 illustrates different dispensers from various function groups may be used to combine into different dispenser sets to produce different dispensed specimen composition.

FIG. 45 illustrates various function groups containing different dispensers which may be selected and combined into different dispenser sets to produce different dispensed specimen having different skin care function with different specimen composition after mixture. For description purpose, three function groups, group-1 4510, group-2 4520 and group-3 4530, with each group containing three types of dispensers, are used for illustration in FIG. 45. In practice, number of groups and type of dispensers within each group may vary. With any one dispenser selected from each of the three different groups, 4510, 4520, 4530, a total of three dispensers may form a single dispenser set. In one embodiment, each of the function groups 4510, 4520, 4530 may contain different types of sub-compartments, whereas sub-compartments from different groups may form a single dispenser with a plurality of sub-compartments, for example sub-compartments 4301, 4302, and 4303 of FIG. 43 may each belong to a different function group of sub-compartments. However, in FIG. 45, groups 4510, 4520, 4530 will be referred to hereafter as groups of dispensers, or cartridges, for the purpose of explanation, but can be similarly described as sub-compartments as shown in FIG. 43. Dispensers as described in FIG. 45 may be applied to dispensers or sub-compartments of any other embodiments or figures of this invention.

Group-1 4510 as shown in FIG. 45 contains cartridges 4511, 4512, and 4513, and Group-2 4520 is shown to contain cartridges 4521, 4522, and 4523, and Group-3 4530 is shown to contain cartridges 4531, 4532, and 4533. Different groups of 4510, 4520 and 4530 may be created according to the skin care function of the cartridges contained in each group, with the cartridges from same group targeting same or similar skin conditions, or providing same or similar skin care functions. For example, group-1 4510 may be targeting "fine line" skin feature on a user's forehead. Group-2 4520 may be targeting "wrinkles" feature that is deeper than "fine lines", for example smile lines around the mouth. Group-3 4530 may be targeting "brown spots" feature that is of general facial area. Different cartridges in the same group, for example cartridges 4511, 4512, and 4513 in group-1 4510, may contain specimen that may be different in "specimen aspects" of: contained specimen volume; specimen dispensing flow rate or dispense speed; specimen composition; specimen skin care function strength; specimen quality or grade; specimen chemical or biological properties; specimen physical properties including, but not limited to, appearance, viscosity, color, texture, smell, contained particle size; specimen response to a skin treatment member physical actions, whereas the skin treatment member may be any of an ultrasound generation plate applying ultrasound vibrations to skin, an electrode providing electric voltage or current to skin, optic component emitting radiation to skin, mechanical vibrator providing local vibration to skin; specimen cost of ownership; specimen response to targeted skin surface condition, including skin properties of, but not limited to, dryness, oiliness, hydration, PH value, or acquired chemicals from environment.

One example of different combination of different cartridges from different groups for different user's unique skin care need is that the composition of different cartridges can be different. For first user, group-1 4510 cartridge 1-1 may have a composition that is suitable for first user's skin condition, which composition can either be matched as closest to first user's skin care need, or can be custom altered or tuned according to the skin condition of the first user, namely hard coding the first user's skin information as the customized composition of specimen within the cartridge 1-1. For second user, group-1 4510 cartridge 1-2 may either be matched as closest to second user's skin care need, or custom altered according to the skin condition of the second user, namely hard coding the second user's skin information as the customized composition of specimen within the cartridge 1-2. Thus, even though cartridges 1-1 and 1-2 are both for the same skin care purpose, for example "fine line" feature reduction, their actual compositions may be different. Similarly, cartridges from other groups may be closely matched to or altered according to different user's skin care need. Composition is used as an example of "specimen aspects" that can be customized. Other "specimen aspects" as described in the above paragraph may also be matched or altered according to different user's own unique skin care need, and may be used a method to hard code user skin care requirement information into the cartridge selection or customization. Cartridges after being selected, altered or customized from each different group may then be used to form a physically matching set to fit into a device cartridge holder, for example as shown in FIG. 36 through FIG. 44.

Different combination of various cartridges from different groups of 4510, 4520 and 4530 may also produce different final specimen mixture percentage when specimens from cartridges selected from the different groups are mixed to produce a final specimen for skin care. Cartridges within any one group of 4510, 4520 and 4530 may have same specimen, but different cartridges may have different contained specimen volume, for example large, medium, small volume, and different cartridges may have different specimen dispense rate or speed, for example fast, normal, and slow speed. For a first user that may require using more than normal amount of group-1 specimen, normal amount of group-2 specimen, and less than normal of group-3 specimen than a typical user, the first user may order or custom combine: a group-1 cartridge 1-1 that has a fast dispense speed and dispenses a larger than normal amount of group-1 specimen in a single dispense or within a unit dispense time, where cartridge 1-1 may also contain a large specimen volume; a group-2 cartridge 2-2 that has a normal dispense speed and dispenses a normal amount of group-2 specimen in a single dispense or within a unit dispense time, where cartridge 2-2 may contain a normal specimen volume; and, a group-3 cartridge 3-3 that has a slow dispense speed and dispenses a less than normal amount of group-3 specimen in a single dispense or within a unit dispense time, where cartridge 3-3 may contain a small specimen volume, such that the combination of the three cartridges, 1-1, 2-2 and 3-3 makes a physically matching set to fit into a device cartridge holder, for example as shown in FIG. 36 through FIG. 44. While a second user that has a skin condition characterized as "typical", may choose cartridges 1-2, 2-2, 3-2, which are cartridges among each group that have normal dispense speed and dispenses a normal amount of specimen of each group in a single dispense or within a unit dispense time, where these cartridges may contain a normal specimen volume. The combination of cartridges with different specimen dispense speed, coupled with different specimen volume contained within the cartridges, as discussed, may achieve not only making final specimen having the desired composition of final specimen mixing for skin care, it may also help achieve all cartridges depletion at roughly same time so that cartridges may be replenished, refilled, re-purchased or replaced as a set, instead of as individual cartridge, such that it saves user's time and effort. Such different combination of cartridges with different dispensing rate may also be used as a method to hard code user skin care requirement information into the selection scheme of the different cartridges from the different groups, whereas different users may have different dispensing rates of same type of cartridges within same group.

The different combination of cartridges from different groups, which may couple with customized alteration of the specimen aspects as described above, may produce final specimen for skin care after mixtures of specimens from the cartridges from different groups to achieve different skin care functions, or for different skin types, skin conditions, and may provide different degree of skin effectiveness, compatible with different environments or seasons, having different grade, price, usage time, produce different user feeling on skin or skin sensation.

Figure 46A:
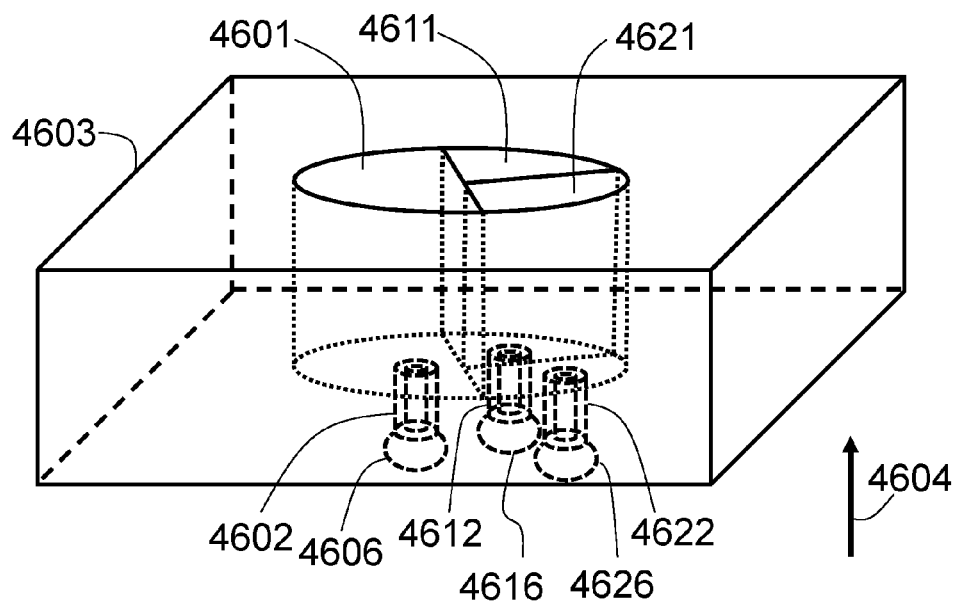
FIG. 46A illustrates each different dispenser of a dispenser set dispenses specimen through a different outlet from the dispensing device.

FIG. 46A illustrates each different dispenser 4601, 4611, or 4621 of a dispenser set dispenses specimen 4606, 4616, or 4626, through a different outlet 4602, 4612, or 4622 from the dispensing device 4603. Specimen dispensers 4601, 4611, and 4621, with dispenser outlets 4602, 4612, and 4622, and device body 4603 of FIG. 46A are substantially similar to the specimen dispensers 3601, 3611, and 3621, with dispenser outlets 3602, 3612, and 3622, and device body 3603 of FIG. 36, except that the dispensers 4601, 4611, and 4621 are inserted in the dispenser slot of device body 4603 in FIG. 46A. In FIG. 46A, specimens 4606, 4616 and 4626 are dispensed out of the device body 4603 through respective dispenser outlets 4602, 4612, and 4622 located at different locations of the device body 4603 and are not mixed immediately after dispensing. FIG. 46A uses dispensers forming a dispenser set as example, but they can be replaced by sub-compartments being part of a single dispenser as in FIG. 43 without limitation.

Figure 46B:
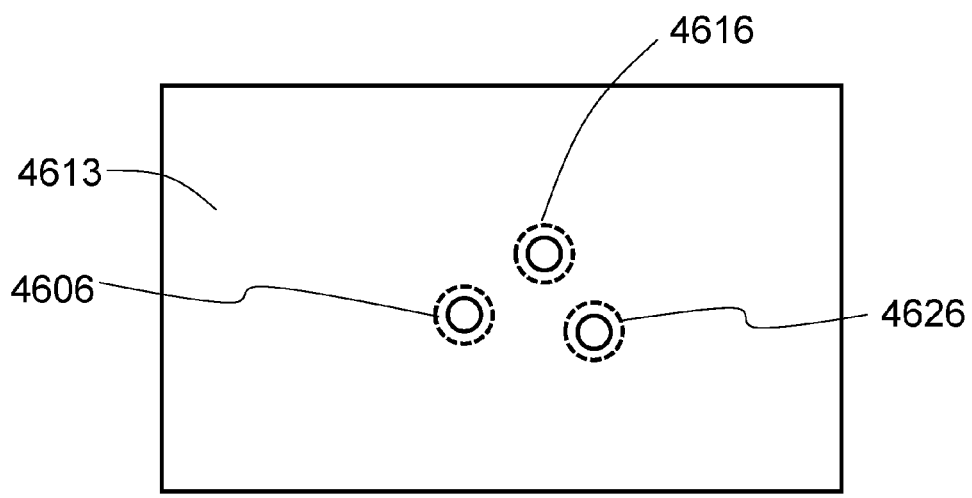
FIG. 46B illustrates a bottom-up view of each different dispenser of a dispenser set dispensing specimen through a different outlet from the dispensing device.

FIG. 46B then illustrates a bottom-up view along the direction 4604 of FIG. 46A of the device body 4603 and the different specimens 4606, 4616 and 4626 dispensed from dispensers 4601, 4611, and 4621 of FIG. 46A and not being mixed. In the example of FIG. 46A and FIG. 46B, specimens 4606, 4616 and 4626 may be mixed manually by a user with hand, or after they are transferred to a skin area of a user and then mixed by another external means, for example massaging the skin area with hand, fingers or a skin treatment member of a skin care device.

Figure 47A:
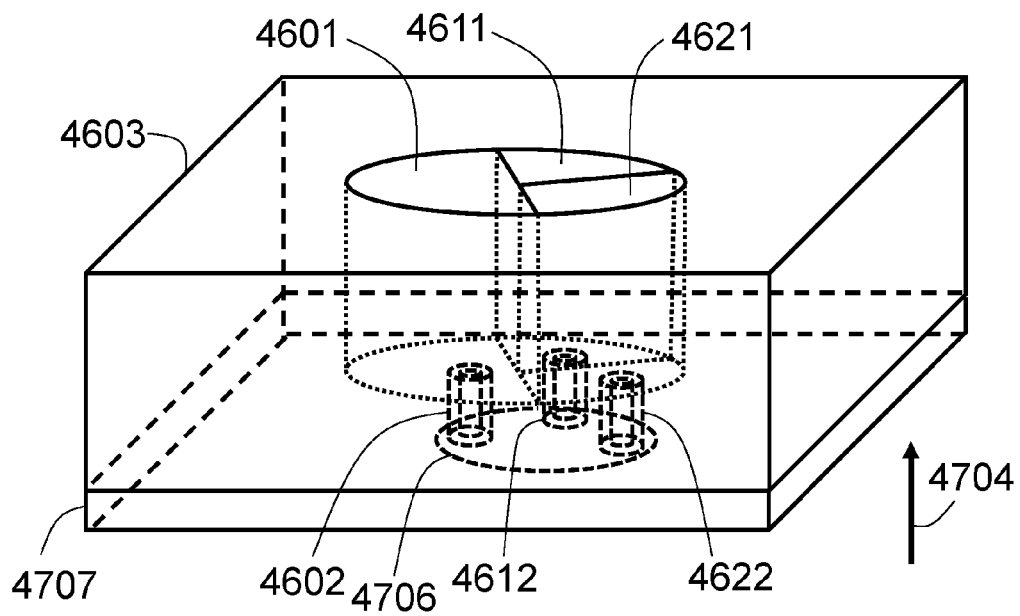
FIG. 47A illustrates each different dispenser of a dispenser set dispenses specimen through a different outlet from the dispensing device, whereas the dispensing device having a surface member that assists mixing the specimen from each dispenser after dispensing.

FIG. 47A illustrates each different dispenser 4601, 4611, or 4621 of a dispenser set dispenses specimen through a different outlet 4602, 4612, or 4622 from the dispensing device 4603, whereas the dispensing device 4603 has a surface member 4707 that assists mixing of the specimens dispensed from dispensers 4601, 4611, and 4621. FIG. 47A is sufficiently similar to FIG. 46, except that the specimen dispensed from outlets 4602, 4612, and 4622 of dispensers 4601, 4611, and 4621 is mixed after exiting the device body 4603 into a final specimen 4706. The surface member 4707 may provide a physical motion that helps mixing of the specimens dispensed from different dispensers of FIG. 47A. Surface member 4707 may be an ultrasound generation plate similar to skin treatment member 1600 of FIG. 16, or a vibration generation tip 1700 of FIG. 17, or a brush head 1800 of FIG. 18, whereas the surface member 4707 may also be used as a skin treatment member that is in contact with user's skin area during a skin care process.

Figure 47B:
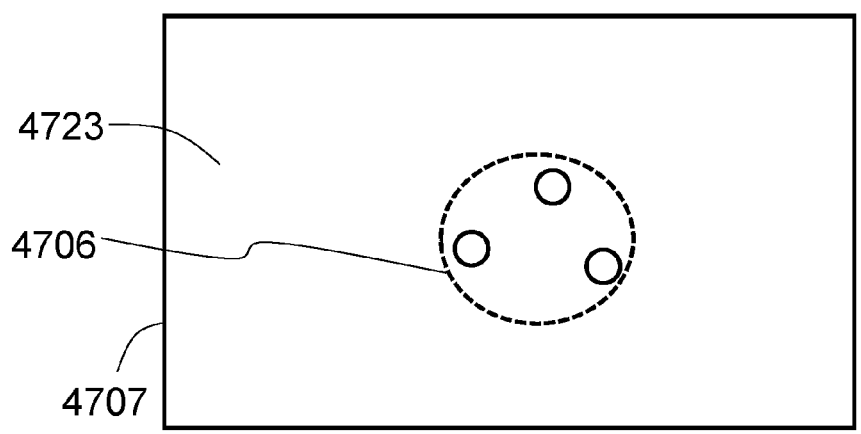
FIG. 47B illustrates a bottom-up view of each different dispenser of a dispenser set dispensing specimen through a different outlet from the dispensing device and being assisted by a surface member to mix.

FIG. 47B illustrates a bottom-up view along direction 4704 of FIG. 47A of dispensing device surface member 4707, and mixed specimen 4706 being mixed by the surface member 4737 on the surface 4723 of the surface member 4706.

Figure 48A:
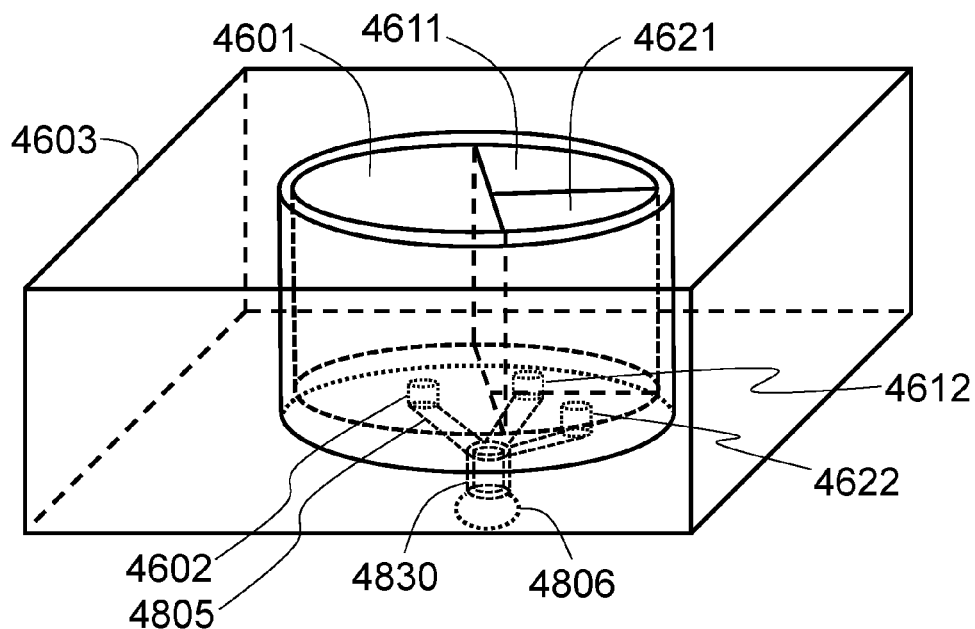
FIG. 48A illustrates dispensers of a dispenser set dispense specimen through the same outlet from the dispensing device.

FIG. 48A illustrates different dispenser 4601, 4611, or 4621 of a dispenser set dispense specimen through the same outlet 4830 from a dispensing device 4603. FIG. 48A is sufficiently similar as FIG. 46A, except that the specimens dispensed from outlets 4602, 4612, and 4622 of dispensers 4601, 4611, and 4621 are passed through conduits 4805 and converged into a single device outlet 4830. Such combined outlet 4830 and conduits 4805 of FIG. 48A are also similar to device outlet 3830 and conduits 3807 of FIG. 38, or cartridge holder outlet 3930 and conduits 3957 of FIG. 39, and any other combined outlet with connected conduits to combine specimen as in any figures or embodiments of this invention. Specimens dispensed from dispensers 4601, 4611 and 4621 are then mixed at and dispense through the combined device outlet 4830, and finally exiting the device body 4603 as mixed specimen 4806.

Figure 48B:
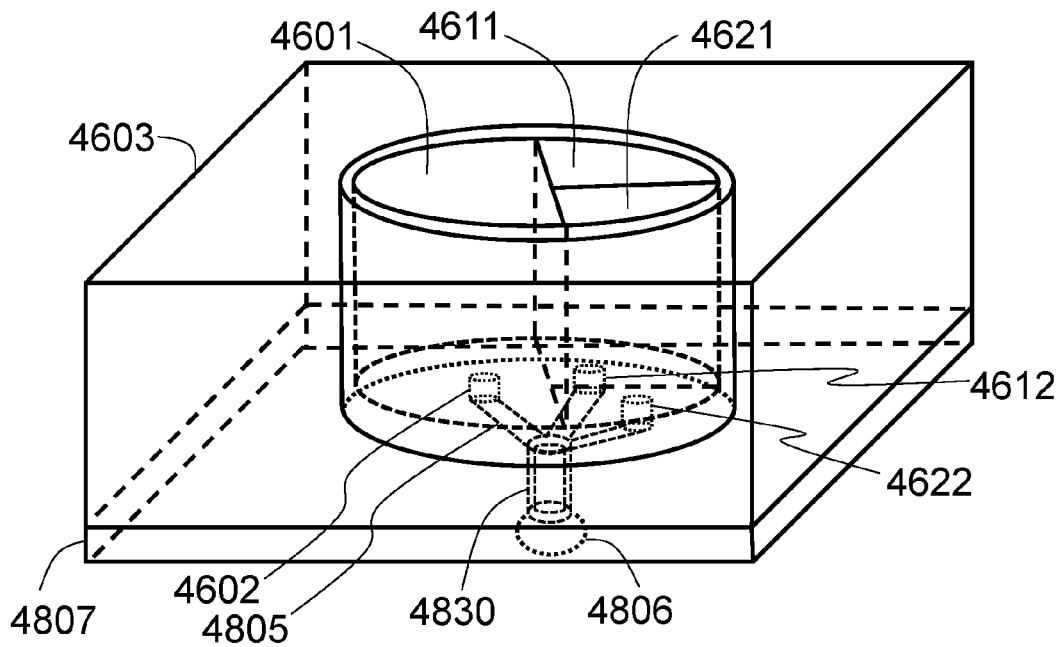
FIG. 48B illustrates dispensers of a dispenser set dispense specimen through the same outlet from the dispensing device, whereas the dispensing device having a surface member that assists mixing the specimen after dispensing.

FIG. 48B illustrates different dispenser 4601, 4611, or 4621 of a dispenser set dispense specimen through the same outlet 4830 from the dispensing device 4603, whereas the dispensing device 4603 has a surface member 4807 that assists mixing the specimen 4806 after dispensing. FIG. 48B is sufficiently similar to FIG. 48A, except that the specimen 4806 dispensed from combined device outlet 4830 is further mixed after exiting the device body 4603 by a surface member 4807, whereas the surface member 4807 may provide a physical motion that helps mixing of the specimen 4806 dispensed upon the surface member 4807. Surface member 4807 may be an ultrasound generation plate similar to skin treatment member 1600 of FIG. 16, or a vibration generation tip 1700 of FIG. 17, or a brush head 1800 of FIG. 18, whereas the surface member 4807 may also be used as a skin treatment member that is in contact with user's skin area during a skin care process.

Now referring back to FIG. 2. The at least one information storage component 142 included in the dispenser 14 can store any of the following listed information, but not limited to: (1) data about the specimen contained within the dispenser 14, which can be, but not limited to, specimen brand, name, type, origin, composition, production date and expiration date, specimen level within the dispenser and ordering information, number of sub-dispensers and compartments, information of specimen within sub-dispensers and compartments; (2) data about optimal or pre-set operational mode of the different sub-dispensers or difference specimen compartments within a single dispenser, where the operational mode can be, but not limited to, timing and/or flow speed of specimen application from each different sub-dispenser or each different compartment, amount of specimen to be dispensed from each different sub-dispenser or each different compartment; (3) information about historic usage of the device, the dispenser and specimen; (4) information that is created or input by the user; (5) information transferred from the control unit 17; (6) biometrics information of the user; and (7) anti-fake, anti-piracy, authenticity confirmation.

The information storage component 142 included in the dispenser 14 can be in the form of, but not limited to: (1) digital data storage device, which can be any of: flash memory, phase-change memory, resistive RAM, MRAM, DRAM, SRAM, magnetic data storage device; (2) analog data storage device; (3) optically recognizable markings which can be any of: letters, numbers, bar code, graphics, color patterns; (4) RF ID; (5) physical indentations or protrusions; and (6) chemicals.

The electronic control unit 17 may receive data stored in the dispenser 14 to convey information to the user through visual, skin contact or sound effects. Alternatively, the electronic control unit 17 may receive data stored in the dispenser 14 to dispense specimen 19 a specific manner determined by the information stored in the received data. The electronic control unit 17 may also send messages, wirelessly to an external device such as, but not limited to, a computer, a mobile device, a smart phone, or a data center.

Figure 21:
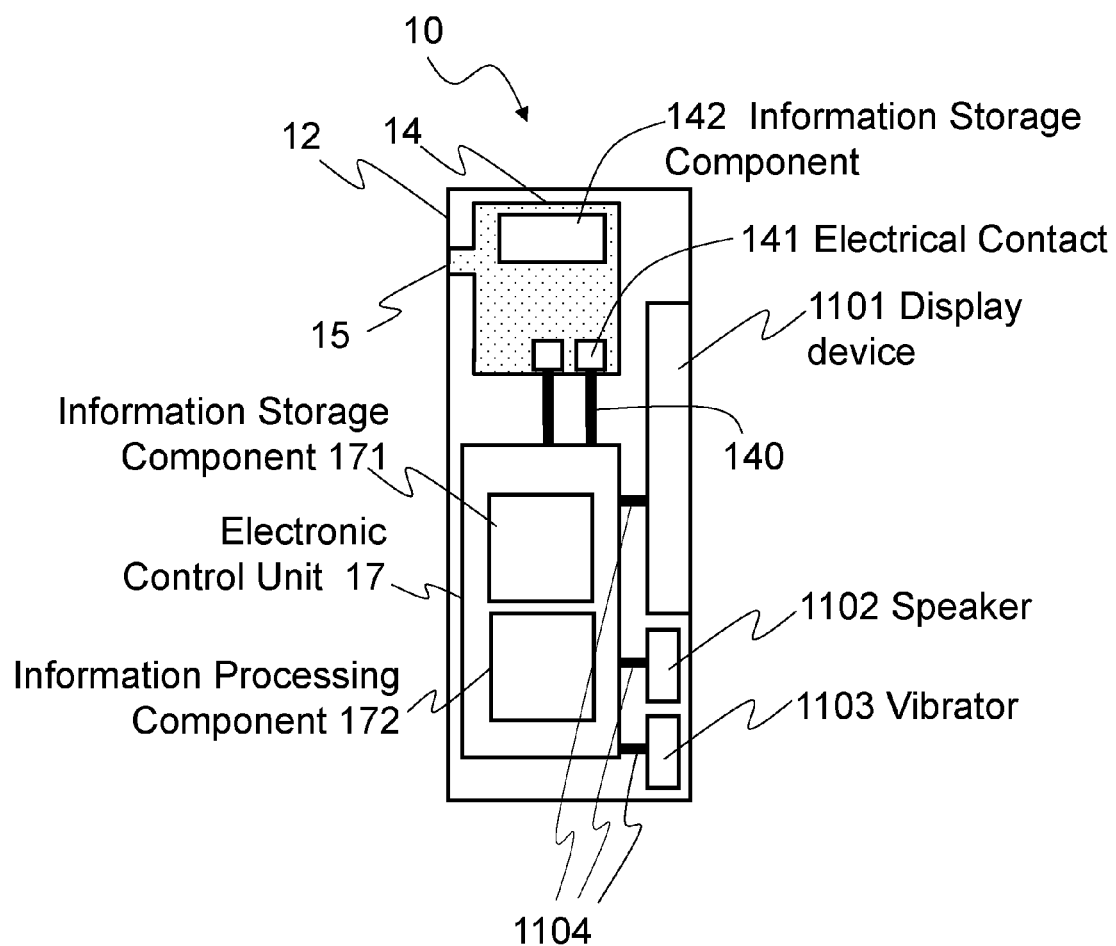
FIG. 21 illustrates a cross-sectional view along the center line 101 of the specimen dispensing device of FIG. 1, which contains electronic components to convey information to a user through visual, skin contact or sounds effects.
Figure 71:
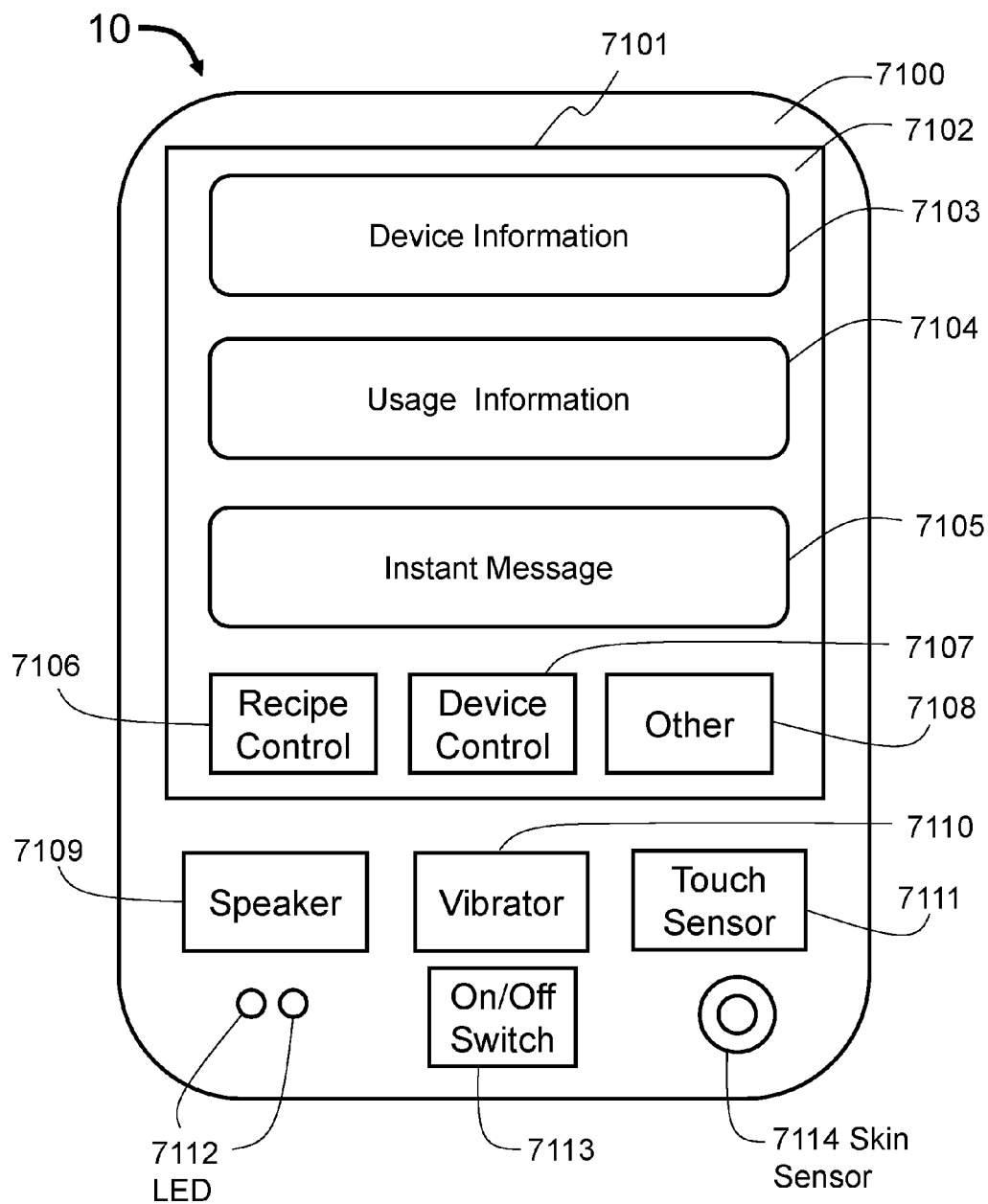
FIG. 71 illustrates components providing user interface of a dispensing device.

FIG. 21 and FIG. 71 illustrate possible components that may be included in the device 10 of FIG. 2 to convey information to a user through visual, skin contact or sound effects.

Now referring to FIG. 21. FIG. 21 illustrates a cross-sectional view along the center line 101 of the specimen dispensing device 10 of FIG. 1, whereas display device 1101, speaker 1102, and vibrator 1103 are shown as examples that may be included in the device 10 to convey information to a user through visual, sound or skin contact effects respectively. The electronic control unit 17 may convey the information that is stored in, and received from, the information storage component 142 of the dispenser 14, or the information stored in the information storage component 171, or the information generated by the information processing component 172, to the user through visual images displayed on display device 1101, or through skin feeling of vibrations produced by vibrator 1103, or through audible sounds produced by speaker 1102, by electrically controlling, or transferring information to, the display device 1101, speaker 1102, or vibrator 1103 via electrical connections 1104.

Now referring to FIG. 71. FIG. 71 illustrates components with detailed functions of a dispensing device 10 that is same as in FIG. 21. FIG. 71 shows possible components of device 10 when viewed upon a device surface 7100, whereas the surface 7100 is different than the specimen dispensing surface 12 and is void of the specimen outlet 15 of FIG. 21, and preferably being a surface that is opposing the surface 12 of device 10 of FIG. 21. The components of device 10 as illustrated in FIG. 71 may consist any one or more of: visual display 7101, touch screen 7102, speaker 7109, vibrator 7110, touch or fingerprint sensor 7111, light emitter 7112, on/off switch 7113, and skin sensor 7114. The display 7101 and touch screen 7102 may be layered into a single touch screen display 7101. Information may be displayed to the user on the display 7101, including any of: device information 7103, usage information 7104, and instant message 7105. Display 7101 may also display visual interfaces that allow user to interact through touch screen display 7102, to achieve various tasks with the visual interfaces including any of: specimen and skin care recipe control 7106, dispensing device control 7107 and other options 7108, whereas a user may use fingers to make contact with display 7101 through touch screen 7102 to interact with the various information displayed on 7101 to achieve desired device 10 setting, performance and dispensed specimen properties.

The display 7101, speaker 7109, and vibrator 7110 of FIG. 71 are same as display device 1101, speaker 1102 and vibrator 1103 of FIG. 21. Components of FIG. 71 may be controlled by the control unit 17 through electrical connections 1104 as shown in FIG. 21. Speaker 7109, vibrator 7110, touch or finger print sensor 7111 may be embedded inside the device 10 body and not visible on the surface 7100. LED 7112 may also be embedded inside device body, but may also exist on surface 7110, whereas LED 7112 may provide light indications to user during usage of device. On/off switch 7113 may be a mechanically operated switch button or lever, or may be a touch sensor, which enables user to turn on or off the device 10 electrically.

Skin sensor 7114 may be an imaging device or a chemical analyzer or a skin surface feature analyzer, which may be used to analyze user's skin of its physical features through image capturing and image processing, or be used to analyze the chemical composition on surface of skin through chemical analysis. When device 10 is in contact with a user skin, for example when device 10 has a skin treatment member, device 10 may locate its position on the user skin of face or body by optical scanning or image capturing of the skin area through skin sensor 7114 that the device 10 is in contact with, followed by an image recognition with comparing and matching pre-recorded user skin feature database of user's face or body that may be stored locally in the device 10, or remotely in a cloud server and accessible through a data network, and then dispensing corresponding skin care specimen, or producing desired skin treatment if device 10 contains a skin treatment member, for the skin of user's that the device is in contact with.

Touch sensor or fingerprint sensor 7111 may provide additional security features to secure user's personal information stored in the device 10, or may assist in identifying user's unique identity and unique skin care need and bring the device 10 into a state or configuration that best meet the user's skin care need.

The components as illustrated in FIG. 71 may provide a user interface through display, sound, vibration, touch screen, vibration or tapping and help dispense a specimen that is adjusted to the unique skin care need of the user. An example of a user using the device 10 through assistance of the illustrated components in FIG. 71 is provided hereafter. The user may charge the battery of the device 10 on a charger, where during charging LED 7112 may provide a light pattern, in color or in intensity, to indicate an on-going charging event or a charging finish event, for example the LED 7112 blinks a colored light during charging, and LED 7112 light goes off, or LED 7112 produces a steady colored light, when charging is completed. User may start using device 10 by turning on the device 10 with the on/off switch 7113 and stop using the device 10 by turning off the device 10 with the on/off switch 7113. The device 10 may automatically turn off by an internal timer of device 10. LED 7112 may produce light patterns, speaker 7109 may produce sounds, and vibrator 7110 may produce vibration patterns, at the beginning, or at the end, or during, the user's using of the device 10. Display 7101 may display information relevant to the device 10, specimen with cartridge that is contained in device 10, and user's usage of the device 10, and may allow user to control the operation of the device 10, information stored in device 10, specimen dispensing through touch screen 7102. Touch sensor or fingerprint sensor 7111 may lock or unlock the device 10 after retrieving correct identification information from user, like touch patterns or fingerprint, and sensor 7111 may cause the device 10 to automatically enter into an operation state, or to automatically load a setting of operation, or a setting of specimen dispensing, from internal storage component 171 in device 10 as shown in FIG. 21, or to provide a user interface or information on display 7101, which are pre-configured to match to the need, or habit, or preference of use, of the user.

Device information 7103 of FIG. 71 may include any of: date and time; battery power; user ID; location of the device 10; environment where the device 10 is being used, including any of temperature, weather, humidity, allergen type and level; and, signal strength of WIFI or Bluetooth.

Usage information 7104 may include any of: specimen and cartridge manufacturer brand and product information; specimen skin care purpose or skin features to treat; direction of using the specimen or the device; specimen volume in cartridge; and user specific specimen recipe information that is unique to the user who is using the device to dispense the specimen according to this specific recipe.

Instant message example 7105 may include any event of: new cartridge installed in device 10; cartridge install in device 10 is close to depletion; order info of cartridge installed in device; advice on modification of specimen dispensing recipe based on that actual using habit of user, or the actual method of use by user; device 10 is overheat; device 10 has low battery; device 10 software system requiring update; and any instructional message to user during use of device 10, for example changing device 10 contact location on the skin of user when the device 10 has a skin treatment member.

During user use of device 10, instructional information, for example changing device 10 contact location on the skin of user when the device 10 is in contact with user skin by a skin treatment member, may also be conveyed to user by device 10 producing specific sound or voice instruction by speaker 7109, or produce vibration pattern through vibrator 7110, or produce light patterns by LED 7112.

Now referring back to FIG. 2. The communication between the information storage component 142 and the control unit 17, especially when data stored in the information storage component 142 of the dispenser 14 are transmitted to the control unit 17, can be achieved by using a standardized protocol, as illustrated in FIG. 53 through FIG. 55B. Such protocol can be designed such that the different specimen information in any individual compartment or individual sub-dispenser is arranged in the same digital format and transmitted to the control unit 17 in sequence or in parallel. The same digital format can be an ordered number and/or character sequence of information that contains an allocate space in the sequence for any of the possibly needed information of any given specimen to be dispensed from the dispensing device 10. Such protocol can also be used to standardize the communication between any specimen dispensers made by different vendors and any dispensing devices made by other vendors, such that they can be easily made compatible and reduce cost of operation, manufacture and ownership.

The information processing component 172 of FIG. 2 included in the control unit 17 may contain embedded programs that utilize all the information stored in the information storage components 142 and 171 in the dispenser 14 and in the control unit 17 to operate and control the serum dispensing from the dispenser 14. Such embedded programs may also be updated for better function from time to time. Update of the information stored in the information storage component 171 of the control unit 17 and the programs in the information processing component 172 can be achieved using a data connection to a computer, a mobile device, a smart phone or a data center. The data connection is preferably through a wireless interface such as wireless internet, Bluetooth or other digital or analog wireless interface. Wireless data transmission can be achieved by a data transmission interface controlled by the control unit 17. Such interface may be an embedded communication component within the control unit 17, like a wireless antenna, or sharing of the wireless charging electronics, where charging and data transmission can be achieved at different frequencies through the same circuit. Otherwise, such update can be done through a direct electric wire connection through electrical contacts that connect to the control unit 17 and can be connected externally.

The electronic control unit 17 may send data to be stored in the dispenser's information storage component 142. The dispenser 14 may be recovered by the manufacture and data stored within the dispenser 14 may be retrieved.

Figure 49:
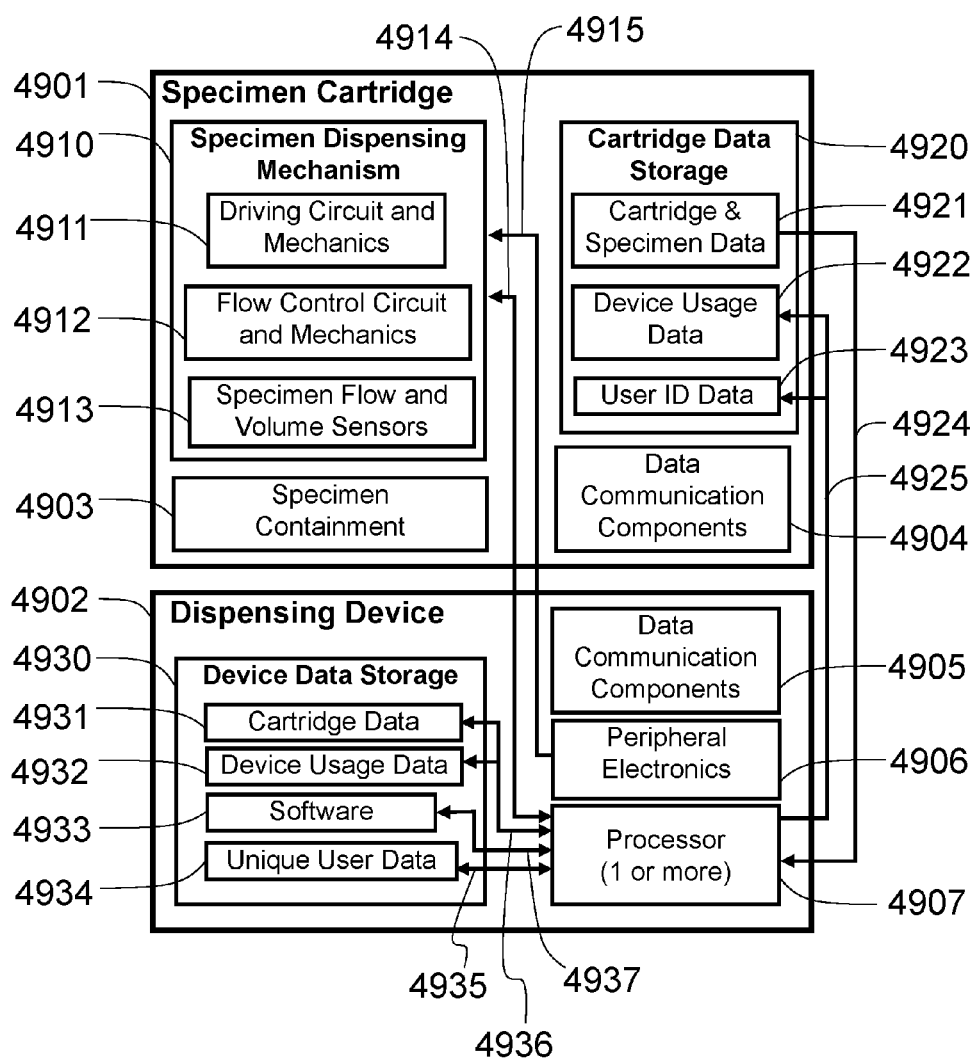
FIG. 49 illustrates components of a specimen dispenser and a dispensing device, and data communications between various components.

Now referring to FIG. 49. FIG. 49 illustrates components of a specimen dispenser or specimen cartridge 4901 that is same as dispenser 14 of FIG. 2, and a dispensing device 4902 that is same as dispensing device 10 of FIG. 2, and data communications between various components of the specimen cartridge 4901 and dispensing device 4902. Dispensing device 4902 of FIG. 49 may contain of any of: (a) device data storage 4930 component, which may store any of, cartridge data 4931, device usage data 4932, software 4933, unique user data 4934; (b) data communication components 4905; (c) data processor 4907; and (d) peripheral electronics 4906. Specimen cartridge 4901, preferably being contained within or attached upon the dispensing device 4902 similarly as dispenser 14 being contained within or attached to device 10 body as in FIG. 14 and FIG. 15, may contain any of: (a) specimen dispensing mechanism 4910, which may be composed of any of driving circuit and mechanics 4911, flow control circuit and mechanics 4912, specimen flow and volume sensors 4913; (b) specimen containment 4903; (c) cartridge data storage component 4920, which may contain any of: cartridge and specimen data 4921, device usage data 4922, and user identification data 4923; and (d) data communication components 4904. Through electrical connections between the dispensing device 4902 and specimen cartridge 4901, or the data communication components 4904 and 4905, processor 4907 within dispensing device 4902 may send electrical signals or digital data to, or receive electrical signals or digital data from, specimen dispensing mechanism 4910, and cartridge data storage 4920 component of specimen cartridge 4901. Specifically, processor 4907 may receive cartridge and specimen data 4921 from the cartridge data storage 4920 by data communication 4924, and may send device usage data 4922 and user ID data 4923 to be stored in cartridge data storage 4920 by data communication 4925. Processor 4907 may also retrieve from, or write to, device data storage 4930 in dispensing device 4902 the software 4933 and unique user data 4934 by data communications 4937 and 4935 respectively, while sending cartridge data 4931 and device usage data 4932 to, or receiving cartridge data 4931 and device usage data 4932 from, the device data storage 4930 by data communication 4936. Peripheral electronics 4906 may contain specimen dispense driving control electronics, which may send commands or electrical signals to the specimen dispensing mechanism 4910 of specimen cartridge 4901 by data communication or electrical connection 4915. Processor 4907 may send data to, or receive data from, the specimen dispensing mechanism 4910 by data communication 4914.

In FIG. 49, the cartridge and specimen data 4921 may contain any of: brand of cartridge 4901 and specimen contained therein; identification of cartridge 4901; authentication code or authentication data of cartridge 4901, with which the dispensing device 4902 or a user can use to confirm authenticity of cartridge 4901 and specimen contained therein; specimen physical form information, for example the specimen being liquid, oil, gel, paste or serum; specimen color; manufacture origin of the specimen cartridge 4901 and specimen contained therein; production date, production place, expiration date of cartridge 4901 and specimen contained therein; intended use of cartridge 4901 and specimen contained therein; specimen composition; method of mixing specimen from multiple sub-dispensers that form a cartridge set being treated as a specimen cartridge 4901; method of mixing specimen from multiple sub-compartments of the specimen cartridge 4901; method to dispense specimen from specimen cartridge 4901; method to use cartridge 4901 and specimen contained therein with a skin treatment member that may be part of dispensing device 4902; recycle information of cartridge 4901, including recycle location, recycle price, and information to be collected during recycle; refill information of cartridge 4901, including refill location and refill price.

Device usage data 4922 within cartridge data storage 4920 of specimen cartridge 4901 may contain any of: the date, the time of day, and the period of time when a user is using dispensing device 4902 with specimen cartridge 4901 installed into or attached upon the dispensing device 4902; dispensing device 4902 use pattern or use habit by a user while specimen cartridge 4901 is installed into or attached upon the dispensing device 4902, including turn on or turn off events of dispensing device 4902, whether the turn off of dispensing device 4902 is automatic turn off by electronics of the dispensing device 4902 or manually turn off by a user, dispensing device 4902 overheat event, dispensing device 4902 battery low power event, dispensing device 4902 charging event, and whether dispensing device 4902 is being charged by a mobile or a stationary battery charger.

User ID data 4923 within cartridge data storage 4920 of specimen cartridge 4901 may containing information or digital data that can be used to identify a specific user that uses the dispensing device 4902 while specimen cartridge 4901 is installed into or attached upon the dispensing device 4902.

Data communication components 4904 and 4905 may be capable of communicating information or data between each other through any means of: Bluetooth, WIFI, infrared optical communication, inductive circuitry, data link through direct electrical connections, visible light optical communication, RF ID, mechanical vibration generation and sensing, and proximity or pressure sensors.

Peripheral electronics 4906 of dispensing device 4902 may comprise any of: circuits for battery charging; circuits for turning on and off the dispensing device 4902; user interface including display, optical emitter, speaker, microphone, vibrator, touch screen, touch sensor; sensors of temperature, humidity, gravity, accelerometer, GPS, proximity to user skin; image or video capturing of skin condition; laser scanning of skin condition; sensors to detect environment infrared radiation, ultraviolet radiation, or water submerge; sensors to detect dispensing device 4902 being opened and internal electronics exposed; circuits to provide electrical power to specimen cartridge 4901; and electrical-mechanical driver or control circuits to dispense specimen from specimen cartridge 4901.

Software 4933 as stored in the device data storage 4930 may be in the form of a device operating system, or as software applications or programs, that may provide functions of any of: operation of dispensing device 4902; software or firmware drivers to operate electrical components of dispensing device 4902 and specimen cartridge 4901; user interface for a user to use the dispensing device 4902; algorithm to compute customized recipe utilizing unique user data 4934 and cartridge and specimen data 4921; identification and authentication of specimen cartridge 4901 and specimen contained in the specimen containment 4903; data encryption of all date communications between dispensing device 4902 and specimen cartridge 4901.

Unique user data 4934 in the device data storage 4903 of the dispensing device 4902 may include any of: user skin information data, user personal and biometrics information, user identification data, and user preference of sharing user's skin care related data with another party. Unique user data 4934 may be identical to, or include any part of, the unique user data 4934 of FIG. 51. Unique user data 4934 is preferred to be encrypted by the function of the software 4933 via the processor 4907.

Device usage data 4932 in the device data storage 4903 of the dispensing device 4902 may include any of: the date, the time of day, the time period, and the location of using dispensing device 4902 by a user; whether a specimen cartridge 4901 is installed into, or attached upon, the dispensing device 4902 during usage of the dispensing device 4902 by a user; use pattern or use habit by a user when using the dispensing device 4902; events during using the dispensing device 4902 by a user, including turn on or turn off events of dispensing device 4902, whether the turn off of dispensing device 4902 is automatic turn off by electronics of the dispensing device 4902 or manually turn off by a user, dispensing device 4902 overheat event, dispensing device 4902 battery low power event, event of a specimen cartridge being installed into, or removed from the dispensing device 4902, dispensing device 4902 charging event, and whether dispensing device 4902 is being charged by a mobile or a stationary battery charger.

Cartridge data 4931 in the device data storage 4903 of the dispensing device 4902 may include any or all of the information as included in the cartridge and specimen data 4921 in cartridge data storage 4920 of specimen cartridge 4901. Cartridge data 4931 may also include any information of: cartridge identification, cartridge and specimen classification, and authenticity of the specimen cartridge 4901 that is installed into, or attached upon the dispensing device 4902; date or time of day when a specimen cartridge 4901 is installed into, or attached upon the dispensing device 4902; how long a specimen cartridge 4901 has been installed into, or attached upon the dispensing device 4902; information of the specimen contained in the specimen cartridge 4901, which is installed into, or attached upon, the dispensing device 4902, including any of: targeted skin condition, mode and method of use and dispensing, manufacturer, origin of manufacture, authenticity information.

Data communications 4935, 4936, 4937, 4924, and 4925 may be accomplished through standard data communication protocols as described in FIG. 53 through FIG. 55B.

Figure 50:
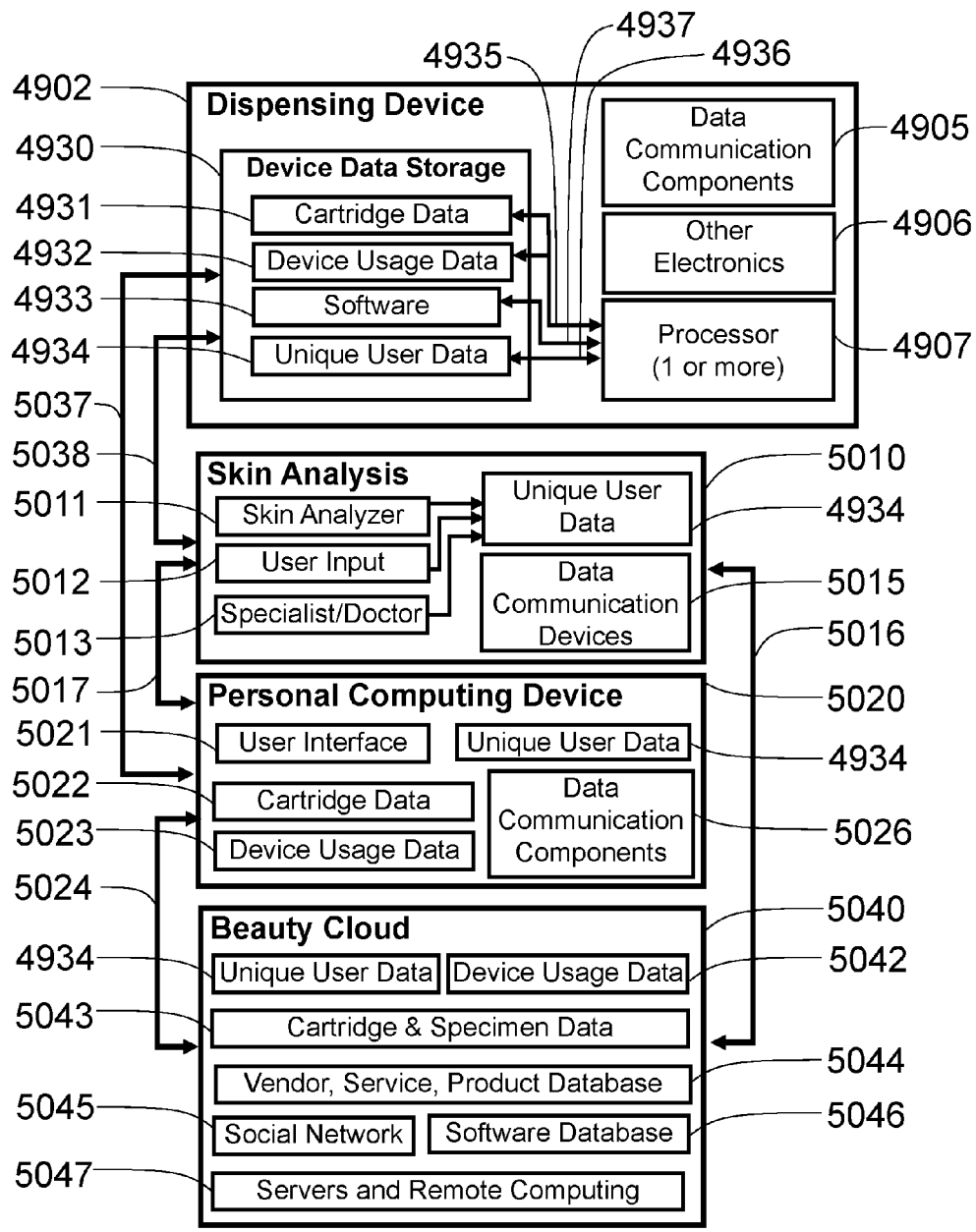
FIG. 50 illustrates components of a dispensing device, parts of a skin analysis process, components of a personal computing device, components of an internet beauty cloud, and data communications between various components and parts.

FIG. 50 illustrates various parts including: a dispensing device 4902 being same as the dispensing device 4902 of FIG. 49 with same internal components and data communications between processor 4907 and device data storage 4930 as in FIG. 49; a skin analysis process 5010 and included parts; a personal computing device 5020; and an internet based beauty cloud 5040; and data communications between various parts.

Skin analysis 5010 is substantially similar as the skin analysis processes as described in FIG. 51 and FIG. 52. Skin analysis 5010 of FIG. 50 may contain the parts of: (a) skin analyzer 5011, which is same as the skin analyzers described in FIG. 52A through FIG. 52F, which analyzes the skin of a user and produces analysis results; (b) user input 5012, which is user's own judgement of opinion of the skin condition, skin features and skin care need of the user's skin; (c) skin care specialist or dermatologist 5013, who provides professional judgement or opinion of the skin condition, skin features and skin care need of the user's skin; (d) unique user data 4934, which may be same, or may include any part of, the unique user data 4934 of device data storage 4930 of dispensing device 4902; (e) data communication devices 5015, which may include any of computer, mobile phone, or data communication devices that utilize Bluetooth, WIFI, infrared communication, inductive circuit, Ethernet, data link through direct electrical connections, visible light optical communication, fiber optics, whereas the data communication through the data communication devices 5015 may be accomplished with data communication protocols, for example internet or Ethernet protocols, or standard data communication protocols as described in FIG. 53 through FIG. 55B. Skin analysis results from skin analyzer 5011 with a process that is substantially similar as described in FIG. 52, may be compiled together with user input 5012 and specialist or dermatologist 5013 input to produce the unique user data 4934 as in FIG. 51, which constitutes the major part of the skin analysis 5010.

Personal computing device 5020 may contain any of: (a) user interface 5021, which allows a user to operate the personal computing device 5020 and perform data management within the personal computing device 5020 and in other devices external to the personal computing device 5020 through data communications; (b) cartridge data 5022, which may be same, or include any of, the cartridge data 4931 in the device storage 4930 of dispensing device 4902; (c) device usage data 5023, which may be same, or include any of, the device usage data 4932 in the device storage 4930 of dispensing device 4902; (d) unique user data 4934, which may be same, or include any of, the unique user data 4934 in the device storage 4930 of dispensing device 4902 or the unique user data 4934 of the skin analysis 5010; (e) data communication components 5026, which may be substantially the same as the data communication components 4905 of the dispensing device 4902.

Personal computing device 5020 may be in the form of any of: computer, smart phone, mobile phone, or specialized personal skin care computing device dedicated to skin care purpose.

Personal computing device 5020 may have embedded software for providing user interface 5021 to interact with user, so that user may customize and command dispensing device 4925, and may access database or digital files within the personal computing device 5020 or within dispensing device 4902, for storing or altering various data types, which may include unique user data 4934, cartridge data 5022 and device usage data 5023. Personal computing device 5020 may provide user access to beauty cloud 5040 for any of the purposes of: (a) uploading, downloading, updating and managing various databases or data files; (b) accessing and sharing such said various databases or data files through a social network; (c) updating software or firmware of personal computing device 5020 and dispensing device 4920; (d) ordering specimen cartridge 4901 of FIG. 49 and specimen products contained therein; (e) selecting service providers for skin analysis 5010 and arranging services of skin analysis 5010; (f) providing feedback to, and getting advices from, vendors or manufacturers of dispensing device 4902 or specimen cartridge 4901 of FIG. 49.

Beauty cloud 5040 is a data network, which provides data cloud service and is composed of data centers, servers and data management software tools. Beauty cloud 5040 may be provided for the purpose of assisting user in skin care and beauty care practice and enhancing personalized skin care for individual users. Beauty cloud 5040 may include any of: (a) unique user data 4934, which may be same, or include any of, the unique user data 4934 in the device storage 4930 of dispensing device 4902, or the unique user data 4934 of the skin analysis 5010, or the unique user data 4934 of the personal computing device 5020; (b) cartridge and specimen data 5043, which may be same, or include any of, the cartridge data 4931 in the device storage 4930 of dispensing device 4902, or the cartridge and specimen data 4921 of cartridge data storage 4920 in specimen cartridge 4901 of FIG. 49; (c) device usage data 5042, which may be same, or include any of, the device usage data 4932 in the device storage 4930 of dispensing device 4902; (d) Vendor, provider, product database 5044, which is a database that may include information about any of: (1) specimen cartridge 4901 vendors, skin analysis 5010 service providers, which are relevant and can be selectively recommended to a user from considering unique user data 4934, device data 5042, and cartridge data 5043; (2) products that can be recommended to a user and user can purchase or order through personal computing device 5020 or by service provider during skin analysis 5010; (3) recipe vendors, who utilize one or more standard sets of basic specimen cartridges, with each cartridge of a standard set specializing in a specific skin treatment function, to create recipes, or methods of combination, of using the basic specimen cartridges based on the skin care knowhow and knowledge-base that the recipe vendors possess, and sell such recipes or methods to a user as a customized skin care recipes to the user, whereas a user may purchase the basic specimen cartridges separately from purchasing the recipes; (e) social network 5045, which is an internet based platform for different users to share and exchange any of: experience and advice of using dispensing device 4902 or specimen cartridge 4901, personally adjusted recipes of using standard specimen cartridges, ideas to adjust recipe or methods of using standard specimen cartridges, as well as providing product and service feedback to vendors, service providers and product manufacturers included in the vendor, service and product database 5044; (f) software database 5046, which may include software, firmware, authentication code, applications or drivers that enable operation of, and communication between, dispensing device 4902, personal computing device 5020 and specimen cartridge 4901; (g) servers and remote computing 5047, which include the hardware and software to enable the other components of beauty cloud 5040 and to allow user to access beauty cloud 5040 remotely through an internet or data network.

Data may be transferred between the skin analysis 5010, utilizing the data communication devices 5015, and the device data storage 4930 of dispensing device 4902 utilizing the data communication components 4905 through data communication 5038, whereas transferred data may include, but not limited to, unique user data 4934. Data may be transferred between the skin analysis 5010, and the personal computing device 5020 utilizing the data communication components 5026, through data communication 5017, whereas transferred data may include, but not limited to, unique user data 4934. Data may be transferred between the device data storage 4930 of dispensing device 4902 utilizing the data communication components 4905, and the personal computing device 5020 utilizing the data communication components 5026, through data communication 5037, whereas transferred data may include, but not limited to, unique user data 4934, cartridge data 4931 and 5022, device usage data 4932 and 5023. Data may be transferred between the beauty cloud 5040 utilizing an internet or a data network, and the personal computing device 5020 utilizing the data communication components 5026, through data communication 5024, whereas transferred data may include, but not limited to, unique user data 4934, cartridge data 5043 and 5022, device usage data 5042 and 5023, vendor, service, product database 5044, social network 5045, and software database 5046. Data may be transferred between the skin analysis 5010, utilizing the data communication devices 5015, and the beauty cloud 5040 utilizing an internet or a data network, through data communication 5016, whereas transferred data may include, but not limited to, unique user data 4934, device usage data 5042, cartridge and specimen data 5043, vendor, service, product database 5044, social network 5045, and software database 5046.

Data communications 5016, 5017, 5024, 5037, and 5038 may be accomplished through standard data communication protocols as described in FIG. 53 through FIG. 55B.

Figure 53:
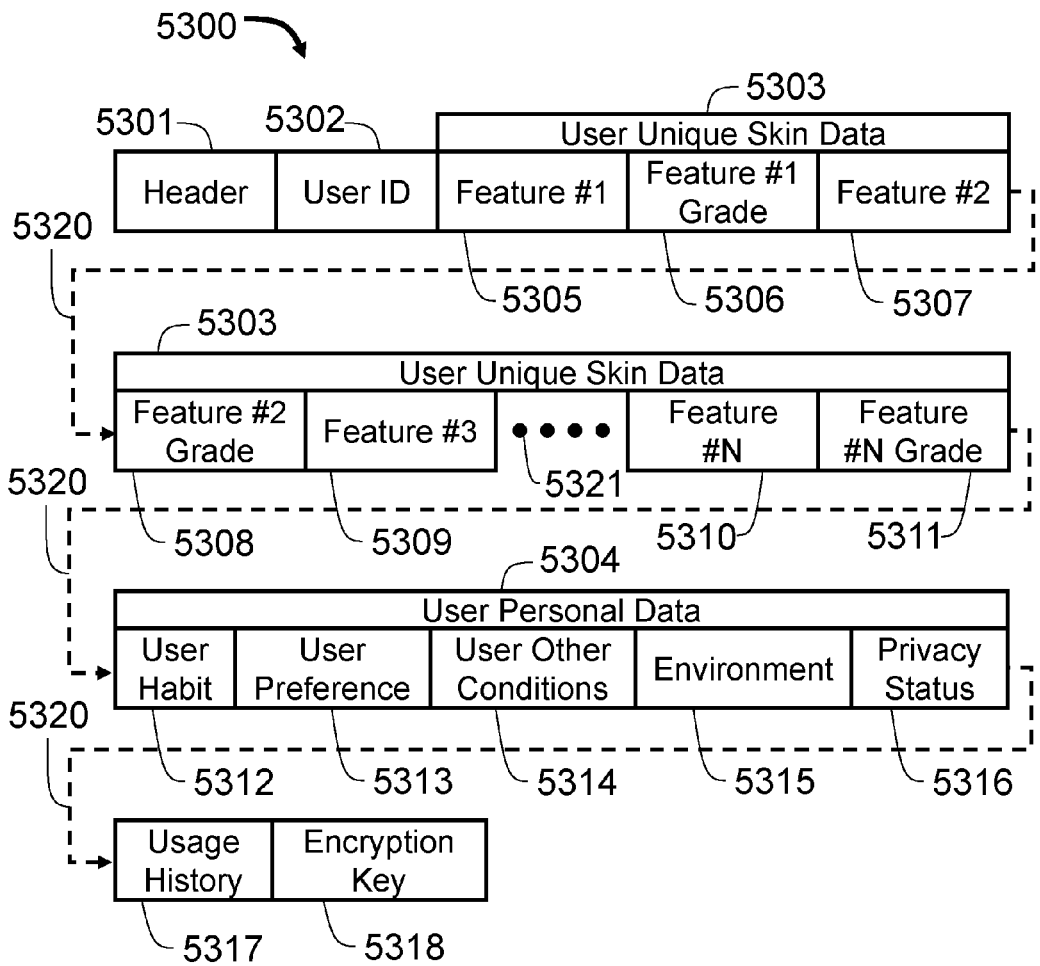
FIG. 53 illustrates user data structure for storing and communication of unique user data and other user related data.

Now referring to FIG. 53. FIG. 53 illustrates a user data structure 5300 for storage and communication of unique user data and other user related data. The user data structure 5300 of FIG. 53 may serve as a standard data communication protocol, or a digital data storage format, as described in other figures or embodiments of this invention. The user data structure 5300 may contain the data sections of: header 5301, user ID 5302, user unique skin data 5303, user personal data 5304, usage history 5317, and encryption key 5318. The sections of user ID 5302, user unique skin data 5303, user personal data 5304, usage history 5317, and encryption key 5318 may be referred to as "unique user data", which term may be referred to in other figures and embodiments of this invention, for example unique user data 4934 of FIG. 49 through FIG. 51. In some embodiment, the entire user data structure 5300, including the header 5301, may be referred to as "unique user data". The user unique skin data 5303 may be further sub-sectioned into a series of: skin features 5305, 5307, 5309, and 5310, having corresponding feature grades 5306, 5308, and 5311 of each skin feature. User personal data 5304 may be further sub-sectioned into more categories of user related data, including any of: user habit 5312, user preference 5313, user other conditions 5314, environment 5315, and privacy status 5316. Dashed lines 5320 are used in FIG. 53 to describe the continuation of user data structure 5300. Dotted line 5321 is used in FIG. 53 to represent a plurality of "feature" and "feature grade" sections in between Feature #3 5309 and Feature #N 5310, where N is an integer larger than 3.

All data in the user data structure 5300 of FIG. 53 are of informational value, but not all data contained in user data structure 5300 may be used for specimen dispensing or skin care processes, while some data sections of user data structure 5300 may be for information collection for user behavior study to better design the dispensing device, skin care and skin analysis service and specimen cartridge to meet user's skin care need.

User data structure 5300 may be used to transmit data to and stored in any of: user's own specimen dispensing device 4902 of FIG. 50; cartridge data storage 4920 of FIG. 49; local server at location of skin analysis 5010 of FIG. 50; a remote server in data center being part of a beauty cloud 5040 of FIG. 50; user's personal computing device 5020 of FIG. 50; and, user's personal data storage device including wearable electronics, memory sticks, hard disk drives, CD, DVD, and any other data storage electronics that may store digital data.

User data structure 5300, besides being used for skin care purpose as described in other embodiments of this invention, may also be used for other purposes, for example medical care, and other user-centric applications, where features may include features of other user body parts or user health related subjects. Such purpose may include any of: medication application to a patient, tanning of a user's body, food control for body weight control, and perfuming for different social events of a user.

Type of sections and sequence of sections of the user data structure 5300, including the sub-sections, as described in FIG. 53, are used as example. Actual sections, and sub-sections, of the user data structure 5300 may be varied of: the content of the section; the sequence of the sections; new sections may be added; listed sections may be omitted; sub-sections of a parent section, for example sub-sections 5305, 5307, 5309, 5310, 5306, 5308, and 5311 of parent section 5303, may be interlaced with sub-sections of another parent section, for example sub-sections 5312, 5313, 5314, 5315, 5316 of parent section 5304, in digitally stored user data structure 5300.

Data of the different sections of the user data structure 5300 may be stored in the same digital data formats, or with different sections of the user data structure 5300 being stored in different digital data formats in various data storage devices or databases, including any of: information storage components 142 and 171 in FIG. 2, cartridge data storage 4920 in FIG. 49, device data storage 4930 in FIG. 49 and FIG. 50, skin analysis 5010 in FIG. 50, personal computing device 5020 in FIG. 50, and beauty cloud 5040 of FIG. 50. For example, header 5301 and user ID 5302 sections may be stored in non-encrypted ASCII format, while user unique skin data 5303 or user personal data 5304 may be stored in binary format or other encrypted data formats. When different sections of the user data structure 5300 are stored in different digital data formats in various data storage devices or databases, the different digital format data may recombine according to the user data structure 5300 of FIG. 53 before the user data structure 5300 is transmitted. For data transmission purpose, user data structure 5300 can be used as a protocol by itself, or treated as a data section of another standard protocol, for example user data structure 5300 being integrated as the data section into protocols of TCP/IP, Bluetooth, 802.11 or other wired or wireless data transmissions protocols.

Header 5301 section of user data structure 5300 may be used to indicate that the user data structure 5300 is "unique user data" and invoke relevant data packaging, data transmission and data extraction actions, based on the known user data structure 5300, from the data transmission hardware, or software, or firmware from a sending party, or a receiving party, of the user data structure 5300. Header 5301 section may contain information regarding how many distinctive sections are included in the user data structure 5300, and the boundaries of each data section in the user data structure 5300. For example, Header 5301 section may indicate existence of User ID 5302 section, existence of User Unique Skin Data 5303, number of features included in User Unique Skin Data 5303 and data boundaries of each feature and its corresponding grade section, existence of User Personal Data Section 5304 and number of sub-sections included in User Personal Data Section 5304. Header 5301 section of user data structure 5300 may be non-encrypted. In another embodiment, any section or sub-section of user data structure 5300 may be encrypted.

User ID 5302 may be data of a unique identification code, numeric or character sequence to specifically and uniquely identify a specific user, whereas the user data structure 5300 may be uniquely describing the skin conditions, skin care need and skin care preference of the said specific user.

Feature sub-sections 5305, 5307, 5308, and 5310 of user unique skin data section 5303 may include identification or description information of any common skin features that may be found on a user's skin and are of importance to skin treatment for a skin care purpose. Feature grade 5306, 5308, and 5311 of user unique skin data section 5303 may include a data sequence that is composed of quantitative numerals, or qualitative numerals, or both, to describe the severity or strength of the corresponding skin features, as in feature sections 5305, 5307, 5308, existing on user's skin. Any known skin feature that may exist on a user's skin may be assigned a sub-section of "feature" in section 5303 of the user data structure 5300, and a "feature grade" accompanying that feature may also be assigned as a sub-section in section 5303 of the user data structure 5300. For a feature that exists on a given user's skin, grade data may be assigned for that feature in section 5303 of the user data structure 5300. While for a feature that does not exist on the user's skin, the feature grade value of that feature may be un-assigned, or may be assigned special numerals or characters to indicate the non-existence of such feature. For example, feature #1 5035 may be assigned to "fine line" feature on a user's face, and feature #2 5307 may be assigned to "wrinkle" feature on a user's face, while feature #1 grade 5306 is used to store grade of "fine line" and feature #2 grade 5308 is used to store grade of "wrinkle". User A may have fine lines but not wrinkles, in which case the fine liner feature grade 5306 may be assigned a grade value, while the wrinkle feature grade 5308 may be left un-assigned or assigned a number zero as an indication of non-existence of wrinkle feature. New found feature of a certain user, which does not exist as a sub-section in the user unique skin data section 5303 of the user data structure 5300 of that user, may be added into the user unique skin data section 5303 of the user data structure 5300 of that user as a new feature having both feature and feature grade sub-sections, with updating the header section 5301 with relevant information that may include: addition of the new sub-sections of the new feature, the location, length and boundaries of the newly added sub-sections in the user data structure 5300.

Each feature sub-section of 5305, 5307, 5308, or 5310 may contain a unique identification code, or data sequence, to specifically identify a known skin feature. Each feature grade sub-section of 5306, 5308, or 5311 may contain grades that are generated by a commonly accepted grading method. The feature identification codes and the grades may serve as part of a universal protocol to communicate the features and their grades across different dispensing devices, specimen cartridges, skin care analysis services, personal computing devices, and beauty clouds. The same method of features identification and grading may be adopted and practiced by different dispensing device makers, specimen cartridge makers, skin care service providers and different users.

User personal data sections 5304 is used to identify the unique skin care need of each user in addition to the user unique skin data section 5303. User personal data 5304 may serve as a reference in producing personalized specimen recipe. User personal data 5304 may be created as part of the user data structure 5300 during the skin analysis 5010 as in FIG. 50. User personal data 5304 may also be created as part of the user data structure 5300 by a user of a dispensing device through the user interface of said dispensing device, for example the display 7101 and touch screen 7102 of device 10 as in FIG. 71. User personal data 5304 may also be created as part of the user data structure 5300 by an external computing device, for example personal computing device 5020 of FIG. 50.

User habit 5312 section as part of user personal data sections 5304 may contain information regarding the habit of a user using a specimen dispensing device where the user data structure 5300 is stored therein. User habit 5312 may include any of: how long a user uses a specimen dispensing device during each time of use; how often within a certain period of time a user uses a specimen dispensing device, for example how many times within a day, or within a week, or within a month; time of the day when a user uses a specimen dispensing device; day of the week when a user uses a specimen dispensing device; day of the month when a user uses the dispensing device; and, whether the dispensing device contains a specimen cartridge therein during each use by a user. User habit 5312 section may have more than one data entry, whereas each data entry may be distinguished by including a unique time stamp, or data entry time section, that is part of the said data entry, and each data entry may contain a complete set of data of user habit 5312 as described above. Existing data entries may be updated or overwritten, and new data entries may be added or appended to the existing data entries, by a dispensing device during or after the usage of the dispensing device by a user to reflect an on-going user habit of using the dispensing device.

User preference 5313 section as part of user personal data sections 5304 may include preference data of a user in improving or diminishing certain skin features that the user "personally" prioritizes. User preference 5313 may include improving skin features to a condition that may be more than necessary or more than clinically required. For example, a user prefers skin fairness to be extremely fair instead of normal skin tone, which may require additional ultraviolet screening ingredients than typically needed in a dispensed specimen for skin care of the user's actual skin fairness condition.

User other conditions 5314 section as part of user personal data sections 5304 may include user personal data, including, but not limited to: age; gender; ethnicity; body weight; height; existing health issues, for example cardiovascular conditions, diabetes, allergy, medication being taken; dietary choices, for example low carbohydrate diet, high protein diet, low fat diet; sleeping habit, for example normal hours of daily sleep, waking up and insomnia conditions; exercise habit, for example excise time, length, type of exercise, and exercise stress level; working schedule, for example time and length of daily work, indoor or outdoor, whether under sun or other electromagnetic radiation exposure and for how long. User other conditions 5314 may also include user related information that is considered part of the conditions that may affect user skin care results and may be quantitatively or qualitatively graded and stored in user other conditions 5314 in a data segment that contains each of the condition and grading of the corresponding condition, whereas said data segment may be in the substantially similar data format as feature 5305 and features grade 5306.

Environment 5315 section as part of user personal data sections 5304 may include descriptions of the environment that the user of the specimen dispensing device is exposed to, including any of: temperature, humidity, sun exposure, indoor or outdoor activities, allergen in air, smog exposure, whereas said descriptions of environment may also be accompanied by a date or time of the year to reflect seasonal changes of said descriptions of environment. Environment 5315 section and descriptions of the environment may be stored in quantitative or qualitative grades. During operation of a specimen dispensing device, environment 5315 section may be updated manually by a user through the user interface of said dispensing device or through a personal computing device 5020 of FIG. 50. Environment 5315 section may also be updated automatically through built-in sensors of the specimen dispensing device, where the built-in sensors may detect the time of the day, date, GPS location of the dispensing device, temperature, humidity, sun exposure, indoor or outdoor activities, allergen in air, smog exposure. Environment 5315 section may also be updated automatically through a data network connecting to the specimen dispensing device, or to a personal computing device 5020 of FIG. 50, and through at least one data server connecting to the data network, with utilizing a GPS type of location tracking service and a weather and environment service, whereas the GPS service locates location of the dispensing device through the data network, and the weather service provides current and future environment information according to that location data provided by the GPS service, and the provided environment information may be updated to the environment 5315 section of FIG. 53.

Privacy status 5316 section as part of user personal data sections 5304 may include information of: user self-determined privacy preference settings regarding the transmission and storage of the user unique skin data 5303 and user personal data 5304. The privacy status 5316 may determine whether data contained in the user unique skin data 5303 and user personal data 5304 can be transmitted to, or stored in any of: beauty cloud 5040 of FIG. 50, computer or server of a service provider during skin analysis 5010 of FIG. 50. The privacy status 5316 may determine whether data contained in the user unique skin data 5303 and user personal data 5304 can be accessed by, or stored in, any of: the dispense device 4902 of FIG. 49, the specimen cartridge 4901 of FIG. 49, or personal computing device 5020 of FIG. 50. The privacy status 5316 may determine whether data contained in the user unique skin data 5303 and user personal data 5304 can be used for the purpose of data collection to study a single user or a group users for any of: specimen skin care effect, user behavior, user preference analysis, for the purpose of providing better service, better specimen cartridge usage projection for the user, better algorithm development to produce better recipe fitting user's unique skin care need. The privacy status 5316 may be used to determine whether data contained in the user unique skin data 5303 and user personal data 5304 can be used for any marketing purpose of the cartridge maker and other product makers providing relevant products, for promotions to users, feedback of cartridge usage behavior of a user, and feedback of user experience of other products related to skin care. The privacy status 5316 may be used to determine whether data contained in the user unique skin data 5303 and user personal data 5304 can be used for any activities that will expose the said data to a party other than the user or skin care products and service providers that the user is using, for the purpose of any of: making, producing, selling products that is relevant to the user, other than for skin care. The privacy status 5316 may contain choice by the user of enabling personal information to be shared at different levels, for example, whether the user can be personally identified, or identified as a group which is based on any of: physiological, sociological, geological parameters, for example gender, ethnicity, location, income, age, type of work, body weight, or choice of not being identifiable. Privacy status 5316 may be stored in data sections that contain various settable properties and corresponding property values that are determined by the user.

Usage history 5317 may contain dispensing device usage history without being associated with a specific user. Usage history 5317 may contain information regarding the usage of the dispensing device that may include any of: usage date, usage time of the day, time length of usage, location of usage, whether a cartridge is installed in the dispensing device, cartridge brand, cartridge type, cartridge purpose, whether cartridge is used with or without a built-in skin treatment member as in FIG. 47A and FIG. 48B, cartridge origin, cartridge authenticity, cartridge use time of the day, cartridge use date, cartridge use location, cartridge's time length of use by a user, events of device turn on, device turn off, device auto turn off, device over heat, device low battery, a cartridge being installed into or uninstalled from device, device charging event, whether the device is being charged on a mobile or a stationary charger. All information included in the usage history 5317 may be accompanied by a time stamp or time data that describes the time sequence of the recorded events or information. Usage history 5317 may be updated manually by a user. Usage history 5317 may be updated automatically by the dispensing device, with utilizing a built-in clock, timer, or GPS sensors within the dispensing device, and upon a new event is detected by the device. Usage history 5317 may also be updated automatically through a data network connecting to the specimen dispensing device, or by a personal computing device 5020 of FIG. 50 connecting to a data network and through at least one data server, with utilizing a GPS type of location tracking service, whereas the GPS service locates location of the dispensing device through the data network, and provides time information at said location. Usage history 5317 may be stored in progressively added data sections with having a unique ID of each different type of usage history event and its value determined by the dispensing device during each event by.

Encryption Key 5318 may include a digital key or data sequence that may be used to encrypt or decrypt all data of the user data structure 5300. In some embodiment, header 5301 is not encrypted. Encryption key 5318 may be a user determined data sequence. Encryption key 5318 data may itself be encrypted by another second key before storing or transmission of user data structure 5300, while the personal computing device 5020 of FIG. 50, the dispensing device 4902 of FIG. 50 and the servers of beauty cloud 5040 of FIG. 50 may have the known second key, and which is not known to any third party, whereas second key can be used to encrypt or decrypt the encryption key 5318 data, and subsequently encryption key 5318 may be used to encrypt or decrypt the rest of the data sections of user data structure 5300.

Figure 54:
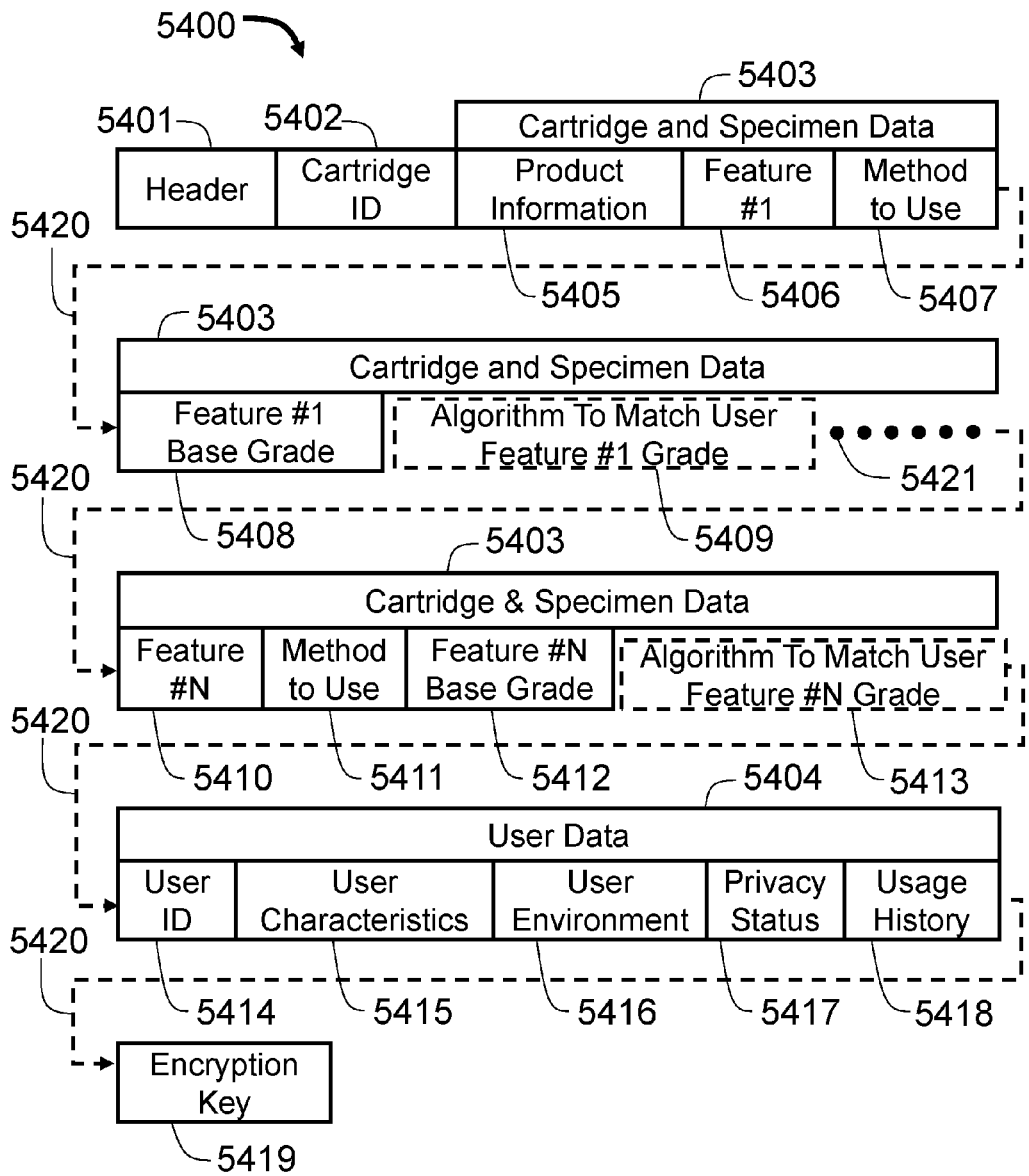
FIG. 54 illustrates dispenser data structure for storing and communication of dispenser and specimen data, and other user related data.

FIG. 54 illustrates a dispenser data structure 5400 for storing and communication of dispenser or cartridge data, specimen data, and other user related data. The dispenser data structure 5400 of FIG. 54 may serve as a standard data communication protocol, or a digital data format for storage, as described in other figures or embodiments of this invention. The data structure 5400 may contain the sections of: header 5401, cartridge ID 5402, cartridge and specimen data 5403, user data 5404, and encryption key 5419. The cartridge and specimen data 5403 may be further sub-sectioned into product information 5405, and a series of skin features, including feature #1 5405 through feature #N 5410, with each skin feature having corresponding method of use 5407 for feature #1 5405 and method of use 5411 for feature #N 5410, feature base grade 5408 for feature #1 5405 and feature base grade 5412 for feature #N 5410, and optional algorithm 5409 to match user feature grade of skin feature #1 5405 and algorithm 5413 for feature #N 5410. Dotted line 5421 is used in FIG. 54 to represent a plurality of "feature", "method to use", "feature base grade" and "algorithm to match user feature grade" sections in between Algorithm 5409 and Feature #N 5410, where N is an integer larger than 1. User data 5404 may be further sub-sectioned into more categories of user related data, including any of: user ID 5414, user characteristics 5415, user environment 5416, privacy status 5417, and usage history 5418. Dashed lines 5420 are used in FIG. 54 to describe the continuation of dispenser data structure 5400.

All data in the data structure 5400 of FIG. 54 are of informational value, but not all data contained in data structure 5400 may be used for specimen dispensing or skin care processes, while some data sections of data structure 5400 may be for information collection for user behavior study to better design the specimen dispenser, specimen and method to dispense specimen to meet user's skin care need.

Dispenser data structure 5400 may be used to transmit cartridge or specimen data to and stored in any of: user's own specimen dispensing device 4902 of FIG. 50 as cartridge data 4931; cartridge data storage 4920 of FIG. 49; local server at location of skin analysis 5010 of FIG. 50; a remote server in data center of a beauty cloud 5040 of FIG. 50 as cartridge and specimen data 5043; user's personal computing device 5020 of FIG. 50; and, user's personal data storage device including wearable electronics, memory sticks, hard disk drives, CD, DVD, and other data storage electronics that stores digital information.

Dispenser data structure 5400, besides for skin care purpose as described in the embodiments of this invention may also be used for other purposes, including medical care, or other user-centric applications, where features 5406 and 5408 of FIG. 54 may include features of other body parts of user, or health related subjects of user. Such purposes may include any of: medication application to a patient, tanning of a user's body, food control for body weight control, and perfuming for different social events of a user.

Sections and sequence of sections of the dispenser data structure 5400, including the sub-sections, as described in FIG. 54, are used as example. Actual sections, and sub-sections, of the dispenser data structure 5400 may be varied of the content of each of the sections, or varied of the sequence of the sections, while as new sections may be added, and existing sections may be removed, and sub-sections of a parent section, for example sub-sections 5405, 5406, 5407, 5408, 5409, 5410, 5411, 5412, and 5413 of parent section 5403, may be interlaced with sub-sections of another parent section, for example sub-sections 5414, 5415, 5416, 5417, and 5418 of parent section 5404, during actual application.

Data of the different sections of the dispenser data structure 5400 may be stored in the same digital data format, or with different sections of the dispenser data structure 5400 stored in different digital data formats, for example ACSII format, binary format, or HEX format, in various data storage devices or databases, including any of: information storage components 142 and 171 in FIG. 2, cartridge data storage 4920 in FIG. 49, device data storage 4930 in FIG. 49 and FIG. 50, skin analysis 5010 in FIG. 50, personal computing device 5020 in FIG. 50, and beauty cloud 5040 of FIG. 50. When different sections of the dispenser data structure 5400 are stored in different digital data formats in various data storage devices or databases, the different digital format data may recombine according to the dispenser data structure 5400 of FIG. 54, before the dispenser data structure 5400 is transmitted. For data transmission purpose, dispenser data structure 5400 can be used as a protocol by itself, or treated as a data section of another standard protocol, for example dispenser data structure 5400 may be integrated as the data section into a data transmission protocol of any of TCP/IP, Bluetooth, 802.11 or other wired or wireless data transmissions protocols.

Header 5401 section of dispenser data structure 5400 may be used to indicate that the dispenser data structure 5400 contains cartridge and specimen data and invoke relevant data packaging, data transmission and data extraction actions, based on the known dispenser data structure 5400, from the data transmission hardware, or software, or firmware from a sending party, or a receiving party, of the dispenser data structure 5400. Header 5401 section may contain information regarding how many distinctive sections are included in the dispenser data structure 5400, and the boundaries of each data section in the dispenser data structure 5400. For example, Header 5401 section may indicate existent of section Cartridge ID 5402, existent of section Cartridge and Specimen Data 5403, number of features and data boundaries of each sub-section in Cartridge and Specimen Data 5403, existence of User Data Section 5404 and number of sub-sections included in User Data Section 5404. Header 5401 section of data structure 5400 may be not encrypted. In another embodiment, any section or sub-section of data structure 5400 may be encrypted.

Cartridge ID 5402 section of dispenser data structure 5400 may be a unique identification code, numeric or character sequence, for example a serial number, which is used to identify information regarding the cartridge and specimen contained therein, including any of: origin, manufacturer identification, date of manufacture, sales and transportation history, whereas such information may be obtained by referring the cartridge ID 5402 to a database included in a specimen dispensing device 4902 of FIG. 50 where the cartridge storing the dispenser data structure 5400 is installed, or a database 5047 of FIG. 50 that is included in a remote server connected to, and accessible through, a data network.

Product information 5405 section of dispenser data structure 5400 may include information regarding the cartridge where the dispenser data structure 5400 is stored, or the specimen contained in the cartridge, including any of: brand of cartridge or specimen; identification information of cartridge or specimen; specimen physical form, for example liquid, gel, powder, serum, lotion, paste; specimen color; origin of manufacture of cartridge or specimen; production date or expiration date of cartridge or specimen; intended skin care purpose of cartridge or specimen; specimen composition; cartridge recycle information, recycle place, and recycle price; cartridge or specimen order information; cartridge specimen refill information, refill place and refill price; cartridge and specimen authentication code, which is a unique code known to a data retriever, or a dispensing device 4902 of FIG. 50, or a beauty cloud server 5047 of FIG. 50, or a personal computing device 5020 of FIG. 50, whereas said authentication code may be generated by referring to a database included in a specimen dispensing device 4902 of FIG. 50 where the cartridge is installed. Said authentication code may also be generated by a database that is included in a remote server 5047 of FIG. 50 which is connected to, and accessible through, a data network, and by utilizing cartridge ID 5402 of FIG. 54 or user ID 5302 of FIG. 53.

Features sub-sections 5406 and 5410 of dispenser data structure 5400 are substantially similar to the feature sub-sections 5305, 5307, 5308, and 5310 of user unique skin data section 5303 as in FIG. 53. Different than the feature sub-sections 5305, 5307, 5308, and 5310 of user unique skin data section 5303 in a dispensing device, which may list all possible skin features that may exist on any user, sub-sections 5406 and 5410 of the dispenser data structure 5400 only include the features that cartridge, or specimen contained therein, is designed to treat. Different cartridges for different skin care purposes may store different features included in their dispenser data structure 5400. In other words, sub-sections 5406 and 5410 of the dispenser data structure 5400 may be regarded as a sub-set of the feature sub-sections 5305, 5307, 5308, and 5310 of user unique skin data section 5303 as in FIG. 53.

Feature base grade 5408 and 5412 of dispenser data structure 5400 are substantially similar to feature grade 5306, 5308, and 5311 of user unique skin data section 5303 in FIG. 53. Feature base grade 5408 and 5412 may include a data sequence that is composed of quantitative numerals, or qualitative numerals, or both. Feature base grade 5408 and 5412 as in dispenser data structure 5400 may be used as reference values for treating corresponding skin feature 5406 and 5410 that a user skin may have, whereas a standard "method of use" 5407 and 5411 may be provided for skin feature 5406 and 5410 at corresponding feature base grade 5408 and 5412. However, in some embodiments, feature base grade 5408 and 5412 may not be needed if "algorithm to match user feature grade" 5409 and 5413 can utilize "method to use" 5407 and 5411 without a reference feature base grade 5408 and 5412. In another embodiment, the dispensing device where the cartridge is installed has an internal built-it algorithm to dispense specimen from cartridge according to the feature 5406 or 5410, and corresponding "method to use" 5407 or 5411.

Same as the feature sub-sections 5305, 5307, 5308, and 5310 of user unique skin data section 5303 as in FIG. 53, each of sub-sections 5406 and 5410 of the dispenser data structure 5400 may contain a unique identification code, or data sequence, to specifically identify a known skin feature. Each feature base grade sub-section of 5408, or 5412 may contain grades that are generated by a commonly accepted grading method. The feature identification codes and the grades may serve as part of a universal protocol, or a standard protocol, to communicate the features and their grades across different dispensing devices, specimen cartridges, skin care analysis, personal computing devices, and beauty clouds, such that the features identification and grading that can be shared among different dispensing device makers, specimen cartridge makers, skin care service providers and different users.

Method to use 5407 and 5411 of dispenser data structure 5400 may include data or algorithms relating to the dispensing of the specimen in the cartridge for the feature 5406 or 5410 having feature base grade 5408 or 5412, whereas the method to use 5407 and 5411 may include any of: specimen dispensing amount per dispense, specimen dispensing flow rate, number of times of specimen dispensing, whether specimen is dispensed in combination within using a skin treatment member, mixture percentage of specimen from different sub-compartments that may exist within the cartridge, modification to specimen dispensing by the time of the day, modification to specimen dispensing by day of the week. The method to use 5407 and 5411 may include modification to specimen dispensing according to user data 5404 by changing any of: specimen dispensing amount per dispense, specimen dispensing flow rate, number of times of specimen dispensing, whether specimen is dispensed in combination within using a skin treatment member, mixture percentage of specimen from different sub-compartments that may exist within the cartridge, modification to specimen dispensing by the time of the day, modification to specimen dispensing by day of the week.

Algorithm to match user feature grade, 5409 and 5413 of dispenser data structure 5400, may contain mathematical algorithms, or mathematical formulae, to decide specimen dispensing method according to the method of use 5407 and 5411, the feature base grade 5408 and 5412, and based on a user's own skin features and the grades for corresponding skin features. Algorithm 5409 and 5413 may be retrieved by a dispensing device as 4924 of FIG. 49, and be used for calculating a final method to use to dispense specimen from cartridge, by controlling any one or more parameters that may be included in method to use 5407 and 5411. Algorithm 5409 and 5413 in another embodiment may already be included in dispensing device software 4933 as in FIG. 49 and thus may be omitted in dispenser data structure 5400, as indicated by the dashed lines of 5409 and 5413 in FIG. 54.

User data 5404 sub-sections are used to identify user, or to record any of: user characteristics, user preference, user behavior, within the dispenser data structure 5400. User data 5404 may be used as a reference in producing personalized recipe.

Sub-sections user ID 5414, user environment 5416 and privacy status 5417 are substantially similar to, or identically same as, the user ID 5302, environment 5315 and privacy status 5316 of FIG. 53, whereas the user ID 5302, environment 5315 and privacy status 5316 of FIG. 53 in user data structure 5300 may be partially or entirely sent to be stored as the user ID 5414, the user environment 5416 and the privacy status 5417 in dispenser data structure 5400 within a cartridge, when the cartridge that stores the dispenser data structure 5400 is installed into and used with a dispensing device that contains user data structure 5300.

User characteristics 5415 sub-section of dispenser data structure 5400 may contain information or data directly related to the user of the dispenser, including any of: user age, user gender, user ethnicity, user body weight and height, user health issues, user diet, user sleep patterns, user exercise habit, user work type and schedule. User characteristics 5415 may include the environmental or life style conditions of the user, which may affect user's skin care results and which may be quantitatively or qualitatively graded and stored in data sections. User characteristics 5415 may be substantially similar to, or identically same as, user other conditions 5314 of FIG. 53, whereas user other conditions 5314 of FIG. 53 in user data structure 5300 may be partially or entirely sent to store as user characteristics 5415 in dispenser data structure 5400 within a cartridge, when the cartridge storing the dispenser data structure 5400 is installed into and used with a dispensing device that contains user data structure 5300.

Usage history 5418 sub-section of dispenser data structure 5400 may contain information, or event, regarding the usage of the dispenser, or the cartridge, with a dispensing device that may include any of: cartridge use time of the day, cartridge use date, cartridge use location, cartridge's time length of use by the user, device turn on event with cartridge installed, device turn off event with cartridge installed, device auto turn off event with cartridge installed, device over heat event with cartridge installed, device low battery event with cartridge installed, device charging event with cartridge installed, information of device charging on a mobile or a stationary charger with cartridge installed. Each recorded event included in the usage history 5418 may be accompanied by a time stamp or time data that describes the time sequence of the recorded events. Usage history 5418 may be updated automatically by a built-in clock, timer, or GPS sensors within the dispensing device. Usage history 5418 may also be updated automatically through a data network by the specimen dispensing device, or by a personal computing device 5020 of FIG. 50, and through at least one data server, with utilizing a GPS type of location tracking service, whereas the GPS service locates location of the dispensing device or its user, and provides time information the location. Usage history 5418 may be stored in progressively added data sections with having a unique ID of each different type of usage history event and its value determined by the dispensing device during each operation of the dispensing device with cartridge installed.

Encryption key 5419 section of dispenser data structure 5400 may include a digital key or data sequence that may be used to encrypt or decrypt all data of the dispenser data structure 5400. In some embodiment, header 5401 is not encrypted. Encryption key 5419 may be a user determined data sequence. Encryption key may also be a data sequence determined by dispenser or specimen manufacture or supplier. Encryption key 5419 data may itself be encrypted by another second key before storing or transmission of data structure 5400, while the second key may be known to any of: dispenser manufacturer; dispenser filling, packaging, or assembly machines; personal computing device 5020 of FIG. 50; the dispensing device 4902 of FIG. 50; and the servers of beauty cloud 5040 of FIG. 50, whereas the second key can be used to encrypt or decrypt the encryption key 5419 data, and subsequently encryption key 5419 may be used to encrypt or decrypt the rest of the data sections of dispenser data structure 5400. Encryption key 5419 of dispenser data structure 5400 may be omitted in some embodiments and where data may not be encrypted. In other embodiments, encryption key 5419 of dispenser data structure 5400 may be omitted, while dispenser data structure 5400 is still encrypted by a key that is known to a dispensing device 4902 of FIG. 50, or a personal computing device 5020 of FIG. 50, or a remote server 5047 of FIG. 50, which may decrypt dispenser data structure 5400 with said known key and retrieve information or data from decrypted dispenser data structure 5400.

Figure 55A:
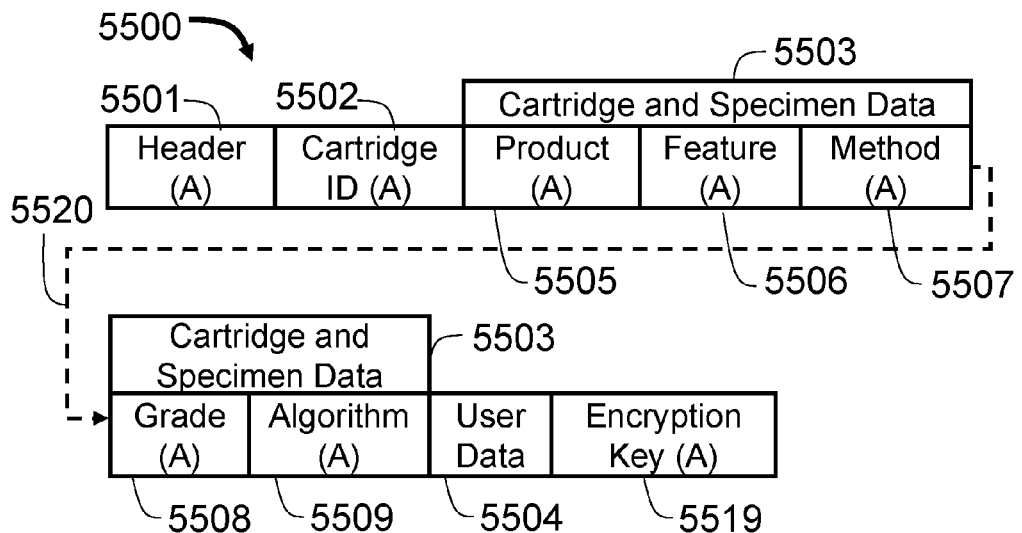
FIG. 55A illustrates dispenser data structure for a first dispenser with specimen contained therein.
Figure 55B:
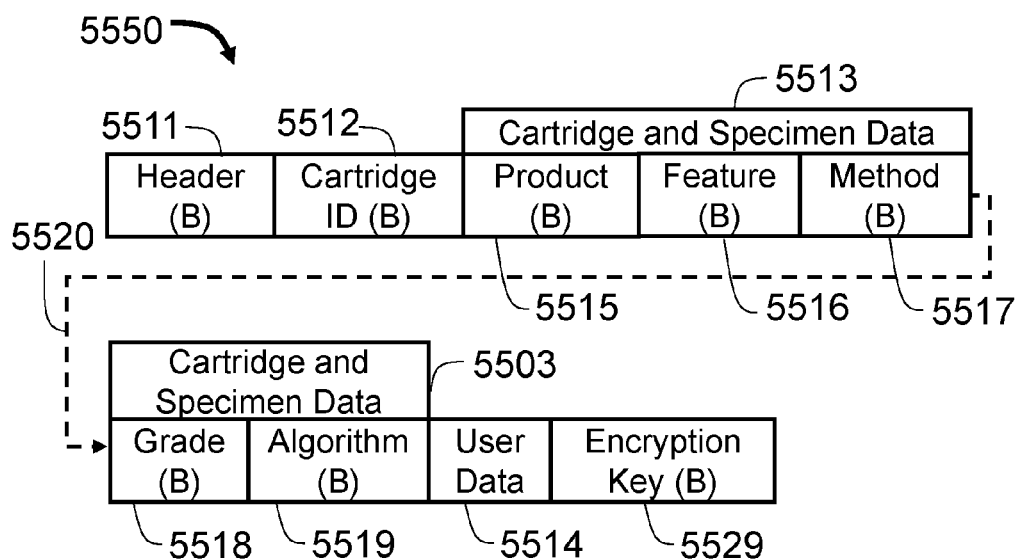
FIG. 55B illustrates dispenser data structure for a second dispenser with specimen contained therein.

FIG. 55A illustrates dispenser data structure 5500 for a first dispenser with a specimen product (A) contained therein. FIG. 55B illustrates dispenser data structure 5550 for a second dispenser with a specimen product (B) contained therein. FIG. 55A and FIG. 55B illustrate examples of using dispenser data structure 5400 of FIG. 54 as a standardized protocol for specifying dispensers and specimen contained therein when they are different products, different brands, or have different methods of use. FIG. 55A and FIG. 55B illustrate two different products, product (A) and product (B), whereas the dispenser data structures 5500 and 5550 are simplified versions of dispenser data structure 5400 of FIG. 54, with each of the dispenser data structures 5500 and 5550 containing a single skin feature 5506 and 5516 representing single skin feature treatment purpose of the specimen contained in the dispensers of product (A) as in FIG. 55A and product (B) as in FIG. 55B. Product (A) of dispenser data structure 5500 as in FIG. 55A and product (B) of dispenser data structure 5550 as in FIG. 55B may be any of: products from different brands having different skin care purposes, products from different brands having the same skin care purpose, products from same brand having different skin care purposes. Header 5501, cartridge ID 5502, product 5505, feature 5506, method 5507, grade 5508, algorithm 5509, user data 5504 and encryption key 5519 of FIG. 55A are same data structure sections as header 5401, cartridge ID 5402, product information 5405, feature #1 5406, method to use 5407, feature #1 base grade 5408, algorithm to match user feature #1 grade 5409, user data 5404 and encryption key 5419 of FIG. 54. Header 5511, cartridge ID 5512, product 5515, feature 5516, method 5517, grade 5518, algorithm 5519, user data 5514 and encryption key 5529 of FIG. 55B are same data structure sections as header 5401, cartridge ID 5402, product information 5405, feature #1 5406, method to use 5407, feature #1 base grade 5408, algorithm to match user feature #1 grade 5409, user data 5404 and encryption key 5419 of FIG. 54.

For illustration purpose, product (A) of FIG. 55A and product (B) of FIG. 55B are assumed to be from different brands. For the same user using product (A) and product (B), head (A) 5501 of FIG. 55A and header (B) 5511 of FIG. 55B may be same if product (A) and product (B) are intended for the same skin care purpose, while head (A) 5501 of FIG. 55A and header (B) 5511 of FIG. 55B may be different if product (A) and product (B) are intended for different skin care purposes. Due to product (A) of FIG. 55A and product (B) of FIG. 55B being from different brands, cartridge ID (A) 5502 and cartridge ID (B) 5512 are different, and product (A) 5505 and product (B) 5515 are different. In the case that if product (A) and product (B) are intended for the same skin care purpose, feature (A) 5506 and feature (B) 5516 may be the same, while as product (A) and product (B) being from different brands, the method (A) 5507, grade (A) 5508, and algorithm (A) 5509, which are used to calculate best method to dispense specimen product (A) according to the user's skin feature, may be different than the method (B) 5517, grade (B) 5518, and algorithm (B) 5519, which are used to calculate best method to dispense specimen product (B) according to the same user's same skin feature. In another embodiment, product (A) and product (B) are intended for different skin care purposes and treating different skin features, feature (A) 5506 and feature (B) 5516 are different, whereas method (A) 5507, grade (A) 5508, and algorithm (A) 5509 are also different than the method (B) 5517, grade (B) 5518, and algorithm (B) 5519. However, as the user is the same, user data 5504 and 5514 may be the same. As the product (A) of FIG. 55A and product (B) of FIG. 55B are from different brands, encryption key (A) 5519 and encryption key (B) 5529 may be different if encryption key is provided by dispenser or specimen manufacturer. Encryption key (A) 5519 and encryption key (B) 5529 may be same if encryption key is provided by the user's dispensing device or provided according to an encryption key provider that specifies the encryption keys 5519 and 5529 being the same for the same user. Encryption key (A) 5519 and encryption key (B) 5529 may be omitted from data structure 5500 and 5550 similarly as encryption key 5419 of FIG. 54.

In the case of a cartridge set, for example a cartridge set containing three cartridges: a cartridge #1 for treating fine lines as cartridge 3601 of FIG. 36 through FIG. 39 or cartridge 4001 of FIG. 40 through FIG. 42, a cartridge #2 for treating deep wrinkles as cartridge 3611 of FIG. 36 through FIG. 39 or cartridge 4011 of FIG. 40 through FIG. 42, a cartridge #3 for treating brown spots as cartridge 3621 of FIG. 36 through FIG. 39 or cartridge 4021 of FIG. 40 through FIG. 42, while cartridge #1 and cartridge #3 may be from brand (A) and cartridge #2 may be from brand (B), all three cartridges have same dispenser data structures similar to FIG. 54, FIG. 55A or FIG. 55B which contain relevant information regarding each of the cartridges, and which enable the three cartridges from different brands (A) and (B) to function together as a single set to be installed in a dispensing device, as in device 3603 of FIG. 36 through FIG. 39, or device 4003 of FIG. 40 through FIG. 42, to dispense a final specimen with a composition that matches to a user's skin features and skin care need.

Figure 56:
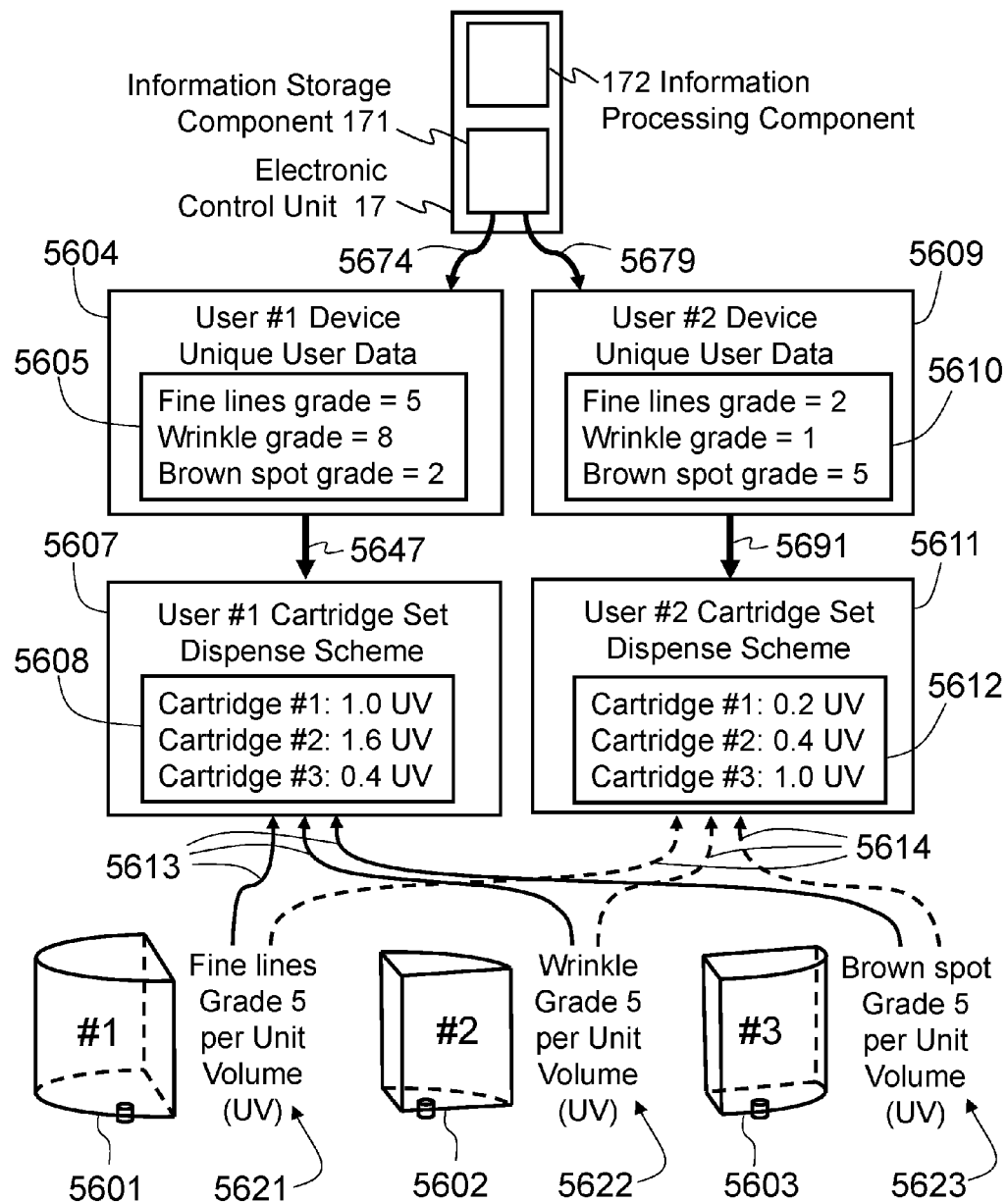
FIG. 56 illustrates methods to provide personalized specimen dispensing schemes for two different users based on the unique user data of each user and dispenser data from a same dispenser set.

FIG. 56 illustrates methods to provide personalized specimen dispense schemes 5607 and 5611 for two different users, user #1 and user #2, based on the unique user data 5604 and 5609 of each user and dispenser data from a same dispenser set, or cartridge set.

FIG. 56 illustrates a cartridge set containing three cartridges: a cartridge #1 5601 which may be similar as cartridge 3601 of FIG. 36 through FIG. 39 or cartridge 4001 of FIG. 40 through FIG. 42, a cartridge #2 5602 which may be similar as cartridge 3611 of FIG. 36 through FIG. 39 or cartridge 4011 of FIG. 40 through FIG. 42, a cartridge #3 5603 which may be similar as cartridge 3621 of FIG. 36 through FIG. 39 or cartridge 4021 of FIG. 40 through FIG. 42, while cartridges 5601, 5602, and 5603 may form a cartridge set to be installed in a dispensing device that is same as device 3603 of FIG. 36 through FIG. 39 or same as device 4003 of FIG. 40 through FIG. 42, or same as the device 10 of FIG. 2, to dispense a final specimen with a composition that matches to a user's own skin care need. Cartridge #1 5601 may be any one of the cartridges of group-1 4510 of FIG. 45, and cartridge #2 5602 may be any one of the cartridges of group-2 4530 of FIG. 45, and cartridge #3 5603 may be any one of the cartridges of group-3 4530 of FIG. 45. Each of the cartridges 5601, 5602, and 5603 may be described similarly as, and may include any functions of, any of the dispensers or cartridges as described in FIG. 22A through FIG. 44.

Cartridge #1 5601 may contain a data storage component that is similar to information storage component 142 of FIG. 2, whereas the data storage component stores specimen information 5621. Specimen information 5621 describes that cartridge #1 5601 contains a specimen that is targeted to treat skin feature of "fine line", with method of use being a Unit Volume ("UV") of specimen contained in cartridge #1 5601 is targeted to treat skin feature "fine line" that is graded as Grade 5. The skin feature of "fine line" and method of use as in specimen information 5621 may be stored in dispenser data structure same as any of the dispenser data structures 5400, 5500, and 5550 of FIG. 54, FIG. 55A and FIG. 55B, whereas skin feature "fine line" is same as any of the features 5406, 5410 of FIG. 54 or any of the features 5506 and 5516 of FIG. 55A and FIG. 55B, and whereas the reference grade "Grade 5" is same as any of the feature base grades 5408, 5412 of FIG. 54 or any of the feature base grades 5508 and 5518 of FIG. 55A and FIG. 55B, and whereas the method to use, "Grade 5 per Unit Volume (UV)" may be defined as any of the "method to use" 5407, 5411 of FIG. 54, or any of the method 5507 and 5517 of FIG. 55A and FIG. 55B.

Cartridge #2 5602 functions similarly as cartridge #1 5601 and may also contain a data storage component, whereas the specimen information 5622 contained in the data storage component of cartridge #2 5602 describes that cartridge #2 5602 contains a specimen that is targeted to treat skin feature of "wrinkle", with method of use being a Unit Volume of the specimen contained in cartridge #2 5602 is targeted to treat skin feature "wrinkle" that is graded as Grade 5.

Cartridge #3 5603 functions similarly as cartridge #1 5601 and may also contain a data storage component, whereas the specimen information 5623 contained in the data storage component of cartridge #3 5603 describes that cartridge #3 5603 contains a specimen that is targeted to treat skin feature of "brown spot", with method of use being a Unit Volume of the specimen contained in cartridge #3 5603 is targeted to treat skin feature "brown spot" that is graded as Grade 5.

The electronic control unit 17 of FIG. 56 is same as the control unit 17 of FIG. 2. For two different users, user #1 and user #2, the information storage component 171 of the control unit 17 of the dispensing device 10 of each of the two users contains different unique user data relating to each of the two users own skin care need.

User #1 device unique user data 5604 may be contained in a data structure same as user data structure 5300 of FIG. 53 and is retrievable from the information storage component 171 of the control unit 17 as shown by step 5674. Unique user data 5604 may describe the user #1 skin condition 5605 by including the existing skin features and the corresponding grades as: feature "fine lines" with a grade of 5, feature "wrinkle" with a grade of 8, and feature "brown spot' with a grade of 2. User #2 device unique user data 5609 may be contained in a data structure same as dispenser data structure 5300 of FIG. 53 and is retrievable from the information storage component 171 of the control unit 17 as shown by step 5679. Unique user data 5609 may describe the user #2 skin condition 5610 by including the existing skin features and the corresponding grades as: feature "fine lines" with a grade of 2, feature "wrinkle" with a grade of 1, and feature "brown spot' with a grade of 5. From the comparison of user #1 skin condition 5605 and user #2 skin condition 5610, if a higher grade number means a stronger skin feature, user #2 skin condition 5610 has less issues of "fine lines" and "wrinkle", but more issues of "brown spot", than user #1 skin condition 5605. Listed features and their grades as in user #1 skin condition 5605 and user #2 skin condition 5610 are same as the features 5305, 5307, 5310, and feature grades 5306, 5308, 5311 of user data structure 5300 of FIG. 53.

Listed features "fine lines", "wrinkle" and "brown spot" as in user #1 skin condition 5605 and user #2 skin condition 5610 are respectively treated by the cartridge #1 5601, cartridge #2 5602 and cartridge #3 5603. Because user #1 skin condition 5605 and user #2 skin condition 5610 are different in the grades of same skin features, for user #1 and user #2 to use the same cartridge set composed of cartridge #1 5601, cartridge #2 5602 and cartridge #3 5603 to treat the different grades skin features of their skin, dispensing scheme needs to be different for user #1 and user #2.

FIG. 56 illustrates that the specimen information 5621 of cartridge #1 5601, specimen information 5622 of cartridge #2 5602 and specimen information 5623 of cartridge #3 5603 are retrieved from cartridge #1 5601, cartridge #2 5602 and cartridge #3 5603 as shown by steps of 5613, and processed together with the unique user data 5604, as shown by step 5647, from user #1 dispensing device, to produce user #1 cartridge set dispensing scheme 5607 that specifies dispensing recipe 5608 as: 1.0 UV specimen dispensing from cartridge #1 5601, 1.6 UV specimen dispensing from cartridge #2 5602 and 0.4 UV specimen dispensing from cartridge #3 5603. Calculation of user #1 dispensing recipe 5608 as illustrated in FIG. 56 is by a proportional calculation, which ratios each skin feature's grade as in user #1 skin condition 5605 relative to the base grade of same skin feature from the corresponding cartridge among the cartridge set. For example, for user #1, as "fine lines" grade on user #1 skin is 5, which is same as the base grade 5 as in the specimen information 5621 of cartridge #1 5601, the dispensed specimen volume from cartridge #1 5601 is then calculated as (5/5×1 UV)=1.0 UV; while "wrinkle" grade on user #1 skin is 8, which is larger than the base grade 5 as in the specimen information 5622 of cartridge #2 5602, the dispensed specimen volume from cartridge #2 5602 is then calculated as (8/5×1 UV)=1.6 UV; "Brown spot" grade on user #1 skin is 2, which is smaller than the base grade 5 as in the specimen information 5623 of cartridge #3 5603, the dispensed specimen volume from cartridge #3 5603 is then calculated as (2/5×1 UV)=0.4 UV. It needs to be noted that the proportional calculation method is only used in FIG. 56 and other figures of this invention as an example and for explanation purpose only. Actual method of calculation of optimal dispensing recipe 5608 may follow a different algorithm, which may be stored in the "Algorithm to Match User Feature" 5409 and 5413 sections of dispenser data structure 5400 of FIG. 54, or sections 5509 and 5519 of data structures 5500 and 5550 of FIG. 55A and FIG. 55B, and which data structures may be the specimen information 5621, 5622, 5623. Calculation of the dispensing recipe 5608 from the specimen information 5621, 5622, 5623 and the user #1 unique user data 5604 may be performed by any of: information processing component 172 of the control unit 17 in the dispensing device of user #1, for example dispensing device 4902 of FIG. 50; a personal computing device 5020 of FIG. 50, which may communicate with the dispensing device 4902 as 5037 of FIG. 50; a remote server of a beauty cloud 5040 of FIG. 50, which may communicate with the dispensing device 4902 of FIG. 50 by a data link directly, or through software and data interface via a personal computing device 5020 as 5024 of FIG. 50.

Follow similar calculation method, user #2 cartridge set dispensing scheme 5611 with dispensing recipe 5612 may also be calculated from the specimen information 5621, 5622, 5623 as shown by 5614 in FIG. 56, together with the user #2 unique user data 5609 as shown by 5691. According to user #2 skin condition 5610, user #2 cartridge set dispensing recipe 5612 specifies as: 0.2 UV specimen dispensing from cartridge #1 5601, 0.4 UV specimen dispensing from cartridge #2 5602 and 1.0 UV specimen dispensing from cartridge #3 5603.

Skin features and their corresponding grades in skin conditions 5605, 5610 and specimen information 5621, 5622, 5623 as in FIG. 56 are used as example for illustration purpose, whereas actual skin features and their grades in application are not limited to listed features in FIG. 56. Examples given in FIG. 56 do not limit how Unit Volume ("UV") is defined for each skin feature. Base grade of specimen information 5621, 5622, 5623 as in FIG. 56 does not limit the actual grading scheme that may be used in application.

Unit Volume ("UV") as used in specimen information 5621, 5622, 5623 in FIG. 56 may be a physical volume, for example a microliter, a milliliter, a five-microliter, a drop, or a single dispense action by a dispensing device, or a specimen volume that is designed for treatment of the base grade, i.e. Grade 5 as in FIG. 56, of each corresponding skin feature. Unit Volume of each of the cartridges 5601, 5602 and 5603 may also be adjusted in consideration of existence of other cartridges in the cartridge set. For a first cartridge, whereas existence of other cartridges in a cartridge set, may increase or decrease the skin feature treatment effectiveness of specimen from said first cartridge after specimen from all cartridges are mixed, due to chemical or physical interactions among the specimen, the UV of said first cartridge specimen dispensing amount will need to be adjusted accordingly. Alternatively, for a first cartridge, existence of other cartridges in a cartridge set, may increase or decrease the skin feature treatment effectiveness of specimen from said first cartridge after specimen from all cartridges are mixed due to same or similar functional elements in specimen from said first cartridge may also exist in specimen from other cartridges, thus the UV of said first cartridge specimen dispensing amount will also need to adjust accordingly.

For a cartridge set, different cartridges can be from different vendors or different brands. For example, cartridges 5601 and 5603 may be from brand A, cartridge 5602 may be from brand B. Cartridge set of cartridges 5601, 5602 and 5603 may be provided to user #1 and user #2 without knowing user skin condition 5605 or 5610, whereas the dispense schemes 5608 and 5612 are obtained by: (1) utilizing user data structure 5300 of FIG. 53, which is stored in cartridges 5601, 5602 and 5603 as specimen information 5621, 5622, 5623, and dispenser data structure 5400 of FIG. 54 which is stored in the information storage component 171; (2) correlating skin features grades in data structures 5300 and 5400; (3) following the method to use 5407, 5411, and algorithm to match user feature 5409, 5413, of data structures 5400; (4) incorporating other relevant information of data structures 5300 and 5400.

Figure 57:
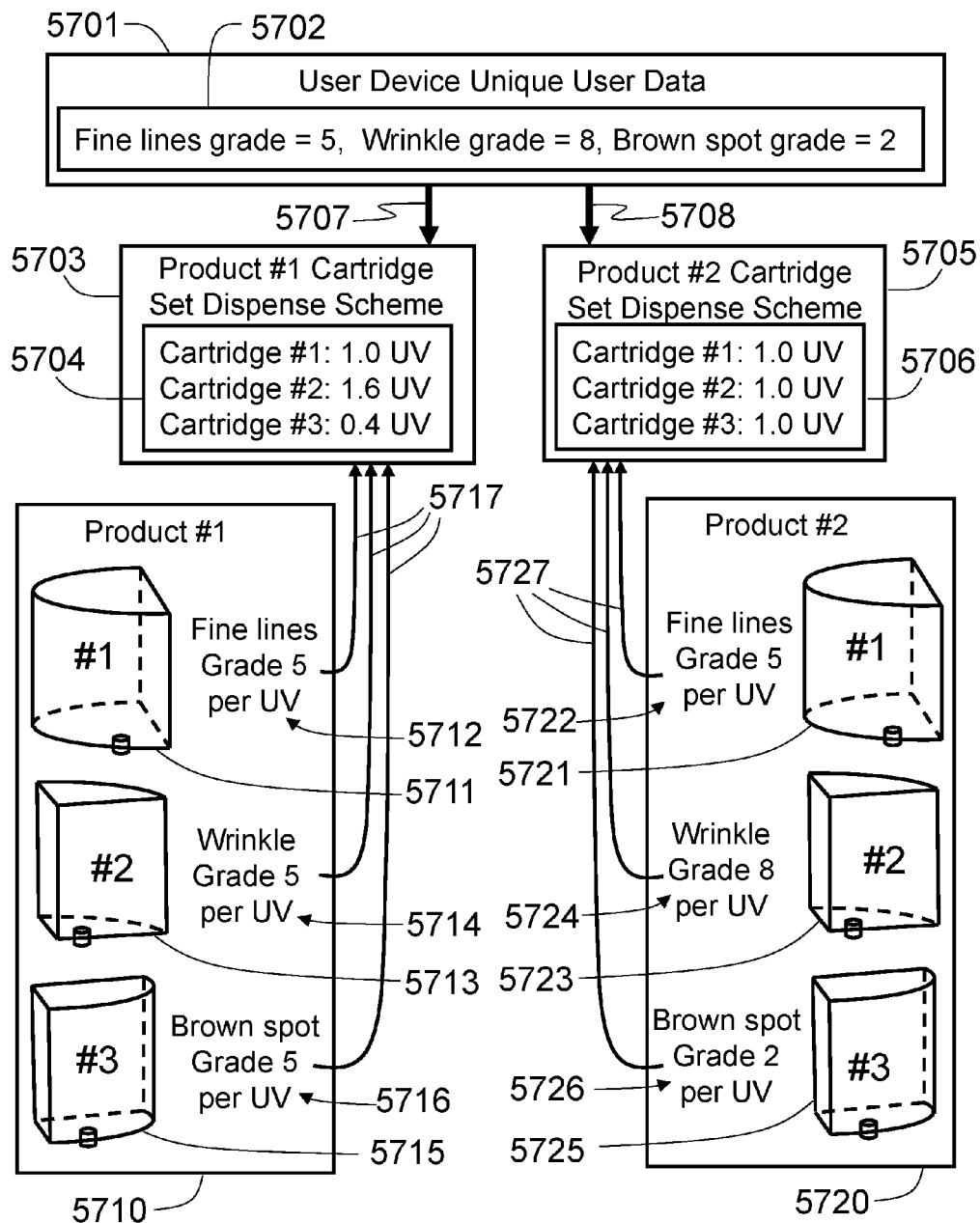
FIG. 57 illustrates methods to provide personalized specimen dispensing schemes for the same user based on the unique user data of the user, and the different dispenser data from two different dispenser sets.

FIG. 57 illustrates examples to provide personalized specimen dispensing schemes 5703 and 5705 for the same user based on the unique user data 5701 of the user and the different dispenser data from two different dispenser sets 5710 and 5720. User device unique user data 5701 and user skin condition 5702 of FIG. 57 are same as user #1 device unique user data 5604 and user #1 skin condition 5605 of FIG. 56. Product #1 5710 cartridge set contains cartridge #1 5711, cartridge #2 5713 and cartridge #3 5715, which are same as cartridge #1 5601, cartridge #2 5602 and cartridge #3 5603 of FIG. 56, whereas the specimen information 5712, 5714 and 5716 are also same as the specimen information 5621, 5622, 5623 of FIG. 56. The product #1 cartridge set dispense scheme 5703 and dispensing recipe 5704 are calculated, with the user device unique user data 5701 as shown by 5707, and with the cartridge specimen information 5712, 5714, 5716 as shown by 5717, using same method as the user #1 cartridge set dispense scheme 5607 and dispensing recipe 5608 are calculated in FIG. 56. In other words, product #1 cartridge set 5710 contains the same cartridges 5601, 5602 and 5603 of FIG. 56, user of FIG. 57 is same as user #1 of FIG. 56, and the product #1 cartridge set dispense scheme 5703 and dispensing recipe 5704 are also same as the user #1 cartridge set dispense scheme 5607 and dispensing recipe 5608 of FIG. 56.

Products #2 cartridge set 5720 contains cartridge #1 5721 that targets same skin feature "fine lines" as cartridge #1 5711 of product #1, and cartridge #2 5723 that targets same skin feature "wrinkle" as cartridge #2 5713 of product #1, and cartridge #3 5725 that targets same skin feature "brown spot" as cartridge #3 5715 of product #1. Cartridges 5721, 5723, and 5725 of product #2 cartridge set 5720 function similarly as cartridges 5711, 5713, and 5715 of product #1 cartridge set 5710. However, cartridge #2 5723 base grade is Grade 8 per UV as compared to cartridge #2 5713 base grade is Grade 5 per UV, indicating each UV of cartridge #2 5723 specimen treats a stronger skin feature of "wrinkle" than each UV of cartridge #2 5713 specimen, if higher grade is regarded a stronger skin feature of "wrinkle". Similarly, cartridge #3 5725 base grade is Grade 2 per UV as compared to cartridge #3 5715 base grade is Grade 5 per UV, indicating each UV of cartridge #3 5725 specimen treats a weaker skin feature than each UV of cartridge #3 5715 specimen. Following same method to obtain product #1 cartridge set dispense scheme 5703, product #2 cartridge set dispense scheme 5705 and dispensing recipe 5706 are calculated with user device unique user data 5701 is acquired as shown by 5708, and with specimen information 5722 of cartridge #1 5721, specimen information 5724 of cartridge #2 5723, specimen information 5726 of cartridge #3 5725 as shown by 5727. From the specimen information 5722, 5724, 5726 and user skin condition 5702, product #2 cartridge set dispensing recipe 5706 specifies as: 1.0 UV specimen dispensing from cartridge #1 5721, 1.0 UV specimen dispensing from cartridge #2 5723 and 1.0 UV specimen dispensing from cartridge #3 5725.

In another embodiment, product #2 may contain different number of cartridges, for example two cartridges, with first cartridge treating both "fine lines" and "wrinkle" features, and second cartridge treating "brown spot". The combination of cartridges in a product cartridge set has no limitation, whereas the method to produce a dispensing recipe according to user skin condition 5702 and specimen information of the cartridges in the cartridge set is the same, as shown in FIG. 57.

Figure 58:
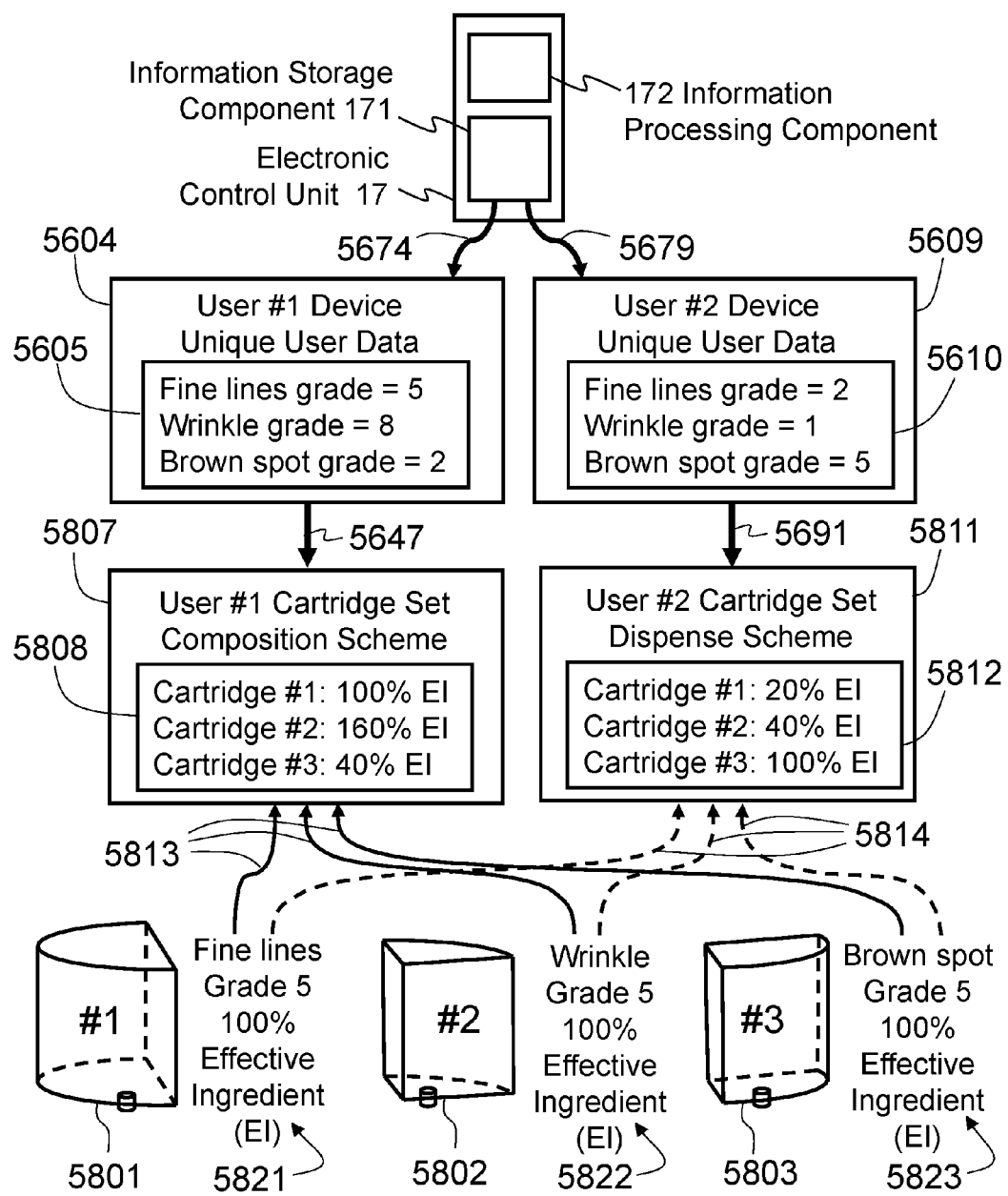
FIG. 58 illustrates methods to provide personalized specimen recipes for two different users based on the unique user data of each user and providing personalized dispenser sets with the same dispensers having different compositions for the two different users.

FIG. 58 illustrates methods to provide personalized specimen composition recipes 5808 and 5812 for two different users, user #1 and user #2, based on the unique user data 5604 and 5609 of each user, and providing personalized dispenser set to the different user with same dispensers that have different compositions. FIG. 58 is substantially similar to FIG. 56, except that the dispense set, or cartridge set, which are composed of cartridge #1 5801, cartridge #2 5802 and cartridge #3 5803, is provided to a user with adjusting the composition of the specimen contained within each cartridge of 5801, 5802, 5803, such that specimen is dispensed from each cartridge in a pre-determined volume, but having a composition that matches to each user's own skin care need. Compared to FIG. 56, FIG. 58 is different in specimen information 5821, 5822, 5823, and also different in method to produce cartridge set composition schemes 5807 and 5811. Cartridges 5801, 5802 and 5803 are substantially same as cartridges 5601, 5602, 5603 in structure, function, components as described in FIG. 56, whereas cartridge 5801 targets same skin feature of "fine lines" as cartridge 5601, cartridge 5802 targets same skin feature of "wrinkle" as cartridge 5602, and cartridge 5803 targets same skin feature of "brown spots" as cartridge 5603.

Specimen information 5821 describes that cartridge #1 5801 contains a specimen that is targeted to treat skin feature of "fine line", with method of use being modifying the Effective Ingredient ("H") of specimen contained in cartridge #1 5801 that is targeted to treat skin feature "fine line" graded as Grade 5 with 100% EI. The skin feature of "fine line" and method of use as in specimen information 5821 may be stored in dispenser data structure same as any of the dispenser data structures 5400, 5500, and 5550 of FIG. 54, FIG. 55A and FIG. 55B, whereas skin feature "fine line" is same as any of the features 5406, 5410 of FIG. 54 or any of the features 5506 and 5516 of FIG. 55A and FIG. 55B, and whereas the reference grade "Grade 5" is same as any of the feature base grades 5408, 5412 of FIG. 54 or any of the feature base grades 5508 and 5518 of FIG. 55A and FIG. 55B, and whereas the method to use, "Grade 5 100% Effective Ingredient (EI)" may be defined as any of the "method to use" 5407, 5411 of FIG. 54, or any of the method 5507 and 5517 of FIG. 55A and FIG. 55B. Specimen information 5822 describes that cartridge #2 5802 contains a specimen that is targeted to treat skin feature of "wrinkle", with method of use being modifying the Effective Ingredient ("EI") of specimen contained in cartridge #2 5802 being targeted to treat skin feature "wrinkle" that is graded as Grade 5 with 100% EI. Specimen information 5823 describes that cartridge #3 5803 contains a specimen that is targeted to treat skin feature of "brown spot", with method of use being modifying the Effective Ingredient ("H") of specimen contained in cartridge #3 5803 is targeted to treat skin feature "brown spot" that is graded as Grade 5 with 100% EI.

Effective ingredient ("EI") of specimen information 5821, 5822, and 5823 is used as an example to describe the effective elements amount, for example by percentage (%), in the composition of the specimen contained in each of the cartridges 5801, 5802 and 5803, whereas the effective elements function to treat skin features of each of the said specimen information to achieve the skin care purpose of each of the said cartridges. Effective ingredient can be described as a certain amount of weight, for example in units of gram, milligram and microgram, or as a certain volume, for example microliter or milliliter, or as other chemical or physical measurements, of the effective skin care elements contained in a unit volume, or unit weight, or a unit measurement of the specimen contained in each of the cartridges 5801, 5802 and 5803. For example, 100% EI may be representing effective elements being in weight of 1 milligram per microliter of specimen contained in a cartridge, or 1 milligram per liquid of specimen contained in a cartridge, or 1 milligram per dispensing action of specimen from a cartridge, whereas a 60% EI represents effective elements being in weight of 0.6 milligrams per microliter of specimen contained in a cartridge, or 0.6 milligrams per liquid of specimen contained in a cartridge, or 0.6 milligrams per dispensing action of specimen from a cartridge. However, other methods to describe a composition of specimen may also be used, without limitation, to describe EI. Different cartridges 5801, 5802, and 5803 specimen information 5821, 5822, 5823 may also have different unit volume, unit weigh or unit measurement in definition of EI.

Similar as in FIG. 56, FIG. 58 illustrates that the specimen information 5821 of cartridge #1 5801, specimen information 5822 of cartridge #2 5802 and specimen information 5823 of cartridge #3 5803 are retrieved from cartridge #1 5801, cartridge #2 5802 and cartridge #3 5803 as shown by 5813, and processed together with the unique user data 5604, as shown by 5647, from user #1 dispensing device to produce user #1 cartridge set composition scheme 5807 that specifies composition recipe 5808 as: 100% EI in specimen of cartridge #1 5801, 160% EI in specimen of cartridge #2 5802 and 40% EI in specimen of cartridge #3 5803. Calculation of user #1 composition recipe 5808 as illustrated in FIG. 58 is also by a proportional calculation as an example, which ratios each skin feature's grade as in user #1 skin condition 5605 relative to the base grade of same skin feature from the corresponding cartridge among the cartridge set. For example, for user #1, as "fine lines" grade on user #1 skin is 5, which is same as the base grade 5 as in the specimen information 5821 of cartridge #1 5801, the desired specimen effective ingredient composition in cartridge #1 5801 is then calculated as (5/5×100% EI)=100% EI; while "wrinkle" grade on user #1 skin is 8, which is larger than the base grade 5 as in the specimen information 5822 of cartridge #2 5802, the desired specimen effective ingredient composition in cartridge #2 5802 is then calculated as (8/5×100% EI)=160% EI; "Brown spot" grade on user #1 skin is 2, which is smaller than the base grade 5 as in the specimen information 5823 of cartridge #3 5803, the desired specimen effective ingredient composition in cartridge #3 5803 is then calculated as (2/5×100% EI)=40% EI. Calculation of the composition recipe 5808 from the specimen information 5821, 5822, 5823 and the user #1 unique user data 5804 may be performed by any of: information processing component 172 of the control unit 17 in the dispensing device of user #1, for example dispensing device 4902 of FIG. 50; a personal computing device 5020 of FIG. 50, which may communicate with the dispensing device 4902 as 5037 of FIG. 50; a remote server of a beauty cloud 5040 of FIG. 50, which may communicate with the dispensing device 4902 of FIG. 50 by a data link directly, or through software and data interface via a personal computing device 5020 as 5024 of FIG. 50.

Following similar calculation method to calculate cartridge set composition recipe 5808, user #2 cartridge set composition scheme 5811 with dispensing recipe 5812 may also be calculated from the specimen information 5821, 5822, 5823 as shown by 5814 in FIG. 58, together with the user #2 unique user data 5609 as shown by 5691. According to user #2 skin condition 5610, user #2 cartridge set composition recipe 5812 specifies as: 20% EI in specimen from cartridge #1 5801, 40% EI in specimen from cartridge #2 5802 and 100% EI in specimen from cartridge #3 5803.

With the same type of cartridges 5801, 5802 and 5803, different than in FIG. 56, a same cartridge from cartridge sets of user #1 and user #2 do not dispense different amount of specimen, as was done in FIG. 56, but rather dispense substantially similar amount of specimen, with specimen having different composition of the effective ingredient for user #1 and user #2 as determined by the composition recipes of 5808 and 5812. In other words, the specimen composition contained in the same type of cartridge may be made different for different user according to each user's own skin feature and skin condition. The different specimen composition in same type of cartridge for different user may be realized by a process of customized specimen composition pre-filling of the cartridge according to the composition scheme 5808 and 5812, such that each of the cartridges 5801, 5802 and 5803 is filled with a composition according to composition recipe 5808 before being provided to user #1 to use, and filled with a composition according to recipe 5812 before being provided to user #2 to use. Alternatively, in the embodiment where at least one of the cartridges 5801, 5802 and 5803 may contain sub-compartments, for example similar to cartridge 4313 containing sub-compartments 4301, 4311 and 4312 as in FIG. 43 as well as other relevant components, wherein some sub-compartment contains effective ingredients, and other compartments contain non-effective ingredients, then the effective ingredient percentage value as specified in composition recipes 5808 and 5812 may be realized by built-in valves, flow gates, or in combination of both, such that dispensed effective ingredients and non-effective ingredients may be dispensed in various amount or relative volume to make the final specimen dispensed from the cartridge contain the correct percentage of the effective ingredient following composition recipes 5808 and 5812.

Skin features and their corresponding grades in specimen information 5821, 5822, 5823 as in FIG. 58 are used as example for illustration purpose, whereas actual skin features and their grades in application are not limited to listed features in FIG. 58. Examples given in FIG. 58 do not limit how composition effective ingredient (EI) is defined for each skin feature. Base grade of specimen information 5821, 5822, 5823 as in FIG. 58 does not limit the actual grading scheme that may be used in application.

Effective ingredient (EI) in the value of 100% percentage as used in specimen information 5821, 5822, 5823 in FIG. 58 may be based on the strength of effective ingredient, or effective elements, in a predetermined physical volume of specimen, for example a microliter, a milliliter, a five-microliter, a drop, or a single dispense action by a dispensing device, or a specimen volume that is designed for treatment of the base grade, i.e. Grade 5 as in FIG. 58, of each corresponding skin feature. Effective ingredient (EI) percentage of each of the cartridges 5801, 5802 and 5803 may also be adjusted in consideration of existence of other cartridges in the cartridge set. For a first cartridge, whereas existence of other cartridges in a cartridge set, may increase or decrease the skin feature treatment effectiveness of specimen effective ingredient from said first cartridge after specimen from all cartridges are mixed, due to chemical or physical interactions among the specimen, the EI of said first cartridge specimen dispensing will need to adjust accordingly. Alternatively, for a first cartridge, existence of other cartridges in a cartridge set, may increase or decrease the skin feature treatment effectiveness of specimen from said first cartridge after specimen from all cartridges are mixed due to same or similar functional elements in specimen from said first cartridge may also exist in specimen from other cartridges, thus the EI of said given cartridge specimen dispensing will need to adjust accordingly.

For a cartridge set, different cartridges can be from different vendors or different brands. For example, cartridges 5801 and 5803 may be from brand A, cartridge 5802 may be from brand B. Cartridge set of cartridges 5801, 5802 and 5803 may be provided to user #1 and user #2 after knowing user skin condition 5605 or 5610 and implementing the composition recipes 5808 and 5812 to the cartridges 5801, 5802 and 5803, whereas the composition recipes 5808 and 5812 are obtained by: (1) utilizing user data structure 5300 of FIG. 53 and dispenser data structure 5400 of FIG. 54; (2) correlating skin features grades in data structures 5300 and 5400; (3) following the method to use and algorithm of data structures 5400; (4) incorporating other relevant information of data structures 5300 and 5400.

In FIG. 58, as cartridges 5801, 5802 and 5803 have the specimen contained therein being adjusted of the composition to match to each individual user, user #1 and user #2, through a possible refill or order with customized compositions recipes 5808 and 5812, cartridges 5801, 5802 and 5803 may not have an embedded data storage device 142 of FIG. 2, as all necessary information required to match to user's skin care need is already included in the various specimen composition, whereas a dispensing device 10 of FIG. 2 only need to dispense the specimen from cartridges 5801, 5802 and 5803 in fixed volume values and final composition of the dispensed specimen will be automatically matching to the each user's own skin condition.

Figure 59:
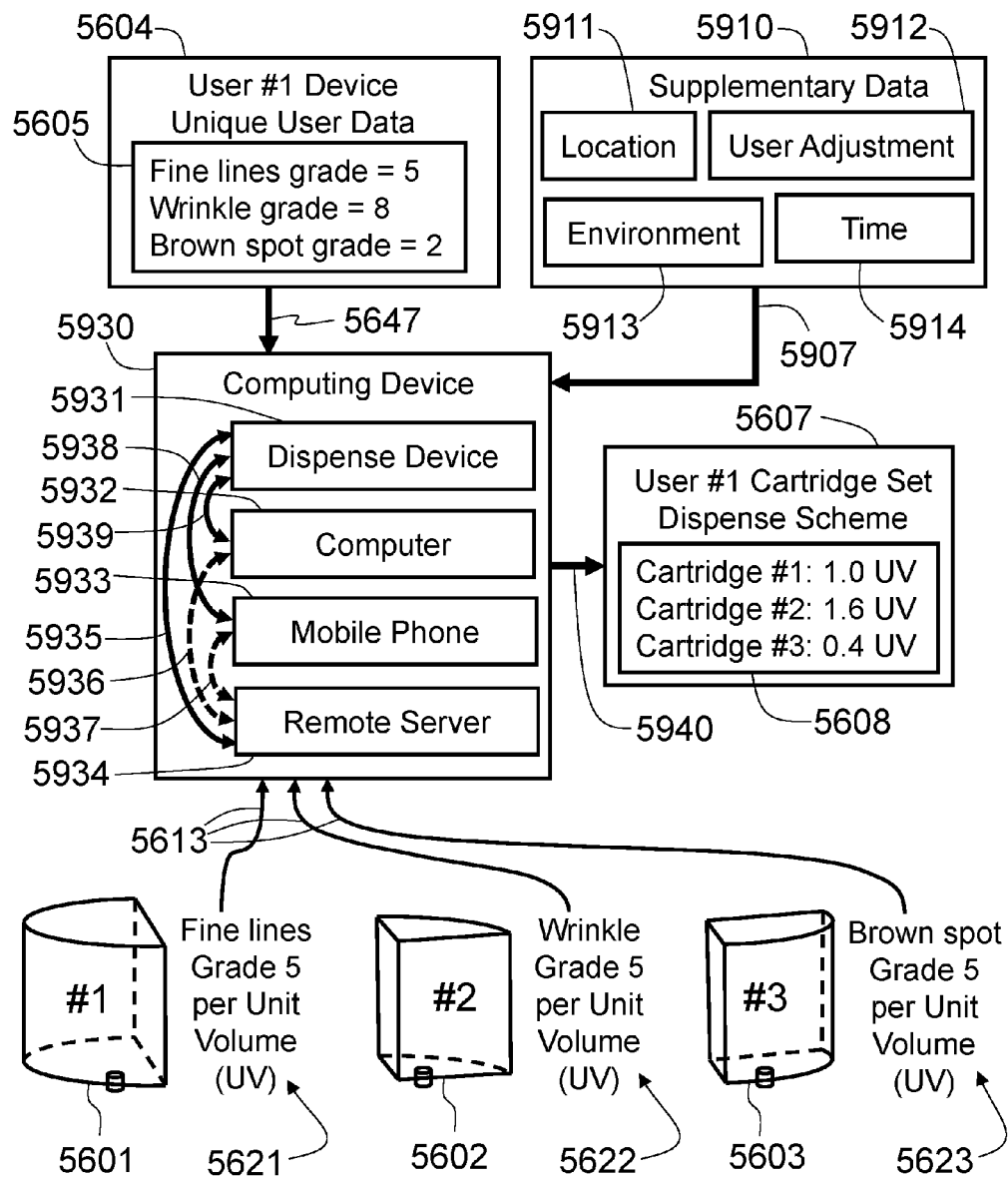
FIG. 59 illustrates methods to calculate personalized dispenser dispensing scheme using unique user data stored in dispensing device, and dispenser data stored in the dispenser set.

FIG. 59 illustrate a method to provide personalized specimen dispensing scheme 5607 with cartridge dispensing recipe 5608 for a user #1 based on the unique user data 5604 from user #1 dispensing device and dispenser data from a dispenser set. FIG. 59 illustrates a more detailed description of one of the methods as illustrated in description of FIG. 56. FIG. 59 illustrates same cartridges 5601, 5602, 5603, same specimen information 5621, 5622 and 5623, same user #1 device unique user data 5604, same user #1 skin condition 5605, same user #1 cartridge set dispense scheme 5607 and same cartridge set dispensing recipe 5608 as illustrated in FIG. 56.

Same as in FIG. 56, FIG. 59 illustrates that the specimen information 5621 of cartridge #1 5601, specimen information 5622 of cartridge #2 5602 and specimen information 5623 of cartridge #3 5603 are retrieved from cartridge #1 5601, cartridge #2 5602 and cartridge #3 5603 as shown by 5613, and processed together with the unique user data 5604, as shown by 5647, in a computing device 5930, to produce user #1 cartridge set dispensing scheme 5607, as shown by 5940, that specifies dispensing recipe 5608 as: 1.0 UV specimen dispensing from cartridge #1 5601, 1.6 UV specimen dispensing from cartridge #2 5602 and 0.4 UV specimen dispensing from cartridge #3 5603, whereas the method of calculation is same as described for FIG. 56. Calculation of the dispensing recipe 5608 from the specimen information 5621, 5622, 5623 and the user #1 unique user data 5604 is performed by a computing device 5930, which may be: (1) dispensing device 5931 of user #1, which may contain an information processing component 172 within a control unit 17 as shown in FIG. 56, for example the dispensing device 4902 of FIG. 50; (2) a computer 5932, for example device 5020 of FIG. 50, or a computer, or a laptop, or a tablet computer; (3) a mobile phone 5933, for example a smart phone; or (4) a remote server 5934 that may be part of the beauty cloud 5040 of FIG. 50. During calculation of dispense scheme 5607, dispensing device 5931 may communicate with the computer 5932 by data link 5939, or with the mobile phone 5933 by data link 5938, or with the remote server 5934, by data links 5935, and the remote server 5934 may communicate with the computer 5932 by data links 5936, with the mobile phone 5933 by data links 5937. The data links 5935, 5936, 5937, 5938, 5939 may be in the form of any of: a wireless data network based on WIFI, Bluetooth, or infrared; a direct physical data connection through electrical wires connected to a computer, a mobile phone; or internet connections to access remote server, whereas the dispensing device 5931 may receive device software or firmware updates through said data links.

During calculation of user #1 cartridge set dispense scheme 5607 by the computing device 5930, supplementary data 5910, which may be part of the user data structure 5300 of FIG. 53, is used as an input in the calculation by computing device 5930 as shown by 5907. Supplementary data 5910 may include any data of: location data 5911, user adjustment data 5912, environment data 5913, time data 5914, whereas supplementary data 5910 may contain data that are substantially included in the user personal data 5304 of FIG. 53.

Location data 5911 may be manually input by user #1. Location data 5911 may also be obtained by computing device 5930 through a data network, for example cell phone network or internet, and retrieved from a location data service provider or a location data server. Location data 5911 may also be obtained by a GPS location tracking service that is included in the computing device 5930.

User adjustment data 5912 is user #1 self-input adjustments to the dispense scheme 5607 after calculation of 5940, to reflect user #1 own preference of skin feature treatment that is different than optimal recipe 5608. User adjustment data 5912 may also be extracted from user preference 5313 section of user data structure 5300 of FIG. 53.

Environment data 5913 may be same as the environment data section 5315 of user data structure 5300 of FIG. 53. Environment 5913 may include descriptions of the environment that the user of the specimen dispensing device is exposed to, including any of: temperature, humidity, sun exposure, indoor or outdoor activities, allergen in air, smog exposure, whereas said descriptions of environment may also be accompanied by a date or time of the year to reflect seasonal changes of said descriptions of environment. Environment 5913 may be provided in 5907 as quantitative or qualitative grades. Environment 5913 may be updated manually by a user through the user interface of computing device 5930. Environment 5913 may also be updated automatically through built-in sensors of the computing device 5930. Environment 5315 may also be updated through a data network by the computing device 5930 and through at least one data server, with utilizing a GPS type of location tracking service contained in computing device 5930 and a weather and environment service, whereas the GPS service locates location of the user #1, and the weather service provides current and future environment information according to that user #1 location data provided by the GPS service, and the provided environment information may be used as environment 5913.

Time data 5914 may be any of: time of day, day of week, day of the month, season. Time data 59 may be input manually by user #1 through computing device 5930, or updated through a data network, for example cell phone network or internet, and retrieved from a time data server. Time data 5914 may also be obtained by a GPS location tracking service that is included in the computing device 5930, whereas the GPS service locates location of the user #1 and provides time as the user #1 location as time data 5914.

Figure 60:
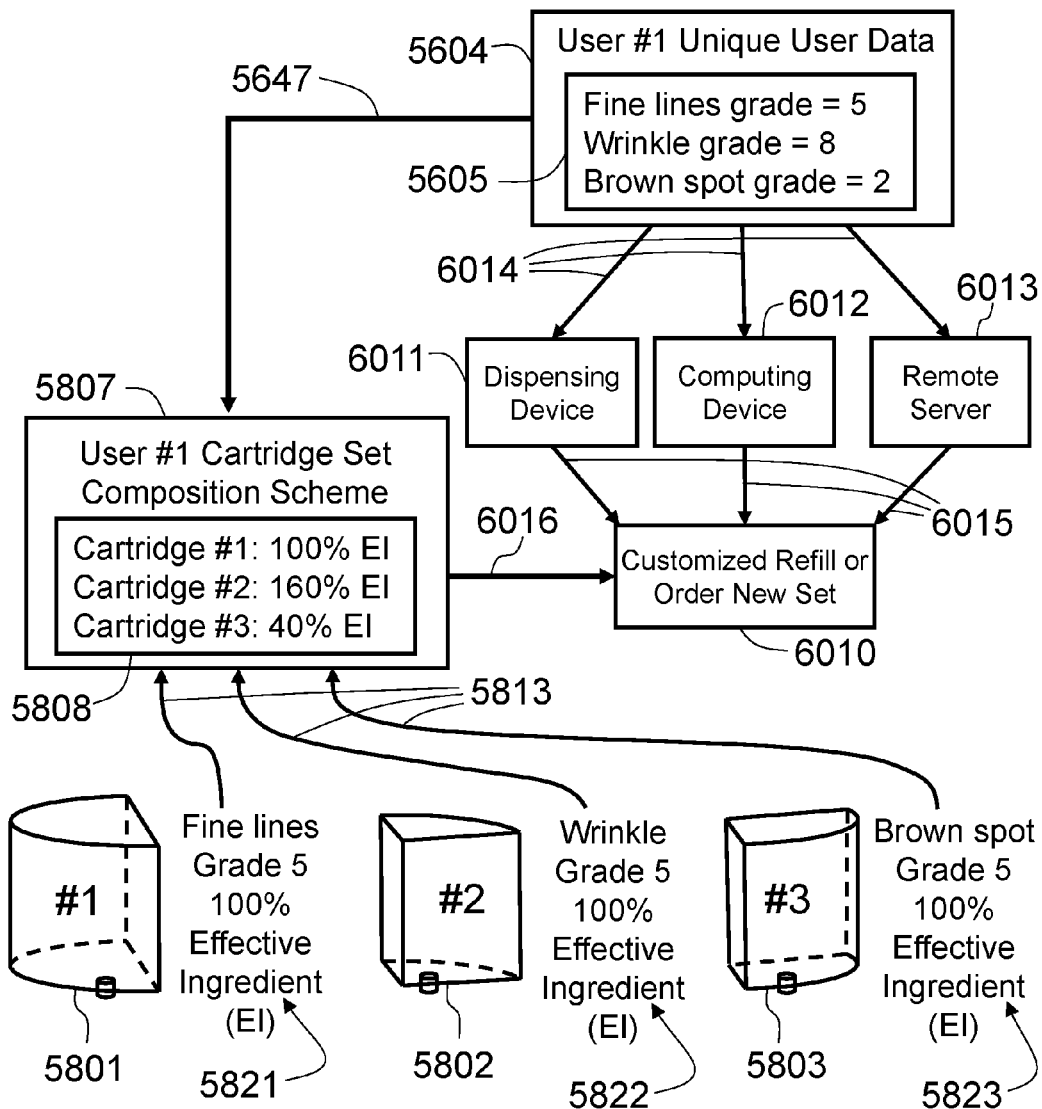
FIG. 60 illustrates process to refill or order personalized composition dispensers using unique user data to realize dispenser composition scheme.

FIG. 60 illustrates a process to refill or order dispenser set as 6010 with personalized composition recipe 5808 using unique user data 5604 to realize dispenser composition scheme 5807. FIG. 60 illustrates a more detailed description of one of the methods as illustrated in description of FIG. 58. FIG. 60 illustrates same cartridges 5801, 5802, 5803, same specimen information 5821, 5822 and 5823, same user #1 device unique user data 5604, same user #1 skin condition 5605, same user #1 cartridge set dispense scheme 5607 and same cartridge set dispensing recipe 5608 as illustrated in FIG. 58. The method of calculating user #1 cartridge set composition scheme 5807, including the cartridge composition recipe 5808, from user #1 unique user data 5604 as shown by 5647, and from the specimen information 5821, 5822, 5823, is same as in FIG. 58 and is similarly described as in FIG. 58, whereas the said calculation may be performed by any of: the dispensing device 6011, a computing device 6012, or a remote server 6013, whereas the 6011, 6012, 6013 devices may be regarded as part of the computing device 5930 of FIG. 59. During said calculation, the user #1 unique user data 5604 are used by a dispensing device 6011, or a computing device 6012, or a remote server 6013, as shown by data input 6014.

After the cartridge set composition scheme 5807, including the cartridge composition recipe 5808, is obtained, a cartridge set of cartridges 5801, 5802, and 5803 may be refiled, or newly ordered, as shown by step 6010, according the composition recipe 5808 of each cartridge for user #1, whereas such refill or new order may be achieved by any of: (a) customized refill or order during skin analysis 5010 of FIG. 50; (b) in a store that supplies the said cartridges set; (c) remote order through a beauty cloud 5040 of FIG. 50 with the dispensing device 6011, or a computing device 6012, or a remote server 6013. Said cartridge set of cartridges 5801, 5802, and 5803 that are customized refilled or newly ordered, may be cartridges that are used with user #1 specimen dispensing device without any data storage device contained in the cartridges 5801, 5802, and 5803. The said customized refill or order new set step 6010 may be initiated and completed by a dispensing device 6011, or a computing device 6012, or a remote server 6013, as shown by data input 6015, utilizing the user #1 cartridge set composition scheme 5807 as shown by data input 6016, whereas the user #1 cartridge set composition scheme 5807 may be either generated by any of the dispensing device 6011, the computing device 6012, and the remote server 6013, or be retrieved from a user personal account 6720 contained in a beauty cloud 6701 of FIG. 67 by any of the dispensing device 6011, the computing device 6012, and the remote server 6013.

Figure 61:
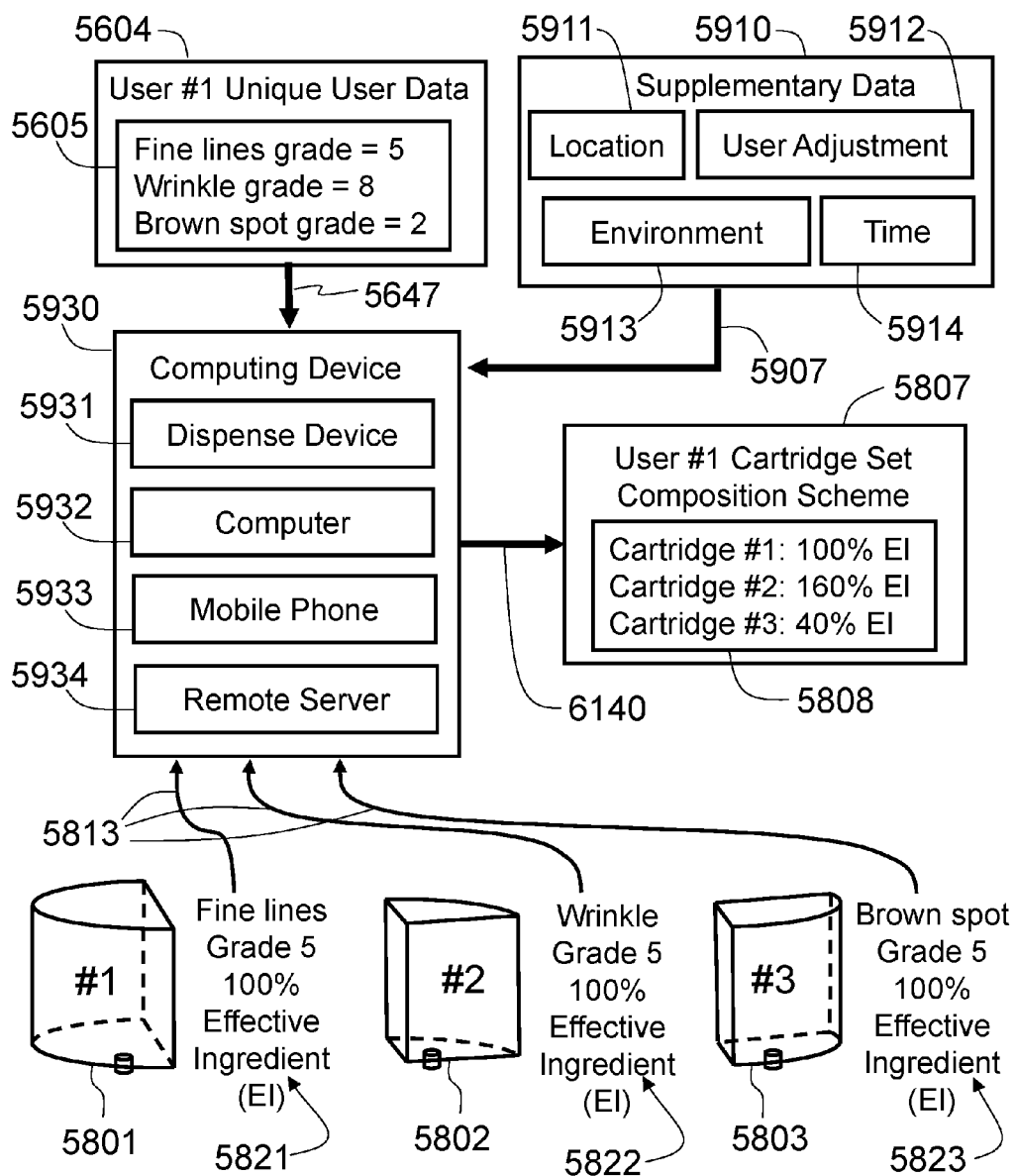
FIG. 61 illustrates methods to realize personalized dispenser composition using unique user data and computing device.

FIG. 61 illustrate a method to provide personalized cartridge set composition scheme 5807 with cartridge composition recipe 5808 for a user #1 based on the unique user data 5604 from user #1 dispensing device and dispenser data from a dispenser set. FIG. 61 illustrates a more detailed description of one of the methods as illustrated in description of FIG. 58, and utilizes the supplementary data 5910 for calculation by the computing device 5930 of FIG. 59. FIG. 61 illustrates same cartridges 5801, 5802, 5803, same specimen information 5821, 5822 and 5823, same user #1 device unique user data 5604, same user #1 skin condition 5605, same user #1 cartridge set dispense scheme 5607 and same cartridge set dispensing recipe 5608 as illustrated in FIG. 58.

Same as in FIG. 58, FIG. 61 illustrates that the specimen information 5821 of cartridge #1 5801, specimen information 5822 of cartridge #2 5802 and specimen information 5823 of cartridge #3 5803 are retrieved from cartridge #1 5801, cartridge #2 5802 and cartridge #3 5803 as shown by 5813, and processed together with the unique user data 5604, as shown by 5647, in a computing device 5930, to produce user #1 cartridge set composition scheme 5807, as shown by 6140, that specifies composition recipe 5808 as: 100% EI of specimen composition in cartridge #1 5801, 160% EI of specimen composition in cartridge #2 5802 and 40% EI of specimen composition in cartridge #3 5803, whereas the method of calculation is same as described for FIG. 58. Calculation of the composition recipe 5808 from the specimen information 5821, 5822, 5823 and the user #1 unique user data 5604 is performed by a computing device 5930 as illustrated in FIG. 59, which may be any of: a dispensing device 5931, a computer 5932, a mobile phone 5933, or a remote server 5934, whereas data links 5935, 5936, 5937, 5938, 5939 in between devices 5931, 5932, 5933 and 5934 may also exist in FIG. 61 and similarly specified as in FIG. 59 description.

During calculation of user #1 cartridge set composition scheme 5807 by the computing device 5930, supplementary data 5910 of FIG. 59, is used as an input in the calculation by computing device 5930 as shown by 5907. Supplementary data 5910 and its components: location data 5911, user adjustment data 5912, environment data 5913, and time data 5914, as same as in FIG. 59 description.

After the user #1 cartridge set composition scheme 5807 and the composition recipe 5808 are obtained, a customized refill or cartridge set ordering as shown by 6010 after 6016 input and 6015 process of FIG. 60 may be performed.

Figure 62:
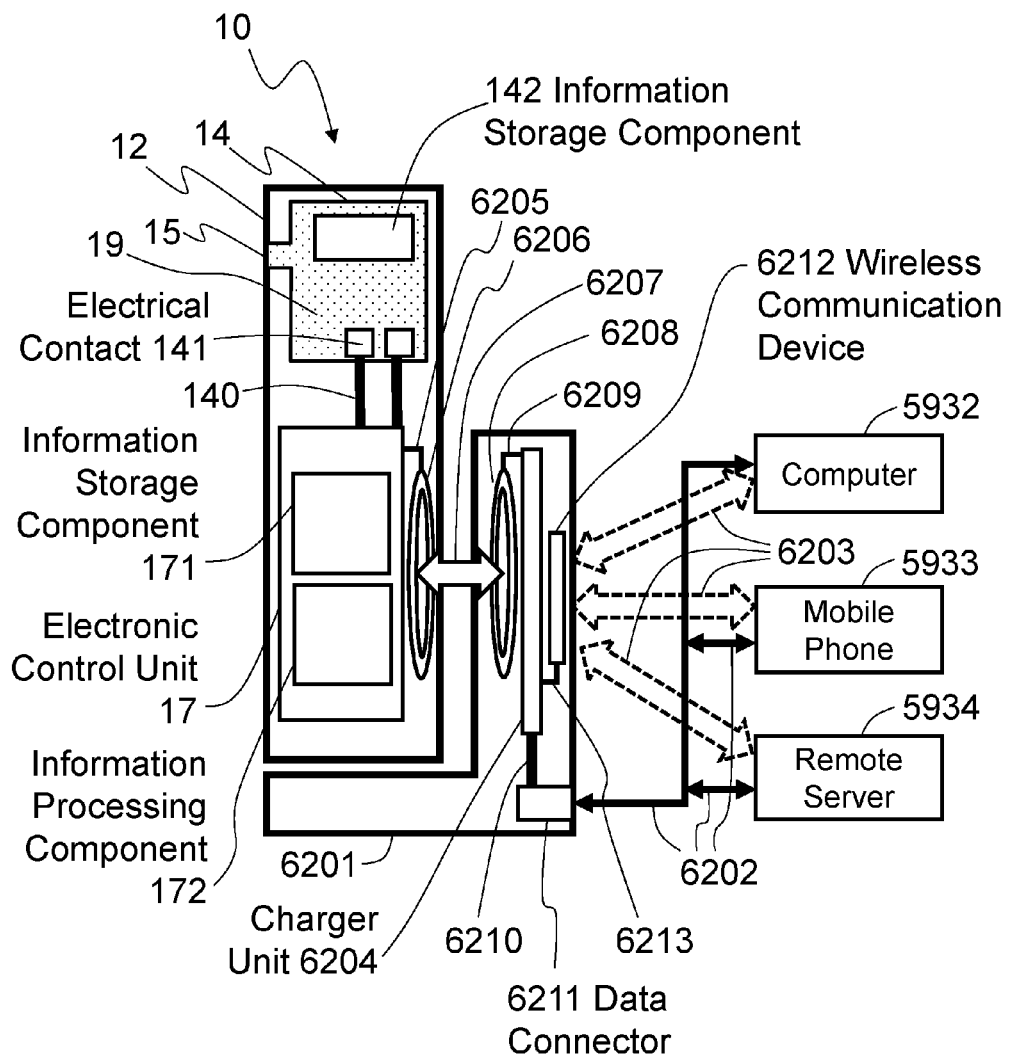
FIG. 62 illustrates data communication methods between computing devices and a dispensing device through a charging station.

FIG. 62 illustrates data communication methods between computing devices and a dispensing device through charging coils. For the data communications 5037 and 5038 between a dispensing device 4902, and skin analysis step 5010 or a personal computing device 5020, as in FIG. 50, or for the data links 5935, 5938 and 5939 between a dispensing device 5931, and a computer 5932, or a mobile phone 5933, or a remote server 5834, as in FIG. 59, the data communications or data links may be accomplished through the dispensing device, illustrated as device 10 in FIG. 62, communicating with a wireless inductive charger 6201 through inductive coupling between a set of charging coils 6206 and 6208. Device 10 of FIG. 62 is same as in FIG. 2, except the device 10 of FIG. 62 contains a charging coil 6206 that is connected to the control unit 17 by electrical connection 6205. The dispensing device 10 is placed in close proximity to a charger 6201, for example with a gap between the opposing surfaces of the device 10 and charger 6201 being less than 5 millimeters, whereas the charger 6201 has another charger circuit 6204 that connects to another charging coil 6208 through electrical connection 6209. In a normal charging operation, the device 10 placed in close proximity to the charger 6201, such that the charging coils 6206 and 6208 are inductively coupled. The charger unit 6204 drives alternating current through the coil 6208 by the electrical connection 6209. Said alternating current in coil 6208 produces alternating electromagnetic field that inductively couples to the coil 6206 through the external bodies of both the charger 6201 and device 10 and generates alternating voltage or current in the coil 6206, whereas the generated alternating voltage or current couples to the control unit 17 through electrical connection 6205 and achieves charging the battery devices that is part of, or connected to, the control unit 17. Inductive charging of device 10 battery device by the charger 6201 through the coils 6206 and 6208 may be achieved by an alternating current applied to the coil 6208 with a first frequency.

In addition to charging function, coils 6206 and 6208 may also provide means for digital data communication to achieve data communications 5037 and 5038 of FIG. 50, or the data links 5935, 5938 and 5939 of FIG. 59. Control unit 17 and charger unit 6204 may also communicate analog or digital data between each other, for example user data structure 5300 of FIG. 53, or dispenser data structure 5400 of FIG. 54, or any wireless communication protocol similar to 802.11, Bluetooth, TCP/IP, and transmit the data protocol from device 10, by inductive coupling between coil 6206 and coil 6208, whereas said analog or digital data transmission is performed by modulating an alternating electrical voltage or current signal with a second frequency. The second frequency is substantially different than the first frequency, for example first frequency may be smaller than 1 MHz that achieves maximum power transfer through inductive coupling of the coils 6206 and 6208, and second frequency may be higher than 10 MHz that is suitable for data transfer through the coils 6206 and 6208 whereas the coils 6206 and 6208 function as transmitting and receiving antennas of a wireless communication in RF frequencies. During operation, charging and data transfer between the coils 6206 and 6208 may be separately operated, whereas charging at first frequency and data transfer at second frequency are always performed separately, and only a single frequency, first frequency or second frequency, voltage or current signal is produced on the coils 6206 and 6208 at any instant time. Alternatively, charging and data transfer between the coils 6206 and 6208 may be concurrent, whereas charging at first frequency and data transfer at second frequency are performed simultaneously, whereas the signal from the two frequencies are modulated in a single analog signal, for example similar to the frequency-modulated (FM) radio signal or GSM signals in mobile phone communication, whereas the analog signal is transmitted through the coils 6206 and 6208. Each of the control unit 17 and charger unit 6204 have embedded circuits that can separate the signals from the first and second frequencies by frequency based filtering techniques, whereas the first frequency signal is separated and directed to the charging circuit of control unit 17 for charging the device 10 battery, while second frequency signal is separated and directed to a data de-modulation circuit where the transmitted data are recovered from second frequency signal. Charger unit 6204 may also electrically connect through connection 6210 to a data connector 6211, whereas the data connector 6211 may be any of: a USB socket, an internet socket, a lightening connector socket, which can connect to an external electronic device for data communication by a data cable. The connection 6202 represents a physical connection between the data connector 6211 to any of: a computer 5932, a mobile phone 5933, and a remote server 5934. Connection 6202 connecting to computer 5932 and mobile phone 5933 may be by direct data cables, and connection 6202 connecting to remote server 5934 may be by first connecting to an internet gateway, or a router, and then by an internet network. Double arrows of connection 6202 represents data being transmitted in both directions between the charger unit 6204 through the data connector 6211, and computer 5932, mobile phone 5933, and remote server 5934.

During data communication between the dispensing device 10, which is same as the dispensing device 5931 of FIG. 59, and the computer 5932, mobile phone 5933, and remote server 5934, which are also described in FIG. 59, the data from the dispensing device 10 are first transmitted to the charger 6201 charger unit 6204 through coils 6206 and 6208 by inductive coupling at second frequency. After data are received from device 10 by the charger unit 6204, the charger unit 6204 may repackage the received data from device 10 into another data transfer protocols, for example USB data transfer protocol. Alternatively, the charger unit 6204 may keep the received data from device 10 without modification. The charger unit 6204 may then send the repackaged data, or data without modifications, to computer 5932, mobile phone 5933, and remote server 5934 through connector 6211 and connection 6202. The data from computer 5932, mobile phone 5933, and remote server 5934 to be sent to the device 10 are first sent to the charger 6201 charger unit 6204 through connection 6202 and connector 6211. After data are received from computer 5932, mobile phone 5933, and remote server 5934 by the charger unit 6204, the charger unit 6204 may un-package the useful data from a data transfer protocol, or may keep the received data without modification, and then send the un-packaged useful data, or data without modifications, to device 10 through oils 6206 and 6208 by inductive coupling at second frequency. Such data communication accomplishes the data communications 5037 and 5038 of FIG. 50, or the data links 5935, 5938 and 5939 of FIG. 59.

Physical connection 6202 may be replaced by a wireless data connection 6203, whereas a wireless communication device 6212, for example a WIFI antenna or a Bluetooth antenna or optical transmitter and receiver, is connected to the charger unit 6204 by electrical connection 6213. When data are transmitted between the device 10 and computer 5932, or mobile phone 5933, or remote server 5934, data are received from, or transmitted to, computer 5932, mobile phone 5933, and remote server 5934 by the wireless communication device 6212 through wireless data connection 6203, whereas the wireless data connection 6203 may be any of: a WIFI, a Bluetooth, an infrared connection, an optical connection. Charger unit 6204 may provide function of packaging data received from device 10 into required wireless communication protocol, before transmitting to computer 5932, mobile phone 5933, and remote server 5934, or un-packaging data received from computer 5932, mobile phone 5933, and remote server 5934 from said protocol, before transmitting to device 10 through the inductively coupled coils 6206 and 6208.

Through the data connections between the device 10, the charger 6204 and computer 5932, mobile phone 5933, or remote server 5934, as described in FIG. 62, the operation software or firmware or database embedded in the device 10 control unit 17, and the operation software or firmware of the charger unit 6204 in charger 6201, may be updated by any of the computer 5932, mobile phone 5933, or remote server 5934.

Figure 16:
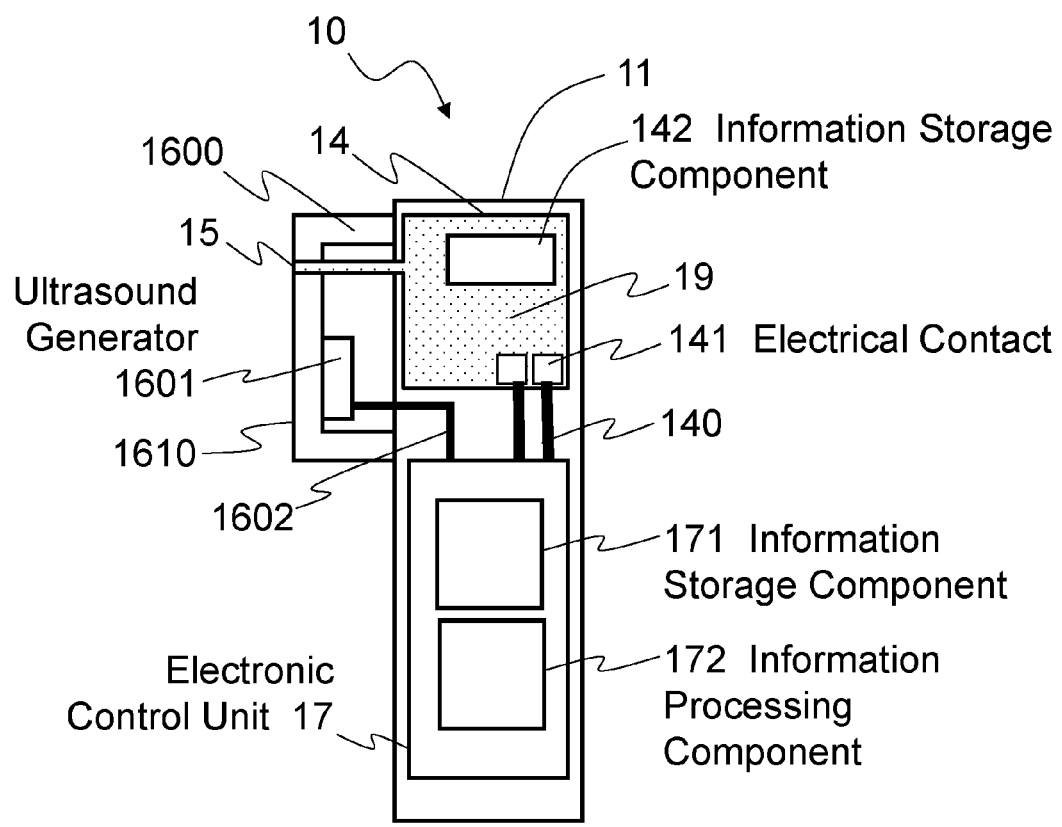
FIG. 16 illustrates a cross-sectional view along the center line 101 of the specimen dispensing device of FIG. 1 that has a skin treatment member, whereas the skin treatment member is an ultrasonic transmission plate.
Figure 63:
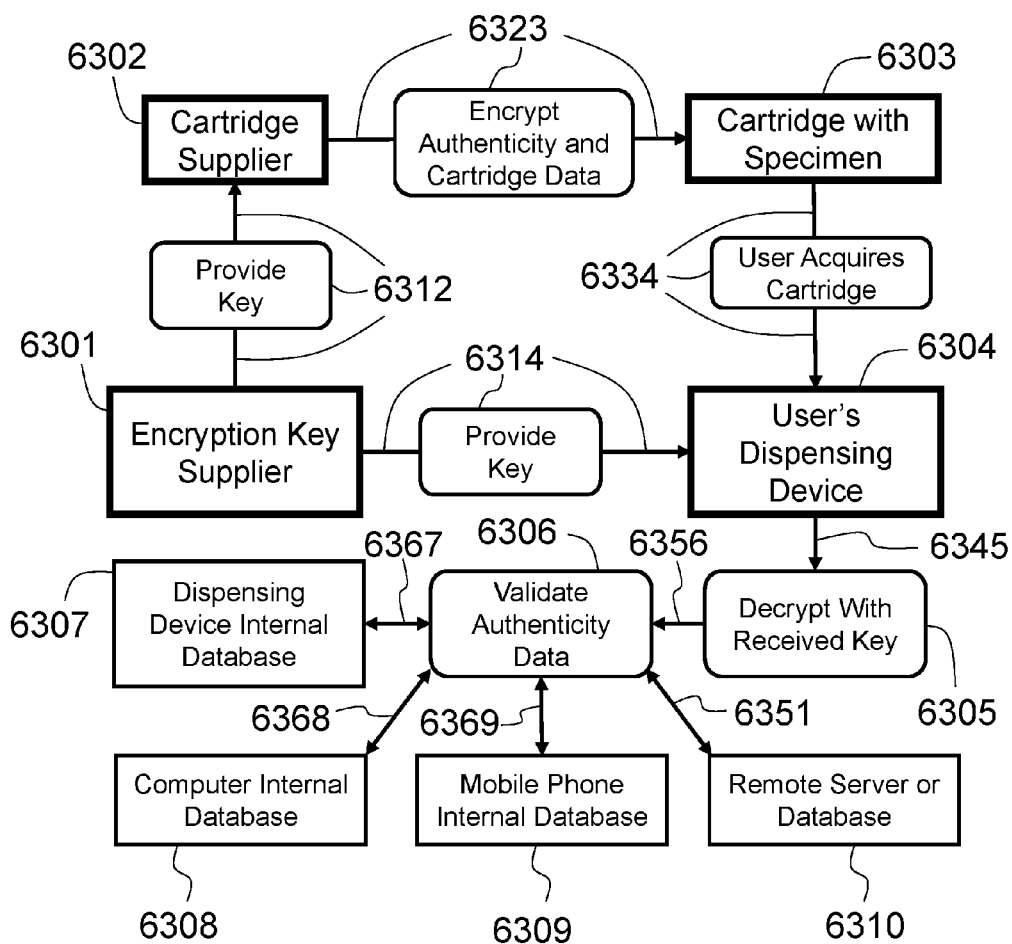
FIG. 63 illustrates a first method to validate the authenticity of a dispenser.

FIG. 63 illustrates a first method to validate the authenticity of a dispenser with information included in the dispenser data structure 5400 of FIG. 54 after the dispenser is installed in a dispensing device, for example after dispenser 14 is installed in the device 10 as in FIG. 15, or after the dispenser 14 is attached to the device 10 as in FIG. 16. Dispenser will be referred to as cartridge in FIG. 63. An encryption key supplier 6301 provides encryption key as shown by step 6312, preferably in digital data format, to a cartridge supplier 6302. Cartridge supplier 6302 encrypts authenticity data and cartridge data of dispenser data structure 5400 of FIG. 54, in step 6323, with the encryption key received in step 6312 and store the dispenser data structure 5400 in a cartridge 6303 containing a specimen that is described by the dispenser data structure 5400. A user acquires cartridge 6303 as in step 6334 and installs cartridge 6303 into the user's dispensing device 6304, as shown by installing cartridge 14 into device 10 in FIG. 14, or attaches cartridge 6303 to the user's dispensing device 6304, as shown by attached cartridge 14 to device 10 in FIG. 15. The encryption key supplier 6301 provides user key as in step 6314 to the user's dispensing device 6304, whereas said user key can be used to decrypt data that are encrypted by the encryption key as provided in step 6312. User key in step 6314 and encryption key in step 6312 may be the same digital information. User key in step 6314 may be provided to user dispensing device 6304 after user dispensing device 6304 extracts cartridge ID information 5402 from the dispenser data structure 5400 of FIG. 54 received from the cartridge 6303, whereas the cartridge ID information 5402 from the dispenser data structure 5400 may be compared to a database maintained in encryption supplier 6301 to retrieve, or compute, the user key to be sent in step 6314. Then user's dispensing device 6304 utilizes the user key received in step 6314, through a data processing unit included in dispensing device 6304 as shown in step 6345, and decrypts the authenticity data and cartridge data of the dispenser data structure 5400 stored in the cartridge 6303 as in step 6305. The decrypted authenticity data of step 6305 are then provided as shown by 6356 to a step 6306 to validate the authenticity data. In step 6306, the decrypted authenticity data may be compared with the dispensing device 6304 internal database 6307 that contains authenticity data information to confirm the validity of the decrypted authenticity data as shown by communication 6367. In step 6306, the decrypted authenticity data may be compared with an internal database 6308 stored in a computer that contains authenticity data information to confirm the validity of the decrypted authenticity data as shown by communication 6368, where communication 6368 may be same as communication 6202 or 6203 of FIG. 62. In step 6306, the decrypted authenticity data may be compared with an internal database 6309 stored in a mobile phone that contains authenticity data information to confirm the validity of the decrypted authenticity data as shown by communication 636, where communication 6369 may be same as communication 6202 or 6203 of FIG. 62. In step 6306, the decrypted authenticity data may be compared with a database 6310 stored in a remote server that contains authenticity data information to confirm the validity of the decrypted authenticity data as shown by communication 6351, where communication 6351 may be same as communication 6202 or 6203 of FIG. 62.

In the case where the cartridge 6303 is not authentic, which may not contain a dispenser data structure 5400, or which may contain a dispenser data structure 5400 that is not encrypted with an encryption key, authenticity of the cartridge 6303 may be invalidated by dispensing device 6304 when dispensing device 6304 does not receive a dispenser data structure 5400 from cartridge 6303, or when dispensing device 6304 detects the dispenser data structure 5400 from cartridge 6303 are not encrypted. In another case where the cartridge 6303 is not authentic, which may contain a dispenser data structure 5400 that is not encrypted with the exact encryption key of step 6312, authenticity of the cartridge 6303 may be invalidated by dispensing device 6304 when dispensing device 6304 cannot decrypt the dispenser data structure 5400 received from cartridge 6303 with the key received in step 6314 as in decryption step 6305 to extract dispenser data structure 5400 in correct data format. In yet another case where the cartridge 6303 is not authentic, which may contain a dispenser data structure 5400 that is encrypted with the exact encryption key of step 6312 and said dispenser data structure 5400 is decrypted by dispensing device 6304 in step 6305, authenticity of the cartridge 6303 may be invalidated by dispensing device 6304 when dispensing device 6304 receives invalid authenticity determination in communications 6367, 6368, 6369 or 6351 in step 6306 after authenticity information of decrypted data structure 5400 is found not authentic by database of 6307, 6308, 6309 or 6310.

Encryption key supplier 6301 may be any of: maker of device 6304; distributor of cartridge 6303 or device 6304; a beauty cloud database or server; a party that is not cartridge maker and not the user, but is capable of providing encryption key; or a mobile phone, or a computer that user uses to order cartridge 6303 from a cartridge supplier 6302.

The encryption key in step 6312 and the user key in step 6314 may be any of: a numerical code, or a character code, or any digital data form. User key of step 6314 may be installed in device during manufacturing of device 6304, for example in the form of a set of keys and the device 6304 chooses the right key for decryption step 6305 from the set of keys. User key of step 6314 may be installed in device 6304 during a software or data file system update of device 6304. User key of step 6314 may be installed in device 6304 by a data transfer protocol during step 6314. User key of step 6314 may be installed in device 6304 during skin analysis 5010 of FIG. 50 through data communication 5038. Both the encryption key of step 6312 and user key of step 6314 may be one of a set of keys maintained by the encryption key supplier 6301, whereas cartridge supplier 6302 may be provided with one of the set of encryption keys, and user device 6304 may be installed with the set of user keys, and during step 6314 encryption key supplier informs device 6304 which one of the installed set of user keys to use to decrypt cartridge data and authenticity data in step 6305.

Both the encryption key of step 6312 and user key of step 6314 may be user specific and may be different for different users, for example they may be generated by user originated seed codes or generated with random seed codes that are produced during each cartridge acquisition transaction by a specific user whereas only a given user's device 6304 and the cartridge 6303 acquired by the same given user have matching encryption key and user key combination, such that decryption in step 6305 may succeed. Both the encryption key of step 6312 and user key of step 6314 may be general keys whereas same keys may be provided for different cartridges in step 6312 or different users in step 6314. Both the encryption key of step 6312 and user key of step 6314 may be generated during a user's ordering of cartridge 6303 with using user data structure 5300 of FIG. 53 to acquire customized cartridges with specimen having customized composition, or cartridge set combination according to methods of FIG. 56 through FIG. 61.

User key of step 6314 may be provided to device 6304 in a communication method that is similar to any of the communications 6367, 6368, 6369 or 6351.

Figure 64:
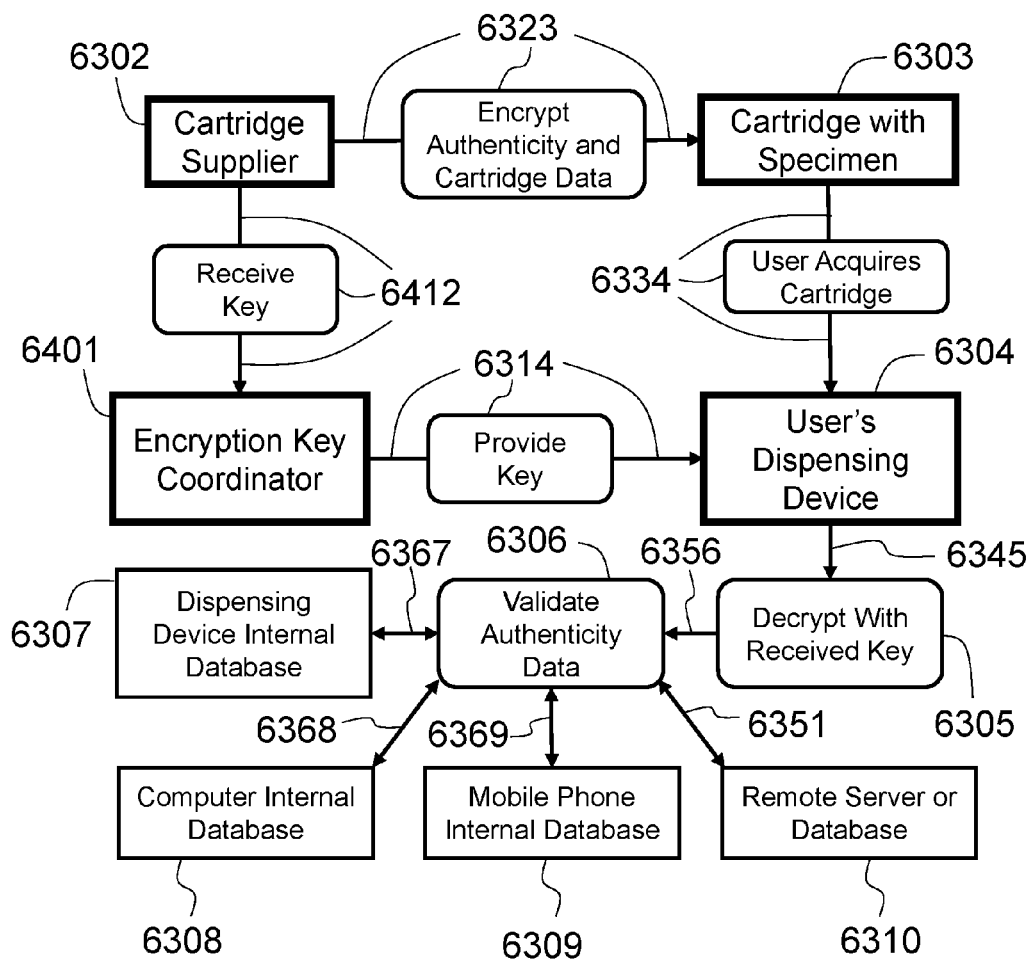
FIG. 64 illustrates a second method to validate the authenticity of a dispenser.

FIG. 64 illustrates a second method to validate the authenticity of a dispenser, whereas every aspect is same as in FIG. 63, except that encryption key supplier 6301 is replaced by an encryption coordinator 6401. During step 6412, cartridge supplier 6302 provides the encryption key it uses in step 6323 to encryption key coordinator 6401. During step 6314, encryption key coordinator 6401 may provide the encryption key it received in step 6412 as user key to device 6304. Alternatively, during step 6314, encryption key coordinator 6401 may provide a user key to device 6304, which user key is generated for, or calculated from, the encryption key received in step 6412, such that the user key may serve the decryption purpose in step 6305. The cartridge supplier 6302 in FIG. 64 may have a set of encryption keys, and cartridge supplier 6302 informs encryption key coordinator 6401 which one of the set of encryption keys it uses in step 6323, whereas the device 6304 in FIG. 64 may store a set of user keys that match to the set of encryption keys that cartridge supplier 6302 has, and whereas in step 6314 encryption key coordinator 6401 informs device 6304 which key of the set of user keys to use for decryption in step 6305, and whereas encryption key coordinator 6401 may not have copies of either the set of the encryption keys that cartridge supplier 6302 has or the set of user keys that device 6305 stores. In FIG. 64 method, encryption key coordinator 6401 may serve as first level authenticity validation, whereas only verified and authentic cartridge supplier 6302, and verified and authentic device 6304 may establish key providing steps of 6412 and 6314 with encryption key coordinator 6401.

Encryption coordinator 6401 may be any of: maker of device 6304; distributor of cartridge 6303 or device 6304; a beauty cloud database or server; a party that is not cartridge maker or the user but is capable of providing encryption key; or a mobile phone, a computer that user uses to order cartridge 6303 from a cartridge supplier 6302.

Figure 65:
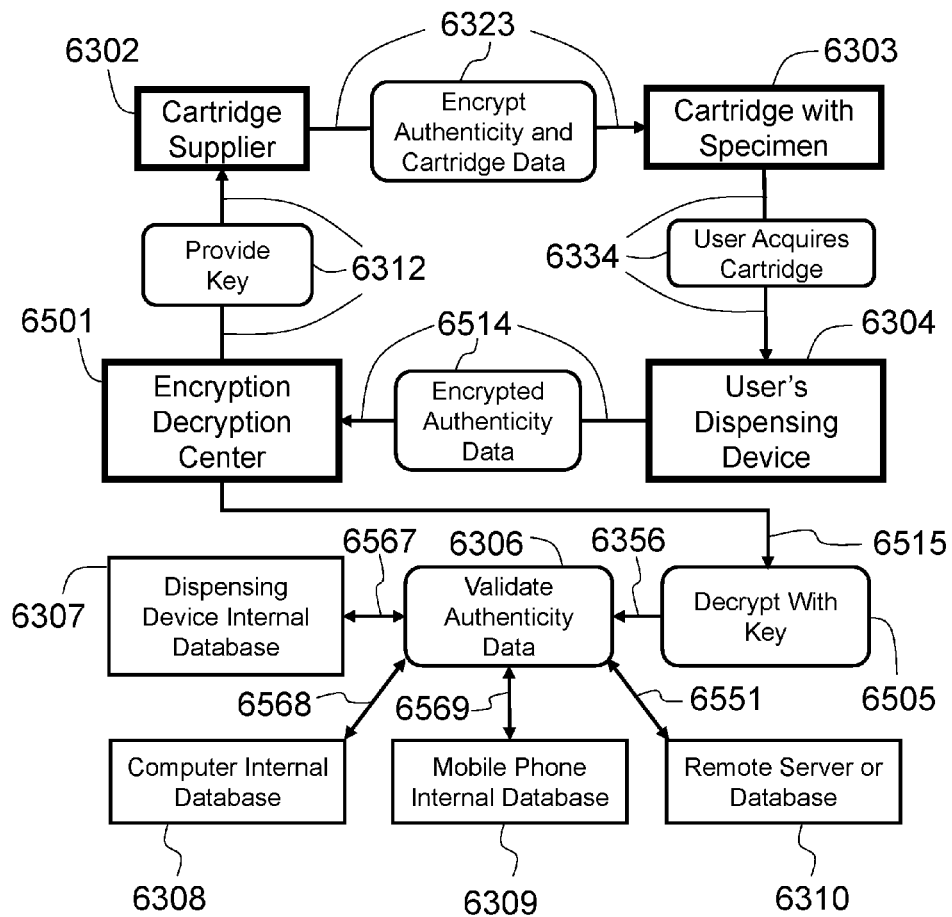
FIG. 65 illustrates a third method to validate the authenticity of a dispenser.

FIG. 65 illustrates a third method to validate the authenticity of a dispenser, whereas every aspect is same as in FIG. 63, except that encryption key supplier 6301 of FIG. 63 is replaced by an encryption/decryption center 6501. After the user's dispensing device 6304 acquires cartridge 6303 in step 6334 and obtained the encrypted dispenser data structure 5400 from cartridge 6303, the dispensing device 6304 sends encrypted authenticity data from the dispenser data structure 5400 as in step 6514 to the encryption/decryption center 6501. Device 6304 may send the encrypted authenticity data from the dispenser data structure 5400 as in step 6514 to the encryption/decryption center 6501 in a communication method that is similar to any of the communications 6367, 6368, 6369 or 6351. After receiving the encrypted authenticity data from the device 6304, encryption/decryption center 6501 provides the decryption service, as shown by step 6515, and decrypts the encrypted authenticity data in step 6505 and forwards to step 6306 for validation of authenticity data similarly as in FIG. 63.

In the case where the cartridge 6303 is not authentic, which may not contain a dispenser data structure 5400, or which may contain a dispenser data structure 5400 that is not encrypted with an encryption key, authenticity of the cartridge 6303 may be invalidated by dispensing device 6304 when dispensing device 6304 does not receive a dispenser data structure 5400 from cartridge 6303, or when dispensing device 6304 detects the dispenser data structure 5400 from cartridge 6303 but encryption/decryption center 6501 finds the dispenser data structure 5400 is not encrypted as expected. In another case where the cartridge 6303 is not authentic, which may contain a dispenser data structure 5400 that is not encrypted with the exact encryption key of step 6312, authenticity of the cartridge 6303 may be invalidated by encryption/decryption center 6501 when encryption/decryption center 6501 cannot decrypt the dispenser data structure 5400 received from device 6304 with the expected decryption key in step 6505 to extract dispenser data structure 5400 in correct data format. In yet another case where the cartridge 6303 is not authentic, which may contain a dispenser data structure 5400 that is encrypted with the exact encryption key of step 6312 and said dispenser data structure 5400 is decrypted by encryption/decryption center 6501 in step 6505, authenticity of the cartridge 6303 may be invalidated by encryption/decryption center 6501 when encryption/decryption center 6501 receives invalid authenticity determination in communications 6567, 6568, 6569 or 6551 in step 6306, whereas communications 6567, 6568, 6569 and 6551 are data connections between the encryption/decryption center 6501 and the database of 6307, 6308, 6309 or 6310, after authenticity information of decrypted data structure 5400 is found not authentic by database of 6307, 6308, 6309 or 6310. After determination of authenticity in step 6306, encryption/decryption center 6501 may send such authenticity determination result back to device 6304 with a data communication similar as any of communications 6367, 6368, 6369 or 6351 of FIG. 63, such that the device 6304 may convey such determination result to the user.

Encryption/decryption center 6501 may be any of: maker of device 6304; distributor of cartridge 6303 or device 6304; a beauty cloud database or server; a party that is not cartridge maker or the user but is capable of providing encryption key and decryption service; or a mobile phone, a computer that user uses to order cartridge 6303 from a cartridge supplier 6302.

Figure 66:
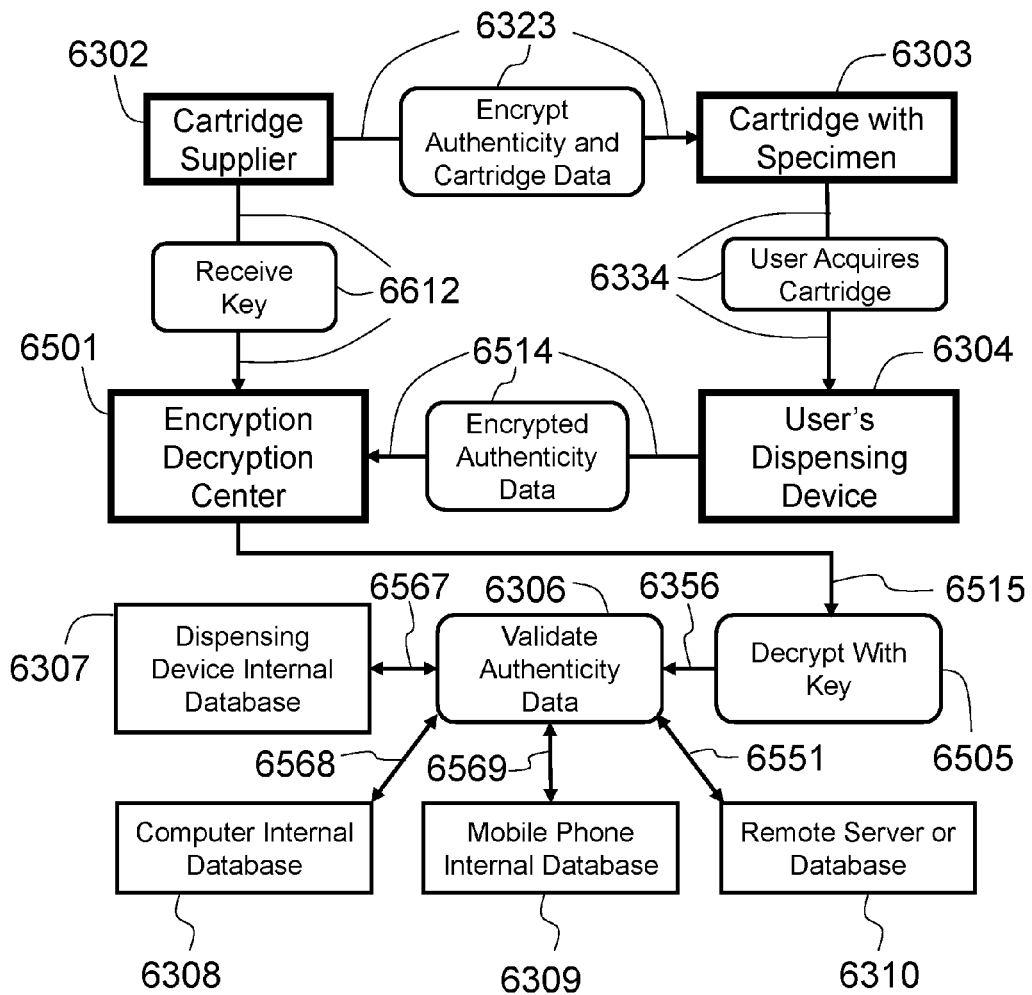
FIG. 66 illustrates a fourth method to validate the authenticity of a dispenser.

FIG. 66 illustrates a fourth method to validate the authenticity of a dispenser, whereas every aspect is same as in FIG. 65, except that during step 6612, cartridge supplier 6302 provides the encryption key it uses in step 6323 to encryption/decryption center 6501. The cartridge supplier 6302 in FIG. 66 may have a set of encryption keys, and cartridge supplier 6302 informs encryption/decryption center 6501 which one of the set of encryption keys it uses in step 6323, whereas the encryption/decryption center 6501 in FIG. 66 may store a set of decryption keys that match to the set of encryption keys that cartridge supplier 6302 has, and whereas in step 6505 the encryption/decryption center 6501 decrypts with the decryption key matching to the received encryption key as in step 6612. In FIG. 66 method, encryption/decryption center 6501 may serve as first level authenticity validation, whereas only verified and authentic cartridge supplier 6302, and verified and authentic device 6304 may establish key providing steps of 6412 and encrypted authenticity data providing step 6514 with encryption/decryption center 6501.

Figure 67:
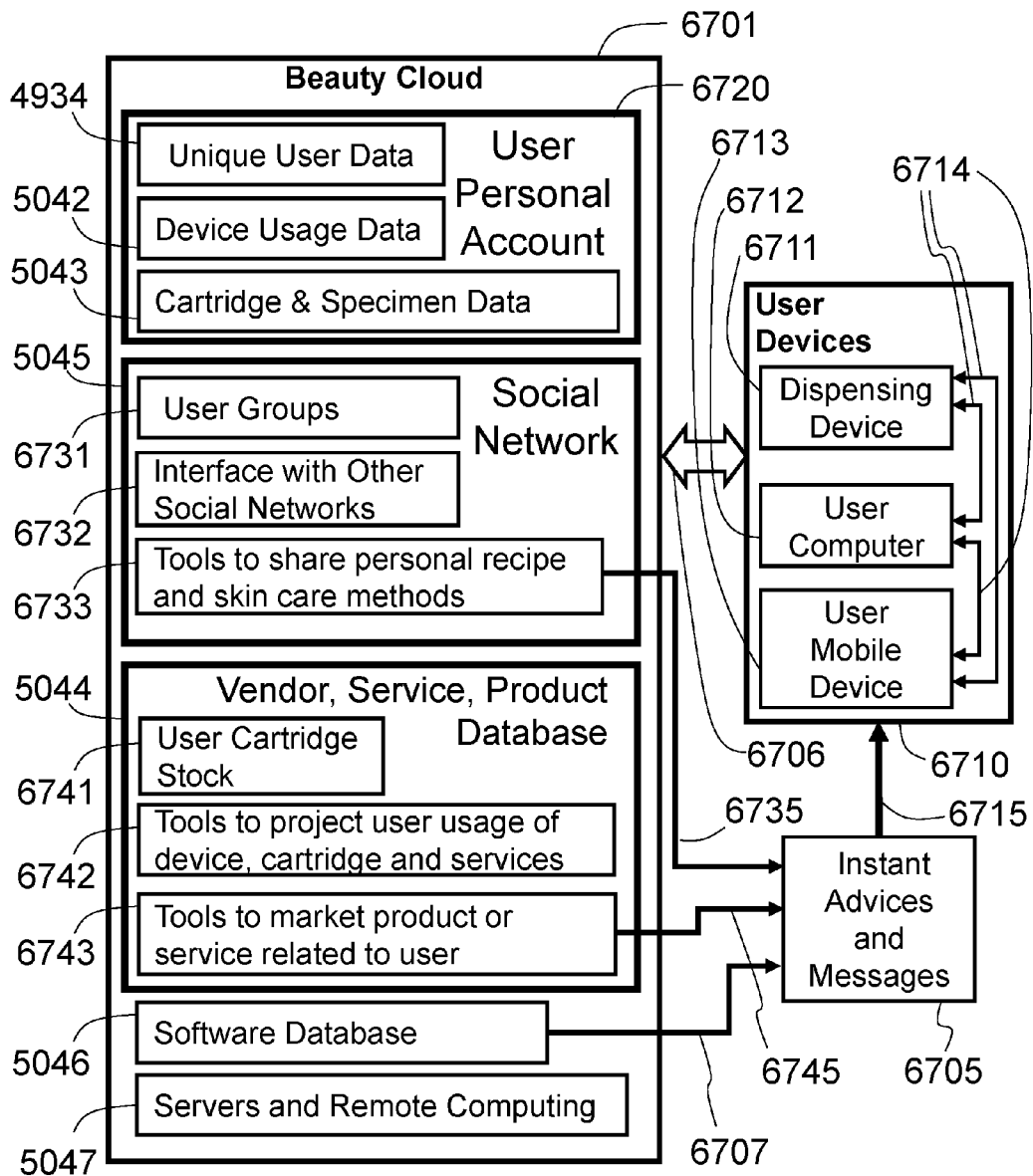
FIG. 67 illustrates components of an internet based beauty cloud and methods of use with user devices.

FIG. 67 illustrates components of an internet beauty cloud 6701 and methods of use with user devices 6710 which includes dispensing device 6711, user computer 6712 and user mobile device 6713. Beauty cloud 6701 is substantially similar to the beauty cloud 5040 of FIG. 50. Dispensing device 6711 is substantially similar to the dispensing device 4902 of FIG. 50. User computer 6712 and user mobile device 6713 are similar to the personal computing device 5020 of FIG. 50. Communication 6706 between beauty cloud 6701 and user devices 6710 is similar to the communication 5024 of FIG. 50. Communications 6714, which are similar to communications 6202 and 6203 of FIG. 62, may exist in between any two of dispensing device 6711, user computer 6712 and user mobile device 6713.

FIG. 67 illustrates that unique user data 4934, device usage data 5042, cartridge and specimen data 5043 of FIG. 50, may be included in a user personal account 6720 maintained in the beauty cloud 6701. Social network 5045 of FIG. 50 is included in beauty cloud 6701 and may have components of: user groups 6731, interface with other social networks 6732 and tools to share personal recipe and skin care methods 6733. Vendor, service, product database 5044 of FIG. 50 is included in beauty cloud 6701 and may have components of: user cartridge stock 6741, tools to project user usage of device, cartridge and service 6742, and tools to market product or service related to user 6743. Software database 5046, as well as servers and remote computing 5047 of FIG. 50 may also be included in beauty cloud 6701. Instant advices and messages 6705 may be initiated by tools to share personal recipe and skin methods 6733 of social network 5045 as shown by 6735, or may be initiated by tools to market product or service related to user 6743 of vendor, service, product database 5044, as shown by 6745, or may be initiated by software database 5046 as shown by 6707. Instant advices and messages 6705 may be displayed or conveyed to a user of the dispensing device 6711, as shown by 6715, similar to instant message 7105 of FIG. 71, or may be displayed or conveyed to a user of the dispensing device 6711 by user computer 6712 and user mobile device 6713. Instant advices and messages 6705 may be initiated by 6735, 6745 and 6707 with consideration of user habit, user location, user time, user environment, and actual dispensing device and cartridge use pattern according to the information stored in unique user data 4934.

User personal account 6720 may be a collection of access rights, passcodes, software features and database that are controllable by each individual user, and also personalized to each individual user's own identification method and access method. For example, the user personal account 6720 may be accessed only by the user owning the user account 6720, whereas the user account 6720 may be an database, which may be secured or encrypted, and accessible with the user providing confidential information, including user name, user password, birthday, identification code or identification digital files, through web pages of an internet browser or through software applications installed in a computer system or mobile communication device. In another embodiment, the user personal account 6720 may be accessed by the user owing the user account 6720 with providing the user's biometrics information, for example the user's finger print, or eye image, or DNA sequence.

Social network 5045 of beauty cloud 6701 has components of user groups 6731, interface with other social networks 6732 and tools to share personal recipe and skin care methods 6733. User groups 6731 are collections of: users who own dispensing device 6711, users who own dispensers and use together with dispensing device 6711, and users who use dispensing device 6711. User groups 6731 may provide an online platform or an online forum for users using same skin care products or sharing same skin care interests to exchange user experience and personalized skin care recipes of using the dispensing device 6711 and cartridges. Interface with other social networks 6732 may be achieved through a software or database tool that can link, exchange, or share activities of each user in user group 6731 with activities of same user in other social networks. For example a user may share the user experience and personalized skin care recipes in user groups 6731 or in other social network platforms with other users. Tools to share personal recipe and skin care methods 6733 may be software or database tools that allow a first user to share or upload skin care related data, for example personalized cartridge set dispensing scheme 5607 or 5611 of FIG. 56, personalized recipe that is adjusted by said first user, or methods of using personalized recipe with dispensing device 6711, to a beauty cloud 6701 or a user groups 6731, and allow a second users to download such skin care related data to the second user's devices 6710. Such sharing of skin care related data by tools to share personal recipe and skin care methods 6733 is further described in FIG. 69. Tools to share personalized recipe and skin care methods 6733 may initiate instant advices as shown by 6735 and messages 6705 to be displayed on user devices 6710 of a user, indicating skin care data or recipes relevant to the said user are uploaded and available for download from, for example, the user groups 5045.

Vendor, service, product database 5044 of FIG. 67 may contain any of: user cartridge stock 6741, tools to project user usage of device, cartridge and service 6742, and tools to market product or service related to user 6743. User cartridge stock 6741 may be a database or software tool that allows a user to access various cartridges available to the user and allows the user to order relevant products according to user's need or desire. User cartridge stock 6741 may also offer venders or service providers the access to the database of the cartridges that a user used or ordered, and evaluate the user's skin care need from the database to provide relevant products and services. Tools to project user usage of device, cartridge and service 6742 may be a database or software tool that allows a user to examine user's own dispensing device and cartridge usage history, usage habit of the user so that user's usage of dispensing device, cartridge and service may be projected and arranged for the user to plan for future product acquisition. Tools to project user usage of device, cartridge and service 6742 may also be a database or software tool that allows vendors or service providers to examine a user's dispensing device and cartridge usage history, usage habit of the user so that user's usage of dispensing device, cartridge and service may be projected and relevant products and service may be recommended to the user. Tools to market product or service related to user 6743 may be a database or software tool that allows vendors or service providers to recommend and provide relevant products and service to a user, utilizing information contained in any of: user personal account 4934, social network 5045, user cartridge stock 6741, and information provided from "Tools that project user usage of device, cartridge and service" 6742. Tools to market product or service related to user 6743 may initiate instant advices and messages 6705 as shown by 6745 to be displayed or conveyed on user devices 6710, indicating relevant products or services being available to said one or more of users.

Software database 5046 may initiate instant advices and messages 6705 as shown by 6707 to be displayed or conveyed on user devices of one or more of users, regarding new software or application update being available for updating the user devices 6710.

Figure 68:
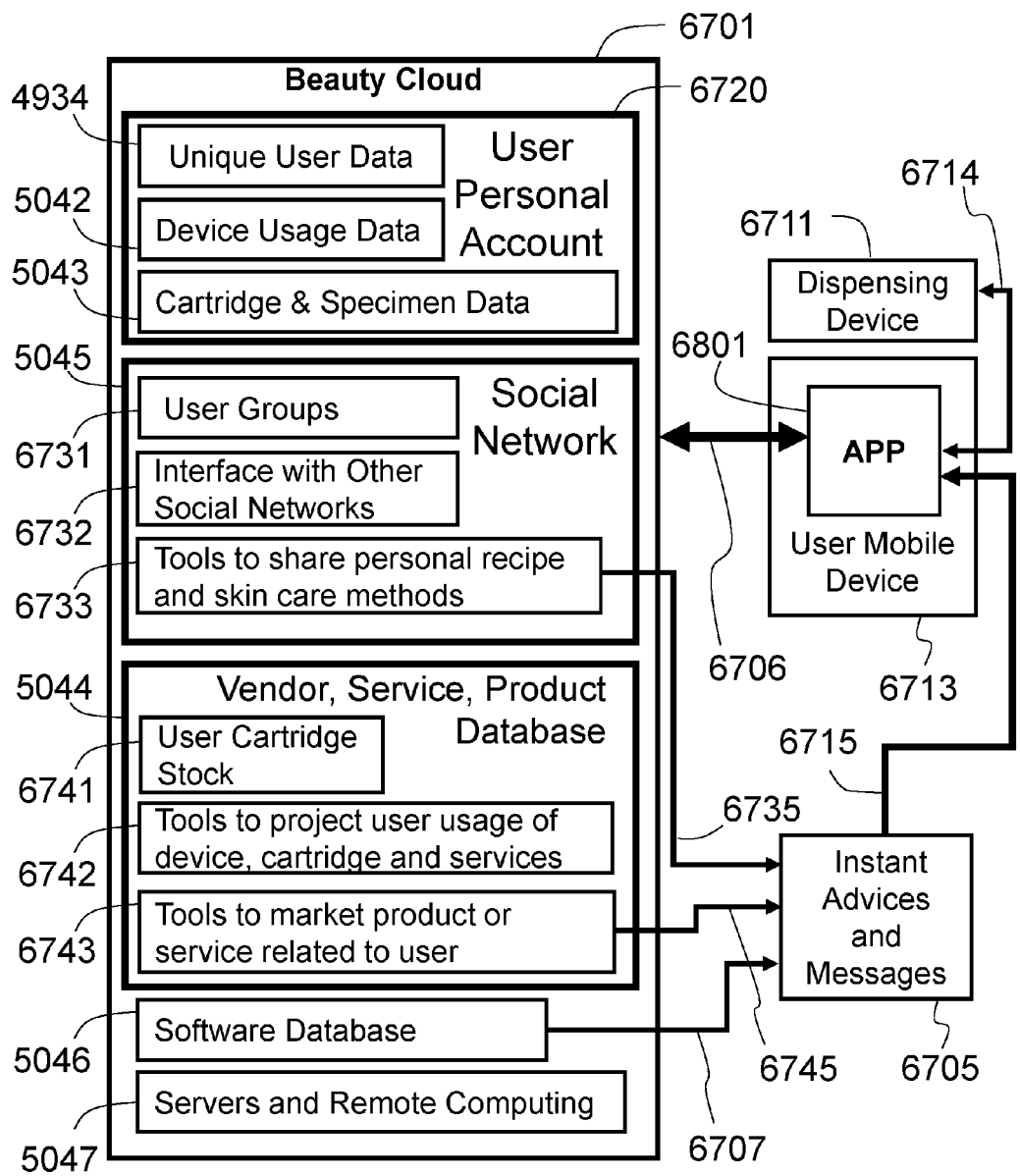
FIG. 68 illustrates components of an internet based beauty cloud and methods of use with an software application on a user mobile device.

FIG. 68 illustrates components of an internet beauty cloud and methods of use with an software application on a mobile computing device. FIG. 68 is same as FIG. 67, except that user devices 6710 of FIG. 67 are now replaced by the user mobile device 6713 as in FIG. 68. The user mobile device 6713 contains a software application ("APP") 6801, whereas the APP 6801 provides interface of data exchange with beauty cloud 6701 through communication 6706. APP 6801 also displays or conveys to the user the instant advices and messages 6705 sent through 6715, and communicates with dispensing device 6711 through communication 6714.

The APP 6801 may also contain the functions that include any of: (a) accessing user personal account 6720; (b) recording data of user habit and usage history of using dispensing device 6711, and pattern of user using dispensing device including time, frequency, period, location and environment, and sending such recorded data to the beauty cloud 6701; (c) tracking user stock of cartridges and projection of usage, and sending such tracking data to the beauty cloud 6701; (d) providing user interface to access user groups 6731, and other social networks, and utilizing interface with other social networks 6732; (e) upload, share, or download skin care related data and personalized recipes, through tools to share personal recipe and skin care methods 6733 of beauty network 6701, to allow a second user of user groups 6731 to obtain personal recipe and skin care methods from a first user; (f) display instant advices and messages 6705 to user.

Figure 69:
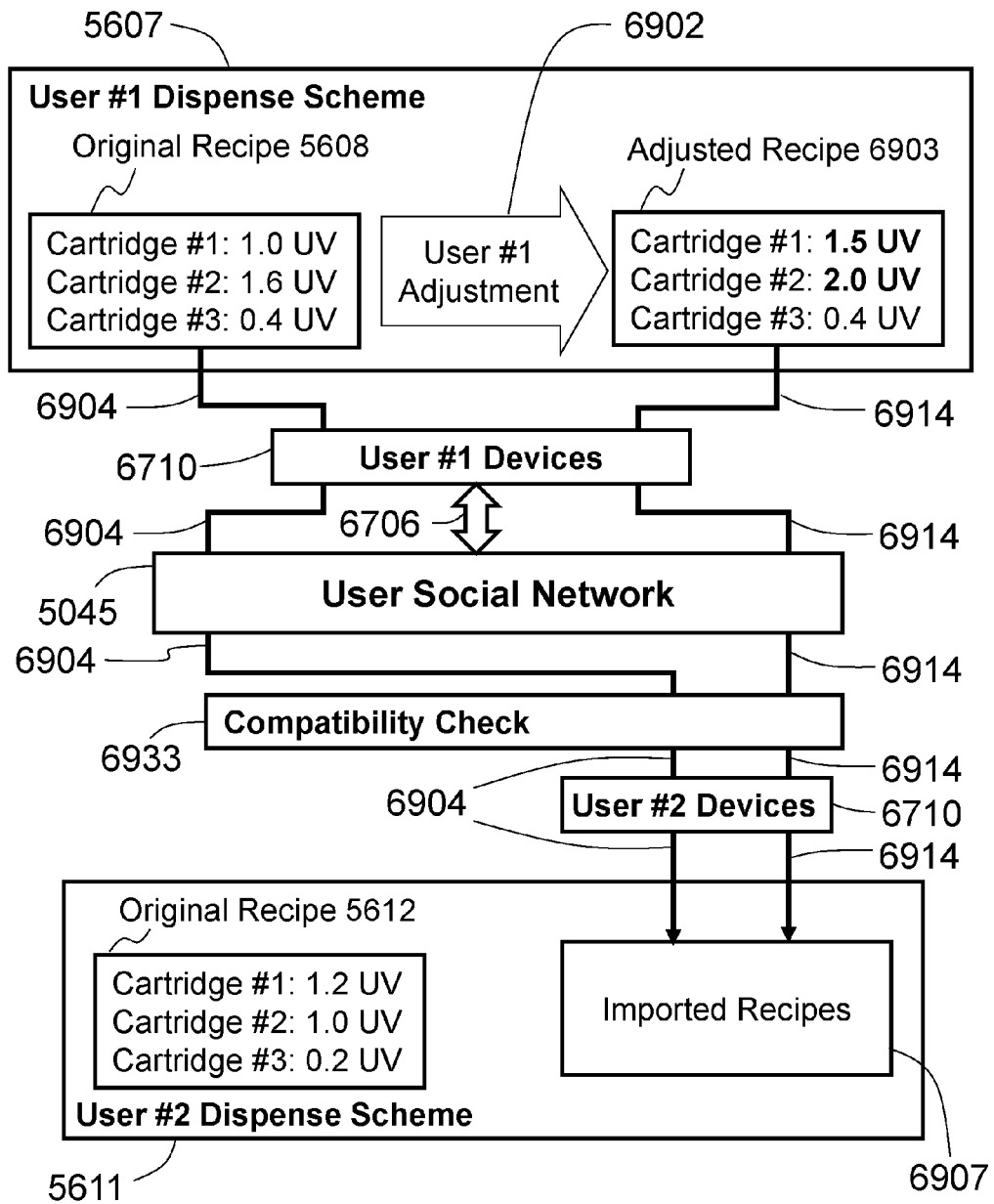
FIG. 69 illustrates a method to share personal recipe and skin care methods through user social network.

FIG. 69 illustrates a method to share personalized recipe and skin care methods through user social network 5045 of FIG. 67 and FIG. 68, with utilizing "tools to share personal recipe and skin care methods" 6733 of FIG. 67 and FIG. 68. User #1 dispensing scheme 5607 of FIG. 69 is same as the user #1 cartridge set dispensing scheme 5607 of FIG. 56. User #2 dispensing scheme 5611 of FIG. 69 is same as the user #2 cartridge set dispensing scheme 5611 of FIG. 56. The original recipe 5608 of user #1 dispense scheme 5607 in FIG. 69 is same as the dispensing recipe 5608 of FIG. 56. The original recipe 5612 of user #2 dispense scheme 5611 in FIG. 69 is same as the dispensing recipe 5608 of FIG. 56. In FIG. 69, user #1 may adjust the original recipe 5608 as shown by user #1 adjustment and may produce an adjusted recipe 6903. Alternatively adjusted recipe 6903 may be created by user #1 or other skin care service providers without referring to original recipe 5608. FIG. 69 illustrates that through the "tools to share personal recipe and skin care methods" 6733 of FIG. 67 and FIG. 68, user #1 may share the original recipe 5608 that was personalized for user #1 as in FIG. 56, and may also share the adjusted recipe 6903, with the user #2. The original recipe 5608 of user #1 may follow data transfer route 6904, and adjusted recipe 6903 of user #1 may follow data transfer route 6914, to be imported into user #2 dispensing scheme as imported recipes 6907. Following routes 6904 and 6914 respectively, original recipe 5608 and adjusted recipe 6903 may first be stored in user #1 devices 6710 which is same as user device 6710 of FIG. 67. Then through the communication 6706, user #1 devices 6710 transfer the original recipe 5608 or adjusted recipe 6903 to user social network 5045, which is same as social network 5045 of FIG. 67 and FIG. 68, through means of any of: (1) upload into user groups 6713; (2) upload through interface with other social networks 6732; and (3) tool to share personal recipe and skin care methods 6733. User #2 then may download the original recipe 5608 or adjusted recipe 6903 from user social network 5045, through means of any of: (1) download from user groups 6713; (2) download through interface with other social networks 6732; and (3) tool to share personal recipe and skin care methods 6733. The "tool to share personal recipe and skin care methods" 6733 may provide a function of compatibility check 6933, which through software, algorithm or database tools may confirm that either one of the original recipe 5608 and adjusted recipe 6903 is compatible with the dispensing device 6710 that user #2 intends to use with the original recipe 5608 or adjusted recipe 6903, or that either one of the original recipe 5608 and adjusted recipe 6903 is compatible with the skin condition or skin features that user #2 has. After compatibility check 6933, the original recipe 5608 and adjusted recipe 6903 may be transferred to, or downloaded into, the user #2 device 6710 from the user social network 5045 and imported into the user #2 dispense scheme as the imported recipes 6907. User #2 then may use imported recipes 6907 for skin care purpose, which may be substantially different than the original recipe 5612 obtained from FIG. 56 method.

User #1 adjustment 6902 may be performed in any of the devices among the user #1 devices 6701 of FIG. 69 and FIG. 67.

Adjusted recipe 6903 may be changes made from original recipe 5608 on any of: (1) method of specimen dispensing, including specimen dispensing amount, dispensing speed, timing of dispensing; (2) sequence of specimen dispensing from different cartridges among a cartridge set or from different compartments contained within a cartridge; (3) specimen composition within one or more cartridges or compartments; (4) methods of using the cartridges, including location of application of recipe with a dispensing device, or time of application of recipe, for example day or night, duration of each of application of recipe, and frequency of application of recipe; (5) methods of application of recipe with a skin treatment member, for example whether using a skin treatment member with application of recipe, location on skin of using a skin treatment member with application of the recipe, physical motion and its strength produced by a skin treatment member with of application of recipe.

Compatibility check 6933 may be provided by a dispensing device supplier, cartridge supplier, skin analysis service provider, user's own computer program, user's own mobile software applications, compatibility test programs existing on beauty cloud 6701 server, or a specialist who is part of social network 5045 and helps check compatibility of user #1 recipes to user #2 skin data. Compatibility check 6933 may performed by user #2 device 6710, or may use user #2 device 6710 as an user interface or platform of such compatibility check. Compatibility check 6933 step may also automatically, or allow user #2 manually, adjust original recipe 5608 and adjusted recipe 6903 to be compatible to user #2 dispensing device, cartridge set, skin condition, or skin features, whereas such adjustment may be assisted by a software tool or through assistance from a skin care specialist.

Adjusted recipe 6903 can be commercialized by user #1 as a product to sell to user #2 through beauty cloud 6701 or social network 5045 as a specialized recipe created by user #1. Adjusted recipe 6903 may not require original recipe 5608 and adjusted recipe 6903 may be formulated by a specialist or a user as a unique method of using any one or more of standard cartridge sets, based on the special skin care know-how of the specialist or the user.

Figure 70:
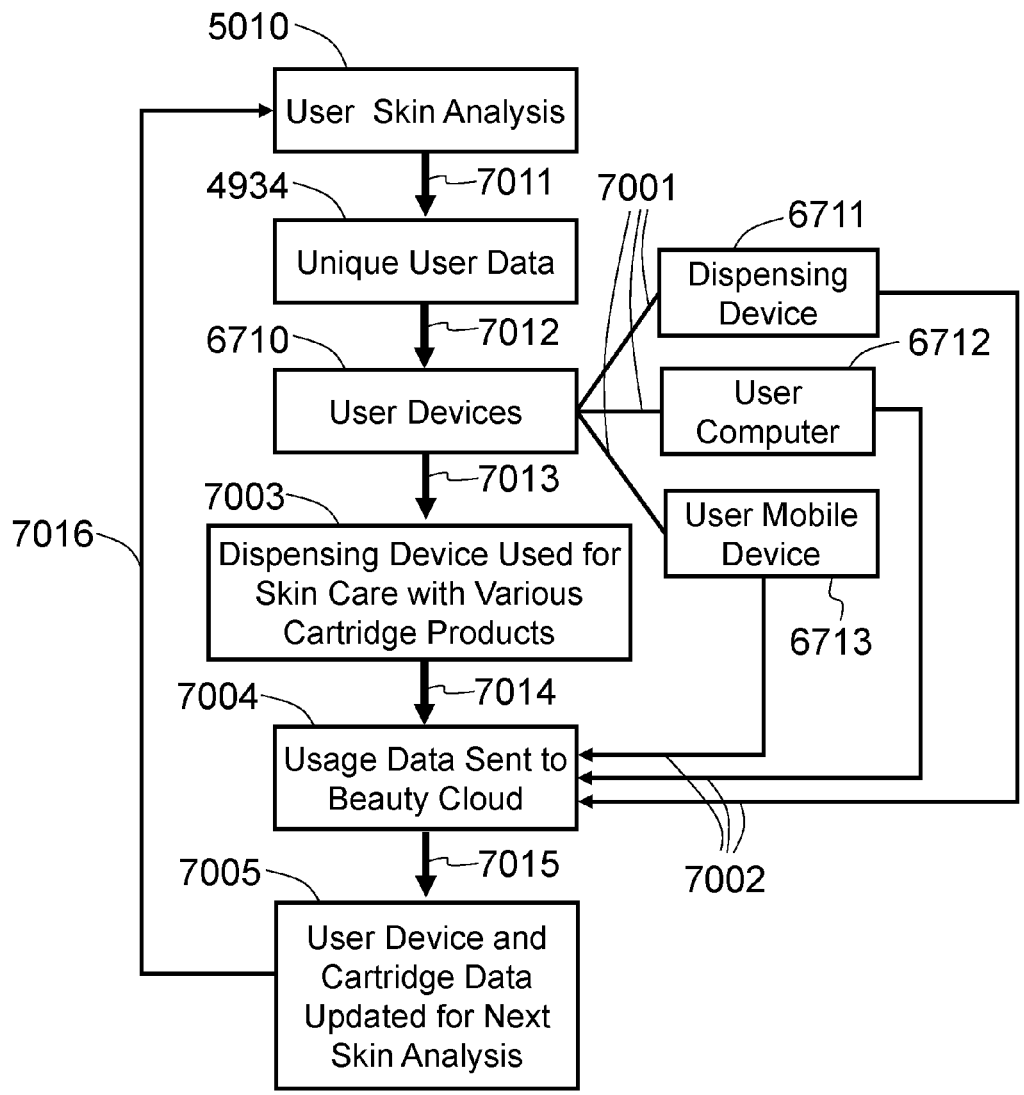
FIG. 70 illustrates a cycle of skin care process of a user.

FIG. 70 illustrates the schematic of the cycle of skin care process of a user based on embodiments of this invention. Skin care process cycle starts with user skin analysis 5010 as described in FIG. 50. User skin analysis 5010 provides data of the user's skin conditions and skin features, as shown by arrow 7011, whereas the data are stored in the form of unique user data 4934 as described in FIG. 49 and FIG. 50. Unique user data 4934 are then further stored, as shown by arrow 7012, in user devices 6710 as described in FIG. 67, which may contain user's dispensing device 6711, user computer 6712 and user mobile device 6713, as shown by relationships of 7001. The process and flow including user skin analysis 5010 to generate unique user data 4934, and then being sent to store in user devices 6710, may also be similar to the skin analysis process as described in FIG. 51. After unique user data 4934 are stored in user devices 6710, arrow 7013 shows the next step 7003 of the cycle of skin care process being dispensing device 6711 being used for skin care with various cartridge products. Arrow 7014 and step 7004 then illustrate the usage data of the dispensing device 6711 and various cartridge products by the user are sent to beauty cloud 5040 of FIG. 50, or beauty cloud 6001 of FIG. 67 and FIG. 58. Arrow 7015 and step 7005 then illustrate the user device and cartridge data, which are part of the usage data of step 7004 are stored in the beauty cloud 5040 of FIG. 50, or beauty cloud 6001 of FIG. 67 and FIG. 58, and ready for use in next skin analysis 5010. Arrow 7016 then illustrates the skin care cycle goes back to user skin analysis step 5010 with using the user device and cartridge data from step 7005 stored in the beauty cloud 5040 of FIG. 50, or beauty cloud 6001 of FIG. 67 and FIG. 58. The usage data of dispensing device and cartridges as in step 7004 may also be sent to beauty cloud by user devices 6710, as shown by arrows 7002, through various data communication means that is similar to communication 5024 and 5037 of FIG. 50.

Figure 72A:
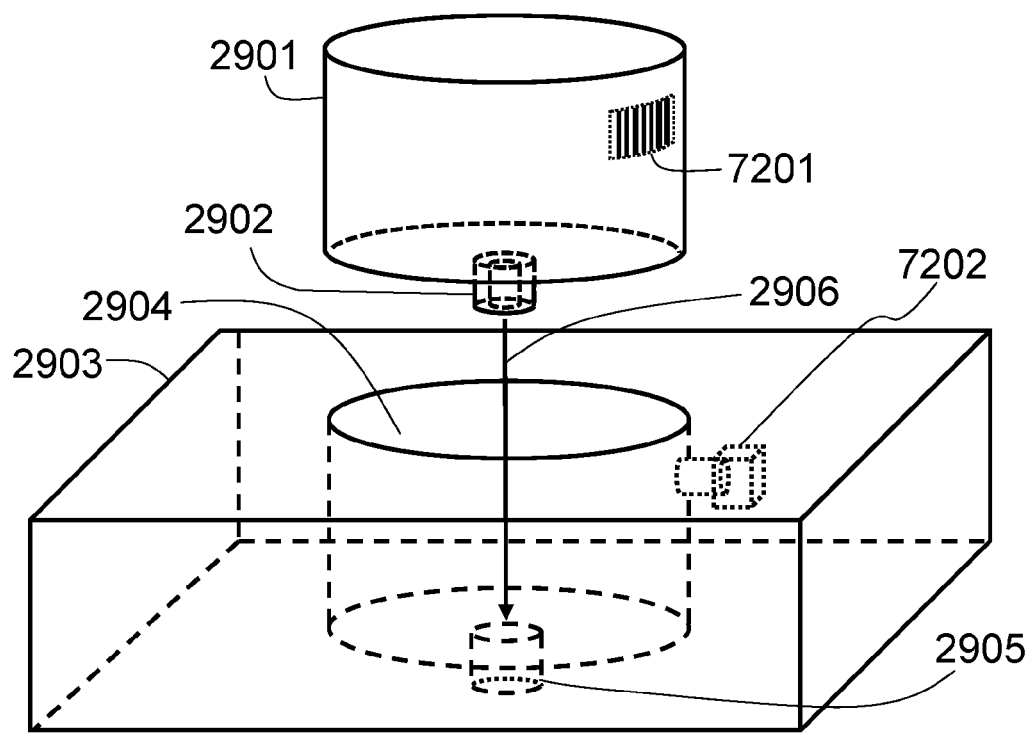
FIG. 72A illustrates a method to identify a dispenser by optical pattern.
Figure 72B:
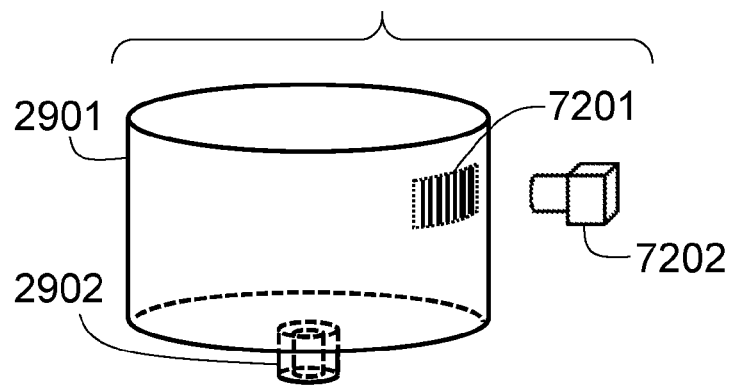
FIG. 72B illustrates a method to identify a dispenser by optical pattern.

FIG. 72A illustrates a method to identify a dispenser by optical scanner. FIG. 72A is substantially similar as FIG. 29. FIG. 72A illustrates a specimen dispenser 2901 in the form of a removable specimen cartridge being inserted into a cartridge slot 2904 in a device body 2903. Specimen dispenser 2901 and slot 2904 are substantially cylindrical shape as in FIG. 72A, which is only for the description purpose, while the actual shapes of specimen dispenser 2901 and slot 2904 may differ from cylindrical shape with only requirement of dispenser 2901 can fit into the slot 2904. Device body 2903 is substantially similar as the device body 11 of device 10 as in FIG. 1. Specimen dispenser 2901 and specimen outlet 2902 at the bottom of the dispenser are substantially similar as specimen dispenser 14 and any of the specimen outlet 2252, 2352 and 2452 in FIG. 22A through FIG. 24B. The nozzle portion of specimen outlet 2902 may have sufficiently similar structures and functions as any of the outlet nozzles 2503, 2506, 2606, 2608, 2703, and 2803 as described in FIG. 25A through FIG. 28D. In FIG. 72A, the dispenser 2901 has an optical marking 7201 on the external wall of the dispenser 2901, whereas the optical marking 7201 may be any of: a bar code, a QC code, an image, a logo, or any other optical patterns that are designed to contain information about the origin of the dispenser 2901 and the specimen contained therein. An image capture device 7202 is embedded in the device body 2903 with an optical opening located at the inside wall of slot 2904 and facing towards inside the slot 2904. The device 7202 may be any of: a laser scanner with optical detector, a camera, an image sensor with optical lenses. Directions 2906 show how specimen dispenser 2901 is inserted into the slot 2904 of the device body 2903. When the dispenser 2901 is inserted into the device body 2903 and positioned into the slot 2904, the image capture device 7202 aligns with the optical marking 7201 as shown in FIG. 72B, which may be an instant time when marking 7201 passes device 7202 optical opening during the insertion procedure of the dispenser 2901, and image capture device 7202 captures the optical marking 7201 and then sends the captured image information to the control unit 17 of FIG. 2 within device body 2903 to be stored in information storage component 171, or to be processed by information processing component 172, or to be stored or processed by personal computing device 5020 of FIG. 50 through communication 5037 of FIG. 50. Information contained in optical marking 7201 may be extracted after image processing. Information contained in optical marking 7201 may include any information that is included in the dispenser data structure 5400 of FIG. 54. Information stored in optical marking 7201 may contain identification information, or authenticity information, of dispenser 2901 and specimen contained therein. Information stored in optical marking 7201 may contain a method that allows personal computing device 5020 of FIG. 50 to access through a data network to obtain any or all information included in the dispenser data structure 5400 of FIG. 54, including identification or authenticity information of dispenser 2901 and specimen contained therein, whereas such method may an internet IP address or a world wide web link.

The optical marking 7201 and image capture of optical marking 7201 by an image capture device 7202 may be applied to all figures of current invention that has a cartridge or sub-cartridge inserted into a device body. For multiple sub-cartridges as in FIG. 36 through FIG. 48B, multiple imaging capture devices 7202 may be embedded in device body 2903 to capture optical marking 7201 on each of the sub-cartridges.

Figure 73:
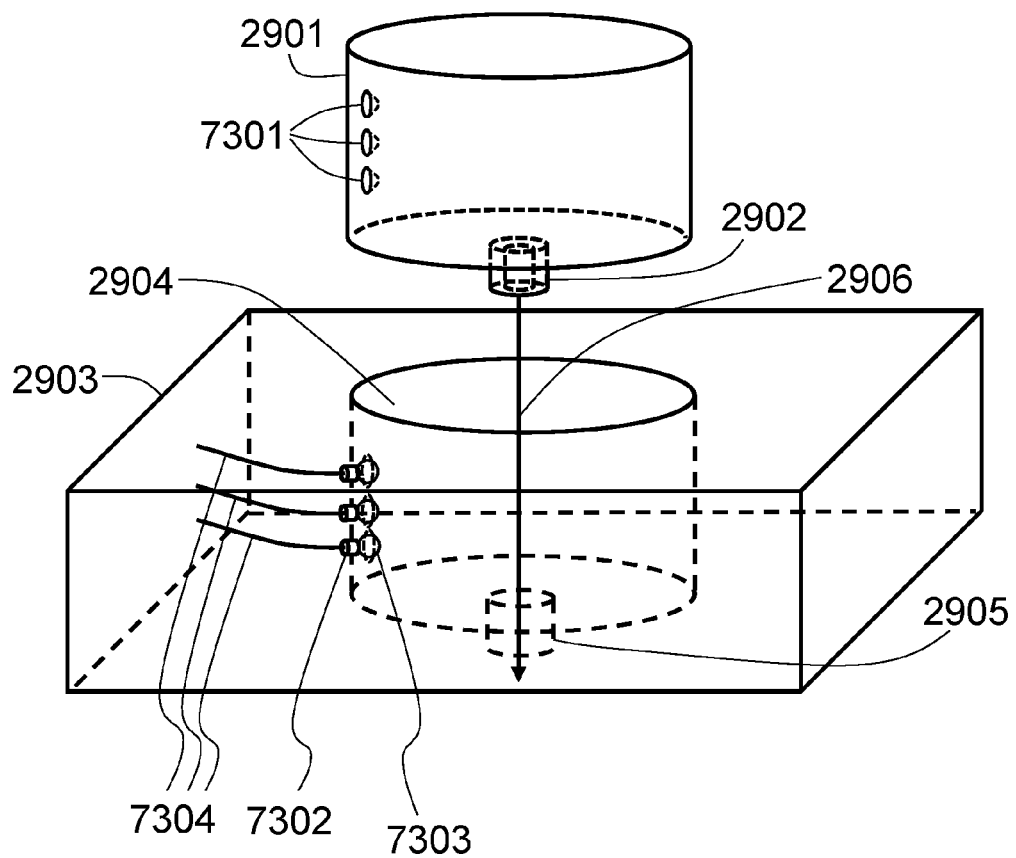
FIG. 73 illustrates a method to identify a dispenser by mechanical features.

FIG. 73 illustrates a method to identify a dispenser by mechanical features. FIG. 73 is sufficiently similar to FIG. 72A, except that optical marking 7201 is replace by mechanical features 7301 on the external surface of dispenser 2901, while image capture device 7202 is replace by mechanical sensors 7302 that are connected to surface feature detectors 7303 within the wall of slot 2904, whereas electrical connections 7304 connecting the mechanical sensors 7302 to power the mechanical sensors 7302 and transmit electrical signals generated by mechanical sensors 7302 to control unit 17 of FIG. 2. The mechanical features 7301 can be any of: surface indentations as shown in FIG. 73, surface protrusions, combination of indentations and protrusions, whereas the number, the locations and the arrangement of the mechanical features 7301 on the surface of dispenser 2901 may be used to store information that is similarly stored in optical marking 7201 of FIG. 72A. The surface feature detectors 7303 may be any of: (1) a surface contact mechanical component, for example spring loaded metal balls that fall in the indentations 7301 when dispenser 2901 is inserted into the slot 2904; (2) an optical laser or scanner with reflected light receiver that detect surface features 7301 of indentation and protrusions and generate various electrical signals according to feature being indentation and protrusions; (3) electrical powered pressure sensors which when pressed against by protrusions of mechanical feature 7301 generate electrical signals in voltage or current. The electrical signals generated by surface feature detectors 7303 and sensors 7302 may be converted into feature information of any of: type of mechanical features 7301, for example indentation or protrusion; number of mechanical features 7301; location and arrangement of mechanical features 7301; height, depth, width, and cluster patterns, of one or more of the mechanical features 7301, whereas feature information is sent by electrical connections 7304 to the control unit 17 of FIG. 2 within device body 2903 to be stored in information storage component 171, or to be processed by information processing component 172, or to be stored or processed by personal computing device 5020 of FIG. 50 through communication 5037 of FIG. 50. Feature information stored in mechanical features 7301 may contain identification information, or authenticity information, of dispenser 2901 and specimen contained therein. Information stored in mechanical features 7301 may contain an internet address or World Wide Web link that allows personal computing device 5020 of FIG. 50 to access through a data network to obtain any or all information included in the dispenser data structure 5400 of FIG. 54, including identification or authenticity information of dispenser 2901 and specimen contained therein. Mechanical features 7301 sensing by mechanical sensors 7302 that are connected to surface feature detectors 7303 may be performed when dispenser 2901 is inserted into slot 2904 and stationary inside 2904, while it may also be performed during the process of dispenser 2901 being inserted into slot 2904 whereas the mechanical features 7301 produces a sequential temporal signal on at least one set of a mechanical sensor 7302 connecting to a surface feature detector 7303, whereas such temporal signal may be used as the feature information. The mechanical sensors 7302 may detect the mechanical features 7301 by monitoring the mechanical movement of the surface feature detectors 7303, for example multiple indentations of feature 7301 passing under a single spring loaded ball bearing 7303 and producing multiple mechanical movements of detector 7303 caused by feature 7301 protrusion or indentation moving under detector 7303 and leading to sensor 7302 producing multiple corresponding electrical pulses as a detection of the mechanical features 7301, whereas the pulses polarity, pulse amplitude, pulses duration correlate with the mechanical features 7301 being protrusion or indentation, mechanical features 7301 height or depth, and physical length of the mechanical features 7301, which are the properties of the mechanical features 7301 that can be used to store information.

The mechanical features 7301 and mechanical feature sensing by mechanical sensors 7302 that are connected to surface feature detectors 7303, may be applied to all figures of current invention that has a cartridge or sub-cartridge inserted into a device body. For multiple sub-cartridges as in FIG. 36 through FIG. 48B, multiple sets of mechanical sensors 7302 that are connected to surface feature detectors 7303 may be embedded in device body 2903 to sense mechanical features 7301 on each sub-cartridge.

Figure 74A:
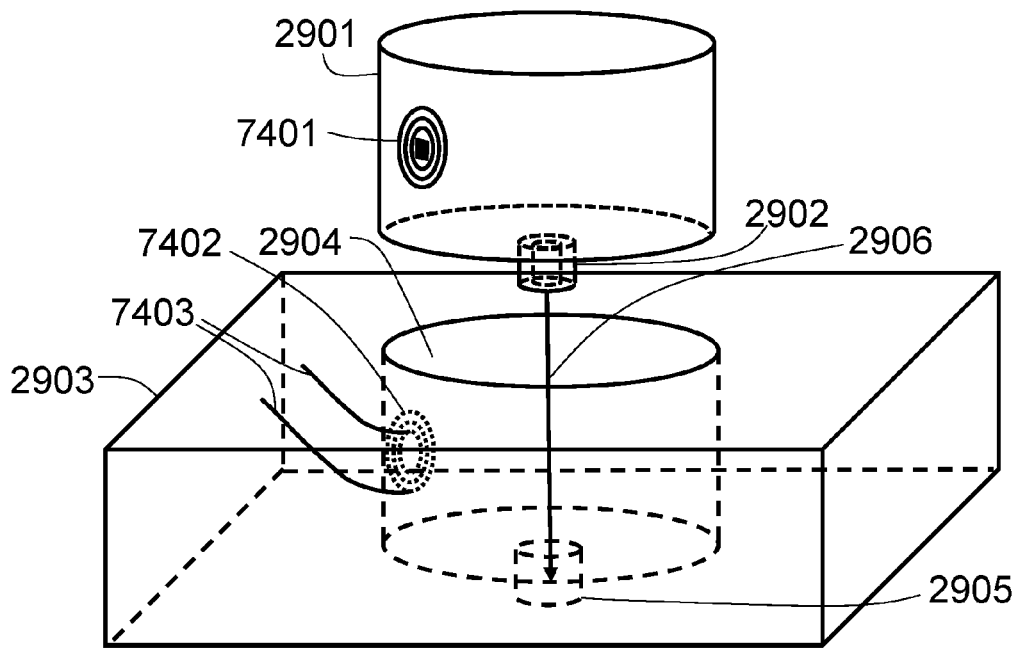
FIG. 74A illustrates a method to identify a dispenser by RFID.

FIG. 74A illustrates a method to identify a dispenser by RFID. FIG. 74A is sufficiently similar to FIG. 72A, except that optical marking 7201 is replace by RFID chip 7401 on the surface of dispenser 2901, while image capture device 7202 is replace by RFID sensors 7402 within the wall of slot 2904, whereas electrical connections 7403 connect RFID sensors 7402 to power the RFID sensors 7402 and transmit electrical signals generated by RFID sensors 7402 to control unit 17 of FIG. 2. The RFID chip 7401 may be an RFID pickup coil electrically connecting to one or more micro-chip as in FIG. 74A, whereas the pickup coil may act as receiving or transmitting antennas and micro-chips of 7401 may have a data storage chip or embedded component that stores information that is similarly stored in optical marking 7201 of FIG. 72A. The RFID sensor 7402 may have any function of: (1) emitting RF frequency microwave towards pickup coils of RFID 7401 to provide power to RFID 7401; (2) sensing of RF frequency microwave signal emitted by RFID 7401 transmitting antennas; (3) converting received microwave signal emitted by RFID 7401 with embedded circuits or micro-chips within RFID sensor 7402 into digital electrical signal. The electrical signals generated by RFID sensors 7402 may be sent through electrical connections 7403 to the control unit 17 of FIG. 2 within device body 2903 to be stored in information storage component 171, or to be processed by information processing component 172, or to be stored or processed by personal computing device 5020 of FIG. 50 through communication 5037 of FIG. 50. Information stored in RFID 7401 may contain identification information, or authenticity information, of dispenser 2901 and specimen contained therein. Information stored in RFID 7401 may contain an internet address or a world wide web link that allows personal computing device 5020 of FIG. 50 to access through a data network to obtain any or all information included in the dispenser data structure 5400 of FIG. 54, including identification or authenticity information of dispenser 2901 and specimen contained therein. RFID 7401 sensing by RFID sensors 7402 may be performed when dispenser 2901 is inserted into slot 2904 and stationary inside 2904, while it may also be performed during the process of dispenser 2901 being inserted into slot 2904 whereas the RFID 7401 receives RF power from RFID sensor 7402 and instantaneously produces a sequenced of RF signal that is pickup and processed by the RFID reader.

The RFID 7401 and RFID sensors 7402 may be applied to all figures of current invention that has a cartridge or sub-cartridge inserted into a device body. For multiple sub-cartridges as in FIG. 36 through FIG. 48B, multiple RFID sensors 7402 may be embedded in device body 2903 to sense RFID 7401 on each sub-cartridge.

Figure 74B:
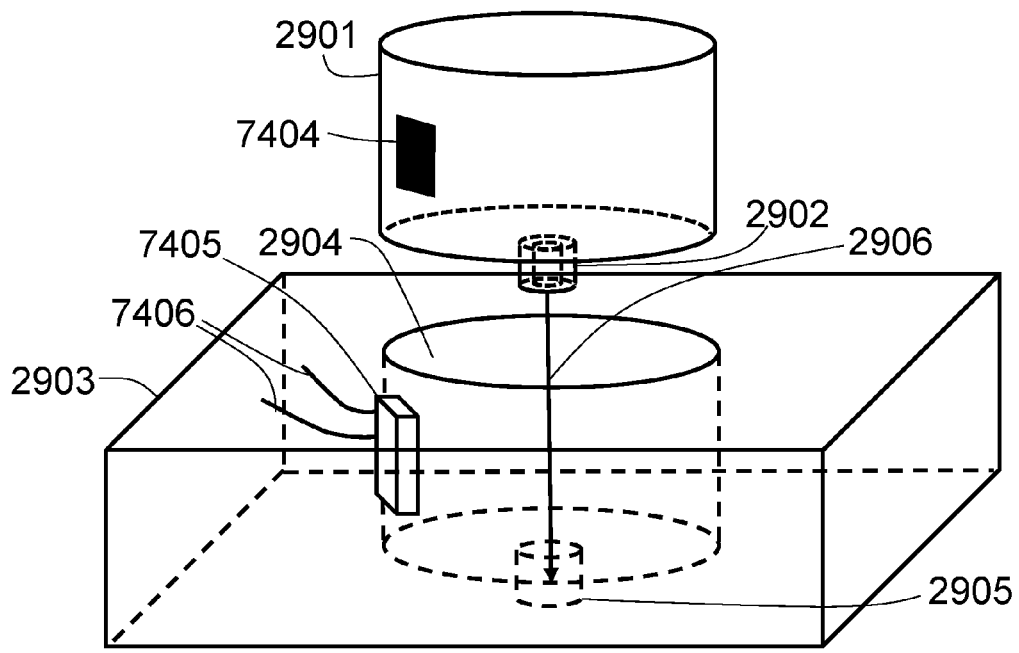

FIG. 74B illustrates a method to identify a dispenser by magnetic sensing. FIG. 74B is sufficiently similar to FIG. 72A, except that optical marking 7201 is replace by a magnetic data storage media 7404 on the surface of dispenser 2901, while image capture device 7202 is replace by magnetic sensors 7405, for example an inductive read head, or a giant-magneto-resistive (GMR) read head, or tunneling-magneto-resistive (TMR) magnetic read head, within the wall of slot 2904, whereas electrical connections 7406 connect to the magnetic sensors 7405 to power the magnetic sensors 7405, for example applying DC current to magnetic sensors 7405, and to transmit electrical signals generated by magnetic sensors 7405, for example voltage change across the magnetic sensors 7405, to control unit 17 of FIG. 2. The magnetic data storage media 7404 may be a magnetic tape with digital or analog data pre-recorded as magnetization data in the magnetic tape as in FIG. 74B. The magnetic sensor 7405 may have any function of: (1) sensing the alternating magnetic field generated by the magnetization data of the magnetic data storage media 7404 when media 7404 moves in close proximity, for example less than 5 mm, to the magnetic sensor 7405 and when the dispenser 2901 is inserted into or removed from the slot 5904; (2) sensing the magnetic field generated by the magnetization data pattern of the magnetic data storage media 7404 when media 7404 is positioned in close proximity to the magnetic sensor 7405, for example less than 5 mm, whereas the magnetic sensors may be an array of GMR or TMR sensors and whereas the magnetic data storage media 7404 may be any of: a magnetic recording media, for example a magnetic tape, a magnetic floppy disk medium, a magnetic hard disk drive medium, a magnetic medium with a plurality of patterned islands composed of magnetic material with each island size between 10 nanometer and 1 micrometer in its largest dimension. Magnetic data storage media 7404 may be a wafer chip composed of a plurality of patterned devices composed of TMR film with each of the device having at least a free magnetic layer, whose magnetization is switchable by a current of different polarities passing through in the direction perpendicular to the TMR film, and a pinning magnetic layer whose magnetization is not changed by the said current, and a tunneling barrier made of non-magnetic oxide material, for example MgO, interposed in between said free layer and pinned layer. The electrical signals generated by magnetic sensors 7405 may be sent through electrical connections 7406 to the control unit 17 of FIG. 2 within device body 2903 to be stored in information storage component 171, or to be processed by information processing component 172, or to be stored or processed by personal computing device 5020 of FIG. 50 through communication 5037 of FIG. 50. Information stored in magnetic data storage media 7404 may contain identification information, or authenticity information, of dispenser 2901 and specimen contained therein. Information stored in magnetic data storage media 7404 may contain an internet address or a world wide web link that allows personal computing device 5020 of FIG. 50 to access through a data network to obtain any or all information included in the dispenser data structure 5400 of FIG. 54, including identification or authenticity information of dispenser 2901 and specimen contained therein. magnetic data storage media 7404 sensing by magnetic sensors 7405 may be performed when dispenser 2901 is inserted into slot 2904 and stationary inside 2904, while it may also be performed during the process of dispenser 2901 being inserted into slot 2904 whereas the magnetic sensor 7402 senses the alternating magnetic field produced by the magnetic data pattern of the magnetic data storage media 7404 produces a data stream of electrical signal that is passed on through electrical connections 7406.

The magnetic data storage media 7404 and magnetic sensors 7405 may be applied to all figures of current invention that has a cartridge or sub-cartridge inserted into a device body. For multiple sub-cartridges as in FIG. 36 through FIG. 48B, multiple magnetic sensors 7405 may be embedded in device body 2903 to sense magnetic data storage media 7404 on each sub-cartridge.

First Preferred Embodiment

Multiple types of device operations can be realized based on the first preferred embodiment of the specimen dispensing device of the current invention.

Figure 5:
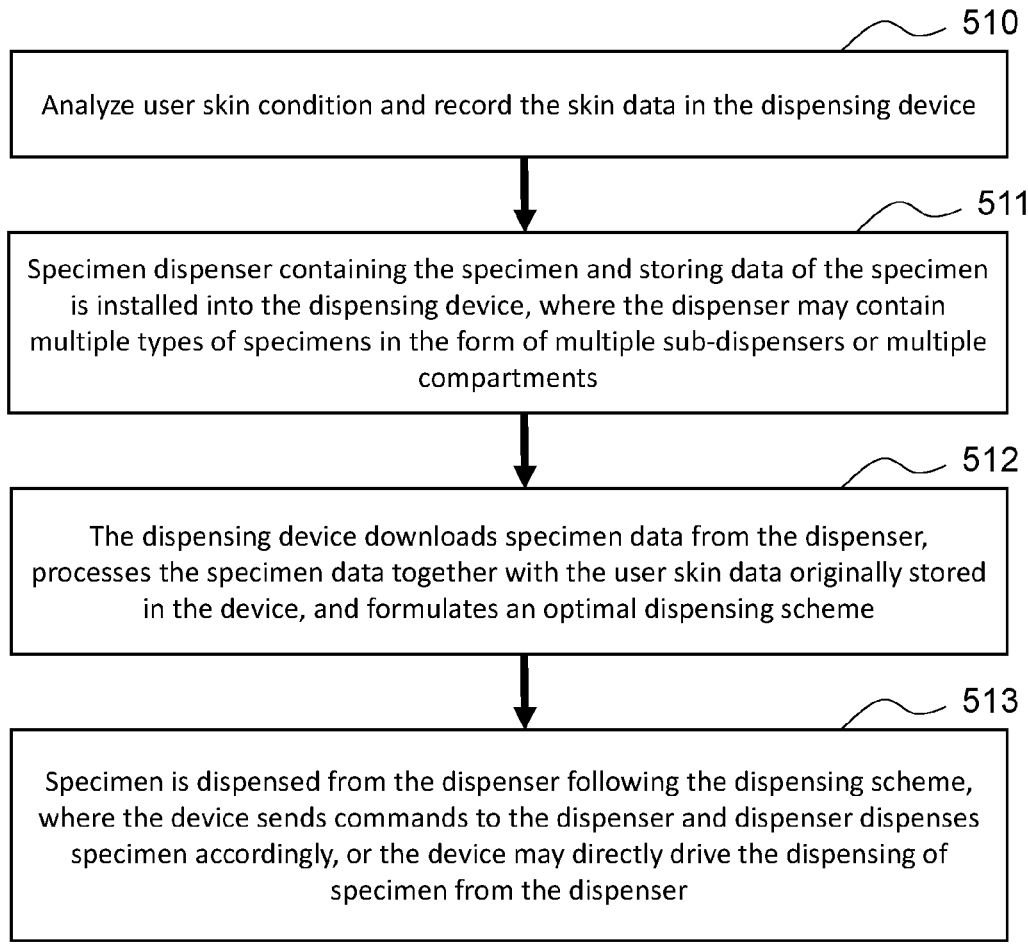
FIG. 5 is a flow diagram illustrating a process of operation of the specimen dispensing device according to the first preferred embodiment of the present invention.

Now referring back to FIG. 5. FIG. 5 is a flow diagram illustrating a process of operation according to the first preferred embodiment. Referring to FIG. 2 and FIG. 5, the information storage component 142 contains information related to the specimen 19, and the information storage component 171 contains information related to how to control the dispensing of the specimen 19 from the dispenser 14, such information can be, but not limited to, user skin information data, user personal and biometrics information, dispenser identification data, date, time, season, and other user-specific data such as preference, schedule, reminder message and avoidance. Information storage component 171 may contain the user data structure 5300 of FIG. 53.

The process of operation as illustrated in FIG. 5 includes steps of:

Step 510: Analyze user skin condition and record the user's skin data in the user's specimen dispensing device.

Step 511: storing data of the specimen in the specimen dispenser, whereas specimen dispenser containing the specimen and storing data of the specimen is installed into the dispensing device, where the dispenser may contain multiple types of specimens in the form of multiple sub-dispensers or multiple compartments.

Step 512: calculating an optimal dispensing scheme according to the specimen data and the user skin data, whereas dispensing device downloads specimen data from the dispenser, processes the specimen data together with the user skin data originally stored in the device, and formulates an optimal dispensing scheme.

Step 513: dispensing specimen according to the dispensing scheme, whereas specimen is dispensed from the dispenser following the dispensing scheme, where the device sends commands to the dispenser and dispenser dispenses specimen accordingly, or the device may directly drive the dispensing of specimen from the dispenser.

Figure 81:
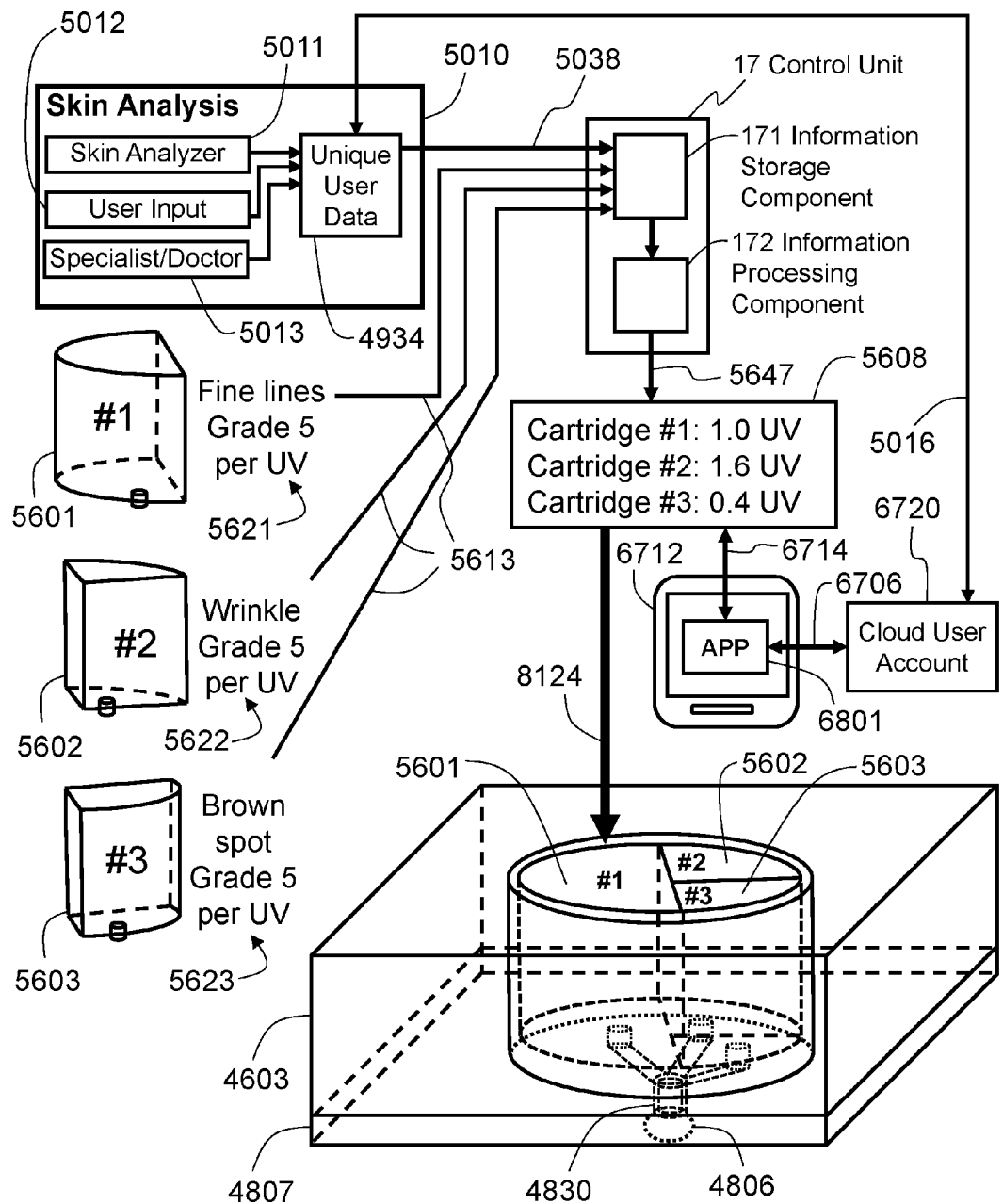

Now referring to FIG. 81. FIG. 81 illustrates a method to realize personalized dispensing scheme utilizing a dispensing device and a set of cartridges according to FIG. 5 process. The step of skin analysis 5010, same as in FIG. 50, may create unique user data 4934 with input from any of: skin analyzer 5011, user input 5012, specialist and dermatologist 5013. The unique user data 4934 may be sent to store in the information storage component 171 of control unit 17 within said dispensing device through communication 5038, same as in FIG. 50, or the unique user data 4934 may also be sent to be stored in a cloud user account 6720 of FIG. 67 through communication 5016 of FIG. 50, to achieve step 510 of FIG. 5, whereas unique user data 4934 may be stored as user data structure 5300 of FIG. 53 in the information storage component 171 or in the cloud user account 6720.

Cartridge #1 5601, cartridge #2 5602 and cartridge #3 5603 with each containing specimen therein and each respectively containing specimen information 5621, 5622 and 5623, same as in FIG. 56, are installed into cartridge slot of the device body 4603 of the said dispensing device as a cartridge set of #1 5601, #2 5602 and #3 5603 cartridges, same as in FIG. 48B. Specimen information 5621, 5622 and 5623 respectively contained in cartridge #1 5601, cartridge #2 5602 and cartridge #3 5603 are transferred to the information storage component 171 of control unit 17 within said dispensing device through communication 5613, same as in FIG. 56, to achieve step 511 of FIG. 5.

Information processing component 172 of control unit 17 within said dispensing device may process information contained in the information storage component 171 of control unit 17, which may include both the unique user data 4934 and specimen information 5621, 5622 and 5623 that are respectively transferred through communication 5038 and communication 5613, to produce or calculate a dispensing recipe 5608 of user #1 cartridge set dispense scheme 5607 of FIG. 56 in step 5647, same as in FIG. 56, to achieve step 512 of FIG. 5. Dispensing recipe 5608 may be stored in information storage component 171.

Dispensing recipe 5608 is then implemented in dispensing of specimen from cartridge #1 5601, cartridge #2 5602 and cartridge #3 5603 as shown by step 8124. Dispensing device dispenses final specimen 4806, which is a mixture of specimen from cartridges 5601, 5602 and 5603 according to the dispensing recipe 5608, through the device outlet 4830, to achieve step 513 of FIG. 5.

Device body 4603 of the dispensing device of FIG. 81, same as in FIG. 48B, may have a surface member 4807, whereas the surface member 4807 may provide a physical motion that helps mixing of the specimen 4806 dispensed upon the surface member 4807. Surface member 4807 may be an ultrasound generation plate similar to skin treatment member 1600 of FIG. 16, or a vibration generation tip 1700 of FIG. 17, or a brush head 1800 of FIG. 18, whereas the surface member 4807 may also be used as a skin treatment member that is in contact with user's skin area during a skin care process.

FIG. 81 also illustrates that, similar to FIG. 68, a mobile device 6712 containing a software application ("APP") 6801 may be used to download and store the dispensing recipe 5608 through communication 6714 between the APP 6801 of the mobile device 6712 and the dispensing device 6711 that contains the control unit 17, whereas the recipe 5608 may be stored in information storage component 171, while mobile device 6712 may also be able to modify the downloaded dispensing recipe 5608 with input from user and upload the modified dispensing recipe 5608 to the dispensing device 6711 and stored in information storage component 171, whereas the dispensing device 6711 control unit 17 may command dispensing of specimen from cartridge #1 5601, cartridge #2 5602 and cartridge #3 5603 according to the modified recipe 5608 thereafter. The mobile device 6712 APP 6801 may also upload dispensing recipe 5608, or modified dispensing recipe 5608, through communication 6706, same as in FIG. 68, to a cloud based user account 6720, which may then be utilized as input parameter or reference information during skin analysis 5010 to update the unique user data 4934 through communication 5016 as shown in FIG. 50.

Figure 6:
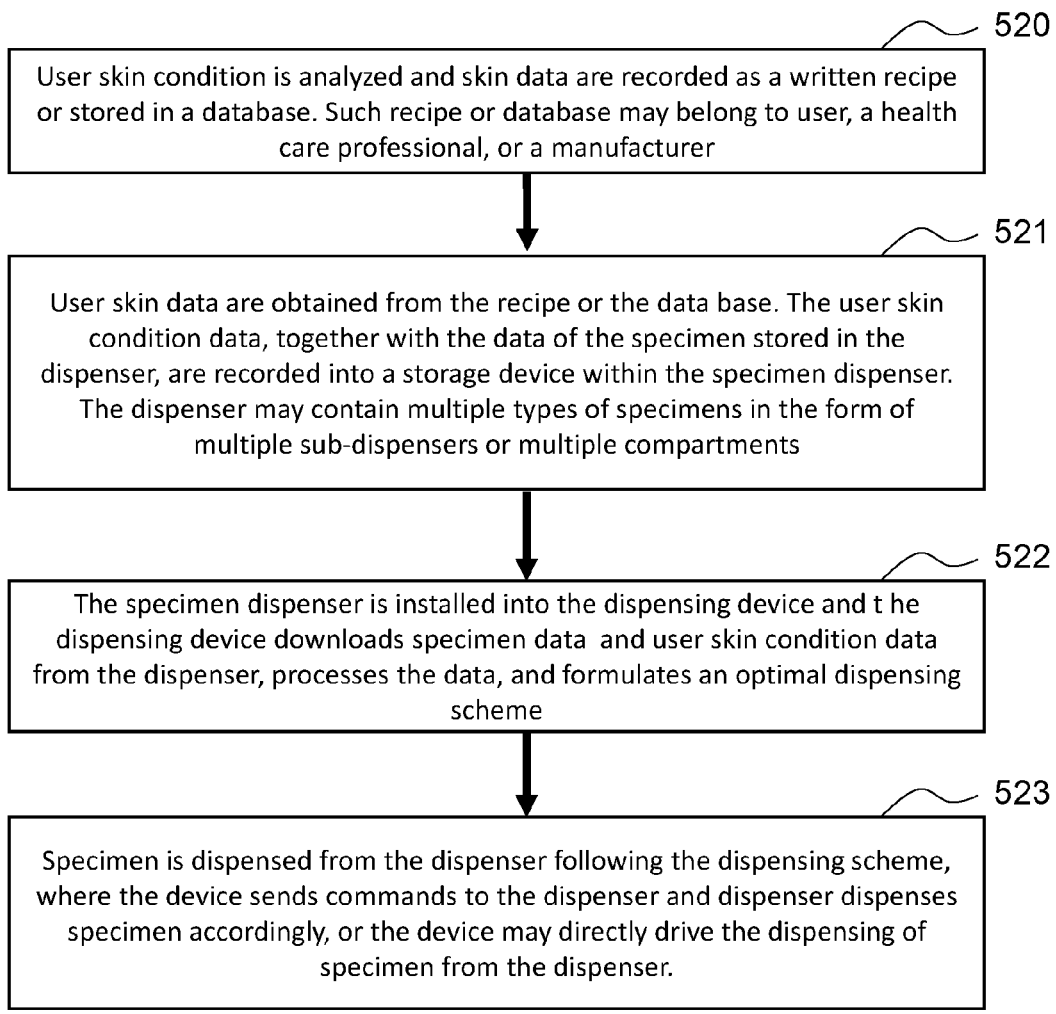
FIG. 6 is a flow diagram illustrating another process of operation of the specimen dispensing device according to the present invention.

Now referring back to FIG. 6. FIG. 6 is a flow diagram illustrating another process of operation according to the first preferred embodiment. Referring to FIG. 2 and FIG. 6, the information storage component 142, in addition to containing information related to the specimen, may also contain information related to how to control the dispensing of the specimen 19 from the dispenser 14, such information can be, but not limited to, user skin information data, user personal and biometrics information, dispenser identification data, date, time, season, and other user-specific data such as preference, schedule, reminder message and avoidance. Such stored information may be configured and updated by user, by manufacturer or by a health care professional. In such embodiment, the information storage component 171 can store any of, but only limited to, device operation data, dispenser operation data, software, firmware or data received from the dispenser 14.

The process of operation as illustrated in FIG. 6 includes the steps of:

Step 520: User skin condition is analyzed and user's skin data are recorded as a written recipe or storing the data in a database. The recipe or database may belong to the user, a health care professional, or a manufacturer.

Step 521: User skin data are obtained from the recipe or the data base. The user skin condition data, together with the data of the specimen stored in the dispenser, are recorded into a storage device within the specimen dispenser. The dispenser may contain multiple types of specimens in the form of multiple sub-dispensers or multiple compartments.

Step 522: The specimen dispenser is installed into the dispensing device and the dispensing device downloads specimen data and user skin condition data from the dispenser, processes the data, and formulates an optimal dispensing scheme.

Step 523: Specimen is dispensed from the dispenser following the dispensing scheme, where the device sends commands to the dispenser and dispenser dispenses specimen accordingly, or the device may directly drive the dispensing of specimen from the dispenser.

Figure 75:
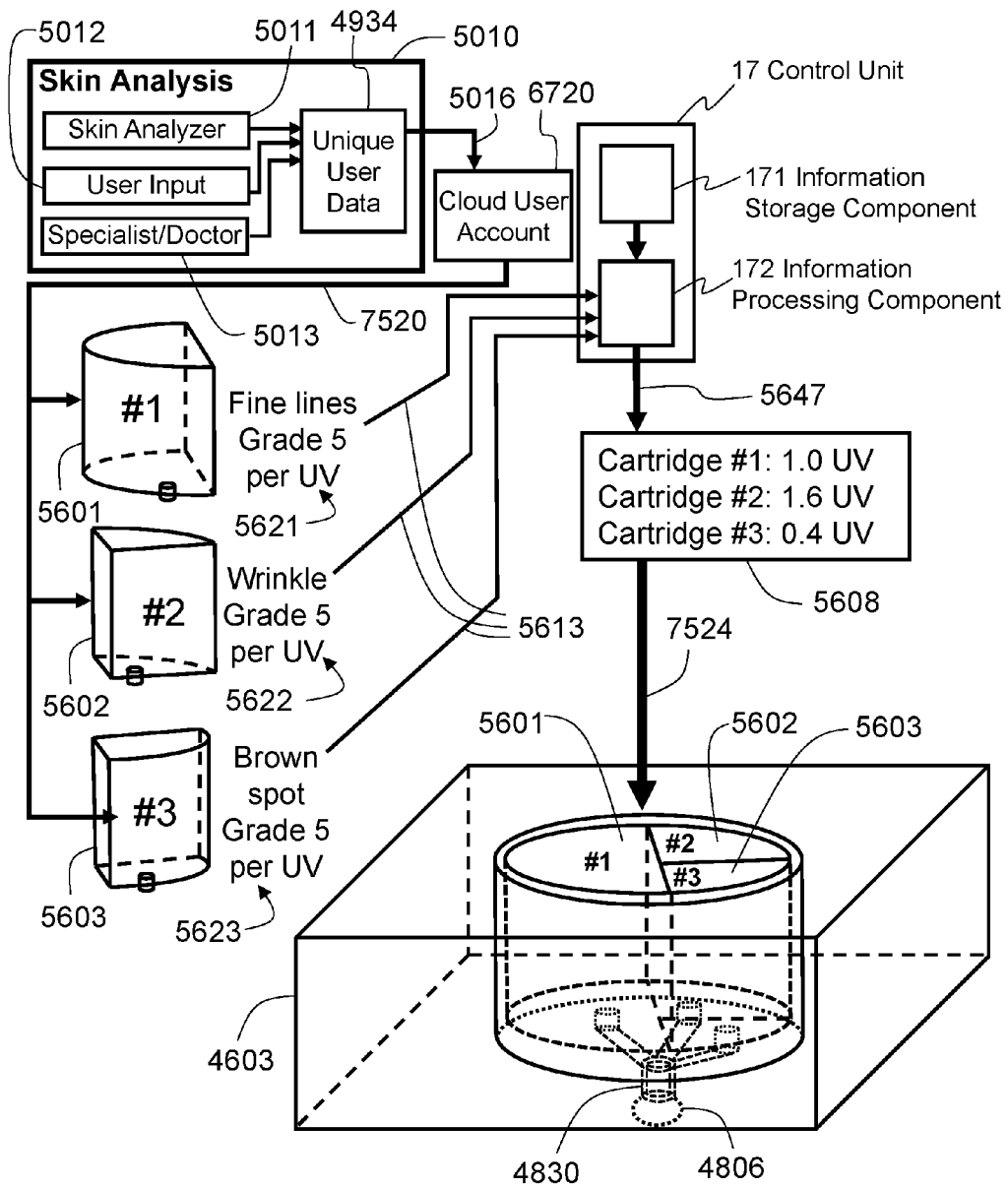

Now referring to FIG. 75. FIG. 75 illustrates a method to realize personalized specimen dispensing scheme utilizing a dispensing device and a set of cartridges according to FIG. 6 process. The step of skin analysis 5010, same as in FIG. 50, may create unique user data 4934 with input from any of: skin analyzer 5011, user input 5012, specialist and dermatologist 5013. The unique user data 4934 may be sent to be stored in a cloud user account 6720 of FIG. 67 through communication 5016 of FIG. 50, to achieve step 520 of FIG. 6.

Each of cartridge #1 5601, cartridge #2 5602 and cartridge #3 5603 contains specimen therein and each respectively contains specimen information 5621, 5622 and 5623, same as in FIG. 56. The unique user data 4934 may be downloaded through communication 7520 from cloud user account 6720 and stored in at least one data storage component embedded in one or more of cartridge #1 5601, cartridge #2 5602 and cartridge #5603, to achieve step 521 of FIG. 6.

Cartridge #1 5601, cartridge #2 5602 and cartridge #3 5603 are then installed into cartridge slot of the device body 4603, same as in FIG. 48A, of the said dispensing device as a cartridge set of #1 5601, #2 5602 and #3 5603 cartridges. Specimen information 5621, 5622 and 5623 respectively contained in cartridge #1 5601, cartridge #2 5602 and cartridge #5603, as well as the unique user data 4934 contained therein are transferred to the information processing component 171 of control unit 17 within said dispensing device through communication 5613, same as in FIG. 56, whereas information processing component 172 may process information including both the unique user data 4934 and specimen information 5621, 5622 and 5623 to produce or calculate a dispensing recipe 5608 of user #1 cartridge set dispense scheme 5607 of FIG. 56 in step 5647, same as in FIG. 56, to achieve step 522 of FIG. 6.

Dispensing recipe 5608 is then implemented in dispensing of specimen from cartridge #1 5601, cartridge #2 5602 and cartridge #3 5603 as shown by step 7524. Dispensing device dispenses final specimen 4806 which is a mixture of specimen from cartridges 5601, 5602 and 5603 according to the dispensing recipe 5608, through the device outlet 4830, to achieve step 523 of FIG. 6.

In FIG. 75, the unique user data 4934 may be downloaded through communication 7520 from cloud user account 6720 and stored in at least one data storage component embedded in one or more of cartridge #1 5601, cartridge #2 5602 and cartridge #5603 during, or after, an acquisition action, for example action of purchasing, initiated by user #1 of the cartridge set composed of cartridge #1 5601, cartridge #2 5602 and cartridge #5603.

Figure 7:
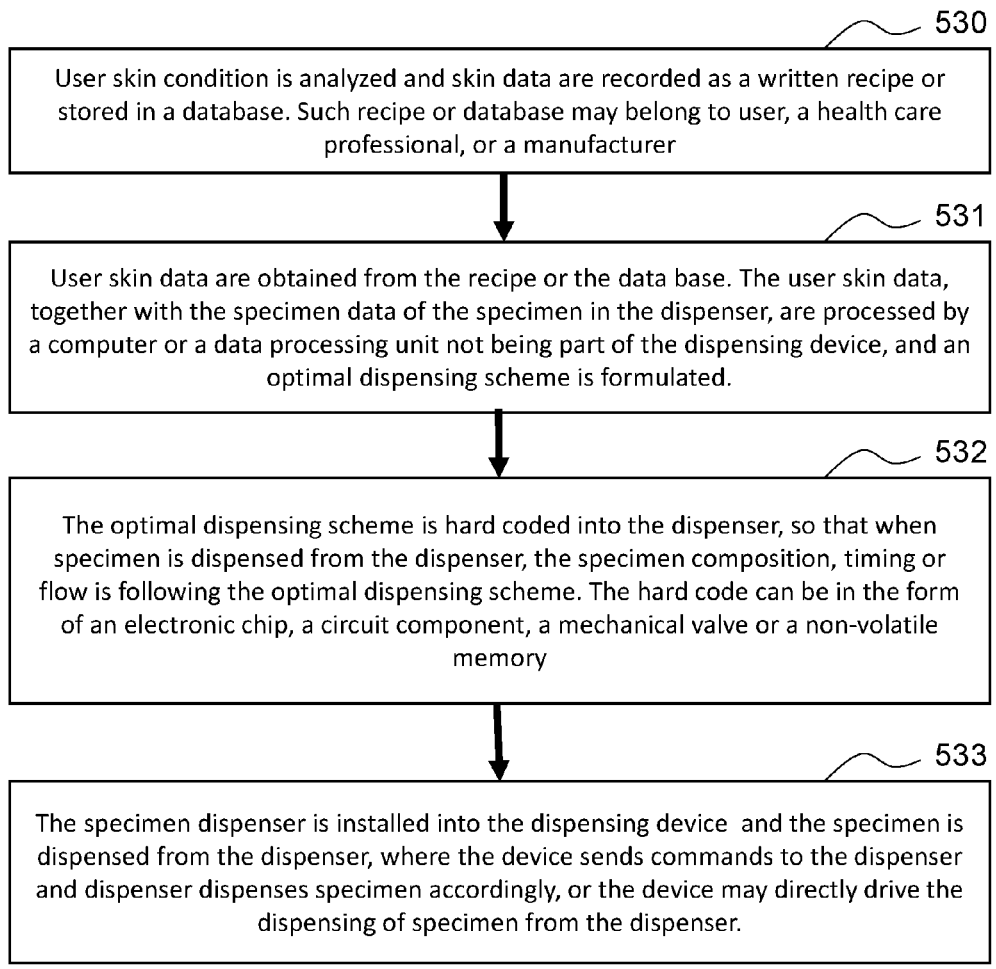
FIG. 7 is a flow diagram illustrating another process of operation of the specimen dispensing device according to the present invention.

Now referring back to FIG. 7. FIG. 7 is a flow diagram illustrating another process of operation according to the first preferred embodiment. Now referring to FIG. 2 and FIG. 7, the information storage component 142 is in the form of a hard coded dispensing mechanism, which regulates the specimen dispensing from the dispenser 14, or any subdispenser and any compartment of the dispenser 14, by any of: specimen composition within each dispenser, specimen outflow speed and specimen dispensing timing. Such hard coded dispensing mechanism is configured with the capacity to store the specimen data, the user data, user skin condition data and any other type of information relating to the proper dispensing of the specimen to meet the user's skin care need. In such configuration, the information storage component 171 can store any of, but not limited to, device operation data, dispenser operation data, software, firmware or data received from the dispenser 14. One of such example is that manufacturer acquires user skin condition and configures the dispenser, electrically or mechanically, in such a way that, when specimen is dispensed from the dispenser when installed in the device, the dispensed specimen is in correct composition to match the user's skin area and condition. The hard code can be, but not limited to, an electronic chip, a circuit component, a mechanical valve or a non-volatile memory.

The process of operation as illustrated in FIG. 7 includes steps of:

Step 530: User skin condition is analyzed and user's skin data are recorded as a written recipe or storing the data in a database. Such recipe or database may belong to the user, a health care professional, or a manufacturer.

Step 531: retrieving the user's skin data from the recipe or the data base, whereas the user skin data, together with the specimen data of the specimen in the dispenser, are processed by a computer or a data processing unit not being part of the dispensing device, and an optimal dispensing scheme is formulated.

Step 532: The optimal dispensing scheme is hard coded into the dispenser, so that when specimen is dispensed from the dispenser, the specimen composition, timing or flow is following the optimal dispensing scheme. The hard code can be in the form of an electronic chip, a circuit component, a mechanical valve or a non-volatile memory.

Step 533: The specimen dispenser is installed into the dispensing device and the specimen is dispensed from the dispenser, where the device sends commands to the dispenser and dispenser dispenses specimen accordingly, or the device may directly drive the dispensing of specimen from the dispenser.

Figure 76:
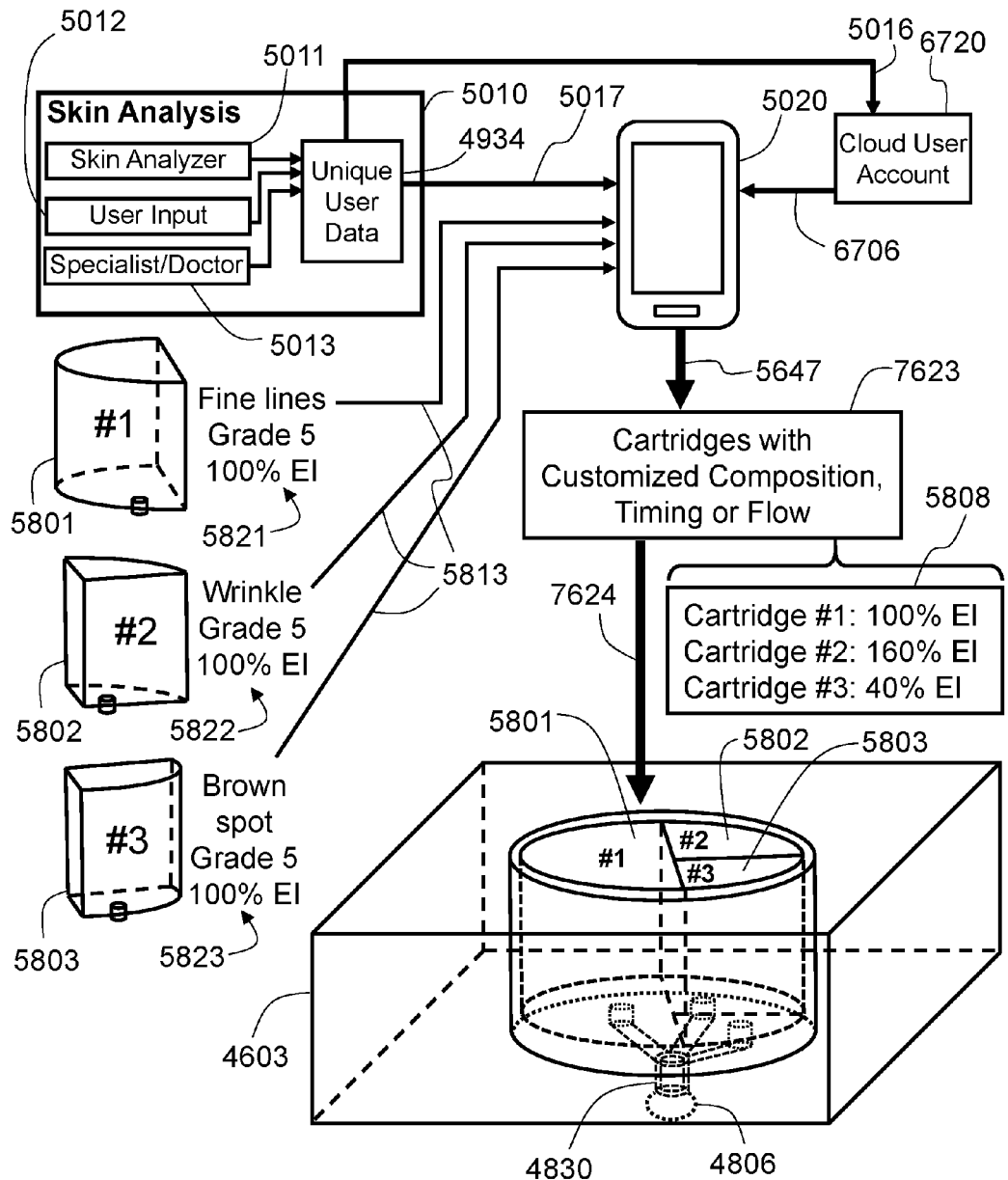

Now referring to FIG. 76. FIG. 76 illustrates a method to realize personalized composition scheme of a dispenser set utilizing a dispensing device and a set of cartridges according to FIG. 7 process. The step of skin analysis 5010, same as in FIG. 50, may create unique user data 4934 with input from any of: skin analyzer 5011, user input 5012, specialist and dermatologist 5013. The unique user data 4934 may be stored in a personal computing device 5020 of FIG. 50, which is also similar to user devices 6710 of FIG. 67. Alternatively, the unique user data 4934 may be sent to be stored in a cloud user account 6720 of FIG. 67 through communication 5016 of FIG. 50, to achieve step 530 of FIG. 7.

Each of cartridge #1 5801, cartridge #2 5802 and cartridge #3 5803 contains specimen therein and each respectively contains specimen information 5821, 5822 and 5823, same as in FIG. 58. The unique user data 4934, which may be contained in personal computing device 5020 or downloaded to the personal computing device 5020 through communication 6706 of FIG. 67 from cloud user account 6720, may be processed together with the specimen information 5821, 5822 and 5823 sent through communication 5813, same as in FIG. 58, to produce or calculate a specimen composition recipe 5808 of user #1 cartridge set composition scheme 5807 of FIG. 58 in step 5647, same as in FIG. 58, to achieve step 531 of FIG. 7.

Cartridge #1 5801, cartridge #2 5802 and cartridge #3 5803 may each be adjusted of the composition of the specimen contained therein, or of the timing of specimen outflow during dispensing, or of the flow rate of the specimen outflow during dispensing, according to the specimen composition recipe 5808 as in step 7623, to achieve step 532 of FIG. 7, whereas such adjustment is regarded as "hardcoding" the specimen composition recipe 5808 into the cartridges 5801, 5802 and 5803. The hardcoding may be achieved with composition adjustment of specimen contained in each of the cartridges 5801, 5802 and 5803. The hardcoding may be achieved with using an electronic chip, a circuit component, a mechanical valve or a non-volatile memory to control composition, timing of outflow, and flow rate of specimen contained in each of the cartridges 5801, 5802 and 5803.

Then cartridge #1 5801, cartridge #2 5802 and cartridge #3 5803 may be installed into cartridge slot of the device body 4603, same as in FIG. 48A, of the said dispensing device as a cartridge set of #1 5801, #2 5802 and #3 5803 cartridges. Composition recipe 5808 is then implemented in dispensing of specimen from cartridge #1 5801, cartridge #2 5802 and cartridge #3 5803 as shown by step 7624, whereas dispensing device dispenses final specimen 4806 which is a mixture of specimen from cartridges 5801, 5802 and 5803 according to the composition recipe 5808 that is hard coded as any of: composition of specimen within each cartridge, timing of specimen outflow, and specimen out flow rate, of specimen contained in each of the cartridges 5801, 5802 and 5803, through the device outlet 4830, to achieve step 533 of FIG. 7.

In FIG. 76, the hardcoding of specimen composition recipe 5808 in the form of composition adjustment of the specimen contained in each of the cartridges 5801, 5802 and 5803 may be achieved after an acquisition action, for example action of purchasing, initiated by user #1 of the cartridge set composed of cartridge #1 5801, cartridge #2 5802 and cartridge #5803, such that said cartridge set composed of cartridges with each containing specimen with a unique specimen composition following the specimen composition recipe 5808 specifically matching to user #1 skin conditions or skin features are provided to user #1 after the acquisition action.

Figure 80:
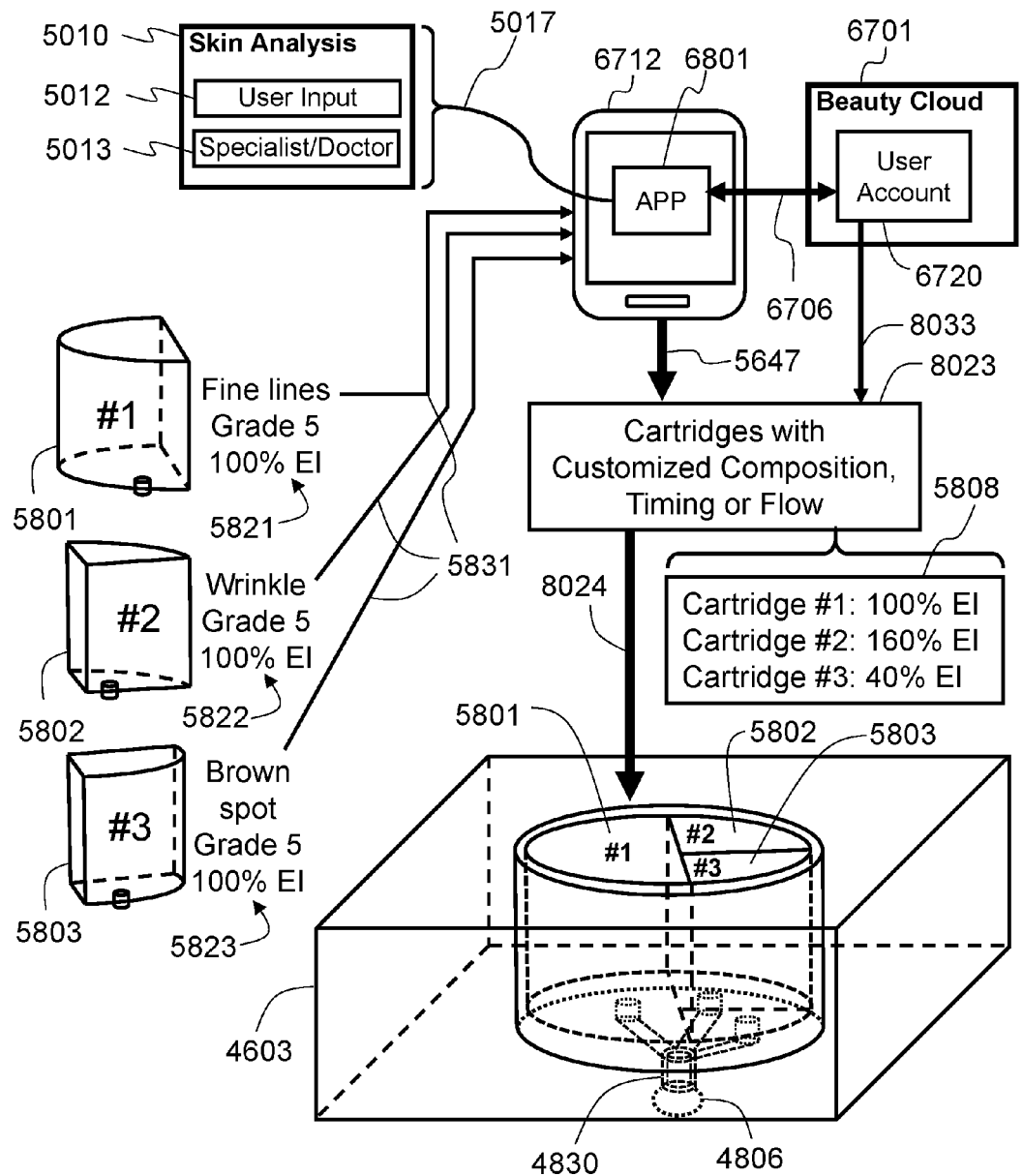

Now referring to FIG. 80. FIG. 80 illustrates another method to realize personalized composition scheme of a dispenser set utilizing a dispensing device and a set of cartridges according to FIG. 7 process. The step of skin analysis 5010, same as in FIG. 50, is performed through a user mobile device 6712 of FIG. 68 with a user interface provided by an APP 6801 that is included in the user mobile device 6712. The APP 6801 creates a unique user data 4934 with input from any of: user input 5012, and input from specialist and dermatologist 5013, whereas such input may be provided through communication 5017 of FIG. 50 between skin analysis 5010 and user personal computing device 5020, which is the user mobile device 6712 as in FIG. 80. After skin analysis step 5010, the unique user data 4934 may be stored in the user mobile device 6712, to achieve step 530 of FIG. 7. The unique user data 4934 may also be sent by the APP 6801 to be stored in a user account 6720 which is part of a beauty cloud 6701 through communication 6706 as in FIG. 68, to achieve step 530 of FIG. 7.

Each of cartridge #1 5801, cartridge #2 5802 and cartridge #3 5803 contains specimen therein and each respectively contains specimen information 5821, 5822 and 5823, same as in FIG. 58. The unique user data 4934, which is stored in user mobile device 6712 or is downloaded to the user mobile device 6712 through communication 6706 of FIG. 68 from user account 6720 by APP 6801 being included in the user mobile device 6712, may be processed together with the specimen information 5821, 5822 and 5823 sent through communication 5813 as in FIG. 58, by the APP 6801 with utilizing the computing components of the user mobile device 6712 to produce or calculate a specimen composition recipe 5808 of user #1 cartridge set composition scheme 5807 of FIG. 58 in step 5647 as in FIG. 58, to achieve step 531 of FIG. 7. The specimen composition recipe 5808 may also be sent by APP 6801 of user mobile device 6712 to be stored in the user account 6720 as cartridge and specimen data 5043 of FIG. 68 through communication 6706.

Cartridge #1 5801, cartridge #2 5802 and cartridge #3 5803 may each be adjusted of the composition of the specimen contained therein, or of the timing of specimen outflow during dispensing, or of the flow rate of the specimen outflow during dispensing, according to the specimen composition recipe 5808 as in step 8023, to achieve step 532 of FIG. 7, whereas such adjustment is regarded as "hard-coding" the specimen composition recipe 5808 into the cartridges 5801, 5802 and 5803. The hardcoding may be achieved with composition adjustment of specimen contained in each of the cartridges 5801, 5802 and 5803. The hardcoding may be achieved with using an electronic chip, a circuit component, a mechanical valve or a non-volatile memory to control composition, timing of outflow, and flow rate of specimen contained in each of the cartridges 5801, 5802 and 5803. Cartridge #1 5801, cartridge #2 5802 and cartridge #3 5803 may each be adjusted of the composition of the specimen contained therein, or of the timing of specimen outflow during dispensing, or of the flow rate of the specimen outflow during dispensing, according to the specimen composition recipe 5808 that may be obtained, as in step 8033, from cartridge and specimen data 5043 of user account 6720 of FIG. 68, to achieve step 532 of FIG. 7.

Then cartridge #1 5801, cartridge #2 5802 and cartridge #3 5803 may be installed into cartridge slot of the device body 4603, same as in FIG. 48A, of the said dispensing device as a cartridge set of #1 5801, #2 5802 and #3 5803 cartridges. Composition recipe 5808 is then implemented in dispensing of specimen from cartridge #1 5801, cartridge #2 5802 and cartridge #3 5803 as shown by step 7624, whereas dispensing device dispenses final specimen 4806 which is a mixture of specimen from cartridges 5801, 5802 and 5803 according to the composition recipe 5808 that is hard coded as any of: specimen composition of each cartridge, timing of specimen outflow, and specimen out flow rate, of specimen contained in each of the cartridges 5801, 5802 and 5803, through the device outlet 4830, to achieve step 533 of FIG. 7.

In FIG. 80, the hardcoding of specimen composition recipe 5808 in the form of composition adjustment of the specimen contained in each of the cartridges 5801, 5802 and 5803 may be achieved after an acquisition action, for example action of purchasing, initiated by user #1 of the cartridge set composed of cartridge #1 5801, cartridge #2 5802 and cartridge #5803, such that said cartridge set composed of cartridges with each containing specimen with a unique specimen composition following the specimen composition recipe 5808 specifically matching to user #1 skin conditions or skin features are provided to user #1 after the acquisition action.

In another embodiment of FIG. 80, whereas specimen composition recipe 5808 being in the form of composition adjustment of the specimen contained in each of the cartridges 5801, 5802 and 5803 before a user acquires the said cartridges, the specimen information 5821, 5822 and 5823 may not be included within the cartridge #1 5801, cartridge #2 5802 and cartridge #5803 when the said cartridges are acquired by user and installed into cartridge slot of the device body 4603. In this case, the dispensing device dispenses one or more pre-determined amounts from each of the said cartridges. With composition of each cartridge adjusted according to recipe 5808 before arriving to the user, the final composition from a mixture of specimen dispensed from said cartridges automatically meet recipe 5808 when pre-determined amounts of specimen are dispensed from each cartridge, whereas the pre-determined amounts, or physical volumes, of specimens dispensed from different cartridge are in constant relative ratios, for example a physical volume of specimen dispensed from cartridge 5801 when divided by the physical volume of specimen dispensed from cartridge 5802, the resulting ratio number is a constant. In this case, specimen information 5821, 5822 and 5823 are not stored in any physical data storage device included in said cartridges, but rather provided as digital information accompanying each of said cartridges when the user orders these cartridges.

Now referring back to FIG. 1 and FIG. 2. Although FIG. 1 and FIG. 2 show the dispenser 14 residing within the device body 11, in practice the dispenser 14 may also be externally attached to the device body 11, as shown by FIG. 15 whereas dispenser 14 is externally attached to the device body 11 of device 10.

Device 10 of FIG. 1 can be used as a stand-alone system, where its function does not depend on other extrinsic components function. Device 10 can also be used as an embedded system, where the function of the dispensing mechanism is an integral part of a larger system. For example, the device 10 of FIG. 1 can be used as a skin care product dispensing sub-system of a skin care device, where the surface 12 can also be a skin treatment member, as illustrated from FIG. 16 through FIG. 20, which can deliver any or all of the physical means of, ultrasonic vibration, sub-sonic vibration, electrical voltage or current application, heating, cooling, light emission, air blowing, brushing, tapping, shaking, pulsating or scrubbing.

FIG. 16 illustrates a cross-sectional view along the center line 101 of the specimen dispensing device of FIG. 1, whereas the skin treatment member is an ultrasonic transmission plate 1600 that produces ultrasonic vibration. The embodiment of FIG. 16 contains the following aspects: (1) an enclosure body 11 which is made of metal, alloy or plastics; (2) an ultrasound transmission plate 1600 for contacting the skin with a treatment surface 1610 and transmitting ultrasonic vibration generated in ultrasound transmission plate 1600 by an ultrasound generator 1601 to the target skin area, whereas the ultrasound generator 1601 may produce one or more ultrasound modes in ultrasound transmission plate 1600 at one or more frequencies from between 20 kHz to 25 MHz and there may be more than one ultrasound generators 1601 attached to the transmission plate 1600; (3) a dispenser 14 contains skin treatment specimen 19 which can be, but not limited to, liquid, gel, cream, paste and powder; (4) a specimen outlet 15 existing on the treatment surface 1610 of the ultrasound transmission plate 1600, through which skin treatment specimen 19 is dispensed close to or, preferably, directly on top of the treatment surface 1610 that is to be in contact with the skin during skin treatment; (5) electronic control unit 17 existing within the enclosure body 11; and (6) an electrical interface 1602 exists between the ultrasound generator 1601 and the electronic control unit 17 so that the operation of the ultrasound generator 1601 can be electrically controlled by the electronic control unit 17.

Figure 82A:
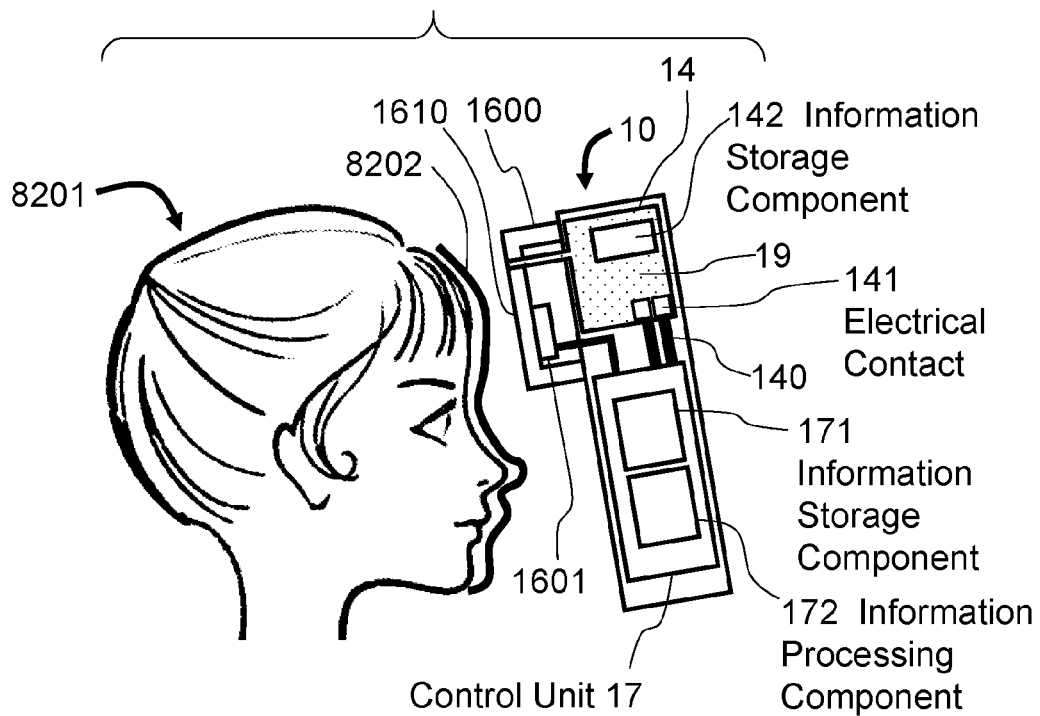

Now referred to FIG. 82A. FIG. 82A illustrates an alternative method to utilize device 10 of FIG. 16 that contains an ultrasound transmission plate 1600 and an ultrasound generator 1601 to apply ultrasound treatment on top of a skin care mask 8202 covering skin area of a user 8201. Different than in FIG. 16, wherein the treatment surface 1610 of ultrasound transmission plate 1600 is in contact with the skin of user 8201 directly during skin treatment, FIG. 82A illustrates a thin mask 8202, which can be a facial mask covering the facial skin of user 8201 as shown in FIG. 82A, being applied over the user facial skin, whereas the treatment surface 1610 of ultrasound transmission plate 1600 of device 10 of FIG. 16 is in contact with the mask 8202 during skin treatment. In the embodiment of FIG. 82A, the specimen 19 may be dispensed from the device 10 onto the mask in any form of: liquid, gel, serum, lotion or paste, whereas the specimen 19 may diffuse within the material of the mask 8202 over a first area of the mask 8202, and whereas treatment surface 1610 of ultrasound transmission plate 1600 is in contact with the mask 8202 at the first area and the ultrasound mode from the treatment surface 1610 may transmit to the mask 8202, whereas the ultrasound mode from the treatment surface 1610 may help specimen 19 contained in material of mask 8202 being absorbed by skin of user 8201 with a higher efficacy, including a longer lasting skin care treatment effect, deeper specimen effective element penetration into user skin, stronger skin treatment effect with better skin feature reduction, and a more uniform skin treatment result across a larger area of the skin of user 8201, than when ultrasound mode is not applied. In another embodiment, treatment surface 1610 of ultrasound transmission plate 1600 is in contact with the mask 8202 at the first area and the ultrasound mode from the treatment surface 1610 may transmit through the mask 8202 and reach the skin of user 8201 underneath skin, whereas the ultrasound mode from the treatment surface 1610 may help specimen 19 contained in material of mask 8202 being absorbed by skin of user 8201 in a higher efficacy. Mask 8202 may be composed of materials of any one or more of: (a) fabrics including cotton, wool, nylon, plastics fibers, fibers, metal fibers, or polymer fibers; (b) paper; (c) membranes of animal skin, plant skin, polymer, cotton, or metal. Mask 8202 may be a material that absorbs the ultrasound energy such that the ultrasound mode from the treatment surface 1610 does not reach user 8201 skin. Mask 8202 may also be a material that transmits the ultrasound energy such that the ultrasound mode from the treatment surface 1610 may reach user 8201 skin.

Figure 17:
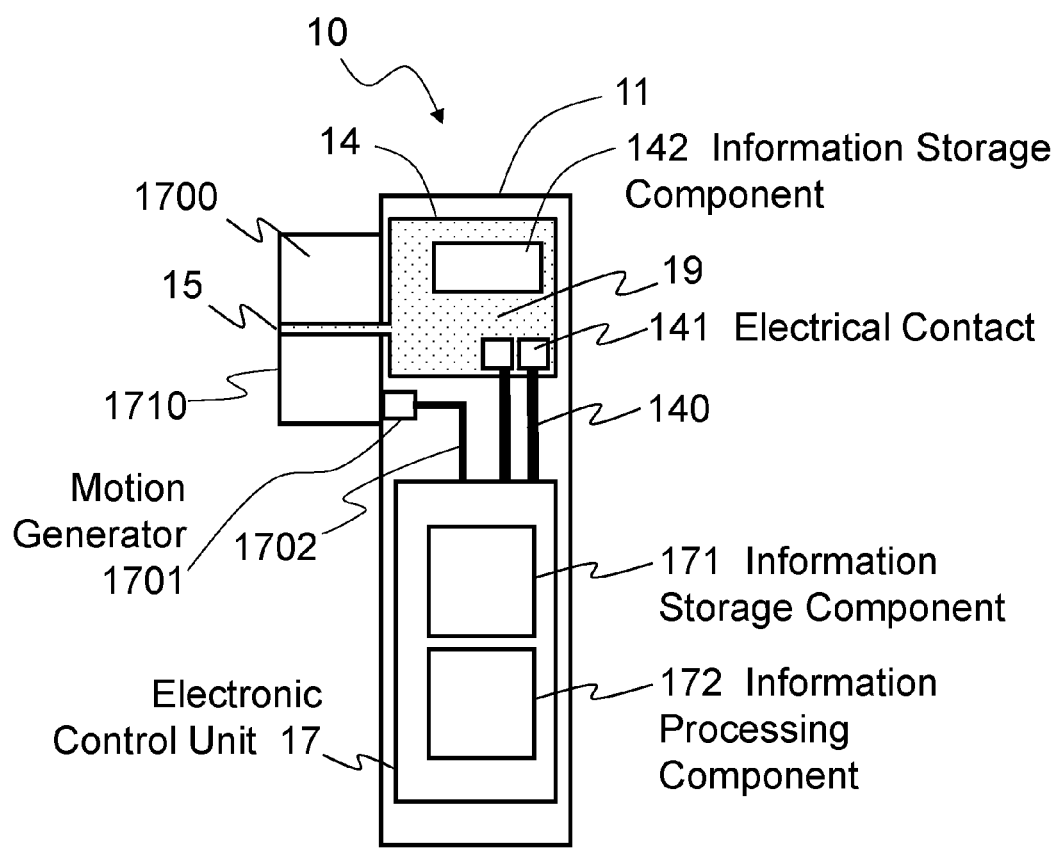
FIG. 17 illustrates a cross-sectional view along the center line 101 of the specimen dispensing device of FIG. 1 that has a skin treatment member, whereas the skin treatment member is a vibration head.

In another embodiment, device 10 of FIG. 82A may be replaced with device 10 of FIG. 17, which has a vibration head 1700 for contacting the skin with a treatment surface 1710 and transmitting mechanical motion generated from vibration head 1700 by a motion generator 1701 to the target skin area, whereas the motion generator 1701 may produce mechanical motions in the vibration head 1700 at one or more frequencies from between 1 Hz to 20 kHz, whereas the mechanical motion generated from vibration head 1700 may be acting on the mask 8202 only, or may be acting on the skin of user 8201 through the mask 8202.

Figure 18:
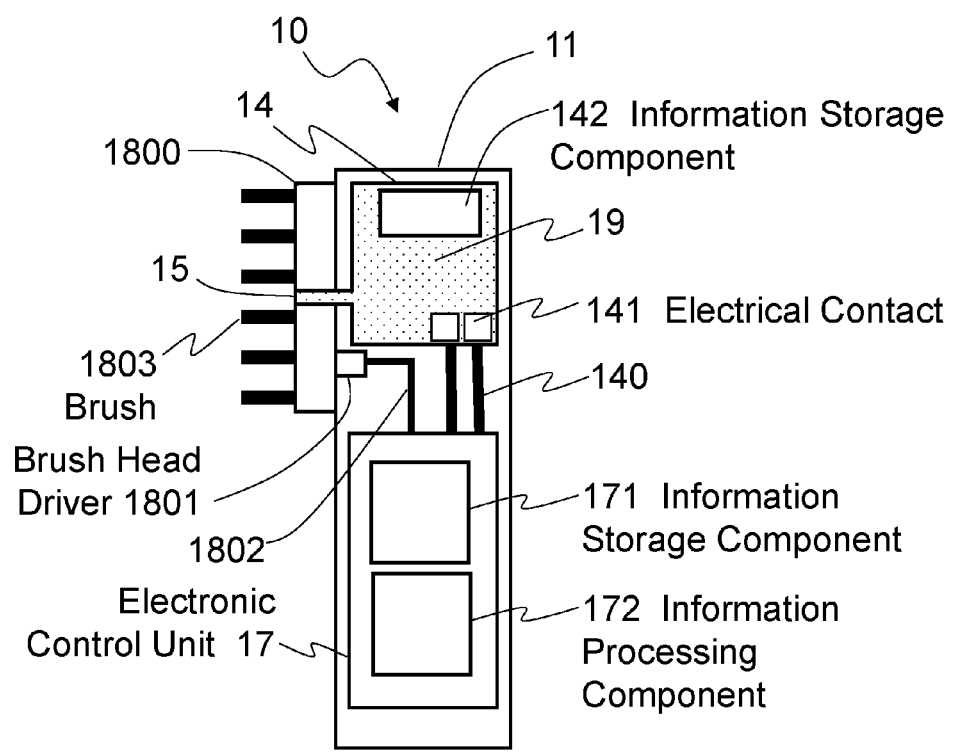
FIG. 18 illustrates a cross-sectional view along the center line 101 of the specimen dispensing device of FIG. 1 that has a skin treatment member, whereas the skin treatment member is a brush head.

In yet another embodiment, device 10 of FIG. 82A may be replaced with device 10 of FIG. 18, which has a brush head 1800 which can produce any motion of: rotational, tapping, pulsating and vibration movements during skin treatment that are powered and controlled by a brush head driver 1801, whereas the head driver 1801 may produce mechanical motions of the brush head 1800 at one or more frequencies from between 1 Hz to 20 kHz, whereas the mechanical motion generated from brush head 1800 and brush fibers 1803 may be acting on the mask 8202 only, or may be acting on the skin of user 8201 through the mask 8202.

Figure 19:
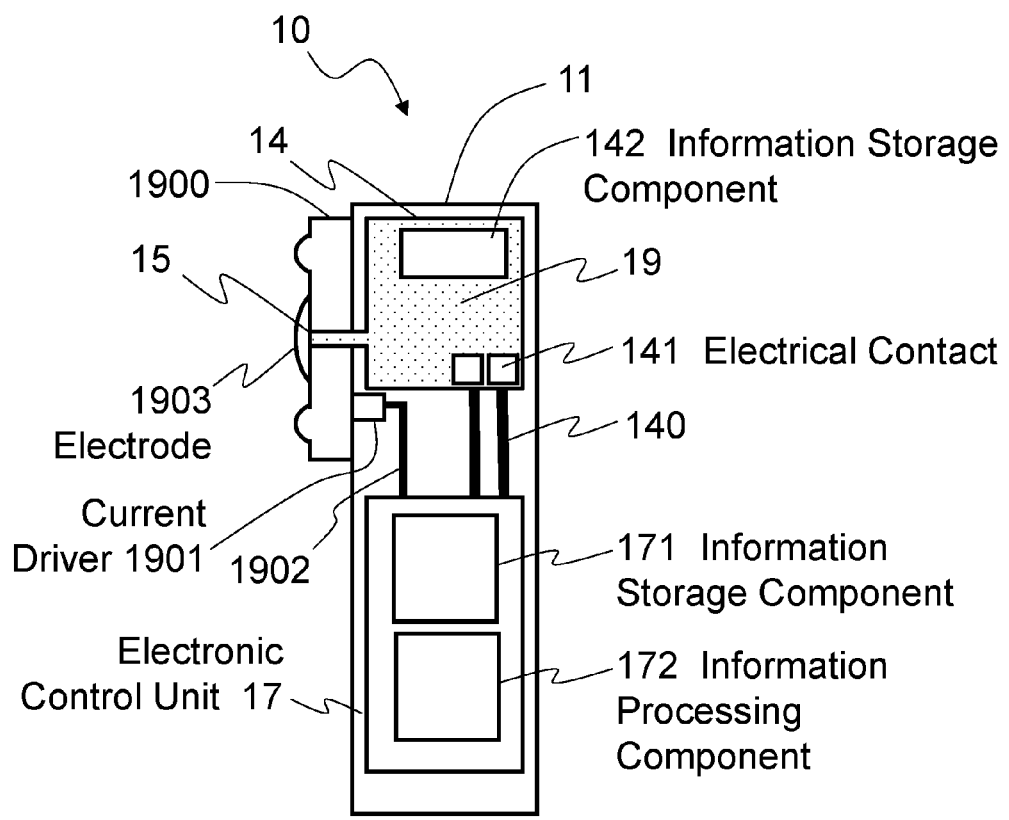
FIG. 19 illustrates a cross-sectional view along the center line 101 of the specimen dispensing device of FIG. 1 that has a skin treatment member, whereas skin treatment member contains one or more electrodes.

In yet another embodiment, device 10 of FIG. 82A may be replaced with device 10 of FIG. 19, which has a galvanic skin treatment head 1900 with one or more electrodes 1903 and producing electric voltage and current on the target skin area, whereas the mask 8202 may provide an additional function of changing the electrical impedance, or electrical resistance, between the user 8201 skin and the electrodes 1903, for example to reduce the electrical shock occurrence during skin treatment, or to make electrical voltage or current application by electrodes 1903 more uniformly distributed around a targeted skin area covered by the mask 8202.

Figure 20:
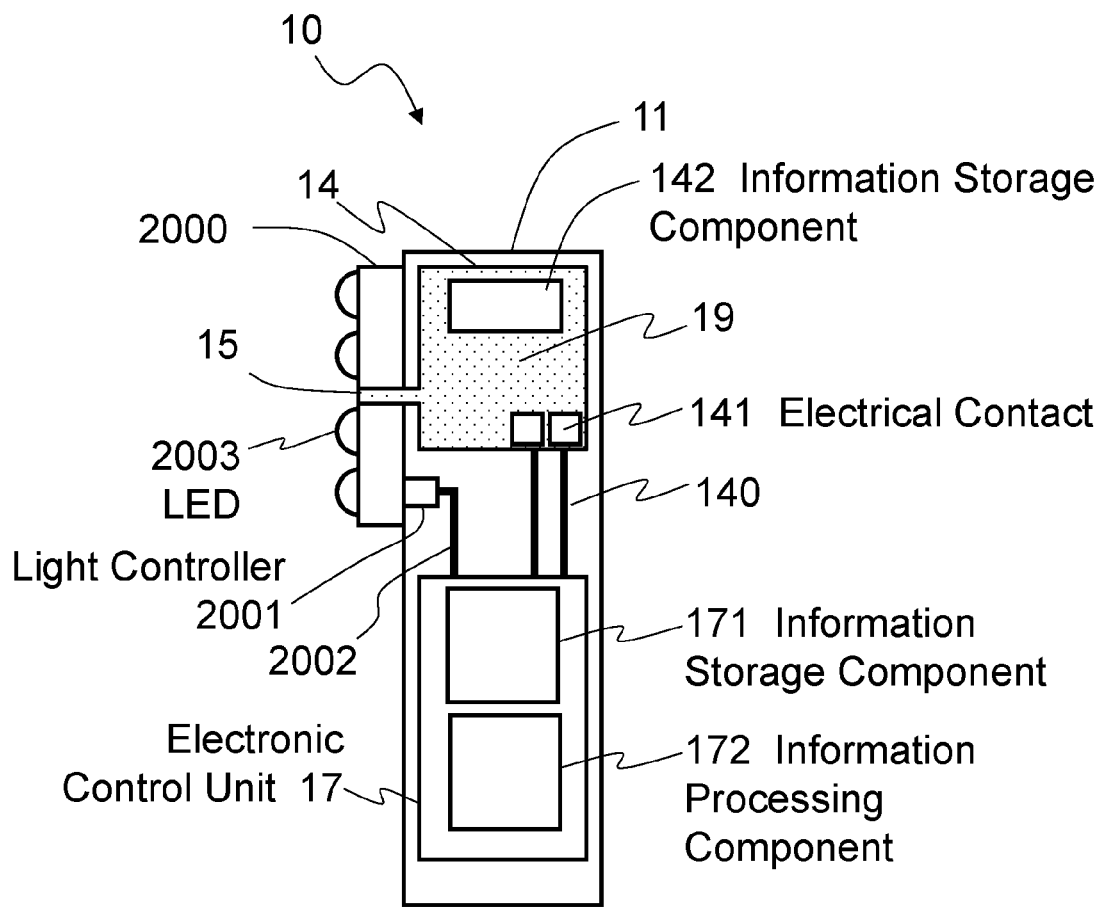
FIG. 20 illustrates a cross-sectional view along the center line 101 of the specimen dispensing device of FIG. 1 that has a skin treatment member, whereas skin treatment member contains one or more light emitting devices (LED) to emit light.

In yet another embodiment, device 10 of FIG. 82A may be replaced with device 10 of FIG. 20, which has a lightening housing 2000 for containing one or more LEDs 2003, and whereas the LEDs 2003 may emit optical radiation towards a user's skin without being in contact with the skin, whereas the mask 8202 may provide an additional function of providing an optical filtering of the optical radiation generated by LEDs 2003, for example to reduce, or block completely, the optical radiations at ultraviolet frequencies, or to make optical heating by the optical radiation from LEDs 2003 more uniformly distributed around a targeted skin area covered by the mask 8202.

Figure 82B:
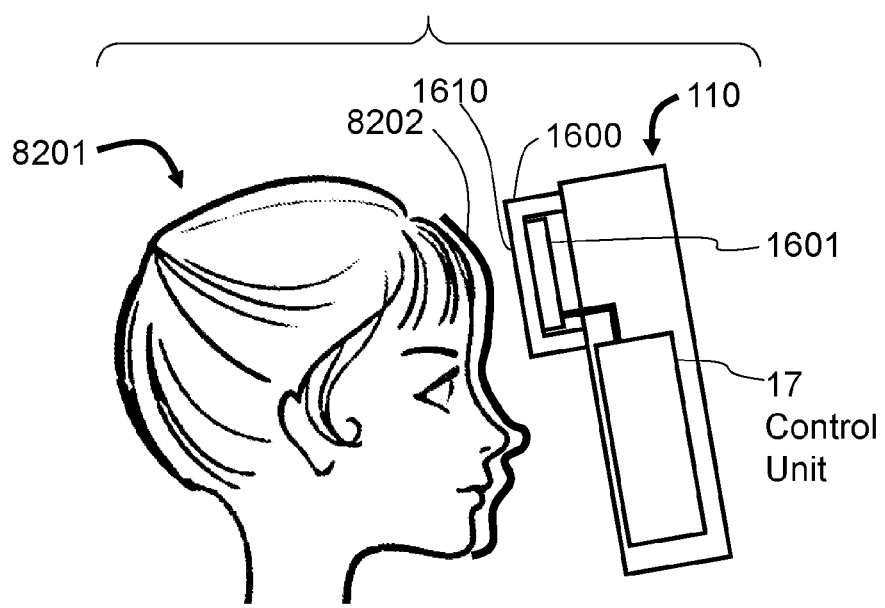

FIG. 82B illustrates a method to utilize device 110 that contains an ultrasound transmission plate 1600 and an ultrasound generator 1601 to apply ultrasound treatment on top of a skin care mask 8202 covering skin area of a user 8201. Compared to FIG. 82A, 82B is identical with the exception of not having embedded dispenser 14 in device 110, and the control unit 17 in device 110 not containing information storage component 171 or information processing component 172, whereas control unit 17 may only control the ultrasound mode generation on treatment surface 1610 of ultrasound transmission plate 1600 by the ultrasound generator 1601. Mask 8202 of FIG. 82B is same as in FIG. 82A. Specimen 19 may be applied to and contained within the mask 8202 through another external method, for example mask 8202 may be partially or entirely soaked by a liquid form specimen 19 before the mask 8202 is applied over the skin of user 8201. Skin treatment method of 82B is identical to FIG. 82A, whereas the treatment surface 1610 of ultrasound transmission plate 1600 is in contact with the mask 8202 at an area containing specimen 19 in the material of the mask 8202, and the ultrasound mode from the treatment surface 1610 may transmit to the mask 8202, or may transmit through the mask 8202 and reaching the skin of user 8201, and help specimen 19 contained in material of mask 8202 being absorbed by skin of user 8201 with a higher efficacy.

In other embodiments, similarly as described in FIG. 82A, device 110 of FIG. 82B may be replaced with any device from: device 10 of FIG. 17, device 10 of FIG. 18, device 10 of FIG. 19, or device 10 of FIG. 20, with the exception that the embedded dispenser 14, information storage component 171 or information processing component 172 contained in these device may not be included in these devices when applied to replace the device 110 of FIG. 82B.

Now referring to FIG. 17. FIG. 17 illustrates a cross-sectional view along the center line 101 of the specimen dispensing device of FIG. 1, whereas the skin treatment member is a vibration head 1700 that produces any mechanical motion of: sub-sonic vibration, tapping, shaking, pulsating or scrubbing, that act upon a user's skin during contact. The embodiment of FIG. 17 contains the following aspects: (1) an enclosure body 11 which is made of metal, alloy or plastics; (2) a vibration head 1700 for contacting the skin with a treatment surface 1710 and transmitting mechanical motion generated from vibration head 1700 by a motion generator 1701 to the target skin area, whereas the motion generator 1701 may produce mechanical motions in the vibration head 1700 at one or more frequencies from between 1 Hz to 20 kHz; (3) a dispenser 14 contains skin treatment specimen 19 which can be, but not limited to, liquid, gel, cream, paste and powder; (4) a specimen outlet 15 existing on the treatment surface 1710 of the vibration head 1700, through which skin treatment specimen 19 is dispensed close to or, preferably, directly on top of the treatment surface 1710 that is to be in contact with the skin during skin treatment; (5) electronic control unit 17 existing within the enclosure body 11; and (6) an electrical interface 1702 exists between the motion generator 1701 and the electronic control unit 17 so that the operation of the motion generator 1701 can be electrically controlled by the electronic control unit 17.

FIG. 18 illustrates a cross-sectional view along the center line 101 of the specimen dispensing device of FIG. 1, whereas the skin treatment member is a brush head 1800 that produces brushing function upon a user's skin during contact. The embodiment of FIG. 18 contains the following aspects: (1) an enclosure body 11 which is made of metal, alloy or plastics; (2) a brush head 1800 which can produce any motion of: rotational, tapping, pulsating and vibration movements during skin treatment that are powered and controlled by a brush head driver 1801, whereas the head driver 1801 may produce mechanical motions of the brush head 1800 at one or more frequencies from between 1 Hz to 20 kHz; (3) a plurality of brush fibers 1803 for contacting user's skin during a skin treatment being attached to the brush head; (4) a dispenser 14 contains skin treatment specimen 19 which can be, but not limited to, liquid, gel, cream, paste and powder; (5) a specimen outlet 15 that is either in the form of a clearance into the brush head 1800 surface where brush fibers 1803 reside, or in the form of a soft tube extruding from the brush head surface to a height slightly shorter than the maximum length of the brush fibers 1803, and the specimen 19 is preferably dispensed to the brush fibers 1803 that are to be in contact with the skin during skin treatment; (6) electronic control unit 17 existing within the enclosure body 11; and (7) an electrical interface 1802 exists between the brush head driver 1801 and the electronic control unit 17 so that the operation of the brush head driver 1801 can be electrically controlled by the electronic control unit 17.

FIG. 19 illustrates a cross-sectional view along the center line 101 of the specimen dispensing device of FIG. 1, whereas skin treatment member is a component that contains, or is comprised of, one or more electrodes 1903 to apply electrical voltage or current to user's skin during contact. The embodiment of FIG. 19 contains the following aspects: (1) an enclosure body 11 which is made of metal, alloy or plastics; (2) a galvanic skin treatment head 1900 for contacting the skin with one or more electrodes 1903 and producing electric voltage and current on the target skin area; (3) a voltage or current driver 1901 which generates the electric voltage or current, whereas the voltage or current driver 1901 may apply electrical voltage between 0.5 Volt (V) to 100 Volt (V), or an electric current between 1 nanoAmpere (nA) to 1 milliAmpere (mA), in between at least two electrode 1903 when the electrodes 1903 are in contact with user's skin, and whereas the applied voltage or current between at least two electrodes 1903 may be a DC voltage or current, or an AC voltage or current at one or more frequencies from between 0.1 Hertz (Hz) to 800 MegaHertz (MHz); (4) a dispenser 14 contains skin treatment specimen 19 which can be, but not limited to, liquid, gel, cream, paste and powder; (5) a specimen outlet 15 existing on the surface of the treatment head 1900 where the electrodes 1903 reside, whereas when the specimen 19 is dispensed through the specimen outlet 15, specimen 19 is disposed close to or, preferably, directly on top of one or more of the electrodes 1903 that are to be in contact with the skin during skin treatment; (6) electronic control unit 17 existing within the enclosure body 11; and (7) an electrical interface 1902 exists between voltage or current driver 1901 and the electronic control unit 17 so that the operation of the voltage or current driver 1901 can be electrically controlled by the electronic control unit 17.

FIG. 20 illustrates a cross-sectional view along the center line 101 of the specimen dispensing device of FIG. 1, whereas skin treatment member is a component that contains, or is comprised of, one or more light emitting devices (LED) 2003 to emit light, or optical radiation, towards a user's skin. The embodiment of FIG. 20 contains the following aspects: (1) an enclosure body 11 which is made of metal, alloy or plastics; (2) a lightening housing 2000 for containing one or more LEDs 2003, and whereas the LEDs 2003 may emit optical radiation towards a user's skin without being in contact with the skin; (3) a light controller 2001 which powers LEDs 2003 with providing electric voltage or current to the LEDs 2003 such that LEDs 2003 may emit optical radiation, whereas light controller 2001 may apply DC voltage or current to the LEDs 2003, or a light controller 2001 may apply AC voltage or current to the LEDs 2003 at one or more frequencies from between 0.1 Hz to 100 MHz, and whereas the optical radiation generated by the LEDs 2003 may have one or more optical wavelengths between 300 nm to 1 mm; (4) a dispenser 14 contains skin treatment specimen 19 which can be, but not limited to, liquid, gel, cream, paste and powder; (5) a specimen outlet 15 existing on the surface of the lighting housing 2000 where LEDs 2003 reside, the specimen 19 may be dispensed through the outlet 15 and disposed either on the surface of the housing unit 2000, or directly onto the skin area to be treated; (6) electronic control unit 17 existing within the enclosure body 11; and (7) an electrical interface 2002 exists between light controller 2001 and the electronic control unit 17 so that the operation of the light controller 2001 and optical radiation emission from LEDs 2003 may be electrically controlled by the electronic control unit 17.

Now referring back to FIG. 2. In the most preferred mode, the device body 11 of the device 10 is in an easy-holding palm-size oval shape and includes two continuous pieces—front and back pieces—which are mechanically coupled together. The specimen outlet 15 is on the front piece immediately coupled to the surface 12. In use, the back piece is for palm-holding. The device includes a wireless charger and thus it can be charged wirelessly.

Second Preferred Embodiment

Figure 8:
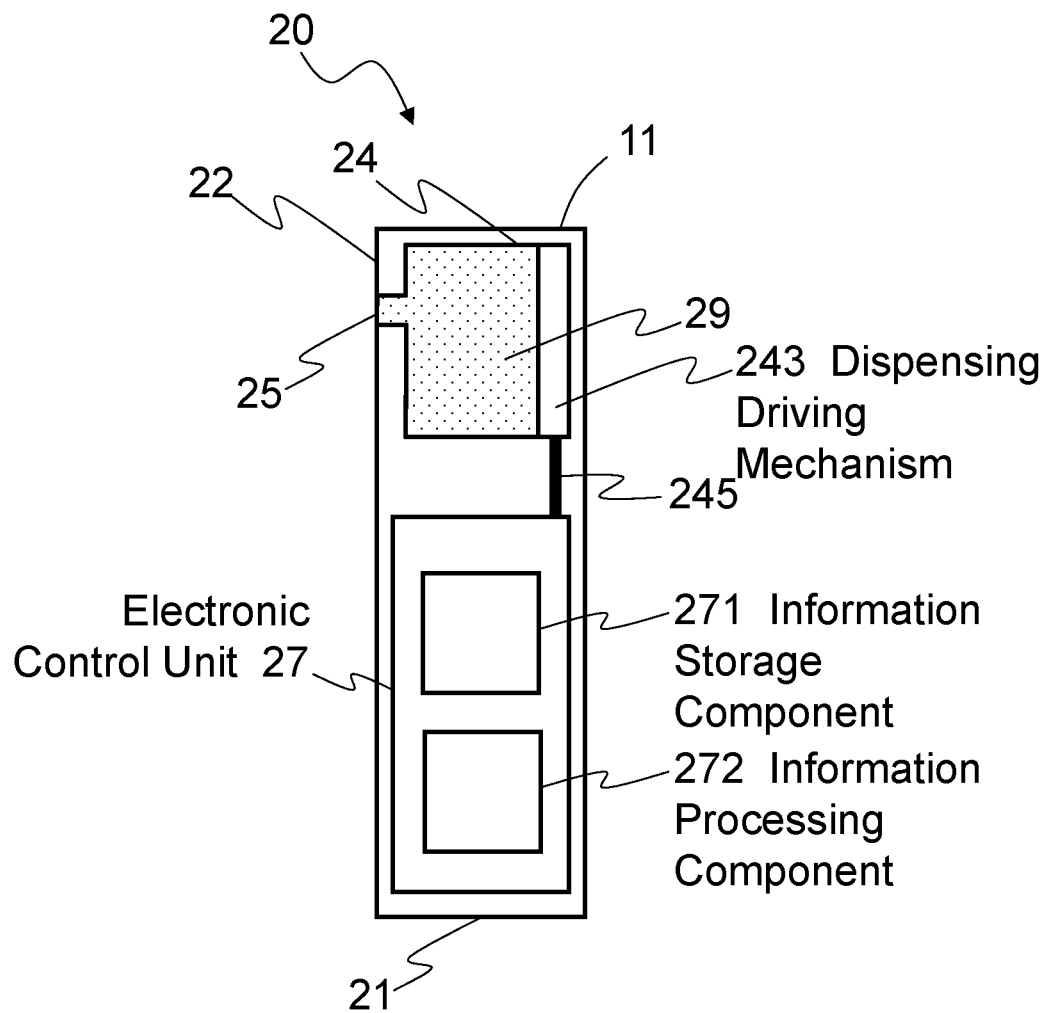
FIG. 8 is a schematic diagram illustrating a cross-sectional view of the specimen dispensing device of FIG. 1 according to the second preferred embodiment of the present invention.

Now referring back to FIG. 8. FIG. 8 is a schematic diagram illustrating a cross-sectional view of a specimen dispensing device 20 according to the second preferred embodiment of the present invention, where a specimen dispenser is integrated within a specimen dispensing device 20. The components 21, 22, 24, 25, 27, 29, 271, and 272 in the second preferred embodiment as illustrated in FIG. 8 are substantially same as the components 11, 12, 14, 15, 17, 19, 171, and 172, respectively, as illustrated in FIG. 2.

However, the dispenser 24 does not include a digital data storage component. A dispensing driving mechanism 243 is coupled to the dispenser 24 to enable dispensing of the specimen 29. The control unit 27 has an information storage component 271 that contains specimen data of the specimen 29. Such specimen data can be recorded into the component 271 when the specimen dispenser 24 is integrated into the dispensing device 20. The recording of specimen data into the component 271 can be achieved electrically by an external data input device. The specimen data can also be automatically recorded into the component 271 by the control unit 27, when the dispenser 24 has non-electrical information containing feature, such as, but not limited to, indentation, protrusion, bar code, RFID, graphic or chemical, which triggers an information retrieval from such feature by the control unit 27. User skin data are imported into the device 20 and stored in the component 271. The information processing component 272 processes the specimen and user skin data from the component 271, and formulates an optimal dispensing scheme. The control unit 27 drives the dispensing mechanism 243 through the electrical interconnect 245 following the optimal scheme to dispense the specimen 29 from the dispenser 24.

Figure 9:
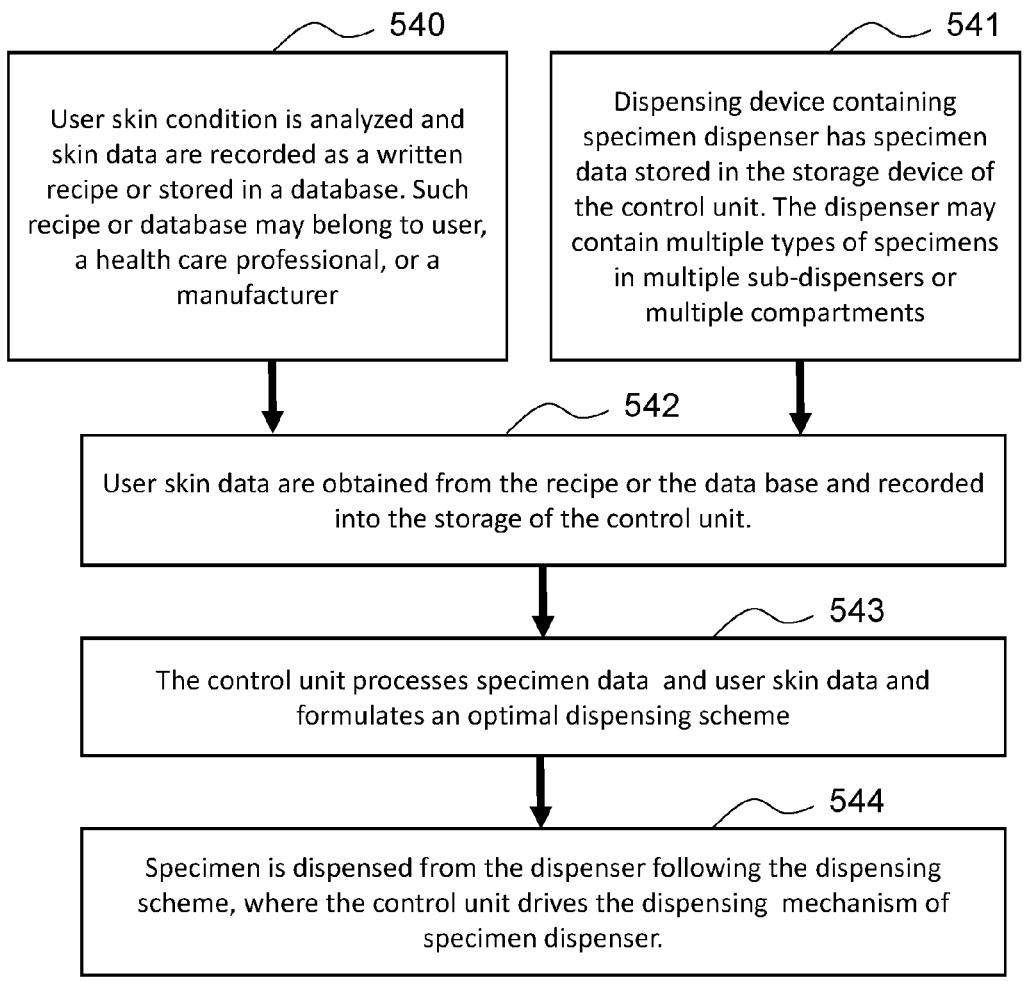
FIG. 9 is a flow diagram illustrating a process of operation of the specimen dispensing device according to the second preferred embodiment of the present invention.

A process of operation according to the second embodiment, as illustrated in FIG. 9, contains steps of:

Step 540: user skin condition is analyzed and skin data are recorded as a written recipe or stored in a database, wherein such recipe or database may belong to user, a health care professional, or a manufacturer.

Step 541: dispensing device containing specimen dispenser has specimen data stored in the storage device of the control unit, wherein the dispenser may contain multiple types of specimens in multiple sub-dispensers or multiple compartments.

Step 542: user skin data are obtained from the recipe or the data base and recorded into the storage of the control unit.

Step 543: the control unit processes specimen data and user skin data and formulates an optimal dispensing scheme.

Step 544: specimen is dispensed from the dispenser following the optimal dispensing scheme, where the control unit drives the dispensing mechanism of specimen dispenser.

Figure 77:
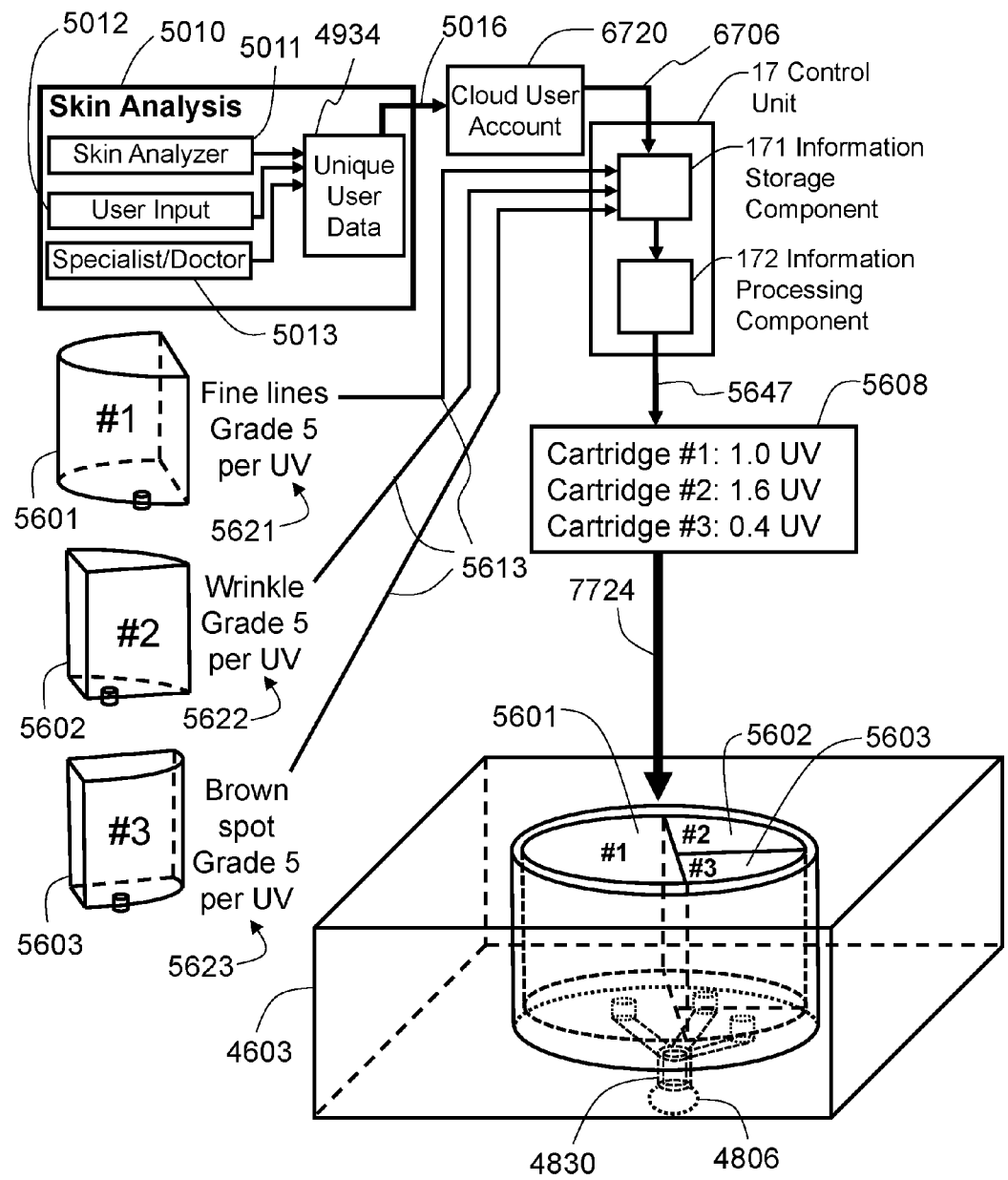

Now referring to FIG. 77. FIG. 77 illustrates a method to realize personalized dispensing scheme utilizing a dispensing device and a set of cartridges according to FIG. 9 process. The step of skin analysis 5010, same as in FIG. 50, may create unique user data 4934 with input from any of: skin analyzer 5011, user input 5012, specialist and dermatologist 5013. The unique user data 4934 may be sent to store in the cloud user account 6720 of FIG. 67 through communication 5016 of FIG. 50, to achieve step 540 of FIG. 9, whereas unique user data 4934 may be stored in cloud user account 6720 as user data structure 5300 of FIG. 53.

Cartridge #1 5601, cartridge #2 5602 and cartridge #3 5603 with each containing specimen therein and each respectively containing specimen information 5621, 5622 and 5623, same as in FIG. 56, are installed into cartridge slot of the device body 4603, same as in FIG. 48A, of the said dispensing device as a cartridge set of #1 5601, #2 5602 and #3 5603 cartridges. Specimen information 5621, 5622 and 5623 respectively contained in cartridge #1 5601, cartridge #2 5602 and cartridge #3 5603 are transferred to the information storage component 171 of control unit 17 within said dispensing device through communication 5613, same as in FIG. 56, to achieve step 541 of FIG. 9.

Unique user data 4934 is downloaded from cloud user account 6720 and stored in the information storage component 171 of control unit 17 within said dispensing device through communication 6706, same as in FIG. 67, to achieve step 542 of FIG. 9.

Information processing component 172 of control unit 17 within said dispensing device may process information contained in the information storage component 171 of control unit 17, which may include both the unique user data 4934 and specimen information 5621, 5622 and 5623 that are respectively transferred through communication 6706 and communication 5613, to produce or calculate a dispensing recipe 5608 of user #1 cartridge set dispense scheme 5607 of FIG. 56 in step 5647, same as in FIG. 56, to achieve step 543 of FIG. 9.

Dispensing recipe 5608 is then implemented in dispensing of specimen from cartridge #1 5601, cartridge #2 5602 and cartridge #3 5603 as shown by step 7724. Dispensing device dispenses final specimen 4806, which is a mixture of specimen from cartridges 5601, 5602 and 5603 according to the dispensing recipe 5608, through the device outlet 4830, to achieve step 544 of FIG. 9.

Third Preferred Embodiment

Figure 10:
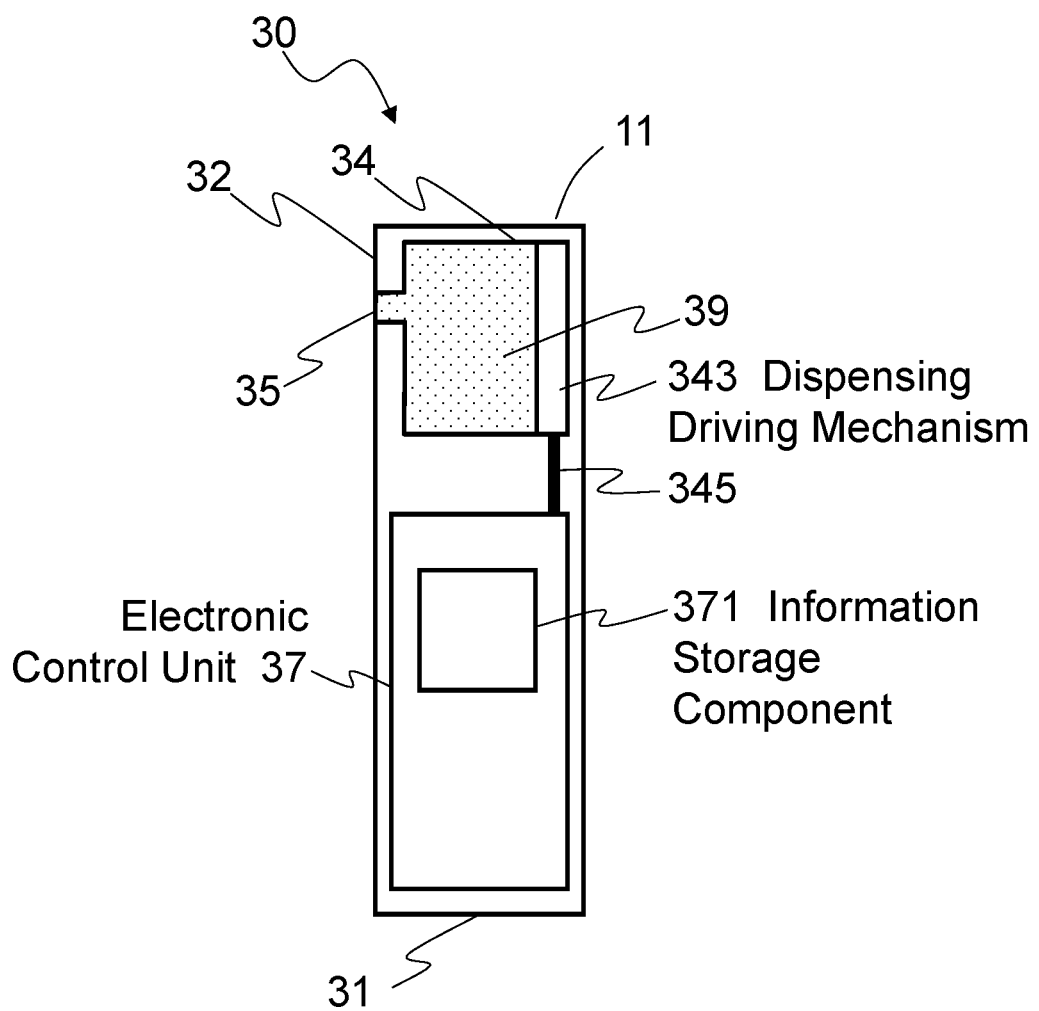
FIG. 10 is a schematic diagram illustrating a cross-sectional view of the specimen dispensing device of FIG. 1 according to the third preferred embodiment of the present invention.

FIG. 10 is a schematic diagram illustrating a cross-sectional view of the specimen dispensing device 30 according to the third preferred embodiment of the present invention, where a specimen dispenser is integrated within a specimen dispensing device 30. The components 31, 32, 34, 35, 37, 39, 343, and 345 in the third preferred embodiment as illustrated in FIG. 8 are substantially same as the components 21, 22, 24, 25, 27, 29, 243, and 245, respectively, as illustrated in FIG. 8.

The control unit 37 has an information storage component 371 that contains the information of the optimal dispensing scheme, with which the control unit 37 drives the dispensing mechanism 343 via an electrical interconnect 345 following the optimal scheme to dispense the specimen 39 from dispenser 34.

The optimal dispensing scheme is formulated outside of the dispensing device. Specimen data and skin data can be similarly stored in the component 371 as in the preferred second embodiment. They may also be stored external to the dispensing device 30. The specimen data and skin data are retrieved and processed by a computer or a data processing unit external for the dispensing device 30 to formulate an optimal dispensing scheme. This optimal dispensing scheme is then imported into the component 371. The control unit 37 reads the optimal scheme data from the component 371 and drives the dispensing mechanism 343 through the electrical interconnect 345 following the optimal scheme to dispense specimen 39 from the dispenser 34.

Figure 11:
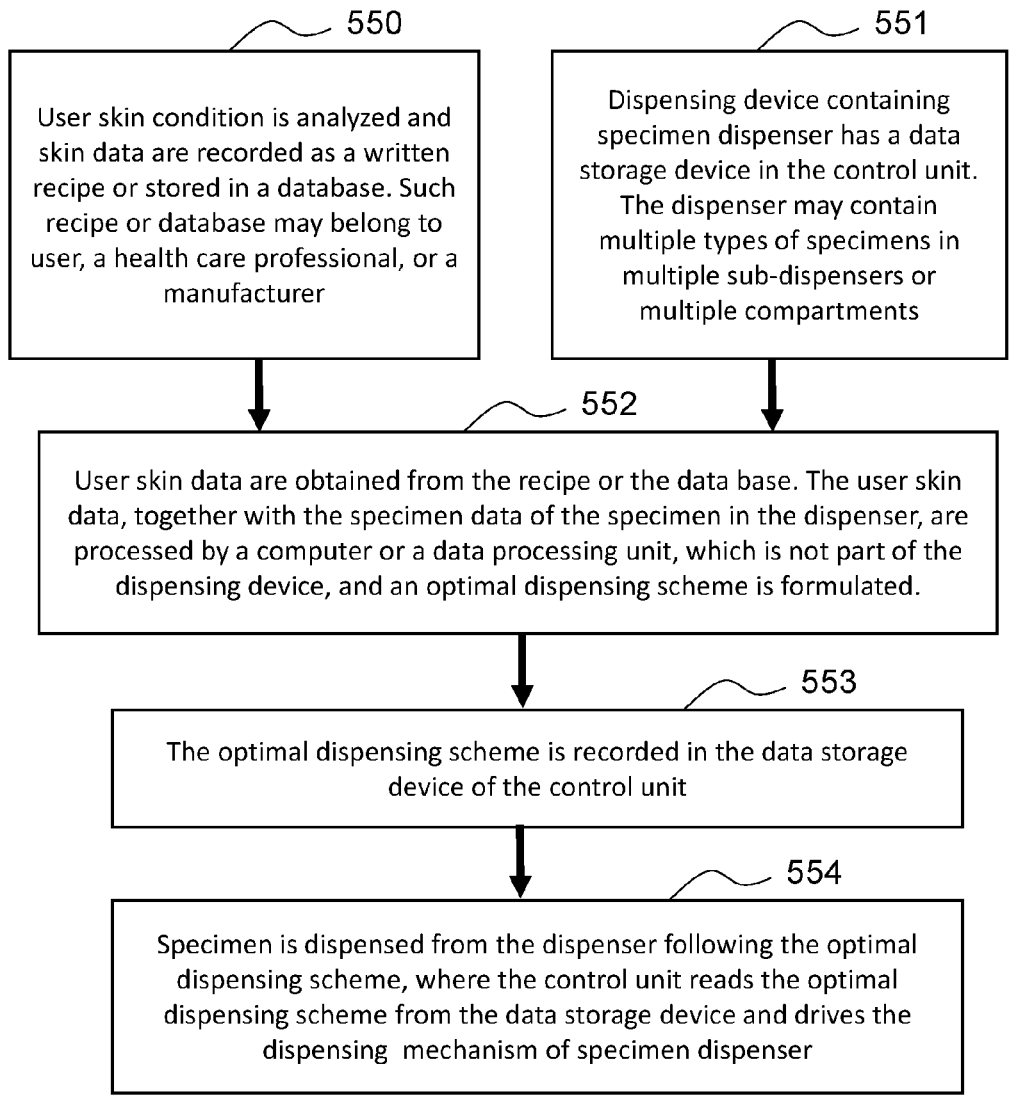
FIG. 11 is a flow diagram illustrating a process of operation of the specimen dispensing device according to the third preferred embodiment of the present invention.

A process of operation according to the second preferred embodiment, as illustrated in FIG. 11, includes the steps of:

Step 550: user skin condition is analyzed and skin data are recorded as a written recipe or stored in a database, wherein such recipe or database may belong to user, a health care professional, or a manufacturer.

Step 551: dispensing device containing specimen dispensers has a data storage device in the control unit. The dispenser may contain multiple types of specimens in multiple sub-dispensers or multiple compartments.

Step 552: retrieving the user skin data from the recipe or the data base. The user skin data, together with the specimen data of the specimen in the dispenser, are processed by a computer or a data processing unit, which is not part of the dispensing device, and an optimal dispensing scheme is formulated.

Step 553: storing the optimal dispensing scheme in the data storage device of the control unit.

Step 554: Specimen is dispensed from the dispenser following the optimal dispensing scheme, where the control unit reads the optimal dispensing scheme from the data storage device and drives the dispensing mechanism of specimen dispenser.

Figure 78:
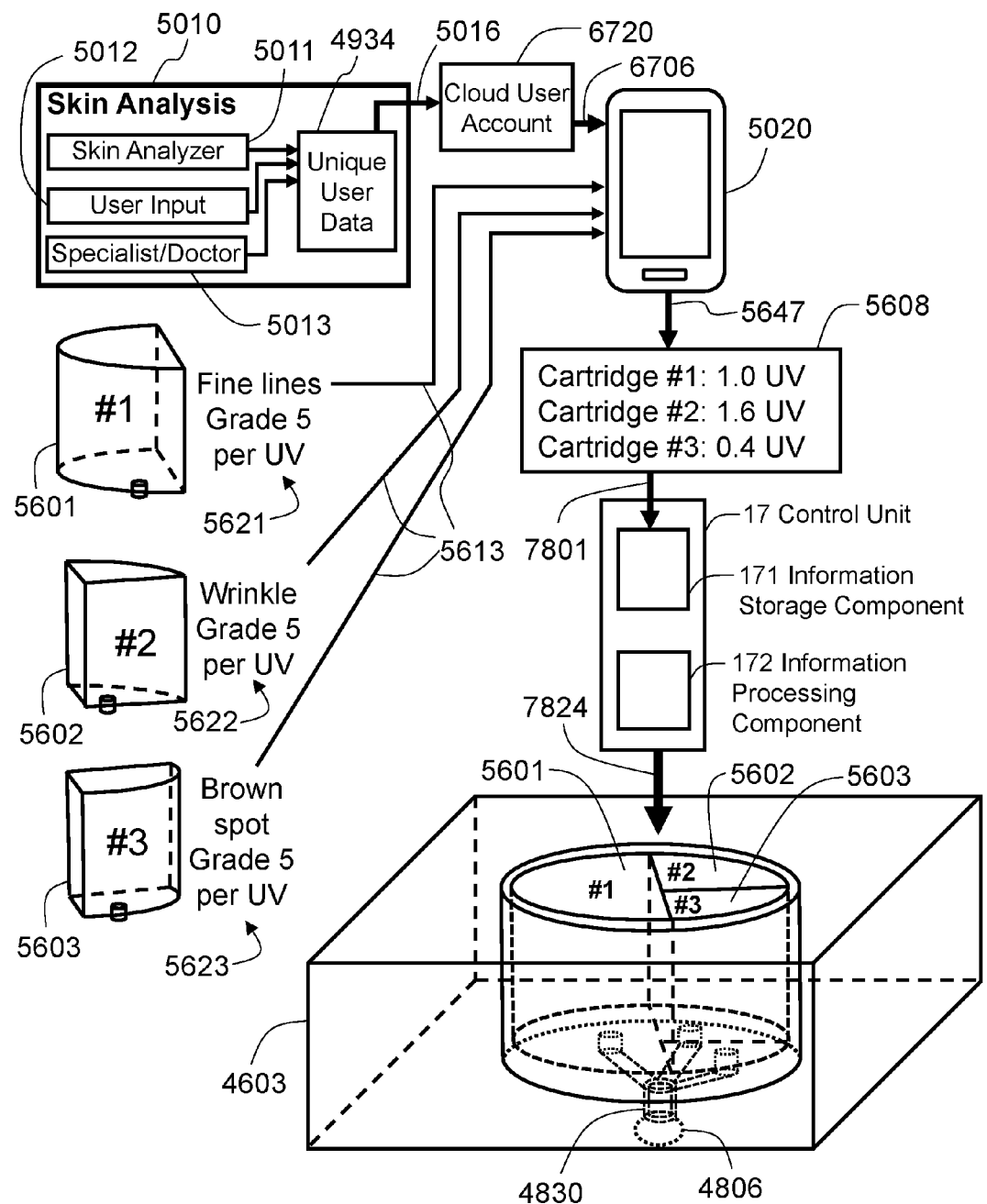

Now referring to FIG. 78. FIG. 78 illustrates a method to realize personalized dispensing scheme utilizing a dispensing device and a set of cartridges according to FIG. 11 process. The step of skin analysis 5010, same as in FIG. 50, may create unique user data 4934 with input from any of: skin analyzer 5011, user input 5012, specialist and dermatologist 5013. The unique user data 4934 may be sent to store in the cloud user account 6720 of FIG. 67 through communication 5016 of FIG. 50, to achieve step 550 of FIG. 11, whereas unique user data 4934 may be stored in cloud user account 6720 as user data structure 5300 of FIG. 53.

Cartridge #1 5601, cartridge #2 5602 and cartridge #3 5603 with each containing specimen therein and each respectively containing specimen information 5621, 5622 and 5623, same as in FIG. 56, are installed into cartridge slot of the device body 4603, same as in FIG. 48A, of the said dispensing device as a cartridge set of #1 5601, #2 5602 and #3 5603 cartridges, whereas an information storage component 171 is contained in control unit 17 within said dispensing device, to achieve step 551 of FIG. 11.

Unique user data 4934 is downloaded from cloud user account 6720 and sent to a personal computing device 5020 of FIG. 50, which may also be a user mobile device 6712 of FIG. 68, through communication 6706. The personal computing device 5020 may acquire specimen information 5621, 5622 and 5623 through communication 5613, which may also be communications 6202 or 6203 of FIG. 62 between a dispensing device that contains the cartridge #1 5601, cartridge #2 5602 and cartridge #5603, and the personal computing device 5020. Communication 5613 of FIG. 78 may also be the communication 5024 of FIG. 50 between a personal computing device 5020 and vender, service, production database 5044 of a beauty cloud 5040. The personal computing device 5020 may process information contained in the personal computing device 5020, which may include both the unique user data 4934 and specimen information 5621, 5622 and 5623 that are respectively transferred through communication 6706 and communication 5613, to produce or calculate a dispensing recipe 5608 of user #1 cartridge set dispense scheme 5607 of FIG. 56 in step 5647, same as in FIG. 56, to achieve step 552 of FIG. 11.

Dispensing recipe 5608 is then sent to be stored in information storage component 171 of control unit 17, as step 7801, to achieve step 553 of FIG. 11.

Control unit 17 controls dispensing of specimen from cartridge #1 5601, cartridge #2 5602 and cartridge #3 5603 by reading dispensing scheme 5608 from information storage component 171, and by implementing dispensing scheme 5608, for example through electrical commands generated by an information processing component 172 of control unit 17, in dispensing of specimen as shown by step 7824. Dispensing device dispenses final specimen 4806, which is a mixture of specimen from cartridges 5601, 5602 and 5603 according to the dispensing recipe 5608, through the device outlet 4830, to achieve step 554 of FIG. 11.

Fourth Preferred Embodiment

Figure 12:
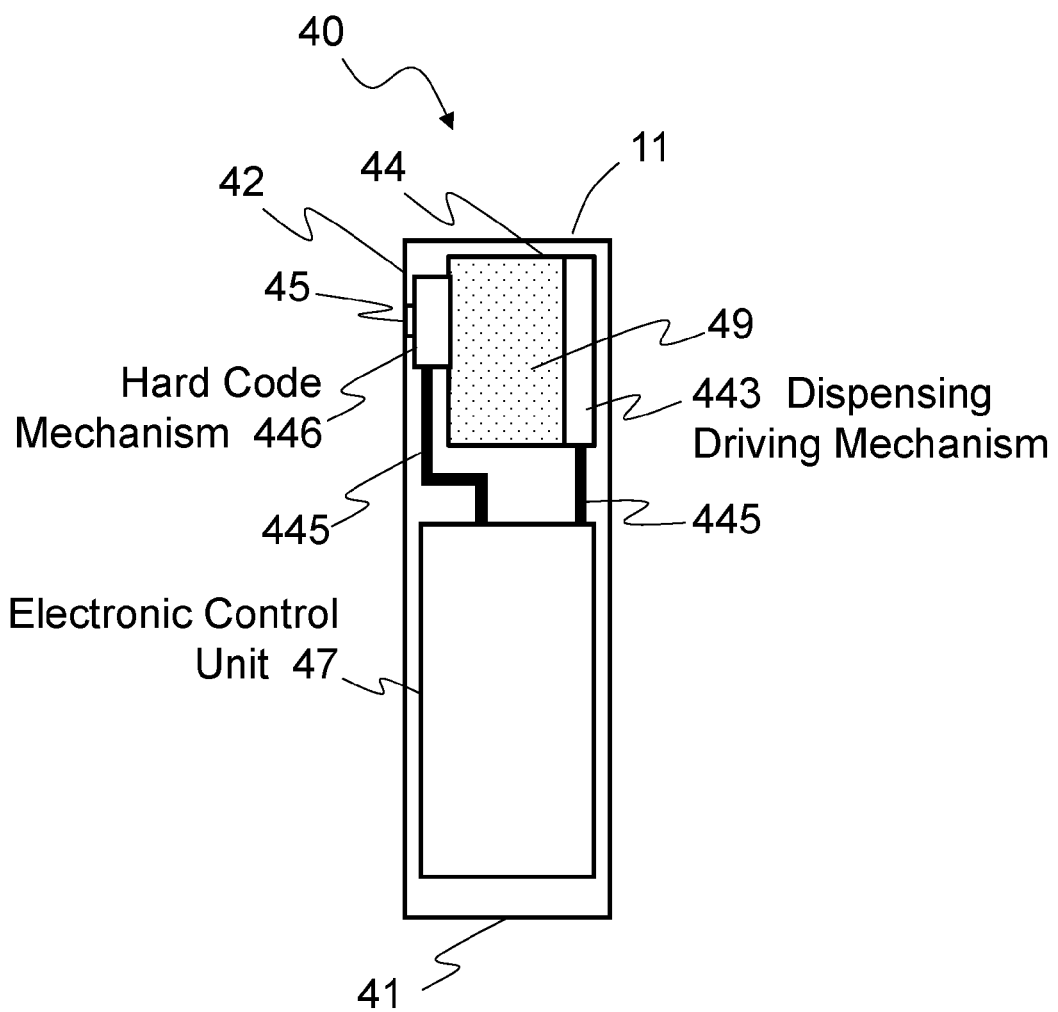
FIG. 12 is a schematic diagram illustrating a cross-sectional view of the specimen dispensing device of FIG. 1 according to the fourth preferred embodiment of the present invention.

FIG. 12 is a schematic diagram illustrating a cross-sectional view of the specimen dispensing device 40 according to the fourth preferred embodiment of the present invention, where a specimen dispenser is integrated within a specimen dispensing device 40. The components 41, 42, 44, 45, 47, 49, 443, and 445 in the fourth preferred embodiment as illustrated in FIG. 12 are substantially same as the components 21, 22, 24, 25, 27, 29, 243, and 245, respectively, as illustrated in FIG. 8.

However, user skin data and specimen data are not stored in digital form within the dispensing device 40. The optimal dispensing scheme is hard coded into the dispensing mechanism, which regulates the specimen dispensing from the dispenser 44, or any sub-dispenser and any compartment of dispenser the 44, by any of: specimen composition within the dispensers, specimen outflow speed and specimen dispensing timing. Such hard coded dispensing mechanism is configured with considering both the specimen data, and the user data, user skin condition and any other type of information relating to the proper dispensing of the specimen to meet user skin care need. The hard code can be in the form of an electronic chip, a circuit component, a mechanical valve or a non-volatile memory.

The optimal dispensing scheme is formulated outside of the dispensing device 40. Specimen data and skin data are stored external to the dispensing device 40. The specimen data and skin data are retrieved and processed by a computer or a data processing unit external to the dispensing device 40 to formulate an optimal dispensing scheme. This optimal dispensing scheme may be then transferred to the control unit 47, whereas control unit 47 may configure the hard code mechanism of the dispenser 446 through an electrical or a mechanical or a chemical or an optical interface 445. During dispensing, the control unit 47 drives the dispensing mechanism 443 through the electrical interconnect or a mechanical interface 445 following the optimal dispensing scheme to dispense the specimen 49 from the dispenser 44 to the device's treatment surface 42.

Figure 13:
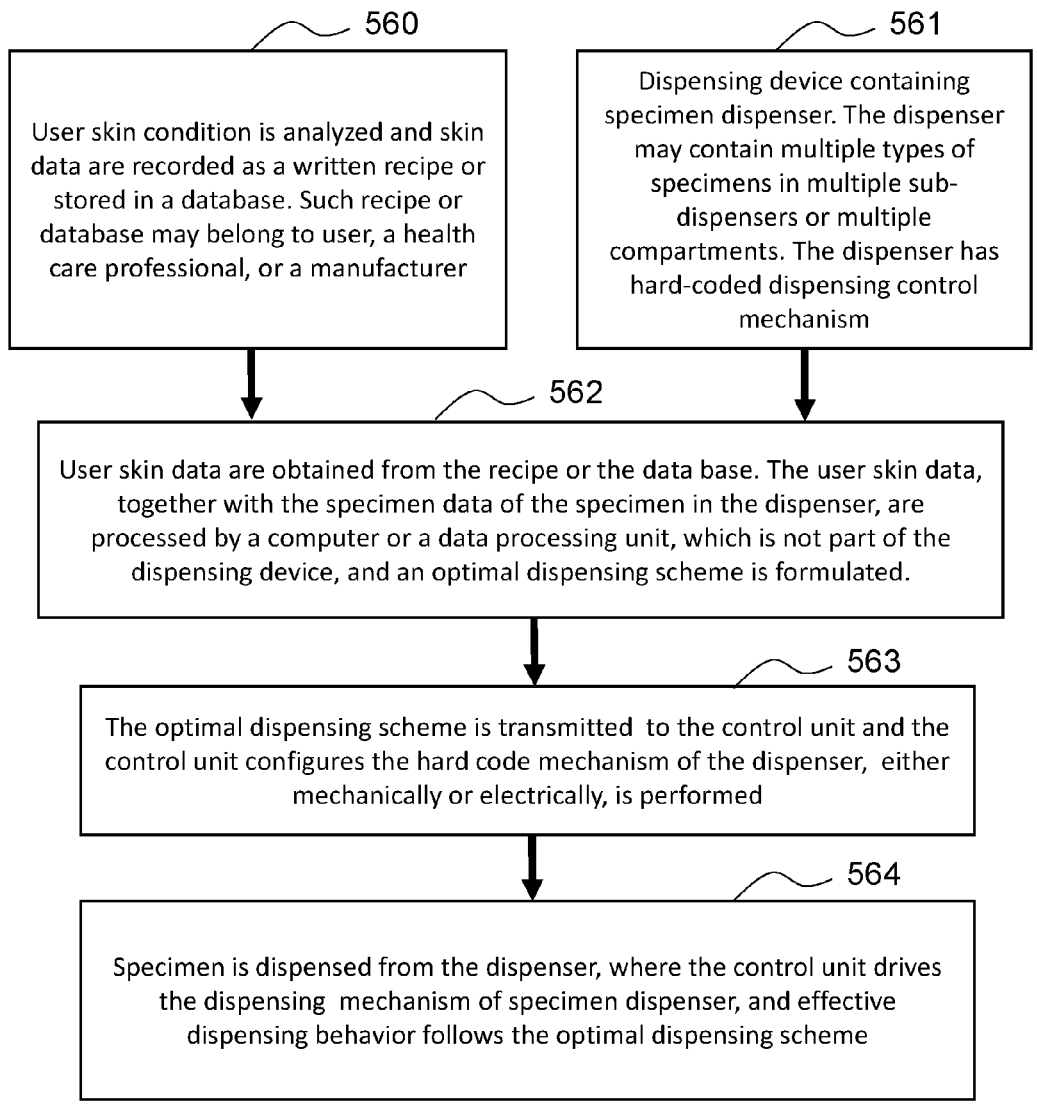
FIG. 13 is the flow of operation of the specimen dispensing device according to the fourth preferred embodiment of the present invention.

A process of operation according to the fourth preferred embodiment, as illustrated in FIG. 13, includes the steps of:

Step 560: User skin condition is analyzed and skin data are recorded as a written recipe or stored in a database, wherein such recipe or database may belong to user, a health care professional, or a manufacturer.

Step 561: Dispensing device contains specimen dispenser. The dispenser may contain multiple types of specimens in multiple sub-dispensers or multiple compartments. The dispenser has hard-coded dispensing control mechanism.

Step 562: User skin data are obtained from the recipe or the data base. The user skin data, together with the specimen data of the specimen in the dispenser, are processed by a computer or a data processing unit, which is not part of the dispensing device, and the optimal dispensing scheme is formulated.

Step 563: The optimal dispensing scheme is transmitted to the control unit and the control unit configures the hard code mechanism of the dispenser, either mechanically or electrically, is performed.

Step 564: Specimen is dispensed from the dispenser, where the control unit drives the dispensing mechanism of specimen dispenser, and effective dispensing behavior follows the optimal dispensing scheme.

Figure 79:
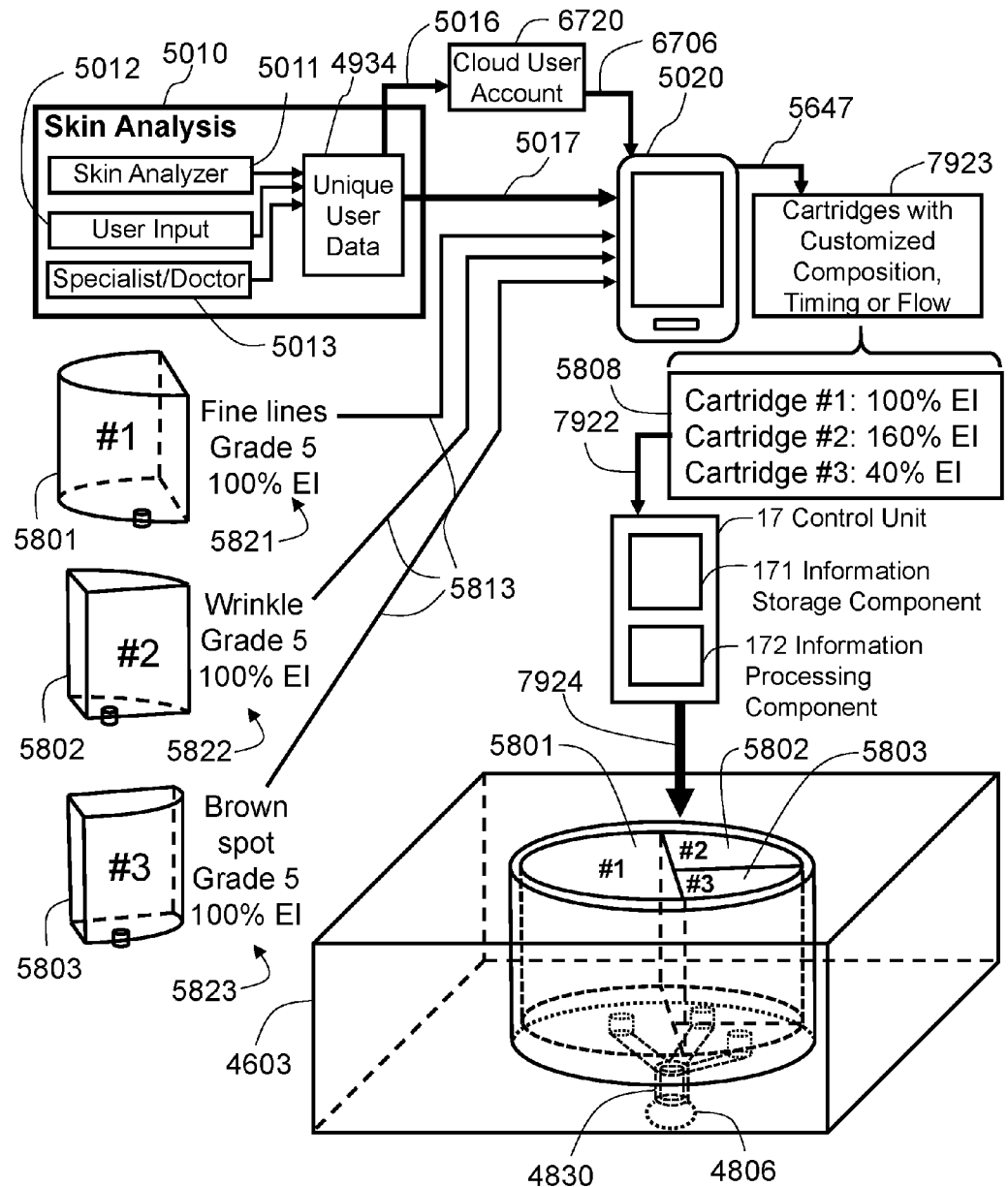

Now referring to FIG. 79. FIG. 79 illustrates a method to realize personalized composition scheme of a dispenser set utilizing a dispensing device and a set of cartridges according to FIG. 7 process. The step of skin analysis 5010, same as in FIG. 50, may create unique user data 4934 with input from any of: skin analyzer 5011, user input 5012, specialist and dermatologist 5013. The unique user data 4934 may be stored in a personal computing device 5020 of FIG. 50, which is also similar to user devices 6710 of FIG. 67, through communication 5017 of FIG. 50, to achieve step 560 of FIG. 13. The unique user data 4934 may also be sent to be stored in a cloud user account 6720 of FIG. 67 through communication 5016 of FIG. 50, to achieve step 560 of FIG. 13. Unique user data 4934 may be stored in personal computing device 5020 or in cloud user account 6720 as user data structure 5300 of FIG. 53.

Cartridge #1 5801, cartridge #2 5802 and cartridge #3 5803 with each containing specimen therein and each respectively containing specimen information 5821, 5822 and 5823, same as in FIG. 58, are installed into cartridge slot of the device body 4603, same as in FIG. 48A, of the said dispensing device as a cartridge set of #1 5801, #2 5802 and #3 5803 cartridges, whereas cartridges 5801, 5802 and 5803 may have hard coded specimen dispensing mechanism, whereas an information storage component 171 is contained in control unit 17 within said dispensing device, to achieve step 561 of FIG. 13.

Unique user data 4934 already stored in personal computing device 5020, or may be downloaded from cloud user account 6720 and sent to a personal computing device 5020 of FIG. 50, which may also be a user mobile device 6712 of FIG. 68, through communication 6706. The personal computing device 5020 may acquire specimen information 5821, 5822 and 5823 through communication 5813, which may also be communications 6202 or 6203 of FIG. 62 between a dispensing device that contains the cartridge #1 5801, cartridge #2 5802 and cartridge #5803, and the personal computing device 5020. Communication 5813 of FIG. 78 may also be the communication 5024 of FIG. 50 between a personal computing device 5020 and vender, service, production database 5044 of a beauty cloud 5040. The personal computing device 5020 may process information contained in the personal computing device 5020, which may include both the unique user data 4934 and specimen information 5821, 5822 and 5823 that are respectively transferred through communication 5017 or 6706, and communication 5813, to produce or calculate a specimen composition recipe 5808 of user #1 cartridge set composition scheme 5807 of FIG. 58 in step 5847 same as in FIG. 58, to achieve step 562 of FIG. 13, and composition recipe 5808 may be hard coded in the cartridge #1 5801, cartridge #2 5802 and cartridge #3 5803 as in step 7923, to achieve step 561 of FIG. 13.

During step 7923 the cartridge #1 5801, cartridge #2 5802 and cartridge #3 5803 may each be adjusted of the composition of the specimen contained in each of the cartridge #1 5801, cartridge #2 5802 and cartridge #3 5803. The cartridge #1 5801, cartridge #2 5802 and cartridge #3 5803 may also each be adjusted of the timing of specimen outflow during dispensing, or of the flow rate of the specimen outflow during dispensing, according to the specimen composition recipe 5808 as in step 7923, whereas said adjustments are regarded as "hardcoding" the specimen composition recipe 5808 into the cartridges 5801, 5802 and 5803. The hardcoding may be achieved with composition adjustment of specimen contained in each of the cartridges 5801, 5802 and 5803. The hardcoding may be achieved with using an electronic chip, a circuit component, a mechanical valve or a non-volatile memory to control composition, timing of outflow, and flow rate of specimen contained in each of the cartridges 5801, 5802 and 5803.

Composition scheme 5808 may also be sent to control unit 17 in step 7922, whereas in the case that composition of the specimen within each cartridge may be electrically configured, control unit may configure the specimen composition within each cartridge, or the outflow specimen composition following composition scheme 5808 to achieve step 563 of FIG. 13. The composition of the specimen within each cartridge may be electrically configured, for example by an electrical voltage or current applied to the specimen contained in any of the cartridge #1 5801, cartridge #2 5802 and cartridge #3 5803 that may cause chemical or physical change of the specimen to alter the composition of the specimen through electro-chemical reactions that may breakdown molecule bonds or produces molecule bonds within the specimen, or the composition of specimen flowing out of each cartridge may be electrically configured. Or for another example, each cartridge of cartridge #1 5801, cartridge #2 5802 and cartridge #3 5803 may contain sub-compartments that store both functional and non-functional elements and a different scheme of dispensing the functional and non-functional elements from various sub-compartments produces different final specimen composition flowing out of each of the cartridge.

Composition recipe 5808 is then implemented in dispensing of specimen from cartridge #1 5801, cartridge #2 5802 and cartridge #3 5803 as shown by step 7924, whereas dispensing device dispenses final specimen 4806 which is a mixture of specimen from cartridges 5801, 5802 and 5803 according to the composition recipe 5808 that is hard coded as any of: specimen composition within each cartridge, timing of specimen outflow, and specimen out flow rate, of specimen contained in each of the cartridges 5801, 5802 and 5803, through the device outlet 4830, to achieve step 564 of FIG. 13.

Although the above description focuses on the application of the device 10 for skin care purpose, it is readily applicable for other health care and personal care needs, where device 10 can be used for dispensing personalized specimen for these other needs. Such needs can be, but not limited to, clinical usage to produce personalized drugs and medications, non-clinical usage for personalized recipes. The subject of treatment can be any biological body area, body function, organ, skin, bone, tissue or cell.

The advantages of the present invention are numerous. For examples, (1) the specimen dispensing device with electrical interface and embedded memory enables customizability of skin care products that are specifically tailored for each individual's own skin care need; and (2) with the electrical dispenser containing product information, best mode of operation, pre-set beautification process and usage data, the specimen dispensing device can greatly increase the treatment effect and user-manufacture interaction of the skin beautification process, reduces the complexity of the user's operation and provides means of feedback from user to manufacture for further improvement on the skin care products.

Methods as described in this invention regarding treating skin features of a user based on unique user data are not limited to skin care only, and may be used for other medical or user-centric applications as well, where user skin as in various embodiments of this invention may be replaced by user's other body parts, and skin features in various embodiments of this invention may be replaced with features or symptoms of other human body parts or body health related subjects or issues.

For example, in the application of same methods for medical purposes: (a) specimen may include medication components in form any of liquid, gel, lotion, oil, paste, power or air sol; (b) unique user data may be user's unique health data regarding users body parts, like muscles, joints, organs, bones, eyes, mouth, or medical issues of body, heart, vascular, diabetes, mental, cancer, flu, infection; (c) user skin features may be replaced with the features of illness, symptoms, or required treatments of corresponding body parts or health issues; (d) dispensing device together with specimen dispenser may be used to produce customized medication for a user's unique medical need. Multiple medications can be dispensed from same dispensing device to form a mixture, or dispensed separately, to treat multiple symptoms or diseases.

In another example application of same methods used for dental care: (a) specimen may include toothpaste components; (b) unique user data can include information of user teeth; (c) features may be conditions of teeth, including holes, degradation, discoloration, material loss, cracking or sensitivity of the teeth.

In another example application of same methods used for tanning: (a) specimen may include tanning material components; (b) unique user data may include desired tanning results, for example, darkness, reflection quality, smoothness, of the skin; (c) features may include the user's skin properties that relate to tanning, for example, fairness, darkness, UV sensitivity, and user desired tanning result.

In another example application of same methods used for perfuming: (a) specimen may include perfume components; (b) unique user data may include user preference of perfuming components, or user perfuming need based on user's own selection or body odor, or what perfume components to dispense for what kind of social event or what time of the day or what day of the week, or method to access user's social network to project timing and location of upcoming social events; (c) features may include what perfume components are not compatible with the user's allergy or skin sensitivity or any health related issues.

In another example application of same methods used for weight control: (a) specimen may be various types of foods; (b) unique user data may include any of user body weight, user body weight target, desired body weight loss speed, user desired time of food intake, user desired type of foods, daily calorie consumption, desired calorie consumption reduction trend; (c) features may include what types of food is preferred, or required, or need to be avoided, by user at what time of the day according to user's health conditions, food allergy, social background, or religion.

While one or more embodiments of the present invention have been illustrated above, the skilled artisan will appreciate that modifications and adoptions to those embodiments may be made without departing from the scope and spirit of the present invention. While the current invention has been shown and described with reference to certain embodiments, it is to be understood that those skilled in the art will no doubt devise certain alterations and modifications thereto which nevertheless include the true spirit and scope of the current invention. Thus the scope of the invention should be determined by the appended claims and their legal equivalents, rather than by examples given.

What is claimed is:

1. A method to provide customized skin care by using a specimen dispensing device to dispense specimens for treating a skin area of a user comprising the steps of:
   a first computing device creating user data during a skin analysis of said user, whereas said user data contains a first identification (ID) of a first skin feature with a first grade, and a second ID of a second skin feature with a second grade;
   said first computing device transferring said user data to a first information storage component included in a control unit enclosed in said specimen dispensing device;
   said user installing a first dispenser containing a first specimen and a second dispenser containing a second specimen into said specimen dispensing device;
   wherein said first dispenser comprising a second information storage component storing a first specimen data including said first ID and a first method of dispensing, and said second dispenser comprising said second information storage component storing a second specimen data including said second ID and a second method of dispensing;
   said control unit acquiring said first and said second specimen data from said second information storage components of said first and second dispensers through a first data connection between said control unit and said first and second dispensers;
   an information processing component included in said control unit calculating a first dispensing recipe with using said first grade, said first method of dispensing, said second grade, and said second method of dispensing;
   said control unit commanding the dispensing of said first and second specimens from said first and said second dispensers according to said first dispensing recipe.

2. The method of claim 1, wherein said first computing device transfers said user data to a first database included in a first server through a first data network connecting said first computing device and said first server during said skin analysis.

3. The method of claim 2, wherein said first dispensing recipe is stored in said first information storage component and a second computing device external to said specimen dispensing device acquires said first dispensing recipe from said first information storage component through a second data connection to said control unit; and wherein said second computing device includes one of: a computer, a mobile phone, and a tablet.

4. The method of claim 3, wherein said second computing device modifies said first dispensing recipe into a second dispensing recipe; wherein said second computing device transfers said second dispensing recipe to said first information storage component through said second data connection; and wherein said control unit commands dispensing of said first and second specimens from said first and second dispensers according to said second dispensing recipe.

5. The method of claim 4, wherein said second computing device transfers said first and second dispensing recipes to second database included in a second server through a second data network connecting said second computing device and said second server.

6. The method of claim 5, wherein said second server is part of a data cloud.

7. The method of claim 1, wherein said user data is transferred by said first computing device in a user data structure including:

a first data section containing data to identify said user;
a second data section containing said first ID;
a third data section containing said first grade describing said first skin feature of said user including severity of said first skin feature;
a fourth data section containing said second ID; and
a fifth data section containing second grade describing said second skin feature on skin of said user including severity of said second skin feature.

8. The method of claim 1, wherein said first specimen data are stored in said second information storage component in a dispenser data structure including:
a first data section containing data to identify said first dispenser and said first specimen;
a second data section containing said first ID;
a third data section containing a first base grade; and
a fourth data section containing information of said first method of dispensing to dispense said first specimen from said first dispenser according to said first base grade.

9. The method of claim 8, wherein said first method of dispensing describes a first amount of said first specimen to be dispensed from said first dispenser when said first grade equals to said first base grade.

10. The method of claim 1, wherein said first dispensing recipe describes a first fixed amount of said first specimen to be dispensed from said first dispenser, and a second fixed amount of said second specimen to be dispensed from said second dispenser.

11. The method of claim 1, wherein said first data connection is one of the following:
wireless data communication between said control unit and said first and second dispensers, including one of: wireless, radio frequency identification (RFID), infrared, inductive coupling, fiber optics interface; and
data communication through one or more electrical wires that connect electrical contacts on the external surfaces of said first and second dispensers to electrical contacts of said control unit.

12. The method of claim 1, wherein each of said second information storage components is one of the following:
a digital storage device;
an analog data storage device;
an optically recognizable marking;
a radio frequency identification (RFID) tag;
a magnetic data storage media; and
physical indentations or protrusions.

13. The method of claim 1, wherein said first computing device contains an imaging device, and said imaging device captures a skin image of said skin area, and said first computing device performs a pattern recognition of said skin image.

14. The method of claim 1, wherein said specimen dispensing device has a skin treatment member for treating said skin area wherein said skin treatment member is one of following:
an ultrasound transmission plate for transmitting ultrasonic vibrations to user's skin during contact with skin of said user;
a vibration head that produces a mechanical motion upon skin of said user during contact;
a brush head that produces a brushing function upon skin of said user during contact;
a component comprising one or more electrodes that apply electrical voltage to skin of said user during contact; and
a component comprising one or more light emitting devices that emit optical radiation towards skin of said user.

15. A method to provide customized skin care by using a specimen dispensing device to dispense specimens for treating a skin area of a user comprising the steps of:
a first computing device creating and storing user data during a skin analysis, wherein said user data contains a first identification (ID) of a first skin feature, a first grade of said first skin feature, a second ID of a second skin feature, and a second grade of said second skin feature;
said first computing device calculating a composition recipe to adjust a first specimen in a first dispenser to a first composition and a second specimen in a second dispenser to a second composition by using said user data, a first specimen data and a second specimen data; wherein said first specimen data includes said first ID and a first method of dispensing, and said second specimen data includes said second ID and a second method of dispensing;
wherein the first dispenser comprises a first data storage component storing said first ID, and wherein the second dispenser comprises a second data storage component storing said second ID; a supplier receiving said composition recipe from said first computing device and adjusting said first specimen to said first composition and said second specimen to said second composition;
then, said user installing said first and second dispensers into said specimen dispensing device; and
a control unit in said dispensing device commands dispensing of said first specimen in said first composition and said second specimen in said second composition.

16. The method of claim 15, wherein said first computing device comprises at least one imaging device to capture skin image of said target skin area of said user, and a pattern recognition software to analyze said skin image to identify existing skin features; wherein said computing device includes one of: a computer, a mobile phone, and a tablet.

17. The method of claim 15, wherein said first method of dispensing describes a first composition percentage of at least one effective element of said first specimen when said first grade equals a first base grade.

18. The method of claim 15, wherein said first specimen is dispensed from said first dispenser in a first physical volume and said second specimen is dispensed from said second dispenser in a second physical volume; and wherein ratio of said first physical volume over said second physical volume is a constant value.

19. A method to provide customized skin care by using a specimen dispensing device to dispense specimens for treating a skin area of a user comprising the steps of:
a first computing device creating user data during a skin analysis, wherein said user data includes a first identification (ID) of a first skin feature;
said first computing device sending said user data to be stored in a database through a data network;
a second computing device acquiring said user data from said database, and using a specimen data to calculate a target composition of a first specimen in a first dispenser; wherein said first dispenser comprises a data storage component storing said first ID and wherein said specimen data include said first ID;
a supplier adjusting said first specimen to said target composition;
then, said user installing said first dispenser into said specimen dispensing device; and said dispensing device dispensing said first specimen from said first dispenser in said target composition.

20. The method of claim 19, wherein said user data are created by said first computing device when said first computing device is utilized by the said user; and wherein said first specimen in said first dispenser is adjusted to said target composition by said supplier who acquires said target composition from said second computing device.

* * * * *